US009321790B2

(12) United States Patent
El-Ahmad et al.

(10) Patent No.: US 9,321,790 B2

(45) Date of Patent: Apr. 26, 2016

(54) PYRIMIDINONE DERIVATIVES AS ANTIMALARIAL AGENTS

(71) Applicant: SANOFI, Paris (FR)

(72) Inventors: Youssef El-Ahmad, Paris (FR); Bruno Filoche-Romme, Paris (FR); Axel Ganzhorm, Paris (FR); Gilbert Marciniak, Paris (FR); Nicolas Muzet, Paris (FR); Baptiste Ronan, Paris (FR); Bertrand Vivet, Paris (FR); Véronique Zerr, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/409,869

(22) PCT Filed: Jun. 21, 2013

(86) PCT No.: PCT/EP2013/063065

§ 371 (c)(1),
(2) Date: Dec. 19, 2014

(87) PCT Pub. No.: WO2013/190123

PCT Pub. Date: Dec. 27, 2013

(65) Prior Publication Data

US 2015/0183804 A1 Jul. 2, 2015

(30) Foreign Application Priority Data

Jun. 22, 2012 (FR) ..................................... 12 55928

(51) Int. Cl.

| | |
|---|---|
| *A61K 31/535* | (2006.01) |
| *C07D 265/36* | (2006.01) |
| *C07D 498/02* | (2006.01) |
| *C07D 519/00* | (2006.01) |
| *A61K 31/519* | (2006.01) |
| *A61K 31/5386* | (2006.01) |
| *C07D 487/04* | (2006.01) |

(52) U.S. Cl.

CPC ............ *C07D 519/00* (2013.01); *A61K 31/519* (2013.01); *A61K 31/5386* (2013.01); *C07D 487/04* (2013.01)

(58) Field of Classification Search

None

See application file for complete search history.

(56) References Cited

FOREIGN PATENT DOCUMENTS

| | | | |
|---|---|---|---|
| EP | 1340761 | A1 | 9/2003 |
| EP | 1454909 | A1 | 9/2004 |
| EP | 1460076 | A1 | 9/2004 |
| WO | 2003/024949 | A1 | 3/2003 |
| WO | 2005/058908 | A1 | 6/2005 |
| WO | 2006/109081 | A1 | 10/2006 |
| WO | 2006/109084 | A1 | 10/2006 |
| WO | 2006/126010 | A2 | 11/2006 |
| WO | 2007/097981 | A2 | 8/2007 |
| WO | 2008/064244 | A2 | 5/2008 |
| WO | 2008/148074 | A2 | 12/2008 |
| WO | 2011/001112 | A1 | 1/2011 |
| WO | 2011/001113 | A2 | 1/2011 |
| WO | 2012/085244 | A1 | 6/2012 |

OTHER PUBLICATIONS

Bi et al. "Proliferative Defect and Embryonic Lethality in Mice Homozygous for a Deletion in the p110a Subunit of Phosphoinositide 3-Kinase" J. Biol. Chem. 274, (1999) 10963-10968.

Bi et al. "Early embryonic lethality in mice deficient in the pll013 catalytic subunit of Pl 3-kinase, Mamm Genome" (2002) 13, 169-172.

Brigaud et al. "Concise Synthesis of Enantiopure a-Trifluoromethyl Alanines, Diamines, and Amino Alcohols via the Strecker-type Reaction" Journal of Organic Chemistry 71(18), 2006 7075-7078.

Cully et al. "Beyond PTEN mutations: the Pl3K pathway as an integrator of multiple inputs during turnorigenesis" Nature Rev. 6, (2006) 184-192.

Doerig et al. "Antimalarial drug discovery: targeting protein kinases" Expert Opinion Ther. Targets 11, (2007) 279-290.

El-Sayed et al. "Nonsteroidal antiinflammatory agents—Part 1: Antiinflammatory, analgesic and antipyretic activity of some new 1-(pyrimidin-2-yl)-3-pyrazolin-5ones and 2-(pyrimidin-2-yl)-l,2,4,5,6,7-hexahydro-3H-indazol-3-ones" Eur. J. Med, Chem., 1998, 33(5), 349-361.

Engelman et al. "The evolution of phosphatdylinostol 3-kinases as regulators of growth and metabolism" Nature Rev. Genetics 7, (2006) 606-619.

Ihle et al. "Take your PlK: phosphatidylinositol 3-kinase inhibitors race through the clinic and toward cancer therapy" Current Opinion in Drug Discovery & Development 13, (2010) 41-49.

Ihle et al. "Take your PlK: phosphatidylinositol 3-kinase inhibitors race through the clinic and toward cancer therapy" Mol Cancer Ther. 8, (2009) 1-9.

Okkenhaug et al. "Impaired B and T Cell Antigen Receptor Signaling in p1108 Pl 3-Kinase Mutant Mice" Science 297, (2002) 1031-1034.

(Continued)

*Primary Examiner* — Jeffrey H Murray

(74) *Attorney, Agent, or Firm* — McDonnell Boehnen Hulbert & Berghoff

(57) ABSTRACT

The invention relates to novel pyrimidinone-based heterocyclic compounds which are parasite growth inhibitors, having the general formula (I) in which Y is a morpholine chosen from three bridged morpholines, L is a bond or a linker, n=0 or 1 and $R_2$ is a methyl group when n=0 and a hydrogen atom when n=1. Process for the preparation thereof and therapeutic use thereof.

(I)

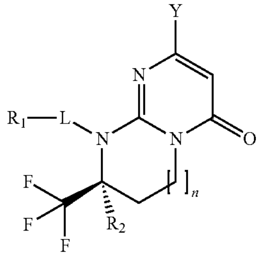

23 Claims, No Drawings

(56) References Cited

OTHER PUBLICATIONS

Ting et al. "Substituted 1,3-Dihydo-2H-pyrrolo[2,3-b]pyridin-2-oneass Potential Antiinflammatory Agents" J. Med. Chem. 33(10) (1990) 2697-2706.

Vaid et al. "PfPI3K, a phosphatidylinositol-3 kinase from *Plasmodium falciparum*, is exported to the host erythrocyte and is involved in hemoglobin trafficking" Blood 115 (2010) 2500-2507.

Ward et al. "Protein kinases of the human malaria parasite *Plasmodium falciparum*: the kinome of a divergent eukabiote" BMC Genomics 5, (2004) 79.

Yamashita et al. "Synthetic Communications: An International Journal for Rapid Communication of Synthetic Organic Chemistry" Syn. Commun. 34(5), (2004) 795-803.

Zhou et al. "Deletion of PIK3C3/Vps34 in sensory neurons causes rapid neurodegeneration by disrupting the endosomal but not the autophagic pathway" PNAS (2010) 107, 9424-9429.

Tanis et al. "Solvent and in situ catalyst preparation impacts upon Noyori reductions of aryl-chloromethyl ketones: application to syntheses of chiral 2-amino-1-aryl-ethanols" Tet. Asymmetry 17 (2006) 2154-2182.

International Search Report for International Patent Application No, PCT/EP2013/063065 dated Jul. 24, 2013 (mailed Aug. 5, 2013) p. 1-8.

Ulmann, "Ueber eine neue Bildungsweise von Diphenylaminderivaten", Chem. Berichte, 36, 2382-2384 (1903).

Johnson et al. "Gene silencing reveals a specific function of hVps34 phosphatidylinositol 3-kinase in late versus early endosomes". Journal of Cell Science 119, 1219-1232 (2006).

Jaber et al. "Class III PI3K Vps34 plays an essential role in autophagy and in heart and liver function." PNAS 109 (6), 2003-2008 (2012).

Apel et al. "Blocked Autophagy Sensitizes Resistant Carcinoma Cells to Radiation Therapy." Cancer Res 68 (5), 1485-1494 (2008).

Zhou et al. "Replication of the Association of a MET Variant with Autism in a Chinese Han Population." PLoS ONE 6(11): e27428, p. 1-5 (2011).

Moon et al. "Class III PI-3-kinase activates phospholipase D in an amino acid-sensing mTORC1 pathway." J. Cell Biol. vol. 195 No. 3 435-447 (2011).

Yang et al. "Eaten alive: a history of macroautophagy." Nat Cell Biol. 12(9), 814-822 (2010).

Tooze et al. "The origin of the autophagosomal membrane." Nature Cell Biology 12 (9), 831-835 (2010).

Vergne et al. "The role of PI3P phosphatases in the regulation of autophagy." FEBS Letters 584, 1313-1318 (2010).

Taguchi-Atarashi et al. "Modulation of Local Ptdlns3P Levels by the PI Phosphatase MTMR3 Regulates Constitutive Autophagy." Traffic 11, 468-478 (2010).

Janku et al. "Autophagy as a target for anticancer therapy." Nat. Rev. Clin. Oncol. 8, 528-539 (2011).

Mosesson et al. "Derailed endocytosis: an emerging feature of cancer." Nature Reviews Cancer 8, 835-850 (2008).

Jaber et al. "Class III PI3K Vps34 plays an essential role in autophagy and in heart and liver function." PNAS Early Edition, p. 1-6, SI 1-5 (2011).

Fan et al. "Akt and Autophagy Cooperate to Promote Survival of Drug-Resistant Glioma." Sci Signal., 3(147), ra81, p. 1-23 (2010).

Sagona et al. "Ptdlns(3)P controls cytokinesis through KIF13A-mediated recruitment of FYVE-CENT to the midbody." Nature Cell Biology, 12(4), 362-373 (2010).

Aliabiev et al. "A Convenient Synthesis of Novel Substituted Isoxazolo[5,4-d]Pyrimidines." Letters in Organic Chemistry, 4, 273-280 (2007).

Yamashita et al. "Improved Procedures for Preparation of Racemic Capreomycidine." Synthetic Communications, 34 (5), 795-803 (2004).

Mitsunobu, Oyo. "The Use of Diethyl Azodicarboxylate and Triphenylphosphine in Synthesis and Transformation of Natural Products." Synthesis, 1981(1), 1-28 (1981).

Lilmann, "Ueber eine neue Bildungsweise von Diphenylaminderivaten", Chem. Berichte, 36, 2382-2384 (1903).

Li et al. "Inhibition of autophagy augments 5-fluorouracil chemotherapy in human colon cancer in vitro and in vivo model." European Journal of Cancer, 46, 1900-1909 (2010).

Li et al. "The EGFR antibody cetuximab induces autophagy in cancer cells by downregulating HIF-1α and Bcl-2 and activating the beclin-1/hVps34 complex." Cancer Res., 70(14), 5942-5952 (2010).

Wu et al. "Autophagy Blockade Sensitizes Prostate Cancer Cells towards Src Family Kinase Inhibitors." Genes & Cancer, 1(1) 40-49 (2010).

Samaddar et al. "A role for macroautophagy in protection against 4-hydroxytamoxifen-induced cell death and the development of antiestrogen resistance." Mol Cancer Ther, 7(9), 2977-2987 (2008).

Raben et al. "Suppression of autophagy permits successful enzyme replacement therapy in a lysosomal storage lisorder—murine Pompe disease." Autophagy, 6(8), 1078-1089 (2010).

Mizushima et al. "Autophagy tights disease through cellular self-digestion." Nature, 451(7182), 1069-1075 (2008).

Hoang et al. "Effect of autophagy on multiple myeloma cell viability." Mol Cancer Ther, 8(7), 1974-84 (2009).

Levine et al. "Autophagy in the Pathogenesis of Disease." Cell, 132(1), 27-42 (2008).

Carew et al. "Targeting autophagy augments the anticancer activity of the histone deacetylase inhibitor SAHAto overcome Bcr-Abl-mediated drug resistance." Blood, 110, 313-322 (2007).

Vazquez-Martin et al. "Autophagy Facilitates the Development of Breast Cancer Resistance to the Anti-HER2 Monoclonal Antibody Trastuzumab." PLoS One, 4(7), e6251, p. 1-13 (2009).

Huguenot et al. "Concise Synthesis of Enantiopure r-Trifluoromethyl Alanines, Diamines, and Amino Alcohols via the Strecker-type Reaction." J. Org. Chem., 71, 7075-7078 (2006).

Gupta et al. "Autophagy inhibition and antimalarials promote cell death in gastrointestinal stromal tumor (GIST)." PNAS, 107(32), 14333-14338 (2010).

Badawey et al. "Nonsteroidal antiinflammatory agents—Part 1: Antiinflammatory, analgesic and antipyretic activity of some new 1-(pyrimidin-2-yl)-3-pyrazolin-5-ones and 2-(pyrimidin-2-yl)-I,2,4,5,6,7-hexahydro-3H-indazol-3-ones." Eul: J. Med. Chem., 33, 349-361 (1998).

Vanhaesebroeck et al. "The emerging mechanisms of isoform-specific PI3K signalling." Nature Reviews Molecular Cell Biology, 11, 329-341 (2010).

Lin, Hong et al. "Synthesis and structure-activity relationships of imidazo[1,2-a]pyrimidin-5(1H)-ones as a novel series of beta isoform selective phosphatidylinositol 3-kinase inhibitors," Bioorganic & Medicinal Chemistry Letters 22 (2012) 2230-2234.

French Search Report issued for priority application FR 1255917, p. 1, dated Sep. 11, 2012.

International Preliminary Report on Patentability issued for parent application PCT/IB2013/055099, p. 1-6.

PYRIMIDINONE DERIVATIVES AS ANTIMALARIAL AGENTS

This application is a national stage application under 35 U.S.C. §371 of International Application No. PCT/EP2013/063065, filed Jun. 21, 2013, which claims priority of France Application No. 1255928 filed on Jun. 22, 2012.

The present invention relates to pyrimidinone derivatives, and to the preparation and therapeutic use thereof.

Malaria is one of the prime causes of infection-mediated mortality worldwide. Infection with the parasite of the type *Plasmodium falciparum* affects close to 225 million people, causes more than 781 000 deaths annually and predominantly concerns children under 5 years old. The substantial return of the disease observed in recent years is due to several factors, including:

- the vectors, namely anopheles, which become resistant to the standard cheap insecticides,
- the increase in the population in the at-risk zones and, mainly,
- the resistance of numerous strains of *Plasmodium falciparum*, the parasite responsible for the mortal forms of the disease, to the medicaments conventionally used, such as chloroquine and mefloquine. Since 2001, artemisinin and derivatives thereof have been considered by the World Health Organization as the treatment of choice for *Plasmodium falciparum*-mediated uncomplicated malaria. However, clear signs of development of resistance to artemisinins have been observed.

The propagation of resistance among *Plasmodium* strains, in particular *P. falciparum*, towards the majority of the antimalarial drugs demonstrates the urgent need to develop novel compounds having a novel mode of action thus enabling a decrease of the risk of cross-resistance. Human kinases are valid targets in the treatment of numerous pathologies and the kinome of *P. falciparum* has been proposed as a reservoir of novel targets for the development of novel medicaments, which have not yet been explored in the treatment of malaria (Doerig and Meijer (2007) Expert Opin. Ther. Targets 11, 279-290).

The kinome of *Plasmodium falciparum* is composed of 64 kinases, some of which are orthologous to human kinases (Ward et al. (2004) BMC Genomics 5,79). Following this orthologous approach, a group of $CF_3$-pyrimidinone derivatives, which are active on human phosphatidylinositol-3-kinases, has been identified as being parasite growth inhibitors in human erythrocytes. Moreover, a plasmodial phosphatidylinositol-3-kinase, known as PfPI3K, has recently been identified, and the existence of a relationship between this kinase and human phosphatidylinositol kinases has been demonstrated (Vaid et al. (2010) Blood 115, 2500-2507). PfPI3K intervenes in the mechanism of endocytosis and in trafficking the host hemoglobin and as such plays an important role in maintaining the parasite growth in the infected human erythrocyte. It might thus be thereby deduced that the plasmodial kinase PfPI3K would be a target for the compounds of the present invention.

Human PI3Ks play a major role in signaling and traffic in human cells (Engelman et al. (2006) Nature Rev. Genetics 7, 606-619). The PI3K/Akt/mTOR signaling mechanism is an essential regulator of cell life, cell proliferation and protein synthesis. The insulin signaling pathway via the PI3K/Akt axis involving class 1A of PI3Ks (PI3Kα and β) is essential in glucose homeostasis. Downstream attenuation of insulin receptor signaling plays an important role in the development of type-2 diabetes. The other isoforms of class I PI3K, PI3Kγ and PI3Kδ, are involved in the immune function and inflammation (Ihle and Povis (2010) Current Opinion in Drug Discovery & Development 13, 41-49). Inhibition of PI3Kα or PI3Kδ in mice results in embryonic lethality (Bi et al. (1999) J. Biol. Chem. 274, 10963-10968; Bi et al. (2002) Mamm Genome 13, 169-172). Moreover, mice showing a deficiency in PI3Kγ or PI3Kδ show deficiences in immune functions (Okkenhaug et al. (2002) Science 297, 1031-1034). A summary of the potential and observable side effects of PI3K inhibition may be found in the articles by Cully et al. ((2006) Nature Rev. 6, 184-192) and Ihle and Powis ((2009) Mol. Cancer Ther. 8, 1-9).

Inhibition of class III PI3K, PIK3C3/VPS34, may also give rise to adverse side effects such as rapid neuron degeneration in mice following the conditional suppression of VPS34 in the sensory neurons (Zhou et al. (2010) PNAS 107, 9424-9429).

In summary, non-limiting examples that may be mentioned of potential side effects due to PI3K inhibition in man include metabolic disturbances associated with inhibition of insulin signaling with an increase of blood glucose, reduction of insulin sensitivity, diabetes, deregulation of the cerebral functions with the potential for inducing symptoms of schizophrenia and of Parkinson's disease, and neurodegeneration, and also immunosuppression. It should also be noted that nausea, diarrhea, tiredness, vomiting, skin eruptions and liver damage have been observed during clinical studies with inhibitors of the PI3K/mTOR axis.

On the basis of these observations, it is obvious that inhibiting human PI3K lipid kinases may have highly undesirable effects and should be avoided when the lipid kinome of *Plasmodium* is targeted for the treatment of malaria.

$CF_3$-pyrimidinone derivatives have been described in patent applications WO 2011/001112 and WO 2011/001113 for the preparation of medicaments for treating various cancers and also for treating parasitic diseases such as malaria. These compounds are described as inhibitors of human PI3Ks.

The compounds of the present invention have the advantage, although being derived from inhibitors of human PI3K and in particular PI3Kα, they do not inhibit this class of human kinases, while nonetheless remaining inhibitors of parasite growth.

Similar kinomes are present in all species of *Plasmodium*, such as *P. falciparum, P. vivax, P. malariae, P. ovale* and *P. knowlesi*. The compounds of the invention may thus be useful in the treatment of malaria induced by all the parasites mentioned above. In addition, the kinases are found in other parasites, such as *Trypanosoma* (for example *T. brucei, T. cruzei*) and *Leishmania* (for example *L. major, L. donovani*). The compounds of the invention may thus be used in the treatment of sleeping sickness, Chagas disease, the various forms of leishmaniasis and other parasitic infections.

Other parasites, such as schistosomes, toxoplasms and *Eimeria*, also use kinases for their cell regulation. Consequently, the compounds of the present invention may be useful in the treatment of schistosomiasis (bilharzia), toxoplasmosis and coccidiosis.

The present invention relates to compounds corresponding to formula (I):

(I)

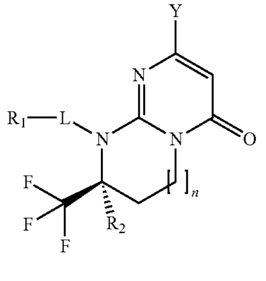

in which:

n represents 0 or 1;

Y represents a bridged morpholine chosen from (a)

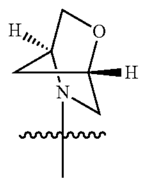

(b)

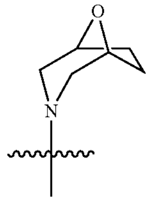

(c)

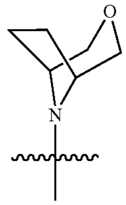

L represents a linker —$CH_2$—CO— such that the carbonyl function is attached to the substituent $R_1$, or a ($C_1$-$C_2$) alkyl, said alkyl being optionally substituted with one or more substituents chosen from a ($C_1$-$C_3$)alkyl group and a hydroxyl group;

$R_1$ represents:

a linear, branched, cyclic or partially cyclic ($C_1$-$C_5$)alkyl group, optionally substituted with one or more substituents chosen from a hydroxyl group, an aryl group, a trifluoromethyl group and a ($C_3$-$C_5$)cycloalkyl group, a ($C_3$-$C_6$)cycloalkyl group, optionally substituted with a hydroxyl group, an aryl group, optionally substituted with one or more substituents chosen from a halogen atom, a hydroxyl group, a cyano group, an —$NH_2$ group, a urea group of formula —NH—CO—NH—($C_1$-$C_4$)alkyl, a morpholine group, a group of formula —$SO_2$—($C_1$-$C_5$)alkyl, a ($C_1$-$C_5$)alkoxy group, said alkoxy being optionally substituted with one or more substituents chosen from:

a halogen atom, a hydroxyl group or a ($C_1$-$C_5$)alkoxy group, a group —$COR_3$, in which $R_3$ represents a substituent chosen from a heterocycloalkyl group and a hydroxyl group, a group —$CONR_4R_{4'}$ in which $R_4$ and $R_{4'}$ are as defined below, a group —$NR_4R_{4'}$ in which $R_4$ and $R_{4'}$ are as defined below, a heterocycloalkyl group comprising one or two heteroelements chosen from a nitrogen atom and an oxygen atom, a heteroaryl group optionally substituted with one or more substituents chosen from a halogen atom, a ($C_1$-$C_3$)alkyl group, a hydroxyl group and an —$NH_2$ group;

a heteroaryl group, comprising one or more heteroatoms chosen from a nitrogen atom, a sulfur atom and an oxygen atom, optionally substituted with one or more substituents chosen from:

a halogen atom, a ($C_1$-$C_3$)alkyl group optionally substituted with one or more halogen atoms, a ($C_1$-$C_5$)alkoxy group, optionally substituted with one or more substituents chosen from a halogen atom, a ($C_3$-$C_5$)cycloalkyl group, a heteroaryl group optionally substituted with one or more substituents chosen from a halogen atom, a ($C_1$-$C_3$)alkyl group, a hydroxyl group and an —$NH_2$ group, a group —$NR_5R_{5'}$ in which $R_5$ and $R_{5'}$, independently, which may be identical or different, represent a substituent chosen from a hydrogen atom, a —$CO_2$—($C_1$-$C_3$)alkyl group, a ($C_3$-$C_5$)cycloalkyl group and a linear or branched ($C_1$-$C_3$)alkyl group, said alkyl group being optionally substituted with one or more hydroxyl groups, a pyridine group bearing two linked adjacent groups forming, together with the two carbons that bear them, a heterocycle comprising a nitrogen atom and an oxygen atom, a heterocycloalkyl group comprising one or more heteroatoms chosen from oxygen and nitrogen atoms, said nitrogen atom being optionally substituted with a substituent chosen from a formyl group, an acetyl group and a —$CO_2$—($C_1$-$C_4$)alkyl group, a group —$NR_6R_{6'}$ in which $R_6$ and $R_{6'}$ which are different, represent a ($C_1$-$C_5$)alkyl group and a ($C_1$-$C_5$)alkoxy group, $R_2$ represents a hydrogen atom when n represents 1 and a methyl group when n represents 0;

$R_4$ and $R_{4'}$, independently, which may be identical or different, represent a hydrogen atom or a ($C_1$-$C_3$)alkyl group, in the form of the base or of an addition salt with an acid or with a base.

The compounds of formula (I) can comprise one or more asymmetric carbon atoms. They can therefore exist in the form of enantiomers or diastereoisomers. These enantiomers, diastereoisomers and also mixtures thereof, including racemic mixtures, are part of the invention.

The compounds of formula (I) may exist in the form of bases or salified with acids or bases, especially pharmaceutically acceptable acids or bases. Such addition salts are part of the invention.

These salts are prepared with pharmaceutically acceptable acids, but salts of other acids that are of use, for example, for purifying or isolating the compounds of formula (I) also form part of the invention. In particular, use will be made in the context of the invention of the hydrogen chloride salt.

In the context of the present invention, and unless otherwise mentioned in the text:

a halogen atom: a fluorine atom, a chlorine atom, a bromine atom or an iodine atom; in particular, the halogen atom is a fluorine atom;

an alkyl group: unless otherwise mentioned in the text, a linear or branched saturated aliphatic group containing from 1 to 5 carbons. Examples that may be mentioned include methyl, ethyl, propyl, isopropyl, butyl, isobutyl, tert-butyl and pentyl groups;

a partially cyclic ($C_1$-$C_5$)alkyl group: unless otherwise mentioned in the text, a linear saturated aliphatic group substituted with a ($C_3$-$C_4$)cycloalkyl group. Examples that may be mentioned include methylcyclopropyl, methylcyclobutyl and ethylcyclopropyl groups;

a cycloalkyl group: a cyclic ($C_3$-$C_6$)alkyl group. Examples that may be mentioned include cyclopropyl, cyclobutyl, cyclopentyl and cyclohexyl groups;

an alkoxy group: a radical —O-alkyl in which the alkyl group is as defined previously, in particular the alkyl group is a methyl or ethyl;

an aryl group: a cyclic aromatic group comprising between 5 and 6 carbon atoms. An example of an aryl group that may be mentioned is the phenyl group;

a heteroaryl group: a monocyclic or bicyclic aromatic group comprising between 2 and 9 carbon atoms and comprising between 1 and 4 heteroatoms, such as nitrogen, oxygen or sulfur. In particular, the bicyclic aromatic groups comprise a phenyl group. Examples of monocyclic heteroaryl groups that may be mentioned include imidazolyl, pyrimidyl, isoxazolyl, thiazolyl, isothiazolyl, pyridyl, pyrazolyl, oxazolyl and 1,2,4-oxadiazolyl groups. Examples of bicyclic heteroaryl groups that may be mentioned include 1H-indazolyl, benzo[1,2,3]thiadiazolyl, benzo[1,2,5]thiadiazolyl, benzothiophenyl, imidazo[1,2-a]pyridyl, quinolinyl and isoquinolinyl groups;

a heterocycloalkyl: a monocyclic or bicyclic alkyl group comprising from 4 to 8 atoms, 1 or 2 of which are heteroatoms, chosen from an oxygen atom and a nitrogen atom. Examples of monocyclic heterocycloalkyl groups that may especially be mentioned include piperidyl, morpholinyl and tetrahydropyranyl groups, and examples of bicyclic heterocycloalkyl groups that may be mentioned include groups of bridged morpholine type: 8-oxa-3-azabicyclo[3.2.1]oct-3-yl, 3-oxa-8-azabicyclo[3.2.1]oct-8-yl.

Among the compounds of the invention, mention may be made of a first subgroup of compounds corresponding to formula (I):

(I)

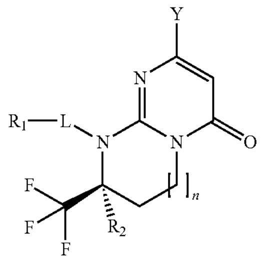

in which:

n represents 0 or 1, and/or

Y represents a bridged morpholine chosen from (a)

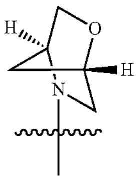

-continued (b)

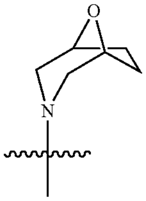

(c)

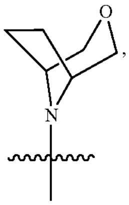

, and/or

L represents a linker —$CH_2$—CO— such that the carbonyl function is attached to the substituent $R_1$, or a ($C_1$-$C_2$) alkyl, said alkyl being optionally substituted with one or more substituents chosen from a ($C_1$-$C_3$)alkyl group and a hydroxyl group, and/or $R_1$ represents:

a linear, branched, cyclic or partially cyclic ($C_1$-$C_5$)alkyl group, optionally substituted with one or more substituents chosen from a hydroxyl group, an aryl group, a trifluoromethyl group and a ($C_3$-$C_5$)cycloalkyl group, a ($C_3$-$C_6$)cycloalkyl group, optionally substituted with a hydroxyl group, an aryl group, optionally substituted with one or more substituents chosen from a halogen atom, a hydroxyl group, a cyano group, an —$NH_2$ group, a urea group of formula —NH—CO—NH—($C_1$-$C_4$)alkyl, a morpholine group, a group of formula —$SO_2$—($C_1$-$C_5$)alkyl, a ($C_1$-$C_5$)alkoxy group, said alkoxy being optionally substituted with one or more substituents chosen from:

a halogen atom, a hydroxyl group or a ($C_1$-$C_5$)alkoxy group, a group —$COR_3$, in which $R_3$ represents a substituent chosen from a heterocycloalkyl group and a hydroxyl group, a group —$CONR_4R_{4'}$ in which $R_4$ and $R_{4'}$ are as defined below, a group —$NR_4R_{4'}$ in which $R_4$ and $R_{4'}$ are as defined below, a heterocycloalkyl group comprising one or two heteroelements chosen from a nitrogen atom and an oxygen atom, a heteroaryl group optionally substituted with one or more substituents chosen from a halogen atom, a ($C_1$-$C_3$)alkyl group, a hydroxyl group and an —$NH_2$ group;

a heteroaryl group, comprising one or more heteroatoms chosen from a nitrogen atom, a sulfur atom and an oxygen atom, optionally substituted with one or more substituents chosen from:

a halogen atom, a ($C_1$-$C_3$)alkyl group optionally substituted with one or more halogen atoms, a ($C_1$-$C_5$)alkoxy group, optionally substituted with one or more substituents chosen from a halogen atom, a ($C_3$-$C_5$)cycloalkyl group, a heteroaryl group optionally substituted with one or more substituents chosen from a halogen atom, a $(C_1-C_3)$alkyl group, a hydroxyl group and an —$NH_2$ group, a group —$NR_5R_{5'}$ in which $R_5$ and $R_{5'}$ independently, which may be identical or different, represent a substituent chosen from a hydrogen atom, a —$CO_2$—$(C_1-C_3)$alkyl group, a $(C_3-C_5)$cycloalkyl group and a linear or branched $(C_1-C_3)$alkyl group, said alkyl group being optionally substituted with one or more hydroxyl groups, a pyridine group bearing two linked adjacent groups forming, together with the two carbons that bear them, a heterocycle comprising a nitrogen atom and an oxygen atom, a heterocycloalkyl group comprising one or more heteroatoms chosen from oxygen and nitrogen atoms, said nitrogen atom being optionally substituted with a substituent chosen from a formyl group, an acetyl group and a —$CO_2$—$(C_1-C_4)$alkyl group, a group —$NR_6R_{6'}$ in which $R_6$ and $R_{6'}$ which are different, represent a $(C_1-C_5)$alkyl group and a $(C_1-C_5)$alkoxy group, and/or $R_2$ represents a hydrogen atom when n represents 1 and a methyl group when n represents 0, and/or $R_4$ and $R_{4'}$, independently, which may be identical or different, represent a hydrogen atom or a $(C_1-C_3)$alkyl group, in the form of the base or of an addition salt with an acid or with a base.

Among the compounds of the present invention, mention may be made of a second subgroup of compounds of formula (I) in which:

n represents 0 or 1;

Y represents a bridged morpholine chosen from (a)

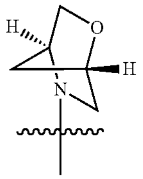

(b)

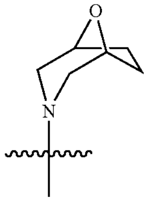

(c)

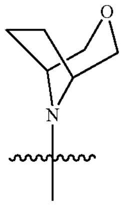

L represents a linker —$CH_2$—CO— such that the carbonyl function is attached to the substituent $R_1$, or a $(C_1-C_2)$ alkyl, said alkyl being optionally substituted with one or more substituents chosen from a $(C_1-C_3)$alkyl group and a hydroxyl group;

$R_1$ represents:

a linear or branched $(C_1-C_5)$ alkyl group, optionally substituted with one or more substituents chosen from a hydroxyl group and an aryl group, a group $(C_3-C_6)$cycloalkyl, an aryl group, optionally substituted with one or more substituents chosen from a halogen atom, a hydroxyl group, a cyano group, an —$NH_2$ group, a urea group of formula —NH—CO—NH—$(C_1-C_4)$alkyl, a morpholine group, a group of formula —$SO_2$—$(C_1-C_5)$alkyl, a $(C_1-C_5)$alkoxy group, said alkoxy being optionally substituted with one or more substituents chosen from:

a halogen atom, a hydroxyl group or a $(C_1-C_5)$alkoxy group, a group —$COR_3$, in which $R_3$ represents a substituent chosen from a heterocycloalkyl group and a hydroxyl group, a group —$CONR_4R_{4'}$ in which $R_4$ and $R_{4'}$ are as defined below, a group —$NR_4R_{4'}$ in which $R_4$ and $R_{4'}$ are as defined below, a heterocycloalkyl group comprising one or two heteroelements chosen from a nitrogen atom and an oxygen atom, a heteroaryl group optionally substituted with one or more substituents chosen from a halogen atom, a $(C_1-C_3)$alkyl group, a hydroxyl group and an —$NH_2$ group, a heteroaryl group, comprising one or more heteroatoms chosen from a nitrogen atom, a sulfur atom and an oxygen atom, optionally substituted with one or more substituents chosen from:

a halogen atom, a $(C_1-C_3)$alkyl group optionally substituted with one or more halogen atoms, a $(C_1-C_5)$alkoxy group, optionally substituted with one or more substituents chosen from a halogen atom, a $(C_3-C_5)$cycloalkyl group, a heteroaryl group optionally substituted with one or more substituents chosen from a halogen atom, a $(C_1-C_3)$alkyl group, a hydroxyl group and an —$NH_2$ group, a group —$NR_5R_{5'}$ in which $R_5$ and $R_{5'}$, independently, which may be identical or different, represent a substituent chosen from a hydrogen atom, a —$CO_2$—$(C_1-C_3)$alkyl group, a $(C_3-C_5)$cycloalkyl group and a linear or branched $(C_1-C_3)$alkyl group, said alkyl group being optionally substituted with one or more hydroxyl groups, a pyridine group bearing two linked adjacent groups forming, together with the two carbons that bear them, a heterocycle comprising a nitrogen atom and an oxygen atom, a heterocycloalkyl group comprising one or more heteroatoms chosen from oxygen and nitrogen atoms, said nitrogen atom being optionally substituted with a substituent chosen from a formyl group and an acetyl group, a group —$NR_6R_{6'}$ in which $R_6$ and $R_{6'}$ which are different, represent a $(C_1-C_5)$alkyl group and a $(C_1-C_5)$alkoxy group, $R_2$ represents a hydrogen atom when n represents 1 and a methyl group when n represents 0;

$R_4$ and $R_{4'}$, independently, which may be identical or different, represent a hydrogen atom or a $(C_1-C_3)$alkyl group, in the form of the base or of an addition salt with an acid or with a base.

Among the compounds of the present invention, mention may be made of a third subgroup of compounds of formula (I) in which:

n represents 0 or 1;

Y represents a bridged morpholine (a)

(a)

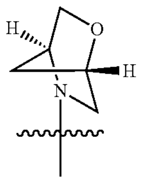

L represents a linker —$CH_2$—CO— such that the carbonyl function is attached to the substituent $R_1$, or ($C_1$-$C_2$) alkyl, said alkyl being optionally substituted with one or more substituents chosen from a ($C_1$-$C_3$)alkyl group and a hydroxyl group;

$R_1$ represents:

a linear, branched, cyclic or partially cyclic ($C_1$-$C_5$)alkyl group, optionally substituted with one or more substituents chosen from a hydroxyl group, an aryl group, a trifluoromethyl group and a ($C_3$-$C_5$)cycloalkyl group, a ($C_3$-$C_6$)cycloalkyl group, optionally substituted with a hydroxyl group, an aryl group, optionally substituted with one or more substituents chosen from a halogen atom, a hydroxyl group, an —$NH_2$ group, a urea group of formula —NH—CO—NH—($C_1$-$C_4$)alkyl, a morpholine group, a group of formula —$SO_2$—($C_1$-$C_5$)alkyl, a ($C_1$-$C_5$) alkoxy group, said alkoxy being optionally substituted with one or more substituents chosen from:

a halogen atom, a hydroxyl group or a ($C_1$-$C_5$)alkoxy group, a group —$COR_3$, in which $R_3$ represents a substituent chosen from a heterocycloalkyl group and a hydroxyl group, a group —$CONR_4R_{4'}$ in which $R_4$ and $R_{4'}$ are as defined below, a group —$NR_4R_{4'}$ in which $R_4$ and $R_{4'}$ are as defined below, a heterocycloalkyl group comprising one or two heteroelements chosen from a nitrogen atom and an oxygen atom, a heteroaryl group optionally substituted with one or more substituents chosen from a halogen atom, a ($C_1$-$C_3$)alkyl group, a hydroxyl group and an —$NH_2$ group, a heteroaryl group, comprising one or more heteroatoms chosen from a nitrogen atom, a sulfur atom and an oxygen atom, optionally substituted with one or more substituents chosen from:

a halogen atom, a ($C_1$-$C_3$)alkyl group optionally substituted with one or more halogen atoms, a ($C_1$-$C_5$)alkoxy group, optionally substituted with one or more substituents chosen from a halogen atom, a ($C_3$-$C_5$)cycloalkyl group, a heteroaryl group optionally substituted with one or more substituents chosen from a halogen atom, a ($C_1$-$C_3$)alkyl group, a hydroxyl group and an —$NH_2$ group, a group —$NR_5R_{5'}$ in which $R_5$ and $R_{5'}$, independently, which may be identical or different, represent a substituent chosen from a hydrogen atom, a —$CO_2$—($C_1$-$C_3$) alkyl group, a ($C_3$-$C_5$)cycloalkyl group and a linear or branched ($C_1$-$C_3$)alkyl group, said alkyl group being optionally substituted with one or more hydroxyl groups, a pyridine group bearing two linked adjacent groups forming, together with the two carbons that bear them, a heterocycle comprising a nitrogen atom and an oxygen atom, a heterocycloalkyl group comprising one or more heteroatoms chosen from oxygen and nitrogen atoms, in particular a morpholinyl group, a bridged morpholinyl group, a tetrahydropyranyl group and a piperidyl group, said nitrogen atom being optionally substituted with a substituent chosen from a formyl group, an acetyl group and a —$CO_2$—($C_1$-$C_4$)alkyl group, a group —$NR_6R_{6'}$ in which $R_6$ and $R_{6'}$, which are different, represent a ($C_1$-$C_5$)alkyl group and a ($C_1$-$C_5$)alkoxy group, $R_2$ represents a hydrogen atom when n represents 1 and a methyl group when n represents 0;

$R_4$ and $R_{4'}$, independently, which may be identical or different, represent a hydrogen atom or a ($C_1$-$C_3$)alkyl group, in the form of the base or of an addition salt with an acid or with a base.

Among the compounds of the present invention, mention may be made of a fourth subgroup of compounds of formula (I) in which:

n represents 0 or 1;

Y represents a bridged morpholine (a)

(a)

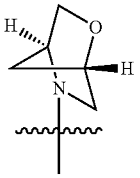

L represents a linker —$CH_2$—CO— such that the carbonyl function is attached to the substituent $R_1$, or ($C_1$-$C_2$) alkyl, said alkyl being optionally substituted with one or more substituents chosen from a ($C_1$-$C_3$)alkyl group and a hydroxyl group;

$R_1$ represents:

a linear or branched ($C_1$-$C_5$)alkyl group, optionally substituted with one or more substituents chosen from a hydroxyl group and an aryl group, a ($C_3$-$C_6$)cycloalkyl group, an aryl group, optionally substituted with one or more substituents chosen from a halogen atom, a hydroxyl group, an —$NH_2$ group, a urea group of formula —NH—CO—NH—($C_1$-$C_4$)alkyl, a morpholine group, a group of formula —$SO_2$—($C_1$-$C_5$)alkyl, a ($C_1$-$C_5$) alkoxy group, said alkoxy being optionally substituted with one or more substituents chosen from:

a halogen atom, a hydroxyl group or a ($C_1$-$C_5$)alkoxy, a group —$COR_3$, in which $R_3$ represents a substituent chosen from a heterocycloalkyl group and a hydroxyl group, a group —$CONR_4R_{4'}$ in which $R_4$ and $R_{4'}$ are as defined below, a group —$NR_4R_{4'}$ in which $R_4$ and $R_{4'}$ are as defined below, a heterocycloalkyl group comprising one or two heteroelements chosen from a nitrogen atom and an oxygen atom, a heteroaryl group optionally substituted with one or more substituents chosen from a halogen atom, a $(C_1-C_3)$alkyl group, a hydroxyl group and an —$NH_2$ group;

a heteroaryl group, comprising one or more heteroatoms chosen from a nitrogen atom, a sulfur atom and an oxygen atom, optionally substituted with one or more substituents chosen from:

a halogen atom, a $(C_1-C_3)$alkyl group optionally substituted with one or more halogen atoms, a $(C_1-C_5)$alkoxy group, optionally substituted with one or more substituents chosen from a halogen atom, a $(C_3-C_5)$cycloalkyl group, a heteroaryl group optionally substituted with one or more substituents chosen from a halogen atom, a $(C_1-C_3)$alkyl group, a hydroxyl group and an —$NH_2$ group, a group —$NR_5R_{5'}$ in which $R_5$ and $R_{5'}$, independently, which may be identical or different, represent a substituent chosen from a hydrogen atom, a —$CO_2$—$(C_1-C_3)$alkyl group, a $(C_3-C_5)$cycloalkyl group and a linear or branched $(C_1-C_3)$alkyl group, said alkyl group being optionally substituted with one or more hydroxyl groups, a pyridine group bearing two linked adjacent groups forming, together with the two carbons that bear them, a heterocycle comprising a nitrogen atom and an oxygen atom, a heterocycloalkyl group comprising one or more heteroatoms chosen from oxygen and nitrogen atoms, in particular a morpholinyl group, a bridged morpholinyl group and a piperidyl group, said nitrogen atom being optionally substituted with a substituent chosen from a formyl group and an acetyl group, a group —$NR_6R_{6'}$ in which $R_6$ and $R_{6'}$ which are different, represent a $(C_1-C_5)$alkyl group and a $(C_1-C_5)$alkoxy group, $R_2$ represents a hydrogen atom when n represents 1 and a methyl group when n represents 0;

$R_4$ and $R_{4'}$, independently, which may be identical or different, represent a hydrogen atom or a $(C_1-C_3)$alkyl group, in the form of the base or of an addition salt with an acid or with a base.

Among the compounds of the present invention, mention may be made of a fifth subgroup of compounds of formula (I) in which:

n represents 0 or 1;

Y represents a bridged morpholine (a)

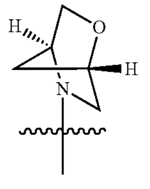

(a)

L represents a linker —$CH_2$—CO— such that the carbonyl function is attached to the substituent $R_1$, or $(C_1-C_2)$ alkyl, said alkyl being optionally substituted with one or more $(C_1-C_3)$alkyl groups;

$R_1$ represents:

a linear, branched, cyclic or partially cyclic $(C_1-C_5)$alkyl group, in particular an isopropyl or tert-butyl group, optionally substituted with one or more substituents chosen from a hydroxyl group, an aryl group, a trifluoromethyl group and a $(C_3-C_5)$cycloalkyl group, a $(C_3-C_6)$cycloalkyl group, optionally substituted with a hydroxyl group, an aryl group, in particular a phenyl group, optionally substituted with one or more substituents chosen from a halogen atom, a cyano group, an —$NH_2$ group, a urea group of formula —NH—CO—NH—$(C_1-C_4)$alkyl, a morpholine group, a group of formula —$SO_2$—$(C_1-C_5)$ alkyl, a $(C_1-C_5)$alkoxy group, in particular a methoxy group, said alkoxy being optionally substituted with one or more substituents chosen from:

a halogen atom, in particular a fluorine atom, a hydroxyl group or a $(C_1-C_5)$alkoxy group, a group —$COR_3$, in which $R_3$ represents a substituent chosen from a heterocycloalkyl group and a hydroxyl group, a heterocycloalkyl group comprising one or two heteroelements chosen from a nitrogen atom and an oxygen atom, in particular a morpholinyl group, a heteroaryl group optionally substituted with one or more substituents chosen from a halogen atom, a $(C_1-C_3)$alkyl group, a hydroxyl group and an —$NH_2$ group;

a heteroaryl group, comprising one or more heteroatoms chosen from nitrogen atoms, in particular a pyridyl group, and sulfur and oxygen atoms, optionally substituted with one or more substituents chosen from:

a halogen atom, a $(C_1-C_3)$alkyl group optionally substituted with one or more halogen atoms, a $(C_1-C_5)$alkoxy group, optionally substituted with one or more substituents chosen from a halogen atom, a $(C_3-C_5)$cycloalkyl group, a heteroaryl group optionally substituted with one or more substituents chosen from a halogen atom, a $(C_1-C_3)$alkyl group, a hydroxyl group and an —$NH_2$ group, a group —$NR_5R_{5'}$ in which $R_5$ and $R_{5'}$, independently, which may be identical or different, represent a substituent chosen from a hydrogen atom, a —$CO_2$—$(C_1-C_3)$alkyl group, a $(C_3-C_5)$cycloalkyl group and a linear or branched $(C_1-C_3)$alkyl group, said alkyl group being optionally substituted with one or more hydroxyl groups, a pyridine group bearing two linked adjacent groups forming, together with the two carbons that bear them, a heterocycle comprising a nitrogen atom and an oxygen atom, in particular a 3,4-dihydro-2H-pyrido[3,2-b][1,4]oxazine group, a heterocycloalkyl group comprising one or more heteroatoms chosen from oxygen and nitrogen atoms, said nitrogen atom being optionally substituted with a substituent chosen from a formyl group, an acetyl group and a —$CO_2$—$(C_1-C_4)$alkyl group, a group —$NR_6R_{6'}$ in which $R_6$ and $R_{6'}$, which are different, represent an alkyl group and a $(C_1-C_5)$alkoxy group, $R_2$ represents a hydrogen atom when n represents 1 and a methyl group when n represents 0;

in the form of the base or of an addition salt with an acid or with a base.

Among the compounds of the present invention, mention may be made of a sixth subgroup of compounds of formula (I) in which:

n represents 0 or 1;

Y represents a bridged morpholine (a)

(a)

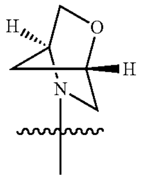

L represents a linker —$CH_2$—CO— such that the carbonyl function is attached to the substituent $R_1$, or ($C_1$-$C_2$) alkyl, said alkyl being optionally substituted with one or more ($C_1$-$C_3$)alkyl groups;

$R_1$ represents:

a linear or branched ($C_1$-$C_5$)alkyl group, in particular an isopropyl or tert-butyl group, optionally substituted with one or more hydroxyl groups, a ($C_3$-$C_6$)cycloalkyl group, an aryl group, in particular a phenyl group, optionally substituted with one or more substituents chosen from a halogen atom, a cyano group, an —$NH_2$ group, a urea group of formula —NH—CO—NH—($C_1$-$C_4$)alkyl, a morpholine group, a group of formula —$SO_2$—($C_1$-$C_5$) alkyl, a ($C_1$-$C_5$)alkoxy group, in particular a methoxy group, said alkoxy being optionally substituted with one or more substituents chosen from:

a halogen atom, in particular a fluorine atom, a hydroxyl group or a ($C_1$-$C_5$)alkoxy, a group —$COR_3$, in which $R_3$ represents a substituent chosen from a heterocycloalkyl group and a hydroxyl group, a heterocycloalkyl group comprising one or two hetero-elements chosen from a nitrogen atom and an oxygen atom, in particular a morpholinyl group, a heteroaryl group optionally substituted with one or more substituents chosen from a halogen atom, a ($C_1$-$C_3$)alkyl group, a hydroxyl group and an —$NH_2$ group;

a heteroaryl group, comprising one or more heteroatoms chosen from nitrogen atoms, in particular a pyridyl group, and sulfur and oxygen atoms, optionally substituted with one or more substituents chosen from:

a halogen atom, a ($C_1$-$C_3$)alkyl group optionally substituted with one or more halogen atoms, a ($C_1$-$C_5$)alkoxy group, optionally substituted with one or more substituents chosen from a halogen atom, a ($C_3$-$C_5$)cycloalkyl group, a heteroaryl group optionally substituted with one or more substituents chosen from a halogen atom, a ($C_1$-$C_3$)alkyl group, a hydroxyl group and an —$NH_2$ group, a group —$NR_5R_{5'}$ in which $R_5$ and $R_{5'}$ independently, which may be identical or different, represent a substituent chosen from a hydrogen atom, a —$CO_2$—($C_1$-$C_3$)alkyl group, a ($C_3$-$C_5$)cycloalkyl group and a linear or branched ($C_1$-$C_3$)alkyl group, said alkyl group being optionally substituted with one or more hydroxyl groups, a pyridine group bearing two linked adjacent groups forming, together with the two carbons that bear them, a heterocycle comprising a nitrogen atom and an oxygen atom, in particular a 3,4-dihydro-2H-pyrido[3,2-b][1,4]oxazine group, a heterocycloalkyl group comprising one or more heteroatoms chosen from oxygen and nitrogen atoms, said nitrogen atom being optionally substituted with a substituent chosen from a formyl group and an acetyl group, a group —$NR_6R_{6'}$ in which $R_6$ and $R_{6'}$, which are different, represent an alkyl group and a ($C_1$-$C_5$)alkoxy group, $R_2$ represents a hydrogen atom when n represents 1 and a methyl group when n represents 0;

in the form of the base or of an addition salt with an acid or with a base.

Among the compounds of the present invention, mention may be made of a seventh subgroup of compounds of formula (I) in which:

Y represents a bridged morpholine (a)

(a)

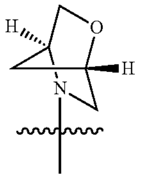

L represents a linker —$CH_2$—CO— such that the carbonyl function is attached the substituent $R_1$, $R_1$ represents:

a linear or branched ($C_1$-$C_5$)alkyl group, in particular an isopropyl or tert-butyl group, a ($C_3$-$C_6$)cycloalkyl group, an aryl group, in particular a phenyl group, optionally substituted with one or more substituents chosen from a halogen atom, a cyano group, an —$NH_2$ group, a urea group of formula —NH—CO—NH—($C_1$-$C_4$)alkyl, a morpholinyl group, a group of formula —$SO_2$—($C_1$-$C_5$) alkyl, a ($C_1$-$C_5$)alkoxy group, in particular a methoxy group, said alkoxy being optionally substituted with one or more substituents chosen from:

a halogen atom, in particular a fluorine atom, a hydroxyl group or a ($C_1$-$C_5$)alkoxy group, a group —$COR_3$, in which $R_3$ represents a substituent chosen from a heterocycloalkyl group and a hydroxyl group, a heterocycloalkyl group comprising one or two hetero-elements chosen from a nitrogen atom and an oxygen atom, in particular a morpholinyl group, a heteroaryl group optionally substituted with one or more substituents chosen from a halogen atom, a ($C_1$-$C_3$)alkyl group, a hydroxyl group and an —$NH_2$ group;

a heteroaryl group, comprising one or more heteroatoms chosen from nitrogen atoms, in particular a pyridyl group, and sulfur and oxygen atoms, optionally substituted with one or more substituents chosen from:

a halogen atom, a ($C_1$-$C_3$)alkyl group optionally substituted with one or more halogen atoms, an alkoxy group, optionally substituted with one or more substituents chosen from a halogen atom, a ($C_3$-$C_5$) cycloalkyl group, a heteroaryl group optionally substituted with one or more substituents chosen from a halogen atom, a ($C_1$-$C_3$)alkyl group, a hydroxyl group and an —$NH_2$ group, a group —$NR_5R_{5'}$ in which $R_5$ and $R_{5'}$, independently, which may be identical or different, represent a substituent chosen from a hydrogen atom, a —$CO_2$—($C_1$-$C_3$)alkyl group, a ($C_3$-$C_5$)cycloalkyl group and a linear or branched ($C_1$-$C_3$)alkyl group, said alkyl group being optionally substituted with one or more hydroxyl groups, a pyridine group bearing two linked adjacent groups forming, together with the two carbons that bear them, a heterocycle comprising a nitrogen atom and an oxygen atom, in particular a 3,4-dihydro-2H-pyrido[3,2-b][1,4]oxazine group, a heterocycloalkyl group comprising one or more heteroatoms chosen from oxygen and nitrogen atoms, said nitrogen atom being optionally substituted with a substituent chosen from a formyl group, an acetyl group and a —$CO_2$—($C_1$-$C_5$)alkyl group, a group —$NR_6R_{6'}$ in which $R_6$ and $R_{6'}$, which are different, represent an alkyl group and a ($C_1$-$C_5$)alkoxy group, in the form of the base or of an addition salt with an acid or with a base.

Among the compounds of the present invention, mention may be made of an eighth subgroup of compounds of formula (I) in which:

Y represents a bridged morpholine (a)

(a)

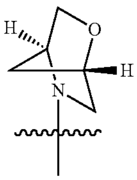

L represents a linker —$CH_2$—CO— such that the carbonyl function is attached to the substituent $R_1$, $R_1$ represents:

a linear or branched ($C_1$-$C_5$)alkyl group, in particular an isopropyl or tert-butyl group, a ($C_3$-$C_6$)cycloalkyl group, an aryl group, in particular a phenyl group, optionally substituted with one or more substituents chosen from a halogen atom, a cyano group, an —$NH_2$ group, a urea group of formula —NH—CO—NH—($C_1$-$C_4$)alkyl, a morpholinyl group, a group of formula —$SO_2$—($C_1$-$C_5$)alkyl, a ($C_1$-$C_5$)alkoxy group, in particular a methoxy group, said alkoxy being optionally substituted with one or more substituents chosen from:

a halogen atom, in particular a fluorine atom, a hydroxyl group or a ($C_1$-$C_5$)alkoxy group, a group —$COR_3$, in which $R_3$ represents a substituent chosen from a heterocycloalkyl group and a hydroxyl group, a heterocycloalkyl group comprising one or two heteroelements chosen from a nitrogen atom and an oxygen atom, in particular a morpholinyl group, a heteroaryl group optionally substituted with one or more substituents chosen from a halogen atom, a ($C_1$-$C_3$)alkyl group, a hydroxyl group and an —$NH_2$ group;

a heteroaryl group, comprising one or more heteroatoms chosen from nitrogen atoms, in particular a pyridyl group, and sulfur and oxygen atoms, optionally substituted with one or more substituents chosen from:

a halogen atom, a ($C_1$-$C_3$)alkyl group optionally substituted with one or more halogen atoms, an alkoxy group, optionally substituted with one or more substituents chosen from a halogen atom, a ($C_3$-$C_5$)cycloalkyl group, a heteroaryl group optionally substituted with one or more substituents chosen from a halogen atom, a ($C_1$-$C_3$)alkyl group, a hydroxyl group and an —$NH_2$ group, a group —$NR_5R_{5'}$ in which $R_5$ and $R_{5'}$, independently, which may be identical or different, represent a substituent chosen from a hydrogen atom, a —$CO_2$—($C_1$-$C_3$)alkyl group, a ($C_3$-$C_5$)cycloalkyl group and a linear or branched ($C_1$-$C_3$)alkyl group, said alkyl group being optionally substituted with one or more hydroxyl groups, a pyridine group bearing two linked adjacent groups forming, together with the two carbons that bear them, a heterocycle comprising a nitrogen atom and an oxygen atom, in particular a 3,4-dihydro-2H-pyrido[3,2-b][1,4]oxazine group, a heterocycloalkyl group comprising one or more heteroatoms chosen from oxygen and nitrogen atoms, in particular a morpholinyl group, a bridged morpholinyl group and a piperidyl group, said nitrogen atom being optionally substituted with a substituent chosen from a formyl group and an acetyl group, a group —$NR_6R_{6'}$ in which $R_6$ and $R_{6'}$, which are different, represent an alkyl group and an alkoxy group, in the form of the base or of an addition salt with an acid or with a base.

A ninth subgroup of compounds of formula (I) according to the invention is such that:

n represents 0 or 1;

Y represents a bridged morpholine chosen from (b) and (c)

(b)

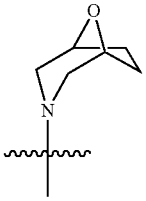

(c)

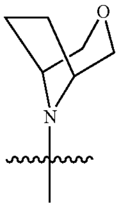

L represents a linker —$CH_2$—CO— such that the carbonyl function is attached to the substituent $R_1$, or ($C_1$-$C_2$)alkyl, said alkyl being optionally substituted with a hydroxyl group;

$R_1$ represents:

a linear or branched ($C_1$-$C_5$)alkyl group, optionally substituted with an aryl group, an aryl group, optionally substituted with one or more substituents chosen from a halogen atom, a hydroxyl group and a ($C_1$-$C_5$)alkoxy group, said alkoxy being optionally substituted with one or more substituents chosen from:

a group —$CONR_4R_{4'}$ in which $R_4$ and $R_{4'}$ are as defined below, a group —$NR_4R_{4'}$ in which $R_4$ and $R_{4'}$ are as defined below, a heteroaryl group comprising one or more heteroatoms chosen from a nitrogen atom, a sulfur atom and an oxygen atom, optionally substituted with one or more ($C_1$-$C_3$)alkyl groups, optionally substituted with one or more halogen atoms, $R_2$ represents a hydrogen atom when n represents 1 and a methyl group when n represents 0;

$R_4$ and $R_{4'}$, independently, which may be identical or different, represent a hydrogen atom or a ($C_1$-$C_3$)alkyl group, in the form of the base or of an addition salt with an acid or with a base.

A tenth subgroup of compounds of formula (I) according to the invention is such that L represents a linker —$CH_2$—CO— such that the carbonyl function is attached to the substituent $R_1$, in the form of the base or of an addition salt with an acid or with a base.

An eleventh subgroup of compounds of formula (I) according to the invention is such that n represents 1, in the form of the base or of an addition salt with an acid or with a base.

A twelfth subgroup of compounds of formula (I) according to the invention is such that n represents 0, in the form of the base or of an addition salt with an acid or with a base.

A thirteenth subgroup of compounds of formula (I) according to the invention is such that $R_1$ represents a heteroaryl group, in particular a pyridyl group, in the form of the base or of an addition salt with an acid or with a base.

A fourteenth subgroup of compounds of formula (I) according to the invention is such that $R_1$ represents a heterocycloalkyl group comprising one or more heteroatoms chosen from oxygen and nitrogen atoms, in particular a morpholinyl group, a bridged morpholinyl group, a tetrahydropyranyl group and a piperidyl group, said nitrogen atom being optionally substituted with a substituent chosen from a formyl group, an acetyl group and a —$CO_2$—($C_1$-$C_4$) alkyl group, in the form of the base or of an addition salt with an acid or with a base.

The subgroups defined above, taken separately or in combination, also form part of the invention. It should be noted that the eleventh and twelfth subgroups cannot be combined together.

Among the compounds of formula (I) that are subjects of the invention, mention may be made especially of the following compounds:

1 (8S)-9-(2-Methyl-2-pyrid-4-ylpropyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 2 (8S)-2-(1S,4S)-2-Oxa-5-azabicyclo[2.2.1]hept-5-yl-9-(2-oxo-2-pyrid-4-ylethyl)-8-trifluoromethyl-6,7,8,9-tetrahydropyrimido[1,2-a]pyrimidin-4-one 3 (8S)-9-[2-(6-Aminopyrid-3-yl)-2-oxoethyl]-2-oxa-5-azabicyclo[2.2.1]hept-5-yl-8-trifluoromethyl-6,7,8,9-tetrahydropyrimido[1,2-a]pyrimidin-4-one 4 (8S)-9-[2-(6-Methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 5 (8S)-9-[2-(6-Methylaminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 6 (8S)-9-[2-(6-Dimethylaminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 7 (8S)-2-(1S,4S)-2-Oxa-5-azabicyclo[2.2.1]hept-5-yl-9-(2-oxo-2-pyrid-3-ylethyl)-8-trifluoromethyl-6,7,8,9-tetrahydropyrimido[1,2-a]pyrimidin-4-one 8 1-[2-(6-Dimethylaminopyrid-3-yl)-2-oxoethyl]-2-(S)-methyl-7-(1S,4S)-2-oxa-5-azabicyclo[2.2.1]hept-5-yl-2-trifluoromethyl-2,3-dihydro-1H-imidazo[1,2-a]pyrimidin-5-one 9 2-(S)-Methyl-1-[2-(6-methylaminopyrid-3-yl)-2-oxoethyl]-7-(1S,4S)-2-oxa-5-azabicyclo[2.2.1]hept-5-yl-2-trifluoromethyl-2,3-dihydro-1H-imidazo[1,2-a]pyrimidin-5-one 10 (8S)-1-[2-(4-Methoxyphenyl)ethyl]-2-methyl-7-(1S,4S)-2-oxa-5-azabicyclo[2.2.1]hept-5-yl-2-trifluoromethyl-2,3-dihydro-1H-imidazo[1,2-a]pyrimidin-5-one 11 (S)-1-[2-(6-Aminopyrid-3-yl)-2-oxoethyl]-2-methyl-7-(1S,4S)-2-oxa-5-azabicyclo[2.2.1]hept-5-yl-2-trifluoromethyl-2,3-dihydro-1H-imidazo[1,2-a]pyrimidin-5-one 12 (8S)-2-(1S,4S)-2-Oxa-5-azabicyclo[2.2.1]hept-5-yl-9-(2-pyrid-3-ylethyl)-8-trifluoromethyl-6,7,8,9-tetrahydropyrimido[1,2-a]pyrimidin-4-one 13 2-Methyl-7-(1S,4S)-2-oxa-5-azabicyclo[2.2.1]hept-5-yl-1-(2-pyrid-3-ylethyl)-2-((S)-trifluoromethyl)-2,3-dihydro-1H-imidazo[1,2-a]pyrimidin-5-one 14 (8S)-9-{2-[6-(2-Hydroxyethylamino)pyrid-3-yl]-2-oxoethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one 15 (8S)-9-[2-(5-Methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 16 2-Methyl-1-[2-(5-methylpyrid-3-yl)-2-oxoethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one 17 2-Methyl-1-[2-(6-methylpyrid-3-yl)-2-oxoethyl]-7-(1S,4S)-2-oxa-5-azabicyclo[2.2.1]hept-5-yl-2-trifluoromethyl-2,3-dihydro-1H-imidazo[1,2-a]pyrimidin-5-one 18 2-Methyl-1-[2-(2-methylpyrid-3-yl)-2-oxoethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one 19 (8S)-9-[2-(2-Methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 20 (8S)-9-[2-(4-Methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 21 2-Methyl-7-(1S,4S)-2-oxa-5-azabicyclo[2.2.1]hept-5-yl-1-(2-oxo-2-pyrid-3-ylethyl)-2-((S)-trifluoromethyl)-2,3-dihydro-1H-imidazo[1,2-a]pyrimidin-5-one 22 (8S)-9-[2-(6-Cyclopropylaminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 23 1-Ethyl-3-{4-[2-((S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)ethyl]phenyl}urea 24 1-Ethyl-3-{4-[2-((S)-2-methyl-7-(1S,4S)-2-oxa-5-azabicyclo[2.2.1]hept-5-yl-5-oxo-2-trifluoromethyl-2,3-dihydro-5H-imidazo[1,2-a]pyrimidin-1-yl)ethyl]phenyl}urea 25 (8S)-9-[2-(4-Methylthiazol-5-yl)ethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 26 2-Methyl-1-[2-(4-methylthiazol-5-yl)ethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one 27 (8S)-9-[2-(3,5-Dimethyl-1H-pyrazol-4-yl)ethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 28 1-[2-(3,5-Dimethyl-1H-pyrazol-4-yl)ethyl]-2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one 29 (8S)-9-(3,3-Dimethyl-2-oxobutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 30 1-(3,3-Dimethyl-2-oxobutyl)-2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one 31 (8S)-9-[2-(6-Amino-5-methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 32 1-[2-(4-Aminophenyl)ethyl]-2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one 33 (8S)-2-(1S,4S)-2-Oxa-5-azabicyclo[2.2.1]hept-5-yl-9-[2-oxo-2-(6-trifluoromethylpyrid-3-yl)ethyl]-8-trifluoromethyl-6,7,8,9-tetrahydropyrimido[1,2-a]pyrimidin-4-one 34 (8S)-9-(2-{6-[(2-Hydroxyethyl)methylamino]pyrid-3-yl}-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 35 (8S)-9-[2-(6-Ethoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 36 (8S)-9-[2-(6-Amino-4,5-dimethylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 37 (S)-9-[2-(4-Difluoromethoxyphenyl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 38 (8S)-9-[2-(3,4-Dihydro-2H-pyrido[3,2-b][1,4]oxazin-7-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 39 (8S)-9-[2-(4-Methyloxazol-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 40 (S)-9-[2-(3,4-Difluorophenyl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 41 (8S)-9-[2-(4-Morpholin-4-ylphenyl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 42 4-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)acetyl]benzonitrile 43 (8S)-9-[2-(4-Methylthiazol-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 44 (8S)-9-[2-(5-Chloropyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 45 (8S)-9-[2-(6-Methoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 46 (8S)-9-[2-(3-Methylisoxazol-4-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 47 (8S)-9-(2-Benzo[1,2,3]thiadiazol-5-yl-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 48 (8S)-9-[2-(2,4-Difluorophenyl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 49 (8S)-9-(3-Ethyl-3-hydroxypentyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 50 (8S)-9-(3-Hydroxy-3-methylbutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 51 (8S)-9-(1-Methyl-1H-indazol-3-ylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 52 (8S)-9-[2-(2-Cyclopropylmethoxypyrimidin-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 53 (8S)-9-[2-(3,5-Dimethylisoxazol-4-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 54 (8S)-9-(2-Ethyl-2-hydroxybutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 55 3-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)acetyl]benzonitrile 56 (8S)-9-(3-Methyl-2-oxobutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 57 {5-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)acetyl]pyrid-2-yl}carbamic acid ethyl ester 58 {5-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)acetyl]pyrid-2-yl}carbamic acid methyl ester 59 (8S)-9-(5-Methyl-[1,2,4]oxadiazol-3-ylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 60 (8S)-2-(1S,4S)-2-Oxa-5-azabicyclo[2.2.1]hept-5-yl-9-[2-oxo-2-(2-trifluoromethylpyrid-3-yl)ethyl]-8-trifluoromethyl-6,7,8,9-tetrahydropyrimido[1,2-a]pyrimidin-4-one 61 (8S)-9-(2-Benzo[1,2,5]thiadiazol-5-yl-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 62 (8S)-2-(1S,4S)-2-Oxa-5-azabicyclo[2.2.1]hept-5-yl-9-[2-oxo-2-(tetrahydropyran-4-yl)ethyl]-8-trifluoromethyl-6,7,8,9-tetrahydropyrimido[1,2-a]pyrimidin-4-one 63 (8S)-9-{2-[6-(2-Fluoroethoxy)pyrid-3-yl]-2-oxoethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one 64 (8S)-9-{2-[3-Fluoro-4-(2-fluoroethoxyl)phenyl]-2-oxoethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one 65 (8S)-9-[2-(2-Methoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 66 (8S)-9-[2-(3-Methyl-3H-imidazol-4-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 67 (8S)-9-(2-Cyclopropyl-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 68 (8S)-2-(1S,4S)-2-Oxa-5-azabicyclo[2.2.1]hept-5-yl-9-(2-oxo-2-pyrid-2-ylethyl)-8-trifluoromethyl-6,7,8,9-tetrahydropyrimido[1,2-a]pyrimidin-4-one 69 (8S)-9-[2-(2-Methyl-2H-pyrazol-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 70 N, N-Dimethyl-2-(4-{2-[(S)-2-methyl-7-(8-oxa-3-azabicyclo[3.2.1]oct-3-yl)-5-oxo-2-trifluoromethyl-2,3-dihydro-5H-imidazo[1,2-a]pyrimidin-1-yl]ethyl}phenoxy)acetamide 71 (8S)-9-[(S)-2-(4-Fluoro-2-methoxyphenyl)-2-hydroxyethyl]-2-(8-oxa-3-azabicyclo[3.2.1]oct-3-yl)-8-trifluoromethyl-6,7,8,9-tetrahydropyrimido[1,2-a]pyrimidin-4-one 72 (2S)-1-[2-(4-Hydroxyphenyl)ethyl]-2-methyl-7-(8-oxa-3-azabicyclo[3.2.1]oct-3-yl)-2-trifluoromethyl-2,3-dihydro-1H-imidazo[1,2-a]pyrimidin-5-one 73 (8S)-2-(8-Oxa-3-azabicyclo[3.2.1]oct-3-yl)-9-(2-oxo-2-phenylethyl)-8-trifluoromethyl-6,7,8,9-tetrahydropyrimido[1,2-a]pyrimidin-4-one 74 (2S)-1-{2-[4-(2-Dimethylaminoethoxyl)phenyl]ethyl}-2-methyl-7-(8-oxa-3-azabicyclo[3.2.1]oct-3-yl)-2-trifluoromethyl-2,3-dihydro-1H-imidazo[1,2-a]pyrimidin-5-one 75 (8S)-2-(8-Oxa-3-azabicyclo[3.2.1]oct-3-yl)-9-(2-oxo-2-pyrid-4-ylethyl)-8-trifluoromethyl-6,7,8,9-tetrahydropyrimido[1,2-a]pyrimidin-4-one 76 (S)-1-[2-(4-Methoxyphenyl)ethyl]-2-methyl-7-(8-oxa-3-azabicyclo[3.2.1]oct-3-yl)-2-trifluoromethyl-2,3-dihydro-1H-imidazo[1,2-a]pyrimidin-5-one 77 (S)-2-Methyl-7-(8-oxa-3-azabicyclo[3.2.1]oct-3-yl)-1-(3-phenylpropyl)-2-trifluoromethyl-2,3-dihydro-1H-imidazo[1,2-a]pyrimidin-5-one 78 (S)-1-{2-[4-(3-Dimethylaminopropoxyl)phenyl]ethyl}-2-methyl-7-(8-oxa-3-azabicyclo[3.2.1]oct-3-yl)-2-trifluoromethyl-2,3-dihydro-1H-imidazo[1,2-a]pyrimidin-5-one 79 (2S)-1-((S)-2-Hydroxy-2-phenylethyl)-2-methyl-7-(8-oxa-3-azabicyclo[3.2.1]oct-3-yl)-2-trifluoromethyl-2,3-dihydro-1H-imidazo[1,2-a]pyrimidin-5-one 80 (8S)-9-((S)-2-Hydroxy-2-phenylethyl)-2-(8-oxa-3-azabicyclo[3.2.1]oct-3-yl)-8-trifluoromethyl-6,7,8,9-tetrahydropyrimido[1,2-a]pyrimidin-4-one 81 (8S)-9-[2-(4-Methoxyphenyl)ethyl]-2-(8-oxa-3-azabicyclo[3.2.1]oct-3-yl)-8-trifluoromethyl-6,7,8,9-tetrahydropyrimido[1,2-a]pyrimidin-4-one 82 (8S)-9-((R)-2-Benzo[b]thiophen-2-yl-2-hydroxyethyl)-2-(8-oxa-3-azabicyclo[3.2.1]oct-3-yl)-8-trifluoromethyl-6,7,8,9-tetrahydropyrimido[1,2-a]pyrimidin-4-one 83 (8S)-9-[2-(4-Hydroxyphenyl)ethyl]-2-(8-oxa-3-azabicyclo[3.2.1]oct-3-yl)-8-trifluoromethyl-6,7,8,9-tetrahydropyrimido[1,2-a]pyrimidin-4-one 84 (8S)-2-(8-Oxa-3-azabicyclo[3.2.1]oct-3-yl)-9-(3-phenylpropyl)-8-trifluoromethylmethyl-6,7,8,9-tetrahydropyrimido[1,2-a]pyrimidin-4-one 85 (8S)-2-(3-Oxa-8-azabicyclo[3.2.1]oct-8-yl)-9-(2-oxo-2-pyrid-3-ylethyl)-8-trifluoromethyl-6,7,8,9-tetrahydropyrimido[1,2-a]pyrimidin-4-one 86 (8S)-9-(1-Difluoromethyl-1H-pyrazol-3-ylmethyl)-2-(8-oxa-3-azabicyclo[3.2.1]oct-3-yl)-8-trifluoromethyl-6,7,8,9-tetrahydropyrimido[1,2-a]pyrimidin-4-one 87 (8S)-2-(8-Oxa-3-azabicyclo[3.2.1]oct-3-yl)-9-(2-oxo-2-pyrid-3-ylethyl)-8-trifluoromethyl-6,7,8,9-tetrahydropyrimido[1,2-a]pyrimidin-4-one 88 (8S)-2-(8-Oxa-3-azabicyclo[3.2.1]oct-3-yl)-9-(2-oxo-2-pyrid-2-ylethyl)-8-trifluoromethyl-6,7,8,9-tetrahydropyrimido[1,2-a]pyrimidin-4-one 89 (S)-9-[2-(1-Acetylpiperid-4-yl)ethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 90 4-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)ethyl]piperidine-1-carbaldehyde 91 4-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)acetyl]piperidine-1-carboxylic acid ethyl ester 92 (8S)-2-(1S,4S)-2-Oxa-5-azabicyclo[2.2.1]hept-5-yl-9-[2-(tetrahydropyran-4-yl)ethyl]-8-trifluoromethyl-6,7,8,9-tetrahydropyrimido[1,2-a]pyrimidin-4-one 93 (8S)-2-(1S,4S)-2-Oxa-5-azabicyclo[2.2.1]hept-5-yl-9-(tetrahydropyran-4-ylmethyl)-8-trifluoromethyl-6,7,8,9-tetrahydropyrimido[1,2-a]pyrimidin-4-one 94 (8S)-9-(1-Acetylpiperid-4-ylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 95 4-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-ylmethyl)piperidine-1-carbaldehyde 96 (8S)-2-(1S,4S)-2-Oxa-5-azabicyclo[2.2.1]hept-5-yl-9-(3,3,3-trifluoro-2-hydroxy-2-trifluoromethylpropyl)-8-trifluoromethyl-6,7,8,9-tetrahydropyrimido[1,2-a]pyrimidin-4-one 97 (8S)-2-(1S,4S)-2-Oxa-5-azabicyclo[2.2.1]hept-5-yl-9-(4,4,4-trifluoro-3-hydroxy-3-trifluoromethylbutyl)-8-trifluoromethyl-6,7,8,9-tetrahydropyrimido[1,2-a]pyrimidin-4-one 98 (8S)-2-(1S,4S)-2-Oxa-5-azabicyclo[2.2.1]hept-5-yl-9-[2-(8-oxa-3-azabicyclo[3.2.1]oct-3-yl)-2-oxoethyl]-8-trifluoromethyl-6,7,8,9-tetrahydropyrimido[1,2-a]pyrimidin-4-one 99 (8S)-2-(1S,4S)-2-Oxa-5-azabicyclo[2.2.1]hept-5-yl-9-[2-(3-oxa-8-azabicyclo[3.2.1]oct-8-yl)-2-oxoethyl]-8-trifluoromethyl-6,7,8,9-tetrahydropyrimido[1,2-a]pyrimidin-4-one 100 (8S)-9-[2-(1-Hydroxycyclopentyl)ethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 101 (8S)-9-(1-Hydroxycyclopentylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 102 (8S)-9-(3,3-Dicyclopropyl-3-hydroxypropyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 103 (8S)-9-(2,2-Dicyclopropyl-2-hydroxyethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 104 (8S)-9-(1-Hydroxycyclopropylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 105 (8S)-9-[2-(1-Hydroxycyclopropyl)ethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 106 (8S)-2-(1S,4S)-2-Oxa-5-azabicyclo[2.2.1]hept-5-yl-9-quinolin-5-ylmethyl-8-trifluoromethyl-6,7,8,9-tetrahydropyrimido[1,2-a]pyrimidin-4-one 107 (8S)-9-[2-(3-Methylisothiazol-4-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 108 (8S)-9-[2-(4-Methanesulfonylphenyl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 109 (8S)-9-Isoquinolin-5-ylmethyl-2-(1S,4S)-2-oxa-5-azabicyclo[2.2.1]hept-5-yl-8-trifluoromethyl-6,7,8,9-tetrahydropyrimido[1,2-a]pyrimidin-4-one 110 (8S)-9-(2-Morpholin-4-yl-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 111 (8S)-9-{2-[4-(2-Morpholin-4-ylethoxy)phenyl]ethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one 112 N-Methoxy-N-methyl-2-((S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)acetamide 113 (8S)-9-(2-Imidazo[1,2-a]pyrid-6-yl-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 114 (8S)-9-[2-(6-Difluoromethoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one 115 (S)-9-{2-[4-(2-Morpholin-4-yl-2-oxoethoxy)phenyl]ethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one 116 (8S)-9-(1-Methyl-3-trifluoromethyl-1H-pyrazol-4-ylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one 117 (8S)-9-{2-[4-(2-Dimethylaminoethoxyl)phenyl]ethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one 118 4-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)acetyl]piperidine-1-carbaldehyde 119 (8S)-9-[2-(1-Acetylpiperid-4-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one in the form of the base or of an addition salt with an acid or with a base.

It should be noted that the above compounds were named according to the IUPAC nomenclature by means of the Autonom software.

In accordance with the invention, the compounds of general formula (I) may be prepared according to the processes that follow.

The synthesis of the intermediate compounds $E_1$ in which n=1 and $R_2$ represents a hydrogen atom is described in Scheme 1:

Scheme 1

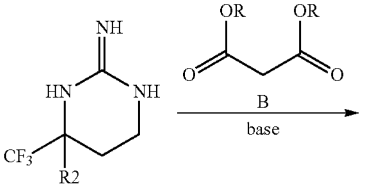

A

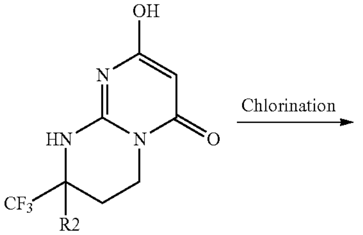

C

-continued

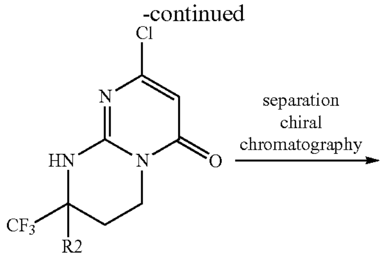

D

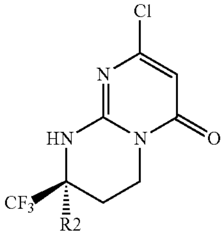

$E_1$

The guanidine A is prepared according to the processes described in patent application EP 1 460 076 by Lochead, A. W. et al. Compound C may be obtained by condensation of a guanidine A with a dialkyl malonate B, in which R is an alkyl group, preferably an ethyl group, in the presence of a strong base such as sodium methoxide, at a temperature of between 60° C. and 100° C., under the conditions described, for example, by Badawey E.-S.A.M. et al. (Eur. J. Med. Chem., 1998, 33(5), 349-361). Compound D may be obtained from a compound C by treatment with a chlorinating agent such as phosphorus oxychloride, in the absence of solvent, at a temperature between 20° C. and 120° C., or in the presence of a polar solvent such as 1,2-dichloroethane, at a temperature of between 20° C. and the boiling point of the solvent, as described by Yamashita, A. et al. (Syn. Commun. (2004), 34(5), 795-803). Compound $E_1$ is obtained after separation of the enantiomers of the compound of formula D by chromatography on a chiral support.

The synthesis of the intermediate compounds $E_0$ in which n=0 and $R_2$ represents a methyl group is described in Scheme 2:

Scheme 2

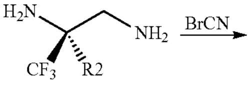

F

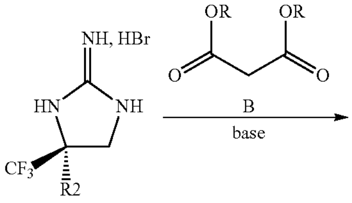

G

-continued

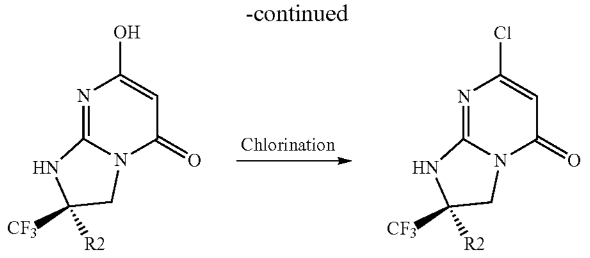

H $E_0$

The diamine F is either commercially available or prepared according to the process described in Journal of Organic Chemistry (2006, 71(18), 7075-7078) by Brigaud, T. et al. The guanidine G is obtained by reacting a diamine F and cyanogen bromide in a polar solvent such as water or acetonitrile, at a temperature of between 0° C. and the boiling point of the solvent, according to the conditions described in patent application EP 1 340 761 by Gallet, T. et al. As previously, the compounds H may be obtained by condensation of a guanidine G with a dialkyl malonate B, in which R is an alkyl group, preferably an ethyl group, in the presence of a strong base such as sodium methoxide, at a temperature of between 60° C. and 100° C.

The compounds $E_0$ are obtained from a compound H by treatment with a chlorinating agent such as phosphorus oxychloride, in the absence of solvent, at a temperature between 20° C. and 120° C., or in the presence of a polar solvent such as 1,2-dichloroethane, at a temperature of between 20° C. and the boiling point of the solvent. Thereafter, the products of formula (I) as defined above according to the present invention may thus be prepared according to Scheme 3.

tion, by addition of a compound J of formula $R_1$-L-Lg with $R_1$ and L as defined above and Lg being a leaving group such as Cl, Br, I or OTf (trifluoromethanesulfonate), with compound I and a base such as sodium hydride, cesium carbonate or potassium tert-butoxide in excess, in a polar solvent such as acetonitrile, N,N-dimethylformamide or tetrahydrofuran, at a temperature of between 0° C. and 150° C., as described by Ting P. C. et al. (J. Med. Chem. (1990), 33(10), 2697-2706). By following the procedure described by E. P. Seest et al. in Tet. Asymmetry 17 (2006) 2154-2182, the compounds J, corresponding to chiral 1-aryl-2-chloroethanols or 1-heteroaryl-2-chloroethanols, were synthesized from the corresponding chloro ketone derivatives, which were themselves derived from chlorination of commercially available acetyl derivatives under standard conditions.

Alternatively, the compounds (I) may be obtained from a compound K by reaction with a bridged morpholine, in the absence of solvent, at a temperature of between 20° C. and 140° C., or in the presence of a solvent such as methyl isobutyl ketone or butyronitrile, at a temperature of between 20° C. and the reflux temperature of the solvent.

The compounds K may be obtained via an alkylation reaction, by addition of a compound J of formula $R_1$-L-Lg with $R_1$ and L as defined above and Lg being a leaving group such as Cl, Br, I or OTf, with compound E and a base such as sodium hydride, cesium carbonate or potassium tert-butoxide in excess, in a solvent such as acetonitrile, N,N-dimethylformamide or tetrahydrofuran, at a temperature of between 0° C. and 150° C., as described, for example, by Ting P. C. et al. (J. Med. Chem. (1990), 33(10), 2697-2706).

The compounds of formula (I) for which the linker L is an ethyl group, $R_1$ is a linear or branched ($C_1$-$C_5$)alkyl group substituted with a hydroxyl group, Y represents a bridged Scheme 3

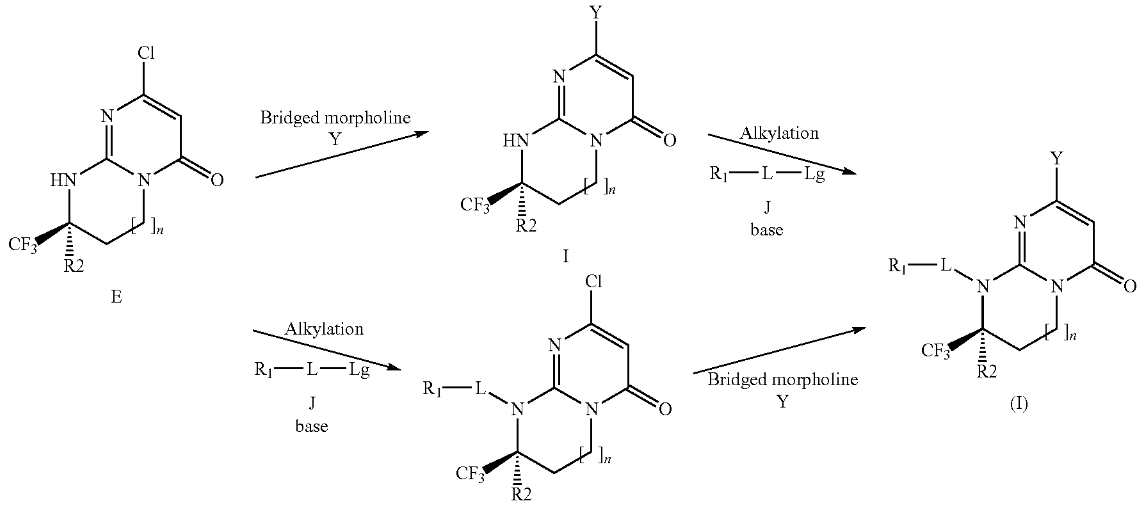

E

I

K (I)

The compounds I are obtained from a compound E, in which n represents 0 or 1, and $R_2$ represents a hydrogen atom if n=1, or a methyl group if n=0, by reaction with a bridged morpholine Y, in the absence of solvent, at a temperature of between 20° C. and 140° C., or in the presence of a polar solvent such as methyl isobutyl ketone or butyronitrile, at a temperature of between 20° C. and the reflux temperature of the solvent. The compounds (I) may then be obtained via an alkylation reacmorpholine chosen from (a), (b) and (c), n represents 1 or 0, and $R_2$ represents a hydrogen atom when n=1 and a methyl group when n=0, are noted (I)-1. The compounds for which the linker L is a methyl group, $R_1$ is a linear or branched ($C_1$-$C_5$)alkyl group substituted with a hydroxyl group, Y represents a bridged morpholine chosen from (a), (b) and (c), n represents 1 or 0, and $R_2$ represents a hydrogen atom when n=1 and a methyl group when n=0, are noted (I)-2. The compounds of formula (I) for which the linker L is a methyl group, $R_1$ is a group —$NR_6R_{6'}$ with $R_6$ et $R_{6'}$ being either different and representing an alkyl group and an alkoxy group, or $R_6$ and $R_{6'}$ together forming a monocyclic or bicyclic heterocycloalkyl, Y represents a bridged morpholine chosen from (a), (b) and (c), n represents 1 or 0, and $R_2$ represents a hydrogen atom when n=1 and a methyl group when n=0, are noted (I)-3. The compounds of formulae (I)-1, (I)-2 and (l)-3 may be obtained according to Scheme 4.

formula $CH_2$═$CH_2$—$CO_2$Alkyl, in the presence of a base such as 1,8-diazabicyclo[5.4.0]undec-7-ene, in a polar aprotic solvent such as N,N-dimethylformamide, at a temperature of 25° C.

Similarly, the compounds (l)-2 may be obtained via an alkylation reaction, by addition of a compound O, as described above, to compound Q, in a polar solvent such as tetrahydrofuran, at a temperature of between 0° C. and 25° C. The compounds Q may be obtained via an alkylation reaction, by Scheme 4

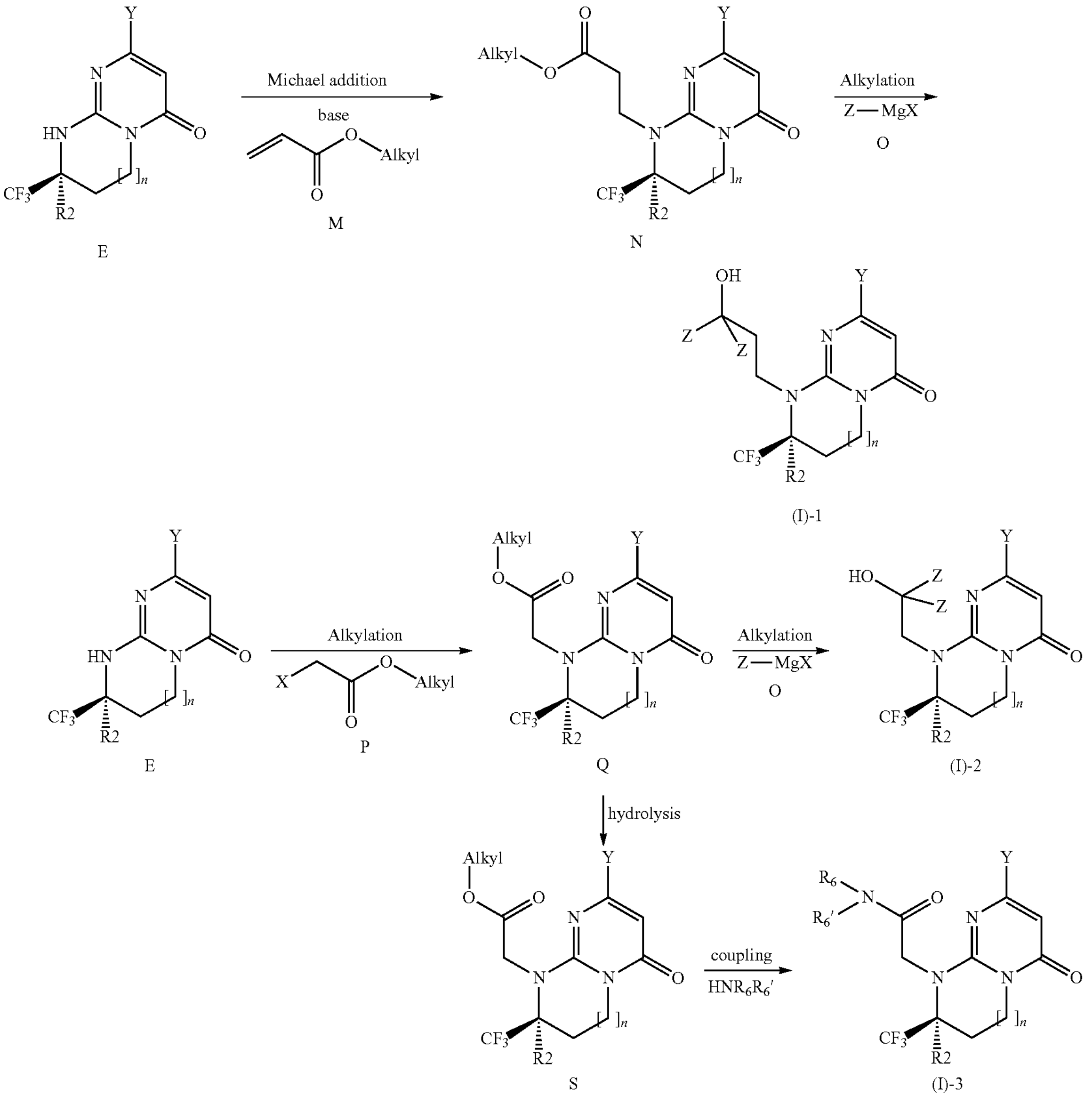

E

M

N (I)-1

E

P

Q (I)-2

S (I)-3

The compounds (l)-1 may be obtained via an alkylation reaction, by addition to a compound N of a compound O, of formula Z—Mg—X in which Z represents a linear or branched alkyl radical and X is a halogen atom such as Cl or Br, in a polar solvent such as tetrahydrofuran, at a temperature of between 0° C. and 25° C., as described, for example, by Ting P. C. et al. (J. Med. Chem. (1990), 33(10), 2697-2706). The compounds N may be obtained via an addition reaction of Michael type of a compound E with a compound M, of addition of a compound P, of formula X—$CH_2$—$CO_2$Alkyl in which X is a halogen atom such as Cl, Br or I, to compound E and an alkaline base such as sodium hydride or cesium carbonate in excess, in a polar solvent such as N,N-dimethylformamide or acetonitrile, at a temperature of 25° C.

The compounds (I)-3 may be obtained via a coupling reaction between a compound S and a compound of formula $HNR_6R_{6'}$ with $R_6$ and $R_{6'}$ being either different and representing an alkyl group and an alkoxy group, or $R_6$ and $R_{6'}$ together forming a monocyclic or bicyclic heterocycloalkyl, in a polar solvent such as N,N-dimethylformamide, in the presence of coupling agents such as 1-hydroxy benzotriazole with 1-(3-dimethylaminopropyl)-3-ethylcarbodiimide hydrochloride. Compound S is obtained by hydrolysis of compound Q, for example using lithium hydroxide monohydrate in a water/tetrahydrofuran mixture.

It is clear to a person skilled in the art that, in order to perform the processes according to the invention described previously, it may be necessary to introduce protecting groups for the amino, carboxyl and alcohol functions in order to avoid side reactions.

Examples of protecting groups and also of protection and deprotection methods are given in *Protective Groups in Organic Synthesis*, Greene et al., 3rd Edition (John Wiley & Sons, Inc., New York). As examples of protection of reactive functions, the following non-exhaustive list may be mentioned:

the hydroxyl groups may be protected, for example, with alkyl radicals such as tert-butyl, trimethylsilyl, tert-butyldimethylsilyl, methoxymethyl, tetrahydropyranyl, benzyl or acetyl, the amino groups may be protected, for example, with acetyl, trityl, benzyl, tert-butoxycarbonyl, benzyloxycarbonyl or phthalimido radicals or other radicals known in peptide chemistry, the acid functions may be protected, for example, in the form of esters formed with readily cleavable esters such as benzyl or tert-butyl esters or esters known in peptide chemistry.

In the text hereinabove, the term "leaving group Lg" means a group that can be readily cleaved from a molecule by breaking a heterolytic bond, with loss of an electron pair. This group can thus be easily replaced with another group in a substitution reaction, for example. Such leaving groups are, for example, halogens or an activated hydroxyl group, such as a mesylate, tosylate, triflate, acetyl, etc. Examples of leaving groups and also references for preparing them are given in *Advanced Organic Chemistry*, J. March, 4th Edition, Wiley Interscience, p. 310-316.

In schemes 1, 2, 3 and 4, the starting compounds and the reagents, when the method for preparing them is not described, are commercially available or described in the literature, or else can be prepared according to methods which are described therein or which are known to those skilled in the art.

According to another of its aspects, a subject of the invention is also the compounds of formulae I, N, Q and S. These compounds are useful as intermediates in the synthesis of the compounds of formula (I).

The following abbreviations and molecular formulae are used:

EtOAc: ethyl acetate
Br: bromine
$CDCl_3$: deuterated chloroform
Cl: chlorine
DBU: 1,8-diazabicyclo[5.4.0]undec-7-ene
DCM: dichloromethane
DMF: N,N-dimethylformamide
DMSO: dimethyl sulfoxide
DMSO-$d_6$: deuterated dimethyl sulfoxide
HPLC: high performance liquid chromatography
HCl: hydrochloric acid
$K_2CO_3$: potassium carbonate
LC/MS: liquid chromatography/mass spectrometry
MeOH: methanol
$MgSO_4$: magnesium sulfate
MHz: Megahertz
$Na_2CO_3$: sodium carbonate
NaCl: sodium chloride
NaOH: sodium hydroxide
$NaHCO_3$: sodium hydrogen carbonate
$Na_2SO_4$: sodium sulfate
Ph: phenyl
Pd/C: palladium-on-charcoal
$Pd(OH)_2$/C: palladium hydroxide-on-charcoal
TFA: trifluoroacetic acid
THF: tetrahydrofuran
° C.: degrees Celsius
Tr: retention time
min: minutes
ESI+: positive-mode electrospray ionization The following examples describe the preparation of certain compounds in accordance with the invention. These examples are not limiting and merely illustrate the present invention. The numbers of the compounds exemplified refer to those given in the table hereinafter, which shows the chemical structures and the physical properties of some compounds according to the invention.

It should be noted that the compounds described in the experimental section were named according to the IUPAC nomenclature by means of the Autonom software.

In the procedures and examples below:

the microwave oven used is a Biotage, Initiator™ Eight, 400 W max, 2450 MHz apparatus.

the proton magnetic resonance spectra ($^1$H NMR), as described below, are recorded at a temperature of 300 K (exchangeable protons not recorded) at 300, 400 or 600 MHz in DMSO-$d_6$ or $CDCl_3$, using the DMSO-$d_6$ or $CDCl_3$ peak as reference. The chemical shifts 6 are expressed in parts per million (ppm). The signals observed are expressed as follows: s=singlet, d=doublet, m=multiplet, bs=broad signal, t=triplet, q=quartet.

the LC/MS characteristics, as described below (A, B, C, D, E, F and G) indicate, successively, the analytical method used and detailed below, the retention time (Tr) of the compound expressed in minutes and the peak [M+H]+ identified by mass spectrometry.

Method A

Instrument: Acquity UPLC chain (Waters); SQD mass spectrometer (Waters)

Column: Ascentis Express C18 50×2.1 mm 2.7 μm, T°=55° C.

Solvent A: $H_2O$+0.02% TFA; Solvent B: acetonitrile+0.014% TFA

Flow rate: 1 mL/min

Gradient A/B: t 0 min 2% B, t 1 min 98% B, t 1.3 min 98% B, t 1.33 min 2% B

Detection: UV 220 nm

Ionization: electrospray positive mode

Method B

Instrument: Acquity UPLC chain (Waters); LCT mass spectrometer (Waters)

Column: BHE C8 50×2.1 mm 1.7 μm, T°=55° C.

Solvent A: $H_2O$+0.02% TFA; Solvent B: acetonitrile+0.014% TFA

Flow rate: 1 mL/min

Gradient A/B: t 0 min 2% B, t 1 min 98% B, t 1.3 min 98% B, t 1.33 min 2% B

Detection: UV 220 nm

Ionization: electrospray positive mode

Method C

Instrument: Acquity UPLC chain (Waters); SQD mass spectrometer (Waters)

Column: BHE C18 50×2.1 mm 1.7 μm, T°=50° C.

Solvent A: $H_2O$+0.02% $HCO_2H$; Solvent B: acetonitrile+0.02% $HCO_2H$

Flow rate: 1 mL/min

Gradient A/B: t 0 min 5% B, t 2 min 100% B, t 2.5 min 100% B

Detection: UV 220 nm

Ionization: electrospray positive mode

Method D

Instrument: Acquity UPLC chain (Waters); SQD mass spectrometer (Waters)

Column: Acquity BHE C18 50×2.1 mm 1.7 μm, T°=50° C.

Solvent A: $H_2O$+0.1% $HCO_2H$; Solvent B: acetonitrile+0.1% $HCO_2H$

Flow rate: 1 mL/min

Gradient A/B: t 0 min 5% B, t 0.8 min 50% B, t 1.2 min 100% B, t 1.85 min 100% B, t 1.95 min 5% B Detection: UV 220 nm Ionization: electrospray positive mode Method E Instrument: HPLC chain (Waters); ZQ mass spectrometer (Waters)

Column: XBridge C18 50×3 mm 2.5 μm, T°=70° C.

Solvent A: $H_2O$+0.1% $HCO_2H$; Solvent B: acetonitrile+0.1% $HCO_2H$

Flow rate: 0.9 mL/min

Gradient A/B: t 0 min 5% B, t 5.3 min 100% B, t 5.5 min 100% B, t 6.3 min 5% B

Detection: UV 220 nm

Ionization: electrospray positive mode

Method F

Instrument: Acquity UPLC type HPLC chain (Waters); SQD mass spectrometer (Waters)

Column: BHE C18 30×2.1 mm 1.7 μm, T°=50° C.

Solvent A: $H_2O$+0.1% $HCO_2H$; Solvent B: acetonitrile+0.1% $HCO_2H$

Flow rate: 1 mL/min

Gradient A/B: t 0 min 5% B, t 2 min 100% B, t 2.5 min 100% B

Detection: UV 220 nm

Ionization: electrospray positive mode

Method G

Instrument: Alliance HPLC chain (Waters); ZQ mass spectrometer (Waters)

Column: X Bridge C18 30×2.1 mm 2.5 μm, T°=55° C.

Solvent A: $H_2O$+0.02% TFA; Solvent B: MeOH

Flow rate: 0.7 mL/min

Gradient A/B: t 0 min 2% B, t 3 min 100% B, t 3.5 min 100% B, t 3.6 min 2% B

Detection: UV 220 nm

Ionization: electrospray positive mode

The optical rotations $[\alpha]_D^{25}$ were measured on a model 341 polarimeter from Perkin-Elmer. Wavelength: sodium α line (589 nm).

EXAMPLE 1

(8S)-9-[2-(2,4-difluorophenyl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 48)

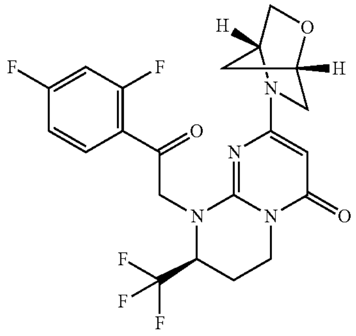 [SMILES: O=C(CN1c2nc(N3C[C@@H]4C[C@@H]3CO4)cc(=O)n2CC[C@H]1C(F)(F)F)c1ccc(F)cc1F]

Step 1.1: 4-trifluoromethyl-1,4,5,6-tetrahydropyrimidin-2-ylamine

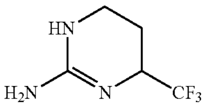

A mixture of 6 g of 10% Pd/C and 60 g (370 mmol) of 2-amino-4-(trifluoromethyl)pyrimidine dissolved in 80 mL of water, 250 mL of isopropanol and 24 mL (370 mmol) of methanesulfonic acid is hydrogenated at 5 bar, at 40° C., for 5 hours in an autoclave. The resulting mixture is then filtered and rinsed with isopropanol and with water. The filtrate is then concentrated under reduced pressure and the residue obtained is dried under vacuum to give 93.5 g of 4-trifluoromethyl-1,4,5,6-tetrahydropyrimidin-2-ylamine methanesulfonate in the form of a white solid. The white solid is dissolved in 250 mL of methyl isobutyl ketone. 100 mL of 10 N sodium hydroxide are then added. The mixture is stirred at room temperature for 15 minutes. The phases are separated by settling and the aqueous phase is re-extracted with methyl isobutyl ketone. The organic phases are combined and then evaporated under vacuum. 59.50 g of 4-trifluoromethyl-1,4,5,6-tetrahydropyrimidin-2-ylamine are thus obtained, the characteristics of which are as follows:

$^1H$ NMR (300 MHz, δ in ppm, DMSO-$d_6$): 1.46 (m, 1H), 1.84 (m, 1H), 3.15 (m, 2H), 3.80 (m, 1H), 4.51-5.20 (bs, 2H), 5.55-6.30 (bs, 1H).

Step 1.2: 2-hydroxy-8-trifluoromethyl-6,7,8,9-tetrahydropyrimido[1,2-a]pyrimidin-4-one

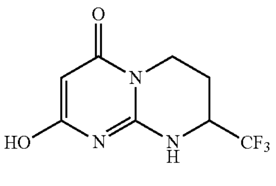 [SMILES: O=c1cc(O)nc2n1CCC(C(F)(F)F)N2]

62.10 g (1150 mmol) of sodium methoxide are added to a mixture of 340 mL (2230 mmol) of diethyl malonate heated to 40° C. The mixture is heated at 100° C. until a clear solution is obtained. 59.50 g (360 mmol) of 4-trifluoromethyl-1,4,5,6-tetrahydropyrimidin-2-ylamine dissolved in 100 mL of methanol are then added to the reaction medium. The mixture obtained is maintained at 100° C. for 1 hour and then cooled to room temperature overnight. The reaction mixture is evaporated to dryness under reduced pressure. The residue obtained is taken up in 250 mL of water. 12 N hydrochloric acid is added to the thick suspension obtained, to pH=5-6. The suspension obtained is filtered through a sinter funnel and the insoluble matter is rinsed with acetonitrile to give 68.10 g of 2-hydroxy-8-trifluoromethyl-6,7,8,9-tetrahydropyrimido[1,2-a]pyrimidin-4-one in the form of a yellow solid, the characteristics of which are as follows:

LC/MS (method D), ESI+: [M+H]+: m/z 236; tr (min)=0.26

$^1$H NMR (300 MHz, δ in ppm, DMSO-$d_6$): 1.46 (m, 1H), 1.84 (m, 1H), 3.15 (m, 2H), 3.80 (m, 1H), 4.51-5.20 (bs, 2H), 5.55-6.30 (bs, 1H).

Step 1.3: 2-chloro-8-trifluoromethyl-6,7,8,9-tetrahydropyrimido[1,2-a]pyrimidin-4-one

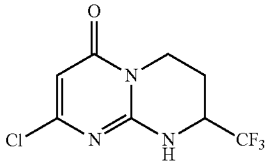 [SMILES: O=c1cc(Cl)nc2n1CCC(C(F)(F)F)N2]

136 mL (1440 mmol) of phosphorus oxychloride are added, at room temperature and under an argon atmosphere, to a suspension of 68.10 g (290 mmol) of 2-hydroxy-8-(trifluoromethyl)-6,7,8,9-tetrahydro-4H-pyrimido[1,2-a]pyrimidin-4-one in 950 mL of 1,2-dichloroethane. The mixture obtained is then heated at 65° C. for 3 hours. After cooling, the reaction mixture is evaporated to dryness under reduced pressure. The residue obtained is taken up in 140 mL of cold water and 430 mL of ethyl acetate. 32% sodium hydroxide is added to the mixture obtained, to pH=5. The resulting organic phase is separated out and then dried over magnesium sulfate, filtered and concentrated under reduced pressure to give 60 g of 2-chloro-8-(trifluoromethyl)-6,7,8,9-tetrahydro-4H-pyrimido[1,2-a]pyrimidin-4-one in the form of an orange solid, the characteristics of which are as follows:

LC/MS (method D), ESI+: [M+H]+: m/z 254; tr (min)=0.51

$^1$H NMR (300 MHz, δ in ppm, DMSO-$d_6$) 2.16 (m, 2H) 3.45 (m, 1H) 4.12 (m, 1H) 4.42 (m, 1H) 5.83 (s, 1H) 9.12 (s, 1H)

Step 1.4: (8S)-2-chloro-8-trifluoromethyl-6,7,8,9-tetrahydropyrimido[1,2-a]pyrimidin-4-one

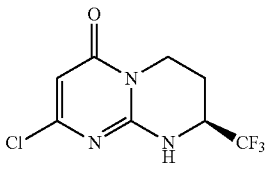

-continued

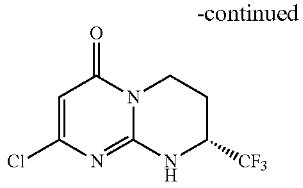

The separation of the two enantiomers of 2-chloro-8-trifluoromethyl-6,7,8,9-tetrahydro-4H-pyrimido[1,2-a]pyrimidin-4-one (100 g) is performed by chiral chromatography: stationary phase: Chiralpak IA (250 mm×4.6) 5 μm; temperature 25° C.; mobile phase: methanol (100%). The levorotatory enantiomer is concentrated to give 49.10 g of (8R)-2-chloro-8-(trifluoromethyl)-6,7,8,9-tetrahydro-4H-pyrimido[1,2-a]pyrimidin-4-one, in the form of a white powder. The dextrorotatory enantiomer is concentrated to obtain 48.5 g of (8S)-2-chloro-8-(trifluoromethyl)-6,7,8,9-tetrahydro-4H-pyrimido[1,2-a]pyrimidin-4-one, in the form of a white powder, the characteristics of which are as follows:

LC/MS (method D), ESI+: [M+H]+: m/z 254; tr (min)=0.51

$^1$H NMR (300 MHz, δ in ppm, DMSO-$d_6$): 2.14 (m, 2H), 3.47 (m, 1H), 4.12 (m, 1H), 4.36 (m, 1H), 5.81 (s, 1H), 9.31 (s, 1H).

$[\alpha]_D^{25}$ at 589 nm=+21.3±0.5° (MeOH)

Step 1.5: (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one

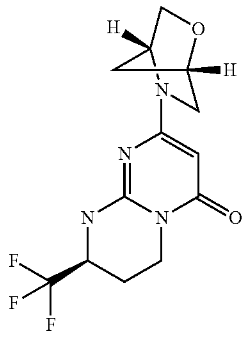 [SMILES: O=c1cc(N2C[C@@H]3C[C@@H]2CO3)nc2n1CC[C@@H](C(F)(F)F)N2]

1.60 g (6.31 mmol) of (8S)-2-chloro-8-trifluoromethyl-6,7,8,9-tetrahydropyrimido[1,2-a]pyrimidin-4-one and 1.30 g (9.46 mmol) of (1S,4S)-2-oxa-5-azabicyclo[2.2.1]heptane hydrochloride are mixed together. The powder obtained is placed in a tube and 2.21 mL (15.77 mmol) of triethylamine are added. The tube is sealed and heated at 130° C. in an oil bath for 6 hours. After cooling, the crude product is purified by chromatography on silica gel (eluent: 95/5 EtOAc/MeOH). After evaporating the fractions under reduced pressure, 1.20 g of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one are obtained, the characteristics of which are as follows:

LC/MS (method G): ESI+: [M+H]+: m/z 317 tr (min)=1.37

$^1$H NMR (300 MHz, δ in ppm, $CDCl_3$): 2 (m, 2H), 2.35 (m, 2H), 3.45 (m, 2H), 3.92 (s, 1H), 3.95-4.32 (m, 4H), 4.78 (s, 1H), 4.89-5.2 (bs, 1H), 5.49-5.77 (bs, 1H).

Step 1.6: (8S)-9-[2-(2,4-difluorophenyl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

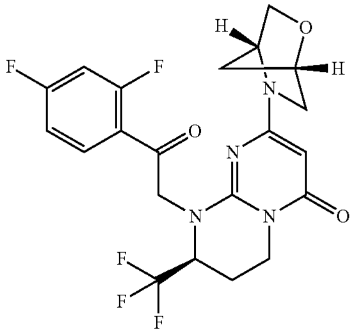 [SMILES: O=C(CN1c2nc(N3C[C@@H]4C[C@@H]3CO4)cc(=O)n2CC[C@H]1C(F)(F)F)c1ccc(F)cc1F]

A suspension of 150 mg (0.47 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one and 463.57 mg (1.42 mmol) of cesium carbonate in 10 mL of acetonitrile is stirred for 15 minutes at room temperature. 222.93 mg (0.95 mmol) of 2-bromo-1-(2,4-difluorophenyl)ethanone are then added. After stirring overnight at room temperature, the reaction mixture is evaporated and the residue is taken up in water and extracted with ethyl acetate. The organic phase is dried over magnesium sulfate and then evaporated to dryness. The residue is purified by chromatography on silica gel (eluent: 95/5 EtOAc/MeOH) to give 130 mg of (8S)-9-[2-(2,4-difluorophenyl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one, the characteristics of which are as follows:

LC/MS (method A): ESI+ [M+H]+: m/z 471 tr (min)=0.68

$^1H$ NMR (600 MHz, δ in ppm, DMSO-$d_6$): 1.58-1.76 (m, 2H), 2.13-2.29 (m, 1H), 2.39-2.47 (m, 1H), 2.95-3.13 (bs, 4H), 3.16-3.29 (m, 1H), 4.34 (m, 1H), 4.41 (s, 1H), 4.51 (s, 1H), 4.58-4.71 (m, 3H), 5.38 (m, 1H), 7.3 (m, 1H), 7.51 (m, 1H), 8 (q, 1H)

EXAMPLE 2

(8S)-9-[2-(4-methylthiazol-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 25)

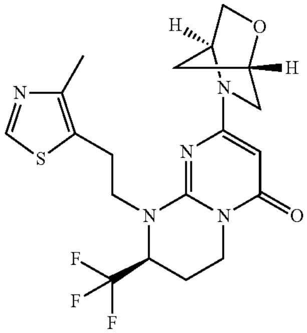 [SMILES: Cc1ncsc1CCN1c2nc(N3C[C@@H]4C[C@H]3CO4)cc(=O)n2CC[C@H]1C(F)(F)F]

Step 2.1: 5-(2-bromoethyl)-4-methylthiazole

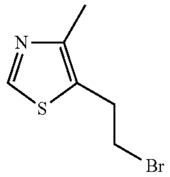

A solution of 1 g (7 mmol) of 4-methyl-5-thiazolylethanol in 15 mL of dichloromethane is cooled to 0° C. under argon. In a first stage, 1.8 g (7 mmol) of triphenylphosphine are added. Next, 1.30 g (7 mmol) of N-bromosuccinimide are added portionwise over 5 minutes. After stirring for 2 hours at 0° C., the solvent is evaporated off under vacuum. The residue obtained is purified by chromatography on silica gel (eluent: 50/50 EtOAc/heptane) to give 900 mg of 5-(2-bromoethyl)-4-methylthiazole, the characteristics of which are as follows:

LC/MS (method G): ESI+ [M+H]+: m/z 207 tr (min)=1.52

$^1H$ NMR (300 MHz, δ in ppm, $CDCl_3$): 2.42 (s, 3H), 3.3-3.35 (t, 2H), 3.5-3.55 (t, 2H), 8.62 (s, 1H).

Step 2.2: (8S)-9-[2-(4-methylthiazol-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

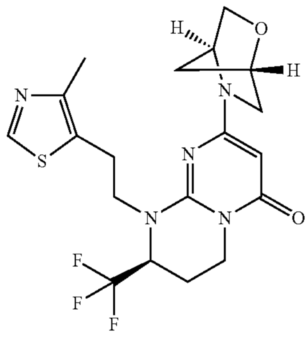 [SMILES: Cc1ncsc1CCN1c2nc(N3C[C@@H]4C[C@H]3CO4)cc(=O)n2CC[C@H]1C(F)(F)F]

A suspension of 160 mg (0.50 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one and 415 mg (1.25 mmol) of cesium carbonate in 4 mL of N,N-dimethylformamide is heated at 80° C. for 15 minutes. After cooling to room temperature, a solution of 150 mg (0.76 mmol) of 5-(2-bromoethyl)-4-methylthiazole in 1 mL of N,N-dimethylformamide is added dropwise. The reaction medium is heated at 80° C. overnight. The reaction mixture obtained is evaporated to dryness. The residue obtained is taken up in water and extracted with ethyl acetate. The organic phase is dried over magnesium sulfate and evaporated to dryness.

The residue is purified by chromatography on silica gel (eluent: 95/5 EtOAc/MeOH) to give 40 mg of (8S)-9-[2-(4-methylthiazol-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one, the characteristics of which are as follows:

LC/MS (method A): ESI+ [M+H]+: m/z 442 tr (min)=0.55

$^1H$ NMR (600 MHz, δ in ppm, DMSO-$d_6$): 1.85 (t, 2H), 2.13 (m, 1H), 2.32 (s, 3H), 2.36 (m, 1H), 3.05-3.32 (m, 4H), 3.36 (d, 1H), 3.45 (m, 1H), 3.67 (d, 1H), 3.75 (d, 1H), 4.15-4.22 (m, 2H), 4.57 (m, 1H), 4.63 (s, 1H), 4.71 (s, 1H), 4.8 (s, 1H), 8.8 (s, 1H).

EXAMPLE 3

(8S)-9-[2-(5-methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 15)

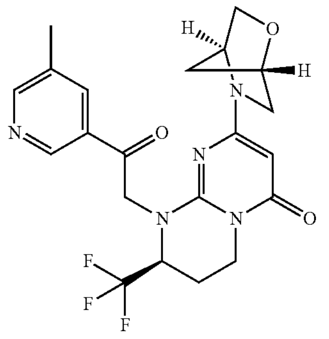 [SMILES: Cc1cncc(C(=O)CN2c3nc(N4C[C@@H]5C[C@H]4CO5)cc(=O)n3CC[C@H]2C(F)(F)F)c1]

Step 3.1: 1-(5-methylpyrid-3-yl)ethanone

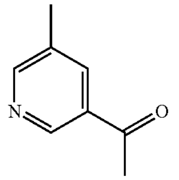

The following are successively introduced into a microwave tube:

484 μl (4.07 mmol) of 3-bromo-5-methylpyridine in 20 mL of $H_2O$/DMF: (1/3: v/v), 2.03 mL (5.70 mmol) of tributyl(1-ethoxyvinyl)tin, 57.12 mg (0.081 mmol) of bis(triphenylphosphine)palladium(II) chloride, 1.12 g (8.14 mmol) of potassium carbonate. This mixture is subjected to microwave irradiation at 110° C. for 1 hour. The reaction mixture is evaporated to dryness and the residue is then taken up in water and extracted with ethyl acetate. The organic phase is dried over magnesium sulfate and evaporated to dryness. The residue obtained is taken up in 6 mL of methanol and 1 mL of 6 N HCl, and the solution is stirred overnight at room temperature. The reaction medium is evaporated to dryness and the residue is taken up in saturated aqueous $NaHCO_3$ solution and extracted with ethyl acetate. The organic phase is dried over magnesium sulfate and evaporated to dryness. The residue is purified by chromatography on silica gel (eluent: 50/50 EtOAc/heptane) to give 300 mg of 1-(5-methylpyrid-3-yl) ethanone, the characteristics of which are as follows:

LC/MS (method G): ESI+ [M+H]+: m/z 136 tr (min)=0.78

$^1$H NMR (300 MHz, δ in ppm, DMSO-$d_6$): 2.37 (s, 3H), 2.62 (s, 3H), 8.1 (s, 1H), 8.63 (s, 1H), 8.93 (s, 1H).

Step 3.2: 2-bromo-1-(5-methylpyrid-3-yl)ethanone hydrobromide

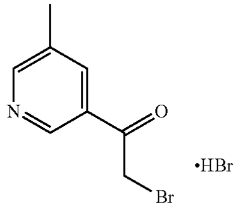

300 mg (2.22 mmol) of 1-(5-methylpyrid-3-yl)ethanone are dissolved in 15 mL of glacial acetic acid. 365 μl (2.22 mmol) of hydrobromic acid and 126 μl (2.44 mmol) of bromine are added to the medium. The reaction mixture is placed under magnetic stirring at room temperature for 2 hours. Ethyl ether is added to the solution until a precipitate appears. The precipitate corresponding to 2-bromo-1-(5-methylpyrid-3-yl)ethanone hydrobromide is filtered off, washed with ether and dried. The 600 mg of product obtained have the following characteristics:

LC/MS (method G): ESI+ [M+H]+: m/z 214 tr (min)=1.17

$^1$H NMR (300 MHz, δ in ppm, DMSO-$d_6$): 2.46 (s, 3H), 5.05 (s, 2H), 8.48 (s, 1H), 8.82 (s, 1H), 9.12 (s, 1H).

Step 3.3: (8S)-9-[2-(5-methyl pyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

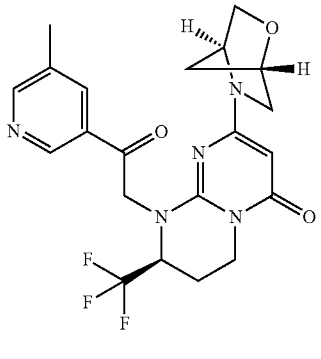 [SMILES: Cc1cncc(C(=O)CN2c3nc(N4C[C@@H]5C[C@H]4CO5)cc(=O)n3CC[C@H]2C(F)(F)F)c1]

150 mg (0.474 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one in 5 mL of DMF are added to a suspension of 50.08 mg (1.04 mmol) of sodium hydride in 5 mL of DMF. The reaction mixture is placed under magnetic stirring at room temperature for 15 minutes. A solution of 153.88 mg (0.522 mmol) of 3-(bromoacetyl)pyridine hydrobromide in 5 mL of DMF is added dropwise to the reaction medium. The reaction is stirred at room temperature overnight. The reaction medium is evaporated to dryness. The crude product is taken up in water and extracted with ethyl acetate. The organic phase is dried over magnesium sulfate and evaporated to dryness. The residue is purified by chromatography on silica gel (eluent: 95/5 EtOAc/MeOH) to give 70 mg of (8S)-9-[2-(5-methylpyrid-3-yl)-2-oxoethyl]-2-(1S, 4S)-2-oxa-5-azabicyclo[2.2.1]hept-5-yl-8-trifluoromethyl-6,7,8,9-tetrahydropyrimido[1,2-a]pyrimidin-4-one, the characteristics of which are as follows:

LC/MS (method A): ESI+ [M+H]+: m/z 450 tr (min)=0.51

$^1$H NMR (600 MHz, δ in ppm, DMSO-$d_6$): 1.62-1.7 (dd, 2H), 2.25 (m, 1H), 2.4 (s, 3H), 2.43 (m, 1H), 2.96-3.2 (m, 3H), 3.2-3.33 (m, 2H), 4.37 (m, 1H), 4.42 (s, 1H), 4.47 (s, 1H), 4.57 (m, 1H), 4.63-4.7 (m, 2H), 5.6 (d, 1H), 8.16 (s, 1H), 8.67 (s, 1H), 8.98 (s, 1H).

EXAMPLE 4

(8S)-9-[2-(3,5-di methylisoxazol-4-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 53)

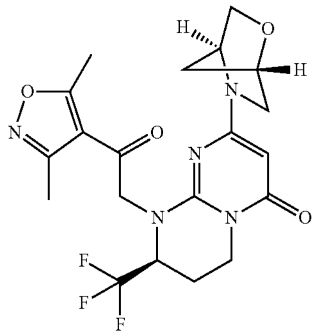 [SMILES: Cc1noc(C)c1C(=O)CN1c2nc(N3C[C@@H]4C[C@H]3CO4)cc(=O)n2CC[C@H]1C(F)(F)F]

Step 4.1: N-methoxy-N-methyl-3,5-dimethylisoxazole-4-carboxamide

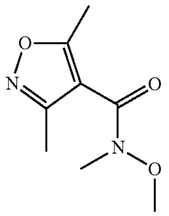

659 µl (8.15 mmol) of pyridine are added to a suspension of 343.07 mg (3.45 mmol) of N,O-dimethylhydroxylamine hydrochloride in 10 mL of dichloromethane. The mixture is stirred at room temperature until fully dissolved. A solution of 526.32 mg (3.13 mmol) of 3,5-dimethylisoxazole-4-carbonyl chloride in 5 mL of dichloromethane is then added. After stirring for 1 hour at room temperature, the reaction mixture is taken up in saturated aqueous $NaHCO_3$ solution and stirred for a few minutes, and the phases are separated by settling. The organic phase is dried over magnesium sulfate and evaporated to dryness. The residue obtained is taken up in toluene and evaporated, the operation being repeated a second time. 570 mg of N-methoxy-N-methyl-3,5-dimethylisoxazole-4-carboxamide are then obtained, corresponding to the following characteristics:

LC/MS (method G): ESI+ [M+H]+: m/z 185 tr (min)=1.08

$^1$H NMR (300 MHz, δ in ppm, $CDCl_3$): 2.32 (s, 3H), 2.46 (s, 3H), 3.34 (s, 3H), 3.52 (s, 3H).

Step 4.2: 1-(3,5-dimethylisoxazol-4-yl)ethanone

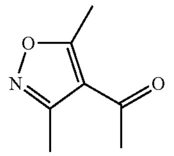

A solution of 580 mg (3.15 mmol) of N-methoxy-N-methyl-3,5-dimethylisoxazole-4-carboxamide in 20 mL of THF is cooled to 0° C. A solution of 1.57 mL (4.72 mmol) of 3 M methylmagnesium bromide in ether is added. After stirring for 4 hours at room temperature, the reaction medium is taken up in 10 mL of 1 N HCl and stirred for a further 1 hour at room temperature. The mixture is then basified with $K_2CO_3$ and extracted with ethyl acetate. The organic phase is dried over magnesium sulfate and evaporated to dryness to give 420 mg of 1-(3,5-dimethylisoxazol-4-yl)ethanone, corresponding to the following characteristics:

LC/MS (method G): [M+H]+: m/z 140 tr (min)=1.06

$^1$H NMR spectrum (300 MHz, δ in ppm, $CDCl_3$): 2.48 (s, 6H), 2.70 (s, 3H).

Step 4.3: 2-bromo-1-(3,5-dimethylisoxazol-4-yl)ethanone

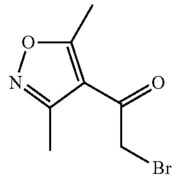

400 mg (2.87 mmol) of 1-(3,5-dimethylisoxazol-4-yl) ethanone are dissolved in 20 mL of glacial acetic acid. 1.42 mL (8.62 mmol) of hydrobromic acid and 163 µl (3.16 mmol) of bromine are added to the medium. The reaction mixture is placed under magnetic stirring at room temperature for 2 hours. The solution is diluted with water, basified with saturated aqueous $NaHCO_3$ solution and extracted with ethyl acetate. The organic phase is dried over magnesium sulfate and evaporated to dryness to give 540 mg of 2-bromo-1-(3,5-dimethylisoxazol-4-yl)ethanone, corresponding to the following characteristics:

LC/MS (method G): ESI+ [M+H]+: m/z 218 tr (min)=1.35

$^1$H NMR (300 MHz, δ in ppm, $CDCl_3$): 2.52 (s, 3H), 2.74 (s, 3H), 4.18 (s, 2H).

Step 4.4: (8S)-2-chloro-9-[2-(3,5-dimethylisoxazol-4-yl)-2-oxoethyl]-8-trifluoromethyl-6,7,8,9-tetrahydropyrimido[1,2-a]pyrimidin-4-one

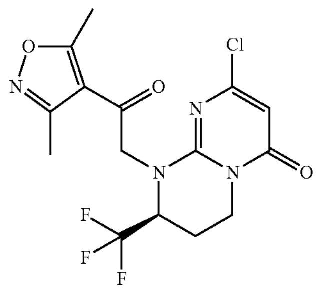 [SMILES: Cc1noc(C)c1C(=O)CN1c2nc(Cl)cc(=O)n2CC[C@H]1C(F)(F)F]

A suspension of 150 mg (0.591 mmol) of (8S)-2-chloro-8-trifluoromethyl-6,7,8,9-tetrahydropyrimido[1,2-a]pyrimidin-4-one and 578.13 mg (1.77 mmol) of cesium carbonate in 10 mL of acetonitrile is stirred for 15 minutes at room temperature. 154.76 mg (0.709 mmol) of 2-bromo-1-(3,5-dimethylisoxazol-4-yl)ethanone are then added. After stirring overnight at room temperature, the reaction mixture is evaporated and the residue is taken up in water and extracted with ethyl acetate. The organic phase is dried over magnesium sulfate and evaporated to dryness to give 230 mg of (8S)-2-chloro-9-[2-(3,5-dimethylisoxazol-4-yl)-2-oxoethyl]-8-trifluoromethyl-6,7,8,9-tetrahydropyrimido[1,2-a]pyrimidin-4-one, corresponding to the following characteristics:

LC/MS (method G): ESI+ [M+H]+: m/z 391 tr (min)=2.06

$^1$H NMR (300 MHz, δ in ppm, $CDCl_3$): 2.44 (s, 2H), 2.7 (s, 3H), 3.46 (m, 1H), 4 (m, 2H), 4.54 (m, 1H), 5.23 (s, 3H), 5.53 (d, 1H), 5.92 (s, 1H).

Step 4.5: (8S)-9-[2-(3,5-dimethylisoxazol-4-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

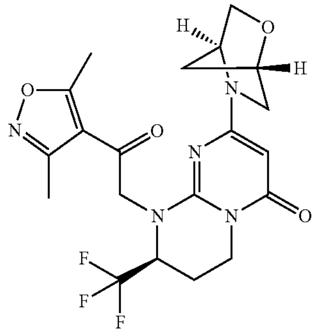 [SMILES: Cc1noc(C)c1C(=O)CN1c2nc(N3C[C@@H]4C[C@H]3CO4)cc(=O)n2CC[C@H]1C(F)(F)F]

200 mg (0.51 mmol) of (8S)-2-chloro-9-[2-(3,5-dimethylisoxazol-4-yl)-2-oxoethyl]-8-trifluoromethyl-6,7,8,9-tetrahydropyrimido[1,2-a]pyrimidin-4-one and 83.28 mg (0.61 mmol) of (1S,4S)-2-oxa-5-azabicyclo[2.2.1]heptane hydrochloride are mixed together. The powder obtained is placed in a tube and 178 μl (1.28 mmol) of triethylamine are added. The tube is sealed and heated at 130° C. in an oil bath for 6 hours. The crude product obtained is taken up in water and extracted with ethyl acetate. The organic phase is dried over magnesium sulfate and then evaporated to dryness. The residue is purified by chromatography on silica gel (eluent: 95/5 EtOAc/MeOH) to give 130 mg of (8S)-9-[2-(3,5-dimethylisoxazol-4-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one, the characteristics of which are as follows:

LC/MS (method A): ESI+ [M+H]+: m/z 454 tr (min)=0.58

$^1$H NMR (300 MHz, δ in ppm, $CDCl_3$): 2.44 (s, 2H), 2.7 (s, 3H), 3.46 (m, 1H), 4 (m, 2H), 4.54 (m, 1H), 5.23 (s, 3H), 5.53 (d, 1H), 5.92 (s, 1H).

EXAMPLE 5

(8S)-9-(3-methyl-2-oxobutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 56)

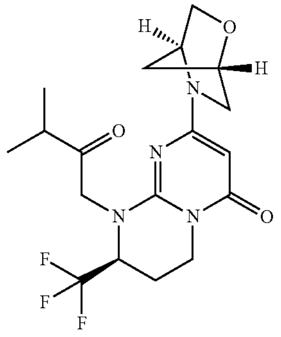 [SMILES: CC(C)C(=O)CN1c2nc(N3C[C@@H]4C[C@H]3CO4)cc(=O)n2CC[C@H]1C(F)(F)F]

Step 5.1: 1-bromo-3-methylbutan-2-one

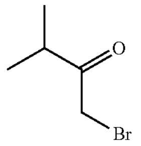

A solution of 1 g (11.61 mmol) of 3-methylbutan-2-one in 6 mL of methanol is cooled to a temperature of 10° C. When the temperature is reached, 597 μl (11.61 mmol) of bromine are added. The reaction mixture is stirred at 10° C. until fully decolorized, and stirring is then continued for 30 minutes at room temperature. After adding 10 mL of water to the solution, stirring is continued for 1 hour at room temperature. The reaction mixture is then taken up in water and extracted with ethyl ether. The organic phase is washed with aqueous 10% $Na_2CO_3$ solution and then with saturated NaCl solution, dried and evaporated to give 1.50 g of 1-bromo-3-methylbutan-2-one, corresponding to the following characteristics:

$^1$H NMR (300 MHz, δ in ppm, $CDCl_3$): 1.15 (s, 3H), 1.18 (s, 3H), 2.92-3.06 (m, 1H), 4 (s, 2H).

Step 5.2: (8S)-2-chloro-9-(3-methyl-2-oxobutyl)-8-trifluoromethyl-6,7,8,9-tetrahydropyrimido[1,2-a]pyrimidin-4-one

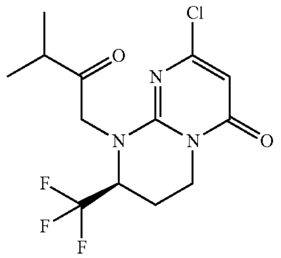 [SMILES: CC(C)C(=O)CN1c2nc(Cl)cc(=O)n2CC[C@H]1C(F)(F)F]

A suspension of 170 mg (0.670 mmol) of (8S)-2-chloro-8-trifluoromethyl-6,7,8,9-tetrahydropyrimido[1,2-a]pyrimidin-4-one and 655.21 mg (2.01 mmol) of cesium carbonate in 10 mL of acetonitrile is stirred for 15 minutes at room temperature. 132.75 mg (0.804 mmol) of 1-bromo-3-methylbutan-2-one are then added. After stirring overnight at room temperature, the reaction mixture is evaporated and the residue is taken up in water and extracted with ethyl acetate. The organic phase is dried over magnesium sulfate and evaporated to dryness to give 220 mg of (8S)-2-chloro-9-(3-methyl-2-oxobutyl)-8-trifluoromethyl-6,7,8,9-tetrahydropyrimido[1,2-a]pyrimidin-4-one, corresponding to the following characteristics:

LC/MS (method G): ESI+ [M+H]+: m/z 338 tr (min)=2.20

$^1$H NMR (300 MHz, δ in ppm, $CDCl_3$): 1.13 (m, 6H), 2.38 (m, 2H), 2.68 (m, 1H), 3.41 (m, 1H), 3.87 (m, 2H), 4.51 (m, 1H), 5.2 (d, 1H), 5.9 (s, 1H).

Step 5.3: (8S)-9-(3-methyl-2-oxobutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one

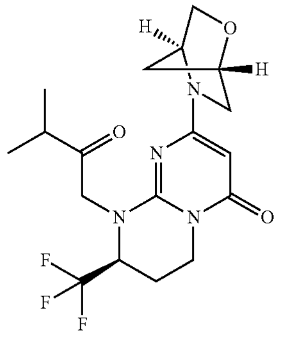 [SMILES: CC(C)C(=O)CN1c2nc(N3C[C@@H]4C[C@H]3CO4)cc(=O)n2CC[C@H]1C(F)(F)F]

220 mg (0.51 mmol) of (8S)-2-chloro-9-(3-methyl-2-oxobutyl)-8-trifluoromethyl-6,7,8,9-tetrahydropyrimido[1,2-a]pyrimidin-4-one and 105.99 mg (0.78 mmol) of (1S,4S)-2-oxa-5-azabicyclo[2.2.1]heptane hydrochloride are mixed together. The powder obtained is placed in a tube and 227 μl (1.63 mmol) of triethylamine are added. The tube is sealed and heated at 130° C. in an oil bath for 3 hours. The crude product obtained is taken up in ethyl acetate and the organic phase is washed with water, dried over magnesium sulfate and then evaporated to dryness. The residue is purified by chromatography on silica gel (eluent: 95/5 EtOAc/MeOH) to give 100 mg of (8S)-9-(3-methyl-2-oxobutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one, the characteristics of which are as follows:

LC/MS (method A): ESI+ [M+H]+: m/z 401 tr (min)=0.6

$^1$H NMR (600 MHz, δ in ppm, DMSO-$d_6$): 1.02 (m, 6H), 1.79 (m, 2H), 2.16 (m, 1H), 2.37 (m, 1H), 2.68 (m, 1H), 2.84-3.26 (bs, 3H), 3.30-3.75 (bs, 2H), 4.18 (d, 1H), 4.30 (m, 1H), 4.46 (m, 1H), 4.60 (s, 1H), 4.63-4.96 (bs, 2H), 5 (m, 1H).

EXAMPLE 6

(8S)-2-(1S,4S)-2-oxa-5-azabicyclo[2.2.1]hept-5-yl-9-(2-oxo-2-pyrid-3-ylethyl)-8-trifluoromethyl-6,7,8,9-tetrahydropyrimido[1,2-a]pyrimidin-4-one (Compound 7)

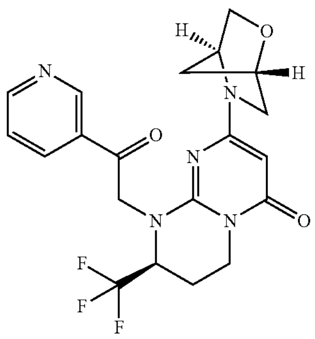 [SMILES: O=C(CN1c2nc(N3C[C@@H]4C[C@H]3CO4)cc(=O)n2CC[C@H]1C(F)(F)F)c1cccnc1]

Step 6.1: (8S)-2-chloro-9-(2-oxo-2-pyrid-3-ylethyl)-8-trifluoromethyl-6,7,8,9-tetrahydropyrimido[1,2-a]pyrimidin-4-one

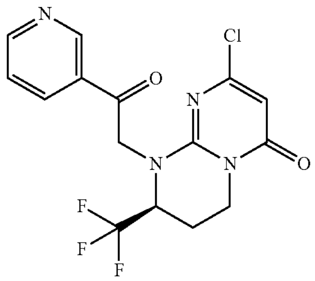 [SMILES: O=C(CN1c2nc(Cl)cc(=O)n2CC[C@H]1C(F)(F)F)c1cccnc1]

A suspension of 750 mg (15.77 mmol) of sodium hydride in 50 mL of DMF is cooled to 0° C. under argon. A solution of 2 g (7.89 mmol) of (8S)-2-chloro-8-trifluoromethyl-6,7,8,9-tetrahydropyrimido[1,2-a]pyrimidin-4-one in 50 mL of DMF is added dropwise. The mixture is stirred for 10 minutes at room temperature. After cooling the reaction medium to 0° C., 2.92 g (9.86 mmol) of 3-(bromoacetyl)pyridine hydrobromide are added portionwise. The reaction mixture is allowed to warm to room temperature and is stirred overnight. The reaction medium is evaporated to dryness and the residue is taken up in water and extracted with EtOAc. The organic phase is dried over magnesium sulfate and evaporated to dryness. The crude product obtained is purified by chromatography on silica gel (eluent: 100% EtOAc). After evaporating the fractions under reduced pressure, 1.90 g of (8S)-2-chloro-9-(2-oxo-2-pyrid-3-ylethyl)-8-trifluoromethyl-6,7,8,9-tetrahydropyrimido[1,2-a]pyrimidin-4-one are obtained, the characteristics of which are as follows:

LC/MS (method G): ESI+ [M+H]+: m/z 373 tr (min)=1.76

$^1$H NMR (300 MHz, δ in ppm, $CDCl_3$): 1.66 (s, 1H), 2.3-2.52 (m, 2H), 3.48 (m, 1H), 4 (m, 1H), 4.37 (d, 1H), 4.56 (m, 1H), 5.92 (s, 1H), 7.45 (m, 1H), 8.22 (m, 1H), 8.81 (s, 1H), 9.15 (s, 1H).

Step 6.2: (8S)-2-(1S,4S)-2-oxa-5-azabicyclo[2.2.1]hept-5-yl-9-(2-oxo-2-pyrid-3-ylethyl)-8-trifluoromethyl-6,7,8,9-tetrahydropyrimido[1,2-a]pyrimidin-4-one

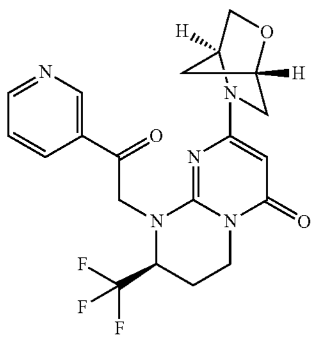 [SMILES: O=C(CN1c2nc(N3C[C@@H]4C[C@H]3CO4)cc(=O)n2CC[C@H]1C(F)(F)F)c1cccnc1]

1 g (2.68 mmol) of (8S)-2-chloro-9-(2-oxo-2-pyrid-3-ylethyl)-8-trifluoromethyl-6,7,8,9-tetrahydropyrimido[1,2-a]pyrimidin-4-one and 545.67 mg (4.02 mmol) of (1S,4S)-2-oxa-5-azabicyclo[2.2.1]heptane hydrochloride are mixed together. The powder obtained is placed in a tube and 934.86 μl (6.71 mmol) of triethylamine are added. The tube is sealed and heated at 130° C. in an oil bath for 6 hours. The crude product obtained is taken up in water and extracted with ethyl acetate. The organic phase is dried over magnesium sulfate and then evaporated to dryness. The residue is purified by chromatography on silica gel (eluent: 95/5 EtOAc/MeOH) to give 980 mg of (8S)-2-(1S,4S)-2-oxa-5-azabicyclo[2.2.1]hept-5-yl-9-(2-oxo-2-pyrid-3-ylethyl)-8-trifluoromethyl-6,7,8,9-tetrahydropyrimido[1,2-a]pyrimidin-4-one, the characteristics of which are as follows:

LC/MS (method A): ESI+ [M+H]+: m/z 436 tr (min)=0.51

$^1$H NMR (600 MHz, δ in ppm, DMSO-$d_6$): 1.67 (d, 1H), 1.75 (d, 1H), 2.32 (m, 1H), 2.5 (m, 1H), 3.04 (d, 1H), 3.17-3.25 (bs, 1H), 3.25-3.4 (bs, 3H), 4.44 (dd, 1H), 4.48 (s, 1H), 4.52 (s, 1H), 4.66 (m, 1H), 4.72 (s, 1H), 4.77 (d, 1H), 5.7 (d, 1H), 7.64 (m, 1H), 8.41 (m, 1H) 8.88 (m, 1H), 9.24 (s, 1H).

EXAMPLE 7

2-methyl-1-[2-(5-methylpyrid-3-yl)-2-oxoethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one (Compound 16)

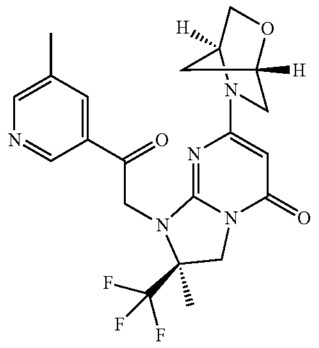 [SMILES: Cc1cncc(C(=O)CN2c3nc(N4C[C@@H]5C[C@H]4CO5)cc(=O)n3C[C@@]2(C)C(F)(F)F)c1]

Step 7.1: (R)-2-methyl-4-phenyl-2-trifluoromethyloxazolidine

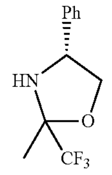

25 g (180 mmol) of (R)-phenylglycinol and then 4 g (16 mmol) of pyridinium para-toluenesulfonate are added to a solution of 25.8 g (230 mmol) of trifluoroacetone in 200 mL of toluene in a three-necked flask on which is mounted Dean-Stark apparatus. The mixture obtained is then heated at 110° C. for 5 hours. After cooling, the reaction mixture is concentrated under reduced pressure. The residue obtained is purified by filtration on silica (eluent: dichloromethane) to give 35.10 g of (R)-2-methyl-4-phenyl-2-trifluoromethyloxazolidine in the form of a colorless liquid, the characteristics of which are as follows:

LC/MS (method D): ESI+ [M+H]+: m/z 232 tr (min)=0.96

$^1$H NMR (300 MHz, δ in ppm, DMSO-$d_6$): 1.55 (s, 3H), 3.58 (m, 1H), 3.80 (m, 1H), 4.28 (m, 1H), 4.42 (m, 1H), 7.34 (m, 5H).

$[\alpha]_D^{25}$ at 589 nm=−23.4±0.8° (c=1.794 mg/0.5 mL MeOH)

Step 7.2: (S)-3,3,3-trifluoro-2-((R)-2-hydroxy-1-phenylethylamino)-2-methylpropionitrile

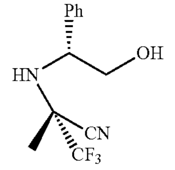

and

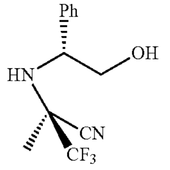

25 mL (200 mmol) of trimethylsilyl cyanide are added dropwise to a solution, cooled to 2° C., of 30.10 g (130 mmol) of (R)-2-methyl-4-phenyl-2-trifluoromethyloxazolidine in 300 mL of dichloromethane in a three-necked flask under argon, followed by dropwise addition of 25 mL (200 mmol) of boron trifluoride etherate. The cold bath is then removed to allow the mixture to warm to room temperature. The resulting mixture is stirred at room temperature for 3 hours, followed by addition of saturated sodium bicarbonate solution to pH=7. The organic phase is separated out and then dried over magnesium sulfate, filtered and concentrated under reduced pressure. The residue obtained is purified by chromatography on silica (eluent A/B: pentane/EtOAc, A/B gradient: t 0 min 0% B, t 20 min 10% B, t 40 min 40% B) to give 3.50 g of (R)-3,3,3-trifluoro-2-((R)-2-hydroxy-1-phenylethylamino)-2-methylpropionitrile in the form of a colorless oil and 10 g of (S)-3,3,3-trifluoro-2-((R)-2-hydroxy-1-phenylethylamino)-2-methylpropionitrile in the form of a white solid, the characteristics of which are:

LC/MS (method D): ESI+ [M+H]+: m/z 259 tr (min)=0.86

$^1$H NMR (300 MHz, δ in ppm, DMSO-$d_6$): 1.71 (s, 3H), 3.43 (m, 2H), 3.57 (m, 1H), 3.96 (m, 1H), 4.97 (m, 1H), 7.29 (m, 5H).

[α]$_D^{25}$ at 589 nm=−77.6±1.4° (c=1.818 mg/0.5 mL DMSO) for (S)-3,3,3-trifluoro-2-((R)-2-hydroxy-1-phenylethylamino)-2-methylpropionitrile Step 7.3: (R)-2-((S)-1-aminomethyl-2,2,2-trifluoro-1-methylethylamino)-2-phenylethanol

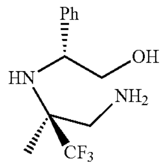

65.10 mL (65.10 mmol) of a 1 M solution of lithium aluminum hydride in tetrahydrofuran are added to a solution, cooled to 2° C., of 16.80 g (65.10 mmol) of (S)-3,3,3-trifluoro-2-((R)-2-hydroxy-1-phenylethylamino)-2-methylpropionitrile in 50 mL of anhydrous tetrahydrofuran in a three-necked flask under argon. At the end of the addition, the reaction mixture is allowed to warm to room temperature and is then stirred overnight. The mixture obtained is cooled to 0° C., followed by very slow dropwise addition of 12 mL of water. Substantial evolution of gas and a temperature rise to 4° C. are observed. 12 mL of 15% potassium hydroxide and then 25 mL of water are added to the resulting mixture, maintained at 0° C. The white precipitate formed is filtered off and the filtrate obtained is dried over magnesium sulfate and then concentrated under reduced pressure to give 10.50 g of (R)-2-((S)-1-aminomethyl-2,2,2-trifluoro-1-methylethylamino)-2-phenylethanol, the characteristics of which are as follows:

LC/MS (method D): ESI+ [M+H]+: m/z 263 tr (min)=0.43

$^1$H NMR (300 MHz, δ in ppm, DMSO-d$_6$): 0.90 (s, 3H), 2.48 (m, 2H), 2.72 (m, 2H), 3.31 (m, 4H), 3.95 (m, 1H), 7.27 (m, 5H).

[α]$_D^{25}$ at 589 nm=−51.2±1.3° (c=1.576 mg/0.5 mL DMSO)

Step 7.4: (S)-3,3,3-trifluoro-2-methylpropane-1,2-diamine

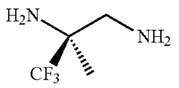

A mixture of 10.50 g (70 mmol) of (R)-2-((S)-1-aminomethyl-2,2,2-trifluoro-1-methylethylamino)-2-phenylethanol in methanol, 4.5 mL (68 mmol) of methanesulfonic acid and 1.50 g of Pd(OH)$_2$/C (20% w/w) is hydrogenated at 25° C. in an autoclave, under a hydrogen pressure of 5 bar, for 24 hours. The mixture obtained is then filtered and the filtrate is evaporated to dryness. The oil obtained is taken up in 3 M hydrochloric acid solution (42 mL). The mixture obtained is extracted with ethyl ether. Ethyl ether and 15 mL of 35% sodium hydroxide are then added to the aqueous phase, to pH 12. The aqueous phase is then separated out by settling and extracted with 3 times 200 mL of ethyl ether. The organic phases are combined, dried over magnesium sulfate, filtered and then concentrated under vacuum to give 4.50 g of (S)-3,3,3-trifluoro-2-methylpropane-1,2-diamine in the form of a pale yellow oil, the characteristics of which are as follows:

LC/MS (method E): ESI+ [M+H]+: m/z 143 tr (min)=0.34

$^1$H NMR (300 MHz, DMSO-d$_6$): 1.10 (s, 3H), 1.60-1.85 (bs, 2H), 2.48 (d, 1H), 2.72 (d, 1H), 3.20-3.50 (bs, 2H).

[α]$_D^{25}$ at 589 nm=−4.3±0.6° (c=1.778 mg/0.5 mL DMSO)

Step 7.5: (S)-4-methyl-4-trifluoromethyl-4,5-dihydro-1H-imidazol-2-ylamine hydrobromide

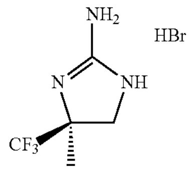

11.60 mL (34.90 mmol) of cyanogen bromide dissolved in dichloromethane are added portionwise to a solution, cooled to 4° C., of 4.50 g (31.70 mmol) of (S)-3,3,3-trifluoro-2-methylpropane-1,2-diamine in 20 mL of acetonitrile, while maintaining the temperature between 5 and 10° C. At the end of the addition, the reaction mixture is left at 5° C. for 30 minutes. The mixture obtained is then stirred at room temperature overnight. The resulting mixture is then concentrated under vacuum. The residue obtained is taken up twice with ethanol and then twice with toluene, and evaporated to dryness each time. The solid obtained is triturated with ethyl ether and then filtered off to give 4.50 g of (S)-4-methyl-4-trifluoromethyl-4,5-dihydro-1H-imidazol-2-ylamine hydrobromide in the form of a white solid, the characteristics of which are as follows:

LC/MS (method D): ESI+ [M+H]+: m/z 168 tr (min)=0.14

$^1$H NMR (300 MHz, DMSO-d$_6$): 1.52 (s, 3H), 3.57 (m, 1H), 3.81 (m, 1H), 7.45 (s, 2H), 8.09 (s, 1H), 9.45 (s, 1H).

[α]$_D^{25}$ at 589 nm: −5.2±0.3° (c=4.909 mg/0.5 mL DMSO)

Step 7.6: (S)-7-hydroxy-2-methyl-2-trifluoromethyl-2,3-dihydro-1H-imidazo[1,2-a]pyrimidin-5-one

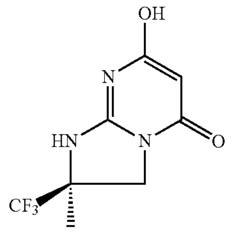 [SMILES: C[C@@]1(C(F)(F)F)Cn2c(nc(O)cc2=O)N1]

36.90 g (148.76 mmol) of (S)-4-methyl-4-trifluoromethyl-4,5-dihydro-1H-imidazol-2-ylamine hydrobromide and 24.10 g (446 mmol) of sodium methoxide are added to a mixture of 29.50 g (216.43 mmol) of diethyl malonate in 200 mL of methanol. The resulting mixture is refluxed for 18 hours. After cooling, the mixture obtained is concentrated to dryness under vacuum. 65 mL of cold water are added to the residue obtained, to obtain a thick suspension, to which is added 25% hydrochloric acid to pH 5. The resulting suspension is stirred in an ice bath for 3 hours and then filtered. The insoluble matter obtained is rinsed with water and then dried to give 37.60 g of (S)-7-hydroxy-2-methyl-2-trifluoromethyl-2,3-dihydro-1H-imidazo[1,2-a]pyrimidin-5-one in the form of a white solid, the characteristics of which are as follows:

LC/MS (method D): ESI+ [M+H]+: m/z 236 tr (min)=0.32

$^{1}$H NMR (400 MHz, DMSO-$d_6$): 1.53 (s, 3H), 3.95 (m, 1H), 4.10 (m, 1H), 4.79 (s, 1H), 5.80-7.01 (bs, 1H), 9.09 (s, 1H).

$[\alpha]_D^{25}$ at 589 nm=−5.6±0.6° (c=1.789 mg/0.5 mL DMSO)

Step 7.7: (S)-7-chloro-2-methyl-2-trifluoromethyl-2,3-dihydro-1H-imidazo[1,2-a]pyrimidin-5-one

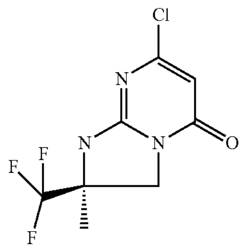 [SMILES: C[C@@]1(C(F)(F)F)Cn2c(nc(Cl)cc2=O)N1]

41.60 mL (446.50 mmol) of phosphorus oxychloride are added, at room temperature and under an argon atmosphere, to a suspension of 35 g (148.80 mmol) of (S)-7-hydroxy-2-methyl-2-trifluoromethyl-2,3-dihydro-1H-imidazo[1,2-a]pyrimidin-5-one in 350 mL of 1,2-dichloroethane. The resulting mixture is then heated at 70° C. for 4 hours. After cooling, the reaction mixture is evaporated to dryness under vacuum. The residue obtained is taken up in 35 mL of cold water and 500 mL of ethyl acetate. 32% sodium hydroxide is added to the mixture obtained, to pH=6-7. The organic phase is then separated out and then dried over magnesium sulfate, filtered and concentrated under reduced pressure to give 20 g of (S)-7-chloro-2-methyl-2-trifluoromethyl-2,3-dihydro-1H-imidazo[1,2-a]pyrimidin-5-one, the characteristics of which are as follows:

LC/MS (method D): ESI+ [M+H]+: m/z 254 tr (min)=0.51

$^{1}$H NMR (400 MHz, DMSO-$d_6$): 1.57 (s, 3H), 4.00 (d, 1H), 4.21 (d, 1H), 5.84 (s, 1H), 9.64 (s, 1H).

$[\alpha]_D^{25}$ at 589 nm=−64.8±1.10 (c=2.2 mg/0.5 mL DMSO)

Step 7.8: 2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one

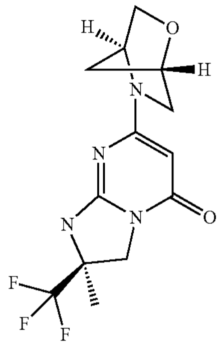 [SMILES: C[C@@]1(C(F)(F)F)Cn2c(nc(N3C[C@@H]4C[C@H]3CO4)cc2=O)N1]

1 g (3.84 mmol) of (S)-7-chloro-2-methyl-2-trifluoromethyl-2,3-dihydro-1H-imidazo[1,2-a]pyrimidin-5-one and 844.18 mg (5.91 mmol) of (1S,4S)-2-oxa-5-azabicyclo[2.2.1]heptane hydrochloride are mixed together. The powder obtained is placed in a tube and 1.38 mL (9.86 mmol) of triethylamine are added. The tube is sealed and heated at 140° C. in an oil bath for 4 hours. After cooling, the crude product is purified by chromatography on silica gel (eluent: 95/5 EtOAc/MeOH). After evaporating the fractions under reduced pressure, 750 mg of 2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one are obtained, the characteristics of which are as follows:

LC/MS (method G): ESI+: [M+H]+: m/z 317 tr (min)=1.34

$^{1}$H NMR (300 MHz, δ in ppm, $CDCl_3$): 1.34 (s, 3H), 1.65 (m, 2H), 3.13 (m, 2H), 3.43 (m, 1H), 3.53 (m, 1H), 3.72 (d, 1H), 3.89 (d, 1H), 4.1-4.81 (bs, 3H), 8.77 (s, 1H).

Step 7.9: 2-methyl-1-[2-(5-methylpyrid-3-yl)-2-oxoethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one

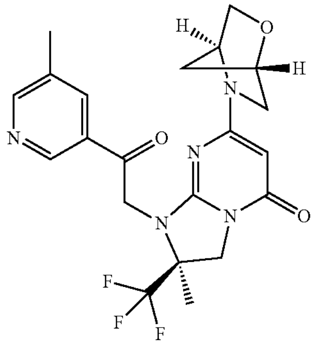 [SMILES: Cc1cncc(C(=O)CN2c3nc(N4C[C@@H]5C[C@H]4CO5)cc(=O)n3C[C@@]2(C)C(F)(F)F)c1]

150 mg (0.474 mmol) of 2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one in 5 mL of DMF are added to a suspension of 50.08 mg (1.04 mmol) of sodium hydride in 5 mL of DMF. The reaction mixture is placed under magnetic stirring at room temperature for 15 minutes. A solution of 153.88 mg (0.521 mmol) of 3-(bromoacetyl)pyridine hydrobromide in 5 mL of DMF is added dropwise to the reaction medium. The reaction is stirred at room temperature overnight. The reaction medium is evaporated to dryness. The crude product is taken up in water and extracted with ethyl acetate. The organic phase is dried over magnesium sulfate and evaporated to dryness. The residue is purified by chromatography on silica gel (eluent: 95/5 EtOAc/MeOH) to give 100 mg of 2-methyl-1-[2-(5-methylpyrid-3-yl)-2-oxoethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one, the characteristics of which are as follows:

LC/MS (method A): ESI+ [M+H]+: m/z 450 tr (min)=0.52

$^{1}$H NMR (600 MHz, δ in ppm, DMSO-$d_6$): 1.65 (s, 3H), 1.71 (m, 2H), 2.4 (s, 3H), 3-3.2 (m, 2H), 3.42 (s, 2H), 4 (d, 1H), 4.24 (d, 1H), 4.52 (t, 3H) 4.81 (d, 1H), 5.12 (d, 1H), 8.19 (s, 1H), 8.67 (s, 1H), 8.99 (s, 1H).

EXAMPLE 8

2-methyl-1-[2-(4-methylthiazol-5-yl)ethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one (Compound 26)

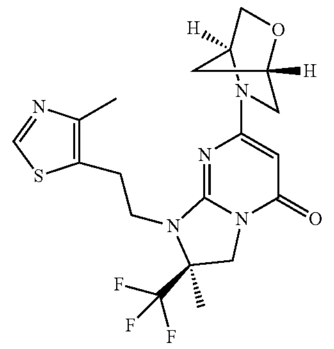 [SMILES: Cc1ncsc1CCN1c2nc(N3C[C@@H]4C[C@H]3CO4)cc(=O)n2C[C@@]1(C)C(F)(F)F]

Step 8.1: 5-(2-bromoethyl)-4-methylthiazole

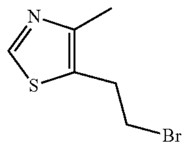

1 g (6.98 mmol) of 2-(4-methylthiazol-5-yl)ethanol is dissolved in 15 mL of dichloromethane. The solution is cooled to 0° C. When the temperature is reached, 1.85 g (6.98 mmol) of triphenylphosphine are added, followed by portionwise addition of 1.30 g (6.98 mmol) of N-bromosuccinimide. After stirring for 2 hours at 0° C., the mixture is evaporated to dryness. The residue is purified by chromatography on silica gel (eluent: 50/50 EtOAc/heptane) to give 900 mg of 5-(2-bromoethyl)-4-methylthiazole, the characteristics of which are as follows:

LC/MS (method G): ESI+ [M+H]+: m/z 206 tr (min)=1.52

$^1$H NMR (300 MHz, δ in ppm, $CDCl_3$): 2.42 (s, 3H) 3.3-3.35 (t, 2H) 3.5-3.55 (t, 2H) 8.62 (s, 1H)

Step 8.2: 2-methyl-1-[2-(4-methylthiazol-5-yl)ethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one

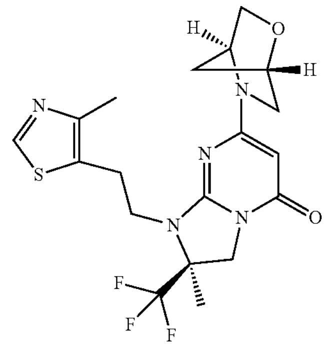 [SMILES: Cc1ncsc1CCN1c2nc(N3C[C@@H]4C[C@H]3CO4)cc(=O)n2C[C@@]1(C)C(F)(F)F]

150 mg (0.474 mmol) of 2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one in 5 mL of DMF are added to a suspension of 45.53 mg (0.95 mmol) of sodium hydride in 5 mL of DMF. The reaction mixture is heated for 15 minutes at 80° C. A solution of 293.24 mg (1.42 mmol) of 5-(2-bromoethyl)-4-methylthiazole in 5 mL of DMF is added dropwise to the reaction medium. The reaction is heated at 80° C. overnight. The reaction medium is evaporated to dryness. The crude product is taken up in water and extracted with ethyl acetate. The organic phase is dried over magnesium sulfate and evaporated to dryness. The residue is purified by chromatography on silica gel (eluent: 95/5 EtOAc/MeOH) to give 45 mg of 2-methyl-1-[2-(4-methylthiazol-5-yl)ethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one, the characteristics of which are as follows:

LC/MS (method A): ESI+ [M+H]+: m/z 442 tr (min)=0.56

$^1$H NMR (600 MHz, δ in ppm, DMSO-$d_6$): 1.55 (s, 3H), 1.86 (m, 2H), 2.34 (s, 3H), 3-3.48 (m, 7H), 3.6 (m, 1H), 3.66 (m, 1H), 3.76 (m, 1H), 3.86 (d, 1H), 4.13 (d, 1H), 4.66 (s, 1H), 8.86 (s, 1H).

EXAMPLE 9

(8S)-9-[2-(2-methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 19)

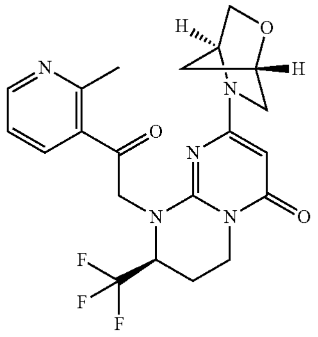 [SMILES: Cc1ncccc1C(=O)CN1c2nc(N3C[C@@H]4C[C@H]3CO4)cc(=O)n2CC[C@H]1C(F)(F)F]

Step 9.1: 1-(2-methylpyrid-3-yl)ethanone

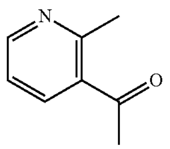

The following are successively introduced into a microwave tube:

469.80 µl (4.07 mmol) of 3-bromo-5-methylpyridine in 20 mL of $H_2O$/DMF: (1/3: v/v), 2.03 mL (5.70 mmol) of tributyl (1-ethoxyvinyl)tin, 57.12 mg (81.38 mmol) of bis(triphenylphosphine)palladium(II) chloride, 1.12 g (8.14 mmol) of potassium carbonate. After irradiating with microwaves for 1 hour at 110° C., the reaction mixture is evaporated to dryness and the residue is taken up in water and extracted with ethyl acetate. The organic phase is dried over magnesium sulfate and evaporated to dryness. The residue is taken up in a solution consisting of 6 mL of methanol and 1 mL of 1 N hydrochloric acid. After stirring overnight at room temperature, the reaction mixture is evaporated to dryness and the residue is taken up in saturated aqueous $NaHCO_3$ solution and extracted with ethyl acetate. The organic phase is dried over magnesium sulfate and evaporated to dryness. The residue is purified by chromatography on silica gel (eluent: 50/50 EtOAc/heptane) to give 160 mg of 1-(2-methylpyrid-3-yl)ethanone, the characteristics of which are as follows:

LC/MS (method G): ESI+ [M+H]+: m/z 136 tr (min)=0.38

$^1$H NMR (300 MHz, δ in ppm, DMSO-$d_6$): 2.58 (s, 3H), 2.61 (s, 3H), 7.38 (m, 1H), 8.2 (m, 1H), 8.57 (m, 1H).

Step 9.2: 2-bromo-1-(2-methylpyrid-3-yl)ethanone hydrobromide

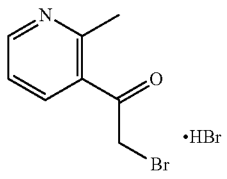

150 mg (1.11 mmol) of 1-(2-methylpyrid-3-yl)ethanone are dissolved in 10 mL of glacial acetic acid. 365 μl (2.22 mmol) of hydrobromic acid and 63 μl (1.22 mmol) of bromine are added to the medium. The reaction mixture is placed under magnetic stirring at room temperature for 1 hour. Ethyl ether is added to the solution until a precipitate appears. The precipitate corresponding to 2-bromo-1-(2-methylpyrid-3-yl)ethanone hydrobromide is filtered off, washed with ethyl ether and dried. The 280 mg of product obtained have the following characteristics:

LC/MS (method G): ESI+ [M+H]+: m/z 214 tr (min)=0.72

$^1$H NMR (300 MHz, δ in ppm, DMSO-$d_6$): 2.73 (s, 3H), 5 (s, 2H), 7.86 (m, 1H), 8.76 (m, 1H), 8.86 (m, 1H).

Step 9.3: (8S)-9-[2-(2-methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

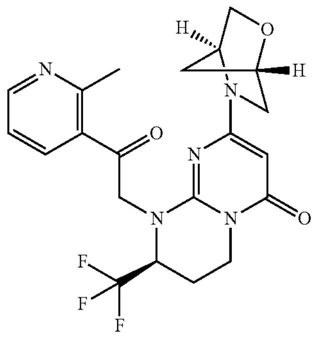 [SMILES: Cc1ncccc1C(=O)CN1c2nc(N3C[C@@H]4C[C@H]3CO4)cc(=O)n2CC[C@H]1C(F)(F)F]

140 mg (0.474 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one in 3 mL of DMF are added to a suspension of 46.74 mg (0.97 mmol) of sodium hydride in 4 mL of DMF. The reaction mixture is placed under magnetic stirring at room temperature for 15 minutes. A solution of 143.62 mg (0.443 mmol) of 2-bromo-1-(2-methylpyrid-3-yl)ethanone hydrobromide in 3 mL of DMF is added dropwise to the reaction medium. The reaction is stirred at room temperature for 1 hour. The reaction medium is evaporated to dryness. The crude product is taken up in water and extracted with ethyl acetate. The organic phase is dried over magnesium sulfate and evaporated to dryness. The residue is purified by chromatography on silica gel (eluent: 95/5 EtOAc/MeOH) to give 100 mg of (8S)-9-[2-(2-methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one, the characteristics of which are as follows:

LC/MS (method A): ESI+ [M+H]+: m/z 450 tr (min)=0.48

$^1$H NMR (600 MHz, δ in ppm, DMSO-$d_6$): 1.71 (m, 2H), 2.25 (m, 1H), 2.43 (m, 1H), 2.6 (s, 3H), 3.1-3.15 (m, 2H), 3.28 (m, 1H), 3.33-3.52 (bs, 2H), 4.37 (m, 1H), 4.52 (d, 2H), 4.59 (m, 1H), 4.64 (d, 1H), 4.69 (s, 1H), 5.5 (d, 1H), 7.4 (m, 1H), 8.28 (m, 1H), 8.61 (m, 1H).

EXAMPLE 10

(8S)-9-[2-(4-methylthiazol-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 43)

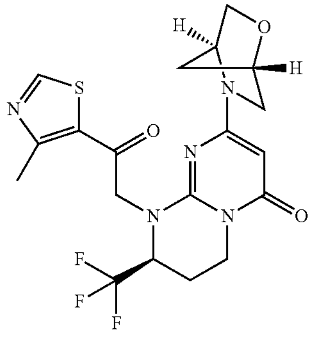 [SMILES: Cc1ncsc1C(=O)CN1c2nc(N3C[C@@H]4C[C@H]3CO4)cc(=O)n2CC[C@H]1C(F)(F)F]

Step 10.1: 2-bromo-1-(4-methylthiazol-5-yl)ethanone hydrobromide

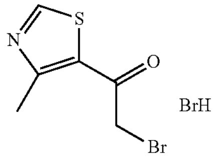

220 mg (1.56 mmol) of 1-(4-methylthiazol-5-yl)ethanone are dissolved in 10 mL of glacial acetic acid. 769 μl (4.67 mmol) of hydrobromic acid and 88 μl (1.71 mmol) of bromine are added to the medium. The reaction mixture is placed under magnetic stirring at room temperature for 2 hours. Ethyl ether is added to the solution until a precipitate appears. The precipitate corresponding to 2-bromo-1-(4-methylthiazol-5-yl)ethanone hydrobromide is filtered off, washed with ethyl ether and dried. The 350 mg of product obtained have the following characteristics:

LC/MS (method G): ESI+ [M+H]+: m/z 220 tr (min)=1.32

$^1$H NMR (300 MHz, δ in ppm, DMSO-$d_6$): 2.67 (s, 3H), 4.79 (s, 2H), 9.31 (s, 1H).

Step 10.2: (8S)-2-chloro-9-[2-(4-methylthiazol-5-yl)-2-oxoethyl]-8-trifluoromethyl-6,7,8,9-tetrahydro-pyrimido[1,2-a]pyrimidin-4-one

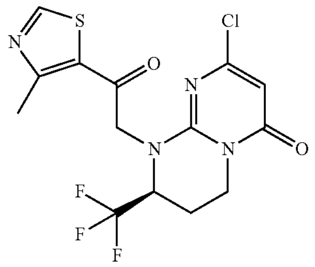 [SMILES: Cc1ncsc1C(=O)CN1c2nc(Cl)cc(=O)n2CC[C@H]1C(F)(F)F]

A suspension of 150 mg (0.591 mmol) of (8S)-2-chloro-8-trifluoromethyl-6,7,8,9-tetrahydropyrimido[1,2-a]pyrimidin-4-one and 578.13 mg (1.77 mmol) of cesium carbonate in 10 mL of acetonitrile is stirred for 15 minutes at room temperature. 213.64 mg (0.709 mmol) of 2-bromo-1-(4-methylthiazol-5-yl)ethanone hydrobromide are then added. After stirring overnight at room temperature, the reaction mixture is evaporated and the residue is taken up in water and extracted with ethyl acetate. The organic phase is dried over magnesium sulfate and evaporated to dryness to give 190 mg of (8S)-2-chloro-9-[2-(4-methylthiazol-5-yl)-2-oxoethyl]-8-trifluoromethyl-6,7,8,9-tetrahydropyrimido[1,2-a]pyrimidin-4-one, corresponding to the following characteristics:

LC/MS (method G): ESI+ [M+H]+: m/z 393 tr (min)=1.95

$^1$H NMR (300 MHz, δ in ppm, DMSO-$d_6$): 2.3 (m, 1H), 2.49 (s, 1H), 2.72 (s, 3H), 3.37 (m, 1H), 4.4 (m, 1H), 4.77 (m, 1H), 4.81 (s, 1H), 5.22 (d, 1H), 5.96 (s, 1H), 9.58 (s, 1H).

Step 10.3: (8S)-9-[2-(4-methylthiazol-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

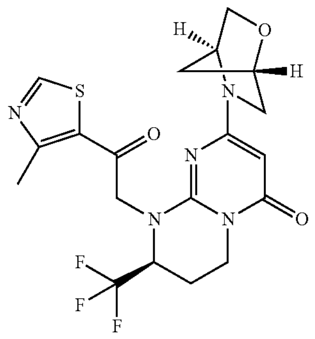 [SMILES: Cc1ncsc1C(=O)CN1c2nc(N3C[C@@H]4C[C@H]3CO4)cc(=O)n2CC[C@H]1C(F)(F)F]

170 mg (0.511 mmol) of (8S)-2-chloro-9-[2-(4-methylthiazol-5-yl)-2-oxoethyl]-8-trifluoromethyl-6,7,8,9-tetrahydropyrimido[1,2-a]pyrimidin-4-one and 70.42 mg (0.52 mmol) of (1S,4S)-2-oxa-5-azabicyclo[2.2.1]heptane hydrochloride are mixed together. The powder obtained is placed in a tube and 151 μl (1.08 mmol) of triethylamine are added. The tube is sealed and heated at 130° C. in an oil bath for 3 hours. The crude product obtained is taken up in water and extracted with ethyl acetate. The organic phase is dried over magnesium sulfate and then evaporated to dryness. The residue is purified by chromatography on silica gel (eluent: 95/5 EtOAc/MeOH) to give 120 mg of (8S)-9-[2-(4-methylthiazol-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one, the characteristics of which are as follows:

LC/MS (method A): ESI+ [M+H]+: m/z 456 tr (min)=0.55

$^1$H NMR (600 MHz, δ in ppm, DMSO-$d_6$): 1.69 (m, 2H), 2.28 (m, 1H), 2.43 (m, 1H), 2.7 (s, 3H), 2.98 (d, 1H), 3.12 (d, 1H), 3.21-3.33 (m, 3H), 4.37 (m, 1H), 4.42 (s, 1H), 4.5 (s, 1H), 4.55-4.62 (m, 2H), 4.67 (s, 1H), 5.22 (d, 1H), 9.19 (s, 1H).

EXAMPLE 11

(8S)-2-(1S,4S)-2-Oxa-5-azabicyclo[2.2.1]hept-5-yl-9-[2-oxo-2-(tetrahydropyran-4-yl)ethyl]-8-trifluoromethyl-6,7,8,9-tetrahydropyrimido[1,2-a]pyrimidin-4-one (Compound 62)

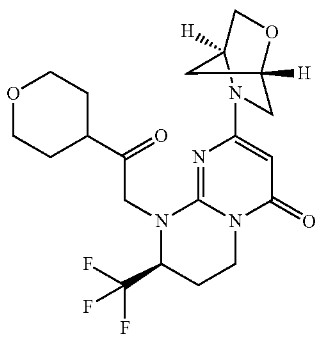 [SMILES: O=C(CN1c2nc(N3C[C@@H]4C[C@H]3CO4)cc(=O)n2CC[C@H]1C(F)(F)F)C1CCOCC1]

Step 11.1: (8S)-2-chloro-9-[2-oxo-2-(tetrahydropyran-4-yl)ethyl]-8-trifluoromethyl-6,7,8,9-tetrahydro-pyrimido[1,2-a]pyrimidin-4-one

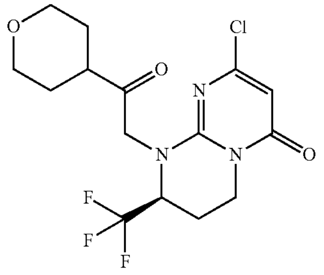 [SMILES: O=C(CN1c2nc(Cl)cc(=O)n2CC[C@H]1C(F)(F)F)C1CCOCC1]

A suspension of 150 mg (0.591 mmol) of (8S)-2-chloro-8-trifluoromethyl-6,7,8,9-tetrahydropyrimido[1,2-a]pyrimidin-4-one and 578.13 mg (1.77 mmol) of cesium carbonate in 10 mL of acetonitrile is stirred for 15 minutes at room temperature. 146.97 mg (0.709 mmol) of 2-bromo-1-(tetrahydropyran-4-yl)ethanone are then added. After stirring overnight at room temperature, the reaction mixture is evaporated and the residue is taken up in water and extracted with ethyl acetate. The organic phase is dried over magnesium sulfate and evaporated to dryness to give 220 mg of (8S)-2-chloro-9-[2-oxo-2-(tetrahydropyran-4-yl)ethyl]-8-trifluoromethyl-6,7,8,9-tetrahydropyrimido[1,2-a]pyrimidin-4-one, corresponding to the following characteristics:

LC/MS (method G): ESI+ [M+H]+: m/z 380 tr (min)=1.94

$^1$H NMR (300 MHz, δ in ppm, $CDCl_3$): 1.58-2.04 (m, 2H), 2.37 (m, 1H), 2.5 (m, 1H), 2.76 (m, 1H), 3.5 (4H), 3.9 (d, 1H), 3.96-4.02 (m, 4H), 4.6 (m, 1H), 5.25 (d, 1H), 5.99 (s, 1H).

Step 11.2: (8S)-2-(1S,4S)-2-Oxa-5-azabicyclo[2.2.1]hept-5-yl-9-[2-oxo-2-(tetrahydropyran-4-yl)ethyl]-8-trifluoromethyl-6,7,8,9-tetrahydropyrimido[1,2-a]pyrimidin-4-one

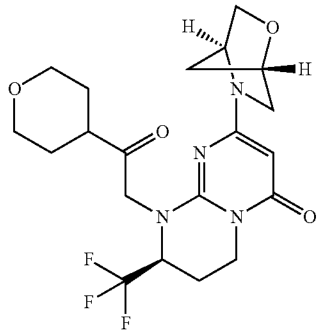 [SMILES: O=C(CN1c2nc(N3C[C@@H]4C[C@H]3CO4)cc(=O)n2CC[C@H]1C(F)(F)F)C1CCOCC1]

220 mg (0.58 mmol) of (8S)-2-chloro-9-[2-oxo-2-(tetrahydropyran-4-yl)ethyl]-8-trifluoromethyl-6,7,8,9-tetrahydropyrimido[1,2-a]pyrimidin-4-one and 94.26 mg (0.69 mmol) of (1S,4S)-2-oxa-5-azabicyclo[2.2.1]heptane hydrochloride are mixed together. The powder obtained is placed in a tube and 202 µl (1.45 mmol) of triethylamine are added. The tube is sealed and heated at 130° C. in an oil bath for 3 hours. The crude product obtained is taken up in water and extracted with ethyl acetate. The organic phase is dried over magnesium sulfate and then evaporated to dryness. The residue is purified by chromatography on silica gel (eluent: 95/5 EtOAc/MeOH) to give 220 mg of (8S)-2-(1S,4S)-2-oxa-5-azabicyclo[2.2.1]hept-5-yl-9-[2-oxo-2-(tetrahydropyran-4-yl)ethyl]-8-trifluoromethyl-6,7,8,9-tetrahydropyrimido[1,2-a]pyrimidin-4-one, the characteristics of which are as follows:

LC/MS (method A): ESI+ [M+H]+: m/z 443 tr (min)=0.52

$^1$H NMR (600 MHz, δ in ppm, DMSO-$d_6$): 1.49 (m, 1H), 1.52 (m, 1H), 1.7 (m, 2H), 1.79 (bs, 2H), 2.15 (m, 1H), 2.36 (m, 1H), 2.7 (m, 1H), 2.84-3.25 (bs, 3H), 3.31-3.59 (bs, 3H), 3.65 (d, 1H), 3.86 (m, 2H), 4.17 (d, 1H), 4.3 (m, 1H), 4.35-5.3 (bs, 5H).

EXAMPLE 12

(8S)-9-[2-(4-methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 20)

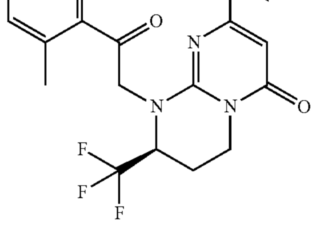

Step 12.1: 1-(4-methylpyrid-3-yl)ethanone

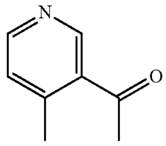

671 µl (5.81 mmol) of 3-bromo-4-methylpyridine in 15 mL of $H_2O$/DMF (1/4: v/v), 1.93 mL (14.53 mmol) of N-butyl vinyl ether, 39.15 mg (0.17 mmol) of palladium(II) acetate, 163.14 mg (0.38 mmol) of 1,3-bis(diphenylphosphino)propane and 973.84 mg (6.98 mmol) of potassium carbonate are placed in a microwave tube. After irradiating with microwaves at 120° C. for 2 hours, 20 mL of 5% hydrochloric acid solution are added. The reaction mixture is stirred for 1 hour at room temperature and then basified with potassium carbonate and extracted with ethyl acetate. The organic phase is dried over magnesium sulfate and evaporated to dryness. The residue is purified by chromatography on silica gel (eluent: 50/50 EtOAc/heptane) to give 320 mg of 1-(4-methylpyrid-3-yl)ethanone, the characteristics of which are as follows:

LC/MS (method G): ESI+ [M+H]+: m/z 136 tr (min)=0.56

$^1$H NMR (300 MHz, δ in ppm, DMSO-$d_6$): 2.46 (s, 3H), 2.62 (s, 3H), 7.35 (d, 1H), 8.56 (d, 1H), 9 (s, 1H).

Step 12.2: 2-bromo-1-(4-methylpyrid-3-yl)ethanone hydrobromide

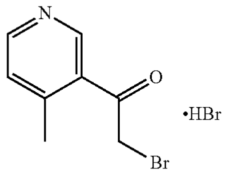

300 mg (2.22 mmol) of 1-(4-methylpyrid-3-yl)ethanone are dissolved in 20 mL of glacial acetic acid. 730 µl (4.44 mmol) of hydrobromic acid and 126 µl (2.44 mmol) of bromine are added to the medium. The reaction mixture is placed under magnetic stirring at room temperature for 2 hours. Ethyl ether is added to the solution until a precipitate appears. The precipitate corresponding to 2-bromo-1-(4-methylpyrid-3-yl)ethanone hydrobromide is filtered off, washed with ethyl ether and dried. The 550 mg of product obtained have the following characteristics:

LC/MS (method G): ESI+ [M+H]+: m/z 214 tr (min)=1.01

$^1$H NMR (300 MHz, δ in ppm, DMSO-$d_6$): 2.59 (s, 3H), 5.04 (s, 2H), 7.85 (d, 1H), 8.84 (d, 1H), 9.25 (s, 1H).

Step 12.3: (8S)-2-chloro-9-[2-(4-methyl pyrid-3-yl)-2-oxoethyl]-8-trifluoromethyl-6,7,8,9-tetrahydropyrimido[1,2-a]pyrimidin-4-one

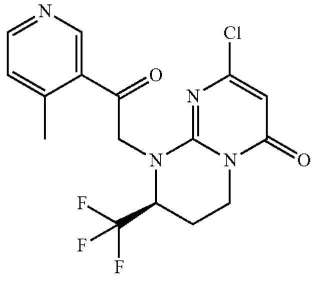 [SMILES: Cc1ccncc1C(=O)CN1c2nc(Cl)cc(=O)n2CC[C@H]1C(F)(F)F]

A suspension of 100 mg (0.394 mmol) of (8S)-2-chloro-8-trifluoromethyl-6,7,8,9-tetrahydropyrimido[1,2-a]pyrimidin-4-one and 385.42 mg (1.18 mmol) of cesium carbonate in 10 mL of acetonitrile is stirred for 15 minutes at room temperature. 139.57 mg (0.473 mmol) of 2-bromo-1-(4-methylpyrid-3-yl)ethanone hydrobromide are then added. After stirring overnight at room temperature, the reaction mixture is evaporated and the residue is taken up in water and extracted with ethyl acetate. The organic phase is dried over magnesium sulfate and evaporated to dryness to give 140 mg of (8S)-2-chloro-9-[2-(4-methylpyrid-3-yl)-2-oxoethyl]-8-trifluoromethyl-6,7,8,9-tetrahydropyrimido[1,2-a]pyrimidin-4-one, corresponding to the following characteristics:

LC/MS (method G): ESI+ [M+H]+: m/z 387 tr (min)=1.87

$^1$H NMR (300 MHz, δ in ppm, $CDCl_3$): 2.27 (m, 1H), 2.44 (s, 3H), 2.5 (m, 1H), 3.4 (m, 1H), 4.4 (m, 1H), 4.77 (m, 1H), 4.86 (d, 1H), 5.32 (d, 1H), 5.97 (s, 1H), 7.4 (d, 1H), 8.6 (d, 1H), 9 (s, 1H).

Step 12.4: (8S)-9-[2-(4-methyl pyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

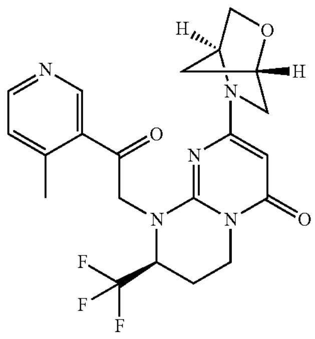 [SMILES: Cc1ccncc1C(=O)CN1c2nc(N3C[C@@H]4C[C@H]3CO4)cc(=O)n2CC[C@H]1C(F)(F)F]

140 mg (0.36 mmol) of (8S)-2-chloro-9-[2-(4-methylpyrid-3-yl)-2-oxoethyl]-8-trifluoromethyl-6,7,8,9-tetrahydropyrimido[1,2-a]pyrimidin-4-one and 94.26 mg (0.69 mmol) of (1S,4S)-2-oxa-5-azabicyclo[2.2.1]heptane hydrochloride are mixed together. The powder obtained is placed in a tube and 126 μl (0.90 mmol) of triethylamine are added. The tube is sealed and heated at 120° C. in an oil bath for 2 hours. The crude product obtained is taken up in water and extracted with ethyl acetate. The organic phase is dried over magnesium sulfate and then evaporated to dryness. The residue is purified by chromatography on silica gel (eluent: 95/5 EtOAc/MeOH) to give 120 mg of (8S)-9-[2-(4-methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one, the characteristics of which are as follows:

LC/MS (method A): ESI+ [M+H]+: m/z 450 tr (min)=0.48

$^1$H NMR (600 MHz, δ in ppm, DMSO-$d_6$): 1.7 (m, 2H), 2.25 (m, 1H), 2.42 (m, 1H), 2.45 (s, 3H), 3-3.2 (m, 2H), 3.24-3.53 (bs, 3H), 3.36 (m, 1H), 4.51 (s, 1H), 4.54 (s, 1H), 4.59 (m, 1H), 4.65-4.76 (m, 2H), 5.55 (d, 1H), 7.37 (d, 1H), 8.59 (d, 1H), 9.05 (s, 1H).

EXAMPLE 13

(8S)-9-(2-methyl-2-pyrid-4-yl propyl)-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 1)

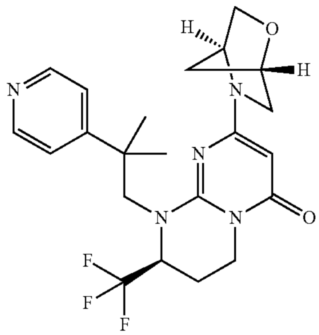 [SMILES: CC(C)(CN1c2nc(N3C[C@@H]4C[C@H]3CO4)cc(=O)n2CC[C@H]1C(F)(F)F)c1ccncc1]

Step 13.1: ethyl 2-methyl-2-pyrid-4-ylpropionate

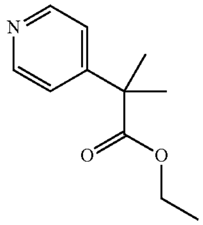

The reaction is performed under argon: 2 g (12.12 mmol) of ethyl pyrid-4-ylacetate are dissolved in 30 mL of DMF. After addition of 15.25 mL (15.15 mmol) of a 1 M solution of lithium bis(trimethylsilyl)amide in THF, the reaction mixture is stirred at room temperature for 30 minutes. 1.21 mL (19.39 mmol) of iodomethane are then added gently, and the solution obtained is stirred at room temperature for 1 hour 30 minutes. A second portion of 15.25 mL (15.15 mmol) of a 1 M solution of lithium bis(trimethylsilyl)amide in THF is added, and the mixture is stirred at room temperature for 1 hour. A second portion of 1.21 mL (19.39 mmol) of iodomethane is also added, and stirring is continued for 2 hours at room temperature. The precipitate formed is filtered off, the filtrate is evaporated to dryness and the residue is taken up in dichloromethane. The organic phase is washed with water and with aqueous ammonium chloride solution, dried and evaporated to dryness to give 1.80 g of ethyl 2-methyl-2-pyrid-4-ylpropionate, corresponding to the following characteristics:

LC/MS (method G): ESI+ [M+H]+: m/z 194 tr (min)=1.03

$^1$H NMR (300 MHz, δ in ppm, DMSO-$d_6$): 1.11 (t, 3H), 1.49 (s, 6H), 4.09 (q, 2H), 7.31 (d, 2H), 8.52 (d, 2H).

Step 13.2: 2-methyl-2-pyrid-4-ylpropan-1-ol

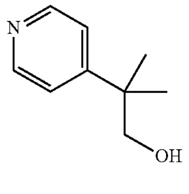

A solution of 1.58 g (7.36 mmol) of ethyl 2-methyl-2-pyrid-4-ylpropionate in 30 mL of THF is cooled to 10° C. When the temperature is reached, 22.08 mL (22.08 mmol) of 1 M diisobutylaluminum hydride solution in toluene are added dropwise. The reaction mixture is allowed to warm to room temperature and is stirred overnight. 1 N hydrochloric acid solution is added to the reaction medium, which is then extracted with ethyl acetate. The organic phase is dried over magnesium sulfate and evaporated to dryness to give 1.60 g of 2-methyl-2-pyrid-4-ylpropan-1-ol, corresponding to the following characteristics:

LC/MS (method G): ESI+ [M+H]+: m/z 152 tr (min)=0.40

$^1$H NMR (300 MHz, δ in ppm, DMSO-$d_6$): 1.19 (s, 6H), 3.42 (d, 2H), 4.76 (t, 1H), 7.34 (d, 2H), 8.44 (d, 2H).

Step 13.3: 2-methyl-2-pyrid-4-ylpropyl benzenesulfonate

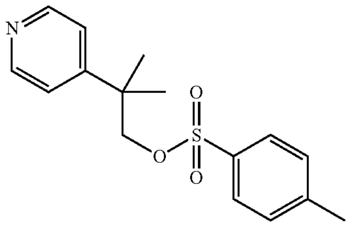 [SMILES: Cc1ccc(S(=O)(=O)OCC(C)(C)c2ccncc2)cc1]

710 μl (4.07 mmol) of N,N-diisopropylethylamine and 33.13 mg (0.27 mmol) of 4-dimethyl amino pyridine are added to a solution of 410 mg (2.71 mmol) of 2-methyl-2-pyrid-4-ylpropan-1-ol in 10 mL of dichloromethane. The mixture is cooled to 0° C. and a solution of 775.42 mg (4.07 mmol) of 4-methylbenzene-1-sulfonyl chloride in 2 mL of dichloromethane is then added. After allowing the reaction medium to warm to room temperature and stirring overnight, it is washed with water and with saturated NaCl solution. The organic phase is dried over magnesium sulfate and evaporated to dryness to give 660 mg of 2-methyl-2-pyrid-4-ylpropyl benzenesulfonate, corresponding to the following characteristics:

LC/MS (method G): ESI+ [M+H]+: m/z 306 tr (min)=1.49

$^1$H NMR (300 MHz, δ in ppm, DMSO-$d_6$): 1.22 (s, 6H), 2.43 (s, 3H), 4.11 (s, 2H), 7.27 (d, 2H), 7.42 (d, 2H), 7.66 (d, 2H), 8.43 (d, 2H).

Step 13.4: (8S)-9-(2-methyl-2-pyrid-4-yl propyl)-2-(1S,4S)-2-oxa-5-azabicyclo[2.2.1]hept-5-yl-8-trifluoromethyl-6,7,8,9-tetrahydropyrimido[1,2-a]pyrimidin-4-one

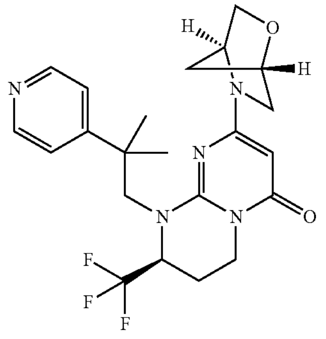 [SMILES: CC(C)(CN1c2nc(N3C[C@@H]4C[C@H]3CO4)cc(=O)n2CC[C@H]1C(F)(F)F)c1ccncc1]

The following are placed in a tube: 130 mg (0.411 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one, 133.92 mg (0.411 mmol) of cesium carbonate, 6.16 mg (0.041 mmol) of sodium iodide and 175.74 mg (0.575 mmol) of 2-methyl-2-pyrid-4-ylpropyl benzenesulfonate in 5 mL of DMF. The reaction mixture is heated overnight at 150° C. in the sealed tube. After allowing the mixture to cool to room temperature, the solvent is evaporated off. The residue is taken up in ethyl acetate, washed with water, dried over magnesium sulfate and evaporated to dryness. The residue is purified by chromatography on silica gel (eluent: 95/5 EtOAc/MeOH) to give 18 mg of (8S)-9-(2-methyl-2-pyrid-4-ylpropyl)-2-(1S,4S)-2-oxa-5-azabicyclo[2.2.1]hept-5-yl-8-trifluoromethyl-6,7,8,9-tetrahydropyrimido[1,2-a]pyrimidin-4-one, the characteristics of which are as follows:

LC/MS (method B): ESI+ [M+H]+: m/z 450 tr (min)=0.53

$^1$H NMR (600 MHz, δ in ppm, DMSO-$d_6$): 1.24 (s, 1H), 1.31 (s, 3H), 1.35 (s, 3H), 1.83 (m, 2H), 2.09 (m, 1H), 2.18 (m, 1H), 3.02 (m, 1H), 3.21 (m, 2H), 3.57 (m, 1H), 3.75 (m, 2H), 3.98 (m, 1H), 4.65 (m, 2H), 4.76 (d, 1H), 4.99 (m, 1H), 7.49 (s, 2H), 8.53 (s, 2H).

EXAMPLE 14

1-ethyl-3-{4-[2-((8S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)ethyl]phenyl}urea (Compound 23)

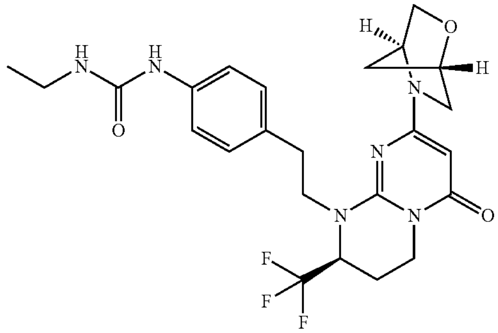 [SMILES: CCNC(=O)Nc1ccc(CCN2c3nc(N4C[C@@H]5C[C@H]4CO5)cc(=O)n3CC[C@H]2C(F)(F)F)cc1]

Step 14.1: tert-butyl [4-(2-hydroxyethyl)phenyl]carbamate

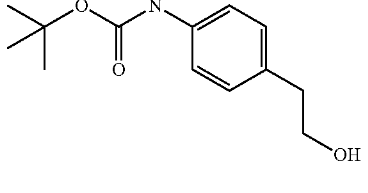

5 g (35.36 mmol) of 2-(4-aminophenyl)ethanol and 6.17 mL (35.36 mmol) of N,N-diisopropylethylamine are added to a solution of 8.49 g (38.89 mmol) of di-tert-butyl dicarbonate in 10 mL of dioxane. After stirring for 4 hours at room temperature, the reaction mixture is evaporated to dryness. The residue is taken up in ethyl acetate and the solution is washed with 1 N hydrochloric acid solution and then with water. The organic phase is dried over magnesium sulfate and evaporated to dryness to give 7.85 g of tert-butyl [4-(2-hydroxyethyl)phenyl]carbamate, the characteristics of which are as follows:

$^1$H NMR spectrum (300 MHz, δ in ppm, DMSO-$d_6$): 1.47 (s, 9H), 2.65 (t, 2H), 3.54 (q, 2H), 4.60 (t, 1H), 7.07 (d, 2H), 7.33 (d, 2H), 9.13-9.3 (bs, 1H).

Step 14.2: tert-butyl [4-(2-bromoethyl)phenyl]carbamate

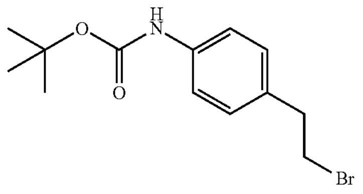 [SMILES: CC(C)(C)OC(=O)Nc1ccc(CCBr)cc1]

8.68 g (33.08 mmol) of triphenylphosphine are added, under an argon atmosphere, to a solution of 7.85 g (33.08 mmol) of tert-butyl [4-(2-hydroxyethyl)phenyl]carbamate in 85 mL of dichloromethane. The mixture is cooled to 0° C. and 5.95 g (33.08 mmol) of N-bromosuccinimide are added portionwise over 25 minutes. Stirring is continued for 3 hours at 0° C. The solvent is then evaporated off, the oil obtained is taken up in ether and the precipitate formed is filtered off and discarded. The filtrate is evaporated and the residue is purified by chromatography on silica gel (eluent: 10/90 EtOAc/heptane) to give 6.90 g of tert-butyl [4-(2-bromoethyl)phenyl] carbamate, the characteristics of which are as follows:

LC/MS (method G): ESI+ [M+Na]+: 322 tr (min)=2.46

$^1$H NMR spectrum (300 MHz, δ in ppm, DMSO-$d_6$): 1.47 (s, 9H), 3.04 (t, 2H), 3.68 (t, 2H), 7.15 (d, 2H), 7.38 (d, 2H), 9.29 (s, 1H).

Step 14.3: tert-butyl {4-[2-((8S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)ethyl]phenyl}carbamate

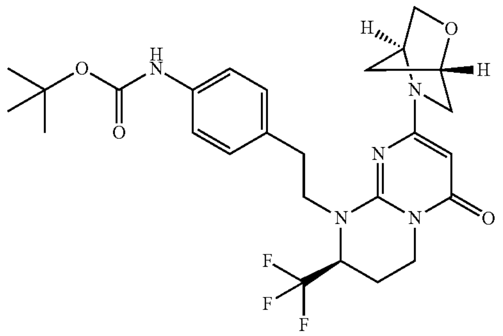 [SMILES: CC(C)(C)OC(=O)Nc1ccc(CCN2c3nc(N4C[C@@H]5C[C@H]4CO5)cc(=O)n3CC[C@H]2C(F)(F)F)cc1]

300 mg (0.95 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one in 3 mL of DMF are added to a suspension of 75.87 mg (1.89 mmol) of sodium hydride in 2 mL of 2-methyltetrahydrofuran. The reaction mixture is placed under magnetic stirring at room temperature for 10 minutes. A solution of 569.48 mg (1.89 mmol) of tert-butyl [4-(2-bromoethyl)phenyl]carbamate in 3 mL of DMF is added dropwise to the reaction medium. The reaction is stirred at room temperature overnight. The reaction medium is evaporated to dryness. The crude product is taken up in water and extracted with ethyl acetate. The organic phase is dried over magnesium sulfate and evaporated to dryness. The residue is purified by chromatography on silica gel (eluent: 95/5 EtOAc/MeOH) to give 240 mg of tert-butyl {4-[2-((8S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)ethyl]phenyl}carbamate, the characteristics of which are as follows:

LC/MS (method G): ESI+ [M+H]+: m/z 536 tr (min)=2.46

$^1$H NMR (300 MHz, δ in ppm, DMSO-$d_6$): 1.45 (s, 9H), 1.9 (s, 3H), 2.32 (m, 1H), 2.70-2.98 (m, 2H), 3.13 (m, 2H), 3.24-3.47 (bs, 2H), 3.7 (m, 1H), 3.77 (m, 1H), 4.17 (m, 2H), 4.47-5 (bs, 4H), 7.01 (d, 2H), 7.38 (d, 2H), 9.28 (s, 1H).

Step 14.4: (8S)-9-[2-(4-aminophenyl)ethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

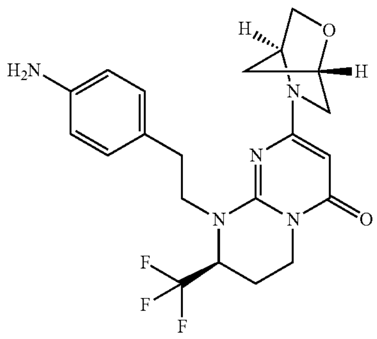 [SMILES: Nc1ccc(CCN2c3nc(N4C[C@@H]5C[C@H]4CO5)cc(=O)n3CC[C@H]2C(F)(F)F)cc1]

4 mL (17.93 mmol of a 4 N HCl/dioxane solution are added to a solution of 240 mg (0.45 mmol) of tert-butyl {4-[2-((8S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)ethyl]phenyl}carbamate. The reaction mixture is stirred for 1 hour 30 minutes at room temperature. The solvent is evaporated off and the residue is taken up in a methanol/dichloromethane mixture and then evaporated to give 245 mg of (8S)-9-[2-(4-aminophenyl)ethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one, the characteristics of which are as follows:

LC/MS (method G): ESI+ [M+H]+: m/z 436 tr (min)=1.60

$^1$H NMR (300 MHz, δ in ppm, DMSO-$d_6$): 1.79-2.12 (m, 3H), 2.33 (m, 1H), 2.82-3.09 (m, 2H), 3.17 (m, 2H), 3.37 (m, 1H), 3.58 (s, 1H), 3.69 (m, 2H), 3.79 (d, 1H), 4.2 (m, 2H), 4.67 (bs, 3H), 7.33 (s, 4H), 9.8-10.6 (bs, 2H).

Step 14.5: 1-ethyl-3-{4-[2-((8S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl) ethyl]phenyl}urea

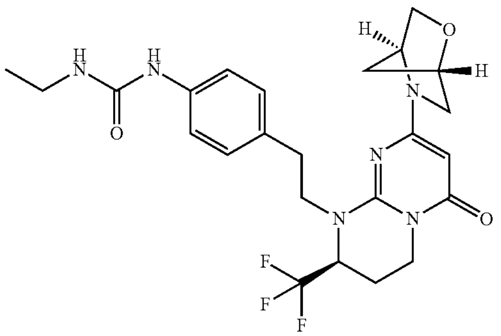 [SMILES: CCNC(=O)Nc1ccc(CCN2c3nc(N4C[C@@H]5C[C@H]4CO5)cc(=O)n3CC[C@H]2C(F)(F)F)cc1]

50 μl (0.63 mmol) of ethyl isocyanate are added to a solution of 150 mg (0.32 mmol) of (8S)-9-[2-(4-aminophenyl) ethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one and 139 μl (0.79 mmol) of N,N-diisopropylethylamine in 1 mL of dichloromethane. After stirring overnight at room temperature, the solvent is evaporated off. The residue is taken up in ethyl acetate and washed with water and with saturated aqueous NaCl solution. The organic phase is dried over magnesium sulfate and evaporated to dryness. The residue is purified by reverse-phase chromatography (RP18 column) (eluent: 50/50 $H_2O$/MeOH) to give 92 mg of 1-ethyl-3-{4-[2-((8S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)ethyl]phenyl}urea, the characteristics of which are as follows:

LC/MS (method A): ESI+ [M+H]+: m/z 507 tr (min)=0.6

$^1$H NMR (600 MHz, δ in ppm, DMSO-$d_6$): 1.05 (t, 3H), 1.88 (m, 3H), 2.31 (m, 1H), 2.78 (m, 1H), 2.9 (m, 1H), 3.1 (m, 4H), 3.36 (m, 2H), 3.71 (d, 1H), 3.79 (d, 1H), 4.18 (d, 2H), 4.55 (m, 1H), 4.6-5.1 (bs, 3H), 6 (t, 1H), 7 (d, 2H), 7.3 (d, 2H), 8.3 (s, 1H).

EXAMPLE 15

1-ethyl-3-(4-{2-[(1S,4S)-2-methyl-7-2-oxa-5-azabicyclo[2.2.1]hept-5-yl-5-oxo-2-((S)-trifluoromethyl)-2,3-dihydro-5H-imidazo[1,2-a]pyrimidin-1-yl] ethyl}phenyl)urea (Compound 24)

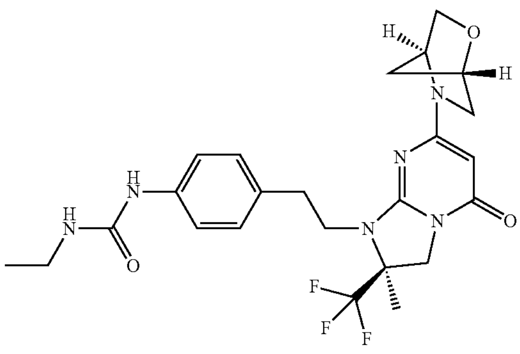 [SMILES: CCNC(=O)Nc1ccc(CCN2c3nc(N4C[C@@H]5C[C@H]4CO5)cc(=O)n3C[C@@]2(C)C(F)(F)F)cc1]

Step 15.1: tert-butyl (4-{2-[(1S,4S)-2-methyl-7-2-oxa-5-azabicyclo[2.2.1]hept-5-yl-5-oxo-2-((S)-trifluoromethyl)-2,3-dihydro-5H-imidazo[1,2-a]pyrimidin-1-yl]ethyl}phenyl)carbamate

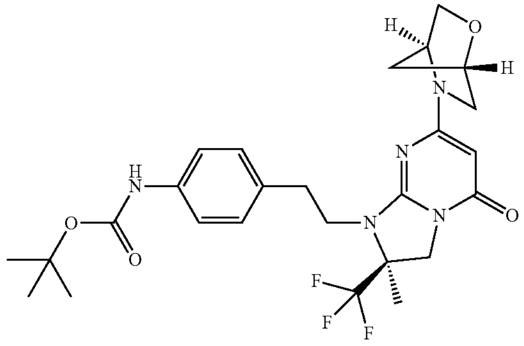 [SMILES: CC(C)(C)OC(=O)Nc1ccc(CCN2c3nc(N4C[C@@H]5C[C@H]4CO5)cc(=O)n3C[C@@]2(C)C(F)(F)F)cc1]

A suspension of 300 mg (0.948 mmol) of 2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one and 309.05 mg (0.948 mmol) of cesium carbonate in 5 mL of DMF is stirred at 85° C. for 15 minutes. A solution of 284.74 mg (0.948 mmol) of tert-butyl [4-(2-bromoethyl)phenyl]carbamate is added dropwise. After reacting overnight at 85° C., the mixture is evaporated and the residue is taken up in water and extracted with ethyl acetate. The organic phase is dried over magnesium sulfate and evaporated to dryness. The residue is purified by chromatography on silica gel (eluent: 95/5 EtOAc/MeOH) to give 385 mg of tert-butyl (4-{2-[(1S,4S)-2-methyl-7-2-oxa-5-azabicyclo[2.2.1]hept-5-yl-5-oxo-2-((S)-trifluoromethyl)-2,3-dihydro-5H-imidazo[1,2-a]pyrimidin-1-yl]ethyl}phenyl)carbamate, the characteristics of which are as follows:

LC/MS (method G): ESI+ [M+H]+: m/z 536 tr (min)=2.48

$^1$H NMR (300 MHz, δ in ppm, $CDCl_3$): 1.47 (s, 9H), 1.53 (s, 3H), 1.85 (s, 2H), 2.77 (m, 1H), 2.93 (m, 1H), 3.29-3.46 (m, 5H), 3.54 (m, 1H), 3.68 (m, 1H), 3.81 (m, 2H), 4.13 (m, 1H), 4.66 (s, 1H), 7.11 (d, 2H), 7.39 (d, 2H), 9.29 (s, 1H).

Step 15.2: 1-[2-(4-aminophenyl)ethyl]-2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one

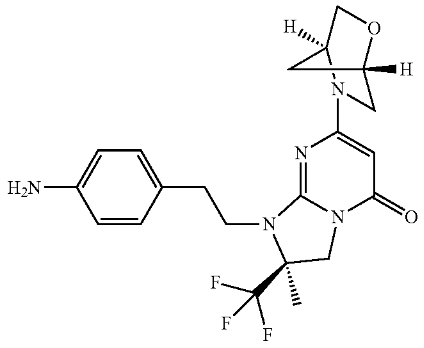 [SMILES: C[C@@]1(C(F)(F)F)Cn2c(nc(N3C[C@@H]4C[C@H]3CO4)cc2=O)N1CCc1ccc(N)cc1]

1 mL of trifluoroacetic acid is added to a solution of 385 mg (0.72 mmol) of tert-butyl (4-{2-[(1S,4S)-2-methyl-7-2-oxa- 5-azabicyclo[2.2.1]hept-5-yl-5-oxo-2-((S)-trifluoromethyl)-2,3-dihydro-5H-imidazo[1,2-a]pyrimidin-1-yl]ethyl}phenyl)carbamate in 4 mL of dichloromethane. After stirring for 1 hour at room temperature, the solvent is evaporated off. The residue is taken up in ethyl acetate and washed with saturated aqueous $NaHCO_3$ solution. The organic phase is dried over magnesium sulfate and evaporated to dryness to give 275 mg of 1-[2-(4-aminophenyl)ethyl]-2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one, the characteristics of which are as follows:

LC/MS (method A): ESI+ [M+H]+: m/z 436 tr (min)=0.48

$^1$H NMR (600 MHz, δ in ppm, DMSO-$d_6$): 1.52 (s, 3H), 1.87 (m, 2H), 2.69 (m, 1H), 2.87 (m, 1H), 3.26-3.53 (bs, 6H), 3.68 (d, 1H), 3.78 (m, 2H), 4.10 (d, 1H), 4.66 (s, 1H), 4.92 (s, 2H), 6.5 (d, 2H), 6.87 (d, 2H).

Step 15.3: 1-ethyl-3-(4-{2-[(1S,4S)-2-methyl-7-2-oxa-5-azabicyclo[2.2.1]hept-5-yl-5-oxo-2-((S)-trifluoromethyl)-2,3-dihydro-5H-imidazo[1,2-a]pyrimidin-1-yl]ethyl}phenyl)urea

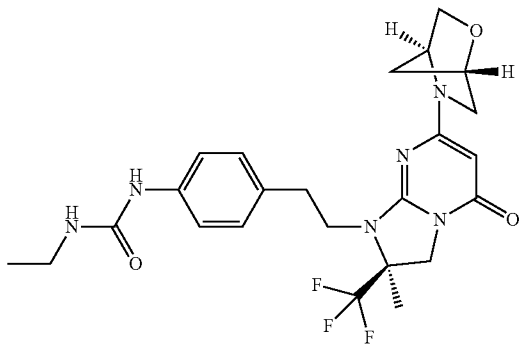 [SMILES: CCNC(=O)Nc1ccc(CCN2c3nc(N4C[C@@H]5C[C@H]4CO5)cc(=O)n3C[C@@]2(C)C(F)(F)F)cc1]

104 μl (1.29 mmol) of ethyl isocyanate are added to a solution of 140 mg (0.32 mmol) of 1-[2-(4-aminophenyl)ethyl]-2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one in 1 mL of dichloromethane. After stirring for 3 hours at room temperature, the solvent is evaporated off. The residue is taken up in ethyl acetate and washed with water and with saturated aqueous NaCl solution. The organic phase is dried over magnesium sulfate and evaporated to dryness. The residue is purified by reverse-phase chromatography (RP18 column) (eluent: 50/50 $H_2O$/MeOH) to give 83 mg of 1-ethyl-3-(4-{2-[(1S,4S)-2-methyl-7-2-oxa-5-azabicyclo[2.2.1]hept-5-yl-5-oxo-2-((S)-trifluoromethyl)-2,3-dihydro-5H-imidazo[1,2-a]pyrimidin-1-yl]ethyl}phenyl)urea, the characteristics of which are as follows:

LC/MS (method A): ESI+ [M+H]+: m/z 507 tr (min)=0.6

$^1$H NMR (600 MHz, δ in ppm, DMSO-$d_6$): 1.08 (t, 3H), 1.55 (s, 3H), 1.88 (m, 2H), 2.82 (m, 1H), 2.97 (m, 1H), 3.12 (m, 2H), 3.19 (m, 1H), 3.39 (d, 1H), 3.43 (m, 1H), 3.58 (m, 1H), 3.7 (d, 1H), 3.78 (d, 1H), 3.82 (d, 1H), 4.12 (d, 1H), 4.58 (s, 1H), 4.64 (s, 1H), 4.82 (bs, 1H), 5.95 (m, 1H), 7.08 (d, 2H), 7.32 (d, 2H), 8.15 (s, 1H).

EXAMPLE 16

(8S)-9-[2-(3,4-dihydro-2H-pyrido[3,2-b][1,4]oxazin-7-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 38)

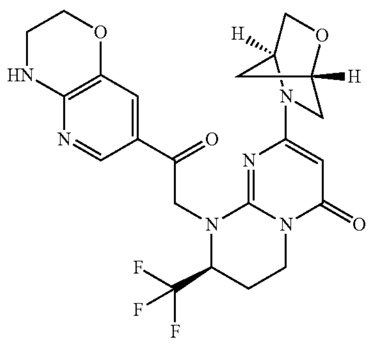 [SMILES: O=C(CN1c2nc(N3C[C@@H]4C[C@H]3CO4)cc(=O)n2CC[C@H]1C(F)(F)F)c1cnc2c(c1)OCCN2]

Step 16.1: 1-(3,4-dihydro-2H-pyrido[3,2-b][1,4]oxazin-7-yl)ethanone

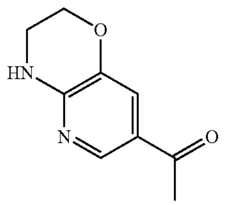

The procedure used is the same as that of step 12.1.

800 mg (3.61 mmol) of 7-bromo-3,4-dihydro-2H-pyrido[3,2-b][1,4]oxazine were used in the reaction. After purification by chromatography on silica gel (eluent: 90/10 DCM/MeOH), 320 mg of 1-(3,4-dihydro-2H-pyrido[3,2-b][1,4]oxazin-7-yl)ethanone were obtained, the characteristics of which are as follows:

LC/MS (method G): ESI+ [M+H]+: m/z 179 tr (min)=0.66

$^1$H NMR (300 MHz, δ in ppm, $CDCl_3$): 2.42 (s, 3H), 3.47 (q, 2H), 4.12 (t, 2H), 7.3 (s, 1H), 7.77 (s, 1H), 8.28 (s, 1H).

Step 16.2: 2-bromo-1-(3,4-dihydro-2H-pyrido[3,2-b][1,4]oxazin-7-yl)ethanone hydrobromide

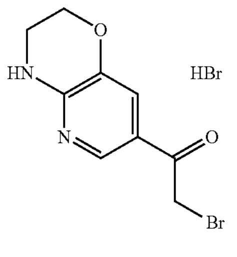 [SMILES: O=C(CBr)c1cnc2c(c1)OCCN2 ; Br]

The procedure used is the same as that of step 12.2.

320 mg (1.80 mmol) of 1-(3,4-dihydro-2H-pyrido[3,2-b][1,4]oxazin-7-yl)ethanone were used in the reaction. After precipitation with ethyl ether and filtration, 690 mg of 2-bromo-1-(3,4-dihydro-2H-pyrido[3,2-b][1,4]oxazin-7-yl) ethanone hydrobromide are obtained, the characteristics of which are as follows:

LC/MS (method G): ESI+ [M+H]+: m/z 257 tr (min)=1.10

$^1$H NMR (300 MHz, δ in ppm, $CDCl_3$): 3.57 (t, 2H), 4.23 (t, 2H), 4.78 (s, 2H), 7.55 (s, 1H), 8.38 (s, 1H), 8.5-9 (bs, 1H).

Step 16.3: (8S)-2-chloro-9-[2-(3,4-dihydro-2H-pyrido[3,2-b][1,4]oxazin-7-yl)-2-oxoethyl]-8-trifluoromethyl-6,7,8,9-tetrahydropyrimido[1,2-a]pyrimidin-4-one

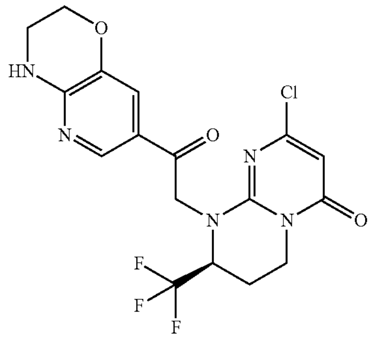 [SMILES: O=C(CN1c2nc(Cl)cc(=O)n2CC[C@H]1C(F)(F)F)c1cnc2c(c1)OCCN2]

The procedure used is the same as that of step 12.3.

200 mg (0.79 mmol) of (8S)-2-chloro-8-trifluoromethyl-6,7,8,9-tetrahydropyrimido[1,2-a]pyrimidin-4-one and 319.86 mg (0.95 mmol) of 2-bromo-1-(3,4-dihydro-2H-pyrido[3,2-b][1,4]oxazin-7-yl)ethanone hydrobromide were used in the reaction. After purification by chromatography on silica gel (eluent: 90/10 DCM/MeOH), 110 mg of (8S)-2-chloro-9-[2-(3,4-dihydro-2H-pyrido[3,2-b][1,4]oxazin-7-yl)-2-oxoethyl]-8-trifluoromethyl-6,7,8,9-tetrahydropyrimido[1,2-a]pyrimidin-4-one are obtained, the characteristics of which are as follows:

LC/MS (method G): ESI+ [M+H]+: m/z 430 tr (min)=1.77

$^1$H NMR (300 MHz, δ in ppm, $CDCl_3$): 2.27 (m, 1H), 2.44 (s, 1H), 3.17 (d, 1H), 3.39 (m, 1H), 3.49 (s, 2H), 4.13 (m, 2H), 4.37 (m, 1H), 4.58-4.77 (m, 2H), 5.48 (d, 1H), 7.36 (s, 1H) 7.97 (s, 1H), 8.38 (s, 1H).

Step 16.4: (8S)-9-[2-(3,4-dihydro-2H-pyrido[3,2-b][1,4]oxazin-7-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

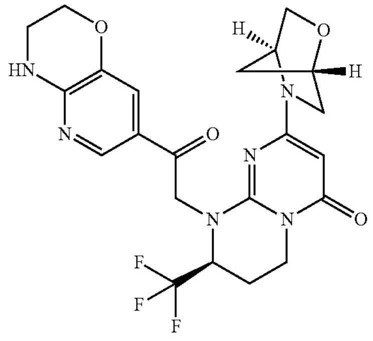 [SMILES: O=C(CN1c2nc(N3C[C@@H]4C[C@H]3CO4)cc(=O)n2CC[C@H]1C(F)(F)F)c1cnc2c(c1)OCCN2]

The procedure used is the same as that of step 12.4.

110 mg (0.25 mmol) of (8S)-2-chloro-9-[2-(3,4-dihydro-2H-pyrido[3,2-b][1,4]oxazin-7-yl)-2-oxoethyl]-8-trifluoromethyl-6,7,8,9-tetrahydropyrimido[1,2-a]pyrimidin-4-one and 41.64 mg (0.31 mmol) of (1S,4S)-2-oxa-5-azabicyclo[2.2.1]heptane hydrochloride were used in the reaction. After purification by passing through an RP18 reverse-phase column (eluent: from 100% $H_2O$ to 100% $CH_3CN$ over 30 minutes), 30 mg of (8S)-9-[2-(3,4-dihydro-2H-pyrido[3,2-b][1,4]oxazin-7-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one are obtained, the characteristics of which are as follows:

LC/MS (method A): ESI+ [M+H]+: m/z 493 tr (min)=0.49

$^1$H NMR (600 MHz, δ in ppm, DMSO-$d_6$): 1.65 (d, 1H), 1.72 (d, 1H), 2.25 (m, 1H), 2.4 (m, 1H), 2.99 (m, 1H), 3.13 (m, 1H), 3.2 (m, 1H), 3.26 (m, 2H), 3.49 (m, 2H), 4.13 (t, 2H) 4.36 (m, 1H), 4.41 (d, 1H), 4.48 (d, 2H) 4.52 (m, 1H), 4.63 (s, 1H), 5.52 (d, 1H), 7.36 (s, 1H), 7.57 (s, 1H), 8.37 (s, 1H).

EXAMPLE 17

(8S)-9-(2-benzo[1,2,3]thiadiazol-5-yl-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 47)

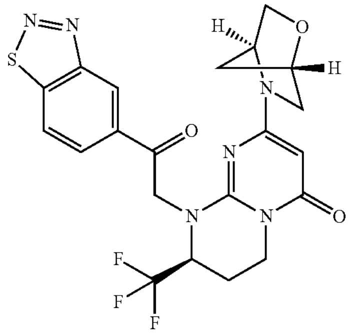 [SMILES: O=C(CN1c2nc(N3C[C@@H]4C[C@H]3CO4)cc(=O)n2CC[C@H]1C(F)(F)F)c1ccc2snnc2c1]

Step 17.1: N-methoxy-N-methylbenzo[1,2,3]thiadiazole-5-carboxamide

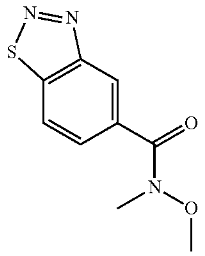

The procedure used is the same as that of step 4.1.

500 mg (2.44 mmol) of benzo[1,2,3]thiadiazole-5-carbonyl chloride are used in the reaction. 620 mg of N-methoxy-N-methylbenzo[1,2,3]thiadiazole-5-carboxamide are obtained, the characteristics of which are as follows:

LC/MS (method G): ESI+ [M+H]+: m/z 224 tr (min)=1.36

$^1$H NMR (300 MHz, δ in ppm, $CDCl_3$): 3.34 (s, 3H), 3.57 (s, 3H), 7.99 (d, 1H), 8.5 (d, 1H), 8.9 (s, 1H).

Step 17.2: 1-benzo[1,2,3]thiadiazol-5-ylethanone

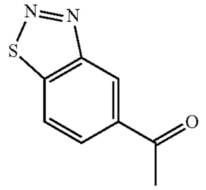

The procedure used is the same as that of step 4.2.

620 mg (2.78 mmol) of N-methoxy-N-methylbenzo[1,2,3]thiadiazole-5-carboxamide were used in the reaction. The mixture is basified with aqueous 1 N NaOH solution and extracted with ethyl acetate. The organic phase is dried over magnesium sulfate and evaporated to dryness to give 430 mg of 1-benzo[1,2,3]thiadiazol-5-ylethanone, corresponding to the following characteristics:

LC/MS (method G): ESI+ [M+H]+: m/z 224 tr (min)=1.49

$^1$H NMR (300 MHz, δ in ppm, $CDCl_3$): 2.78 (s, 3H), 8.29 (d, 1H), 8.53 (d, 1H), 9.32 (s, 1H).

Step 17.3: 1-benzo[1,2,3]thiadiazol-5-yl-2-bromoethanone

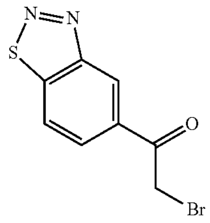 [SMILES: O=C(CBr)c1ccc2snnc2c1]

The procedure used is the same as that of step 12.2.

430 mg (2.41 mmol) of 1-benzo[1,2,3]thiadiazol-5-ylethanone were used in the reaction. The reaction mixture is evaporated to dryness and taken up in dichloromethane. The organic phase is washed with aqueous $NaHCO_3$ solution and with saturated NaCl solution, dried and evaporated to dryness to give 300 mg of 1-benzo[1,2,3]thiadiazol-5-yl-2-bromoethanone, corresponding to the following characteristics:

LC/MS (method G): ESI+ [M+H]+: m/z 257 tr (min)=1.71

$^1$H NMR (300 MHz, δ in ppm, $CDCl_3$): 5.19 (s, 2H), 8.31 (d, 1H), 8.57 (d, 1H), 9.43 (s, 1H).

Step 17.4: (8S)-9-(2-benzo[1,2,3]thiadiazol-5-yl-2-oxoethyl)-2-chloro-8-trifluoromethyl-6,7,8,9-tetrahydropyrimido[1,2-a]pyrimidin-4-one

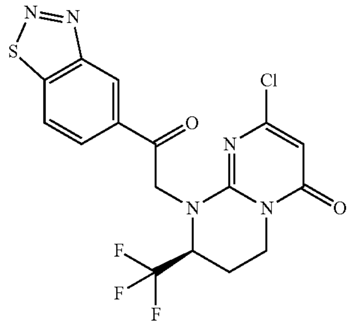 [SMILES: O=C(CN1c2nc(Cl)cc(=O)n2CC[C@H]1C(F)(F)F)c1ccc2snnc2c1]

The procedure used is the same as that of step 12.3.

150 mg (0.59 mmol) of (8S)-2-chloro-8-trifluoromethyl-6,7,8,9-tetrahydropyrimido[1,2-a]pyrimidin-4-one and 167.25 mg (0.65 mmol) of 1-benzo[1,2,3]thiadiazol-5-yl-2-bromoethanone were used in the reaction. After purification by chromatography on silica gel (eluent: 90/10 DCM/MeOH), 210 mg of (8S)-9-(2-benzo[1,2,3]thiadiazol-5-yl-2-oxoethyl)-2-chloro-8-trifluoromethyl-6,7,8,9-tetrahydropyrimido[1,2-a]pyrimidin-4-one are obtained, the characteristics of which are as follows:

LC/MS (method G): ESI+ [M+H]+: m/z 430 tr (min)=2.29

$^1$H NMR (300 MHz, δ in ppm, $CDCl_3$): 2.32 (m, 1H), 2.42-2.62 (m, 2H), 3.36-3.48 (m, 1H), 4.42 (m, 1H), 4.8 (m, 1H), 5.14 (d, 1H), 5.76 (m, 1H), 8.35 (d, 1H), 8.61 (d, 1H), 9.51 (s, 1H).

Step 17.5: (8S)-9-(2-benzo[1,2,3]thiadiazol-5-yl-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one

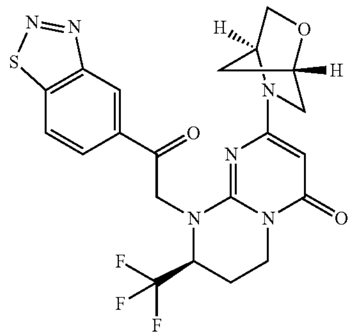 [SMILES: O=C(CN1c2nc(N3C[C@@H]4C[C@H]3CO4)cc(=O)n2CC[C@H]1C(F)(F)F)c1ccc2snnc2c1]

The procedure used is the same as that of step 12.4.

210 mg (0.49 mmol) of (8S)-9-(2-benzo[1,2,3]thiadiazol-5-yl-2-oxoethyl)-2-chloro-8-trifluoromethyl-6,7,8,9-tetrahydropyrimido[1,2-a]pyrimidin-4-one and 79.50 mg (0.58 mmol) of (1S,4S)-2-oxa-5-azabicyclo[2.2.1]heptane hydrochloride were used in the reaction. After purification by chromatography on silica gel (eluent: 60/40 DCM/MeOH), 100 mg of (8S)-9-(2-benzo[1,2,3]thiadiazol-5-yl-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one are obtained, the characteristics of which are as follows:

LC/MS (method A): ESI+ [M+H]+: m/z 493 tr (min)=0.64

$^1$H NMR (600 MHz, δ in ppm, DMSO-$d_6$): 1.36-1.78 (bs, 2H), 2.27 (m, 1H), 2.45-2.5 (m, 2H), 2.75-3.25 (bs, 4H), 4.23-4.98 (bs, 6H), 5.9 (m, 1H), 8.34 (d, 1H), 8.58 (d, 1H), 9.5 (s, 1H).

EXAMPLE 18

(8S)-9-(1-methyl-1H-indazol-3-ylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 51)

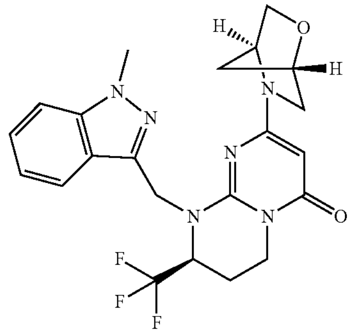 [SMILES: Cn1nc(CN2c3nc(N4C[C@@H]5C[C@H]4CO5)cc(=O)n3CC[C@H]2C(F)(F)F)c2ccccc21]

Step 18.1: (8S)-2-chloro-9-(1-methyl-1H-indazol-3-ylmethyl)-8-trifluoromethyl-6,7,8,9-tetrahydropyrimido[1,2-a]pyrimidin-4-one

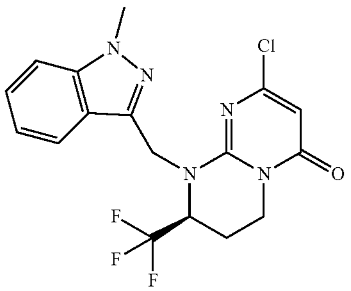 [SMILES: Cn1nc(CN2c3nc(Cl)cc(=O)n3CC[C@H]2C(F)(F)F)c2ccccc21]

The procedure used is the same as that of step 12.3.

180 mg (0.71 mmol) of (8S)-2-chloro-8-trifluoromethyl-6,7,8,9-tetrahydropyrimido[1,2-a]pyrimidin-4-one and 145.39 mg (0.78 mmol) of 3-chloromethyl-1-methyl-1H-indazole were used in the reaction. After purification by chromatography on silica gel (eluent: 80/20 DCM/MeOH), 250 mg of (8S)-2-chloro-9-(1-methyl-1H-indazol-3-ylmethyl)-8-trifluoromethyl-6,7,8,9-tetrahydropyrimido[1,2-a]pyrimidin-4-one are obtained, the characteristics of which are as follows:

LC/MS (method G): ESI+ [M+H]+: m/z 398 tr (min)=2.2

$^1$H NMR (300 MHz, δ in ppm, $CDCl_3$): 2.01 (m, 1H), 2.44 (m, 1H), 3.24-3.41 (m, 2H), 4.02 (s, 3H), 4.23 (m, 1H), 4.66 (d, 1H), 4.75 (m, 1H), 5.89 (d, 1H), 7.15 (t, 1H), 7.42 (t, 1H), 7.62 (d, 1H), 7.84 (d, 1H).

Step 18.2: (8S)-9-(1-methyl-1H-indazol-3-ylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one

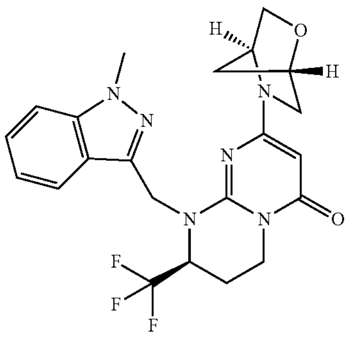 [SMILES: Cn1nc(CN2c3nc(N4C[C@@H]5C[C@H]4CO5)cc(=O)n3CC[C@H]2C(F)(F)F)c2ccccc21]

The procedure used is the same as that of step 12.4.

250 mg (0.63 mmol) of (8S)-2-chloro-9-(1-methyl-1H-indazol-3-ylmethyl)-8-trifluoromethyl-6,7,8,9-tetrahydropyrimido[1,2-a]pyrimidin-4-one and 102.26 mg (0.75 mmol) of (1S,4S)-2-oxa-5-azabicyclo[2.2.1]heptane hydrochloride were used in the reaction. After purification by chromatography on silica gel (eluent: 60/40 DCM/MeOH), 230 mg of (8S)-9-(1-methyl-1H-indazol-3-ylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one are obtained, the characteristics of which are as follows:

LC/MS (method A): ESI+ [M+H]+: m/z 461 tr (min)=0.68

$^1$H NMR (600 MHz, δ in ppm, DMSO-$d_6$): 1.75 (m, 2H), 2.08 (m, 1H), 2.4 (d, 1H), 2.6-3.3 (bs, 5H), 3.99 (s, 3H), 4.2 (m, 1H), 4.4-4.67 (t, 3H), 4.66-4.9 (bs, 2H), 5.89 (d, 1H), 7.11 (t, 1H), 7.39 (t, 1H), 7.58 (d, 1H), 7.73 (d, 1H).

EXAMPLE 19

(8S)-9-[2-(2-Cyclopropylmethoxypyrimidin-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 52)

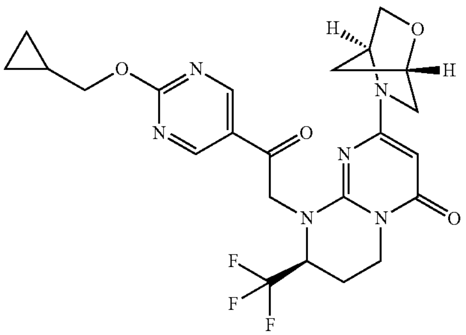 [SMILES: O=C(CN1c2nc(N3C[C@@H]4C[C@H]3CO4)cc(=O)n2CC[C@H]1C(F)(F)F)c1cnc(OCC2CC2)nc1]

Step 19.1: 5-bromo-2-cyclopropylmethoxypyrimidine

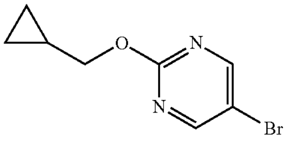 [SMILES: Brc1cnc(OCC2CC2)nc1]

A suspension of 607.92 mg (15.20 mmol) of sodium hydride in 50 mL of THF is prepared under argon. A solution of 1.10 g (15.20 mmol) of cyclopropanemethanol in 5 mL of THF is added dropwise. The mixture is stirred for 50 minutes at room temperature. 1 g (5.07 mmol) of 5-bromo-2-chloropyrimidine in 5 mL of THF is then added. The mixture is stirred at room temperature overnight. The reaction mixture is taken up in water and extracted with ethyl acetate. The organic phase is washed with aqueous $NaHCO_3$ solution and with saturated aqueous NaCl solution, dried and evaporated to dryness to give 1.10 g of 5-bromo-2-cyclopropylmethoxypyrimidine, corresponding to the following characteristics:

LC/MS (method G): ESI+ [M+H]+: m/z 229 tr (min)=2.06

$^1$H NMR (300 MHz, δ in ppm, $CDCl_3$): 0.33 (m, 2H), 0.55 (m, 2H), 1.23 (m, 1H), 4.12 (d, 2H), 8.74 (s, 2H).

Step 19.2: 2-cyclopropylmethoxy-5-(1-ethoxyvinyl)pyrimidine

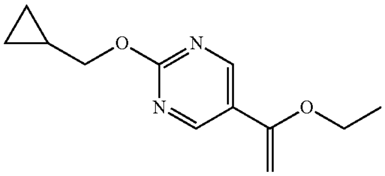 [SMILES: C=C(OCC)c1cnc(OCC2CC2)nc1]

The following are successively introduced into a microwave tube:

760 mg (3.32 mmol) of 5-bromo-2-cyclopropylmethoxypyrimidine in 15 mL of dioxane, 1.36 mL (3.82 mmol) of tributyl(1-ethoxyvinyl)tin, 58.22 mg (0.08 mmol) of bis (triphenylphosphine)palladium(II) chloride, 1.12 g (7.30 mmol) of cesium fluoride. This mixture is subjected to microwave irradiation at 110° C. for 1 hour. The reaction mixture is evaporated to dryness and the residue is taken up in 100 mL of ethyl ether. A solution of 2.80 g of cesium fluoride in 10 mL of water is added. After stirring for 1 hour at room temperature, the mixture is filtered through Celite. The filtrate is washed with aqueous $NaHCO_3$ solution and then with saturated NaCl solution. The organic phase is dried over magnesium sulfate and evaporated to dryness. The residue is purified by chromatography on silica gel (eluent: 10/90 EtOAc/heptane) to give 480 mg of 2-cyclopropylmethoxy-5-(1-ethoxyvinyl)pyrimidine, the characteristics of which are as follows:

LC/MS (method G): ESI+ [M+H]+: m/z 221 tr (min)=2.34

$^1$H NMR (300 MHz, δ in ppm, $CDCl_3$): 0.35 (m, 2H), 0.57 (m, 2H), 0.86 (m, 1H), 1.34 (t, 3H), 3.91 (q, 2H), 4.16 (d, 2H), 4.35 (s, 1H), 4.85 (s, 1H), 8.78 (s, 2H).

Step 19.3: 2-bromo-1-(2-cyclopropylmethoxypyrimidin-5-yl)ethanone

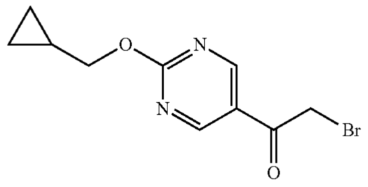 [SMILES: O=C(CBr)c1cnc(OCC2CC2)nc1]

A solution of 480 mg (2.18 mmol) of 2-cyclopropylmethoxy-5-(1-ethoxyvinyl)pyrimidine in 8 mL of a THF/$H_2O$ mixture: (6/2: v/v) is cooled to 0° C. under argon. After addition of 380.02 mg (2.11 mmol) of N-bromosuccinimide, the reaction mixture is maintained at 0° C. for 1 hour. The solution obtained is taken up in ethyl acetate and washed with aqueous $NaHCO_3$ solution and then with saturated NaCl solution. The organic phase is dried over magnesium sulfate and evaporated to dryness. The residue is purified by chromatography on silica gel (eluent: 80/20 DCM/MeOH) to give 410 mg of 2-bromo-1-(2-cyclopropylmethoxypyrimidin-5-yl) ethanone, the characteristics of which are as follows:

LC/MS (method G): ESI+ [M+H]+: m/z 271 tr (min)=1.87

$^1$H NMR (300 MHz, δ in ppm, $CDCl_3$): 0.38 (m, 2H), 0.58 (m, 2H), 1.29 (m, 1H), 4.27 (d, 2H), 4.94 (s, 2H), 9.15 (s, 2H).

Step 19.4: (8S)-2-chloro-9-[2-(2-cyclopropylmethoxypyrimidin-5-yl)-2-oxoethyl]-8-trifluoromethyl-6,7,8,9-tetrahydropyrimido[1,2-a]pyrimidin-4-one

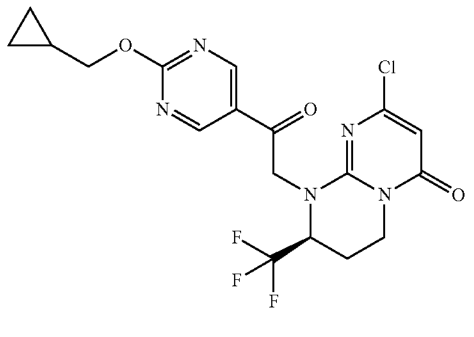 [SMILES: O=C(CN1c2nc(Cl)cc(=O)n2CC[C@H]1C(F)(F)F)c1cnc(OCC2CC2)nc1]

The procedure used is the same as that of step 12.3.

180 mg (0.71 mmol) of (8S)-2-chloro-8-trifluoromethyl-6,7,8,9-tetrahydropyrimido[1,2-a]pyrimidin-4-one and 211.66 mg (0.78 mmol) of 2-bromo-1-(2-cyclopropylmethoxypyrimidin-5-yl)ethanone were used in the reaction. After purification by chromatography on silica gel (eluent: 80/20 DCM/MeOH), 160 mg of (8S)-2-chloro-9-[2-(2-cyclopropylmethoxypyrimidin-5-yl)-2-oxoethyl]-8-trifluoromethyl-6,7,8,9-tetrahydropyrimido[1,2-a]pyrimidin-4-one are obtained, the characteristics of which are as follows:

LC/MS (method G): ESI+ [M+H]+: m/z 444 tr (min)=2.33

$^1$H NMR (300 MHz, δ in ppm, $CDCl_3$): 0.38 (m, 2H), 0.58 (m, 2H), 1.30 (m, 1H), 2.25 (m, 1H), 2.51 (m, 1H), 3.35 (m, 2H), 4.28 (d, 2H), 4.50 (m, 1H), 4.70 (m, 1H), 4.90 (d, 1H), 5.53 (d, 1H), 9.21 (s, 2H).

Step 19.5: (8S)-9-[2-(2-cyclopropylmethoxypyrimidin-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

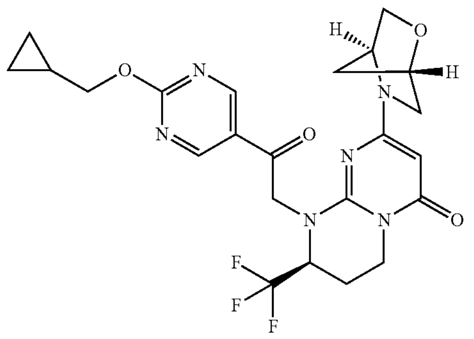 [SMILES: O=C(CN1c2nc(N3C[C@@H]4C[C@H]3CO4)cc(=O)n2CC[C@H]1C(F)(F)F)c1cnc(OCC2CC2)nc1]

The procedure used is the same as that of step 12.4.

160 mg (0.36 mmol) of (8S)-2-chloro-9-[2-(2-cyclopropylmethoxypyrimidin-5-yl)-2-oxoethyl]-8-trifluoromethyl-6,7,8,9-tetrahydropyrimido[1,2-a]pyrimidin-4-one and 58.66 mg (0.43 mmol) of (1S,4S)-2-oxa-5-azabicyclo[2.2.1]heptane hydrochloride were used in the reaction. After purification by chromatography on silica gel (eluent: 60/40 DCM/MeOH), 125 mg of (8S)-9-[2-(2-cyclopropylmethoxypyrimidin-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one are obtained, the characteristics of which are as follows:

LC/MS (method A): ESI+ [M+H]+: m/z 507 tr (min)=0.65

$^1$H NMR spectrum (600 MHz, δ in ppm, DMSO-$d_6$): 0.38 (m, 2H), 0.6 (m, 2H), 1.30 (m, 1H), 1.54-1.76 (m, 2H), 2.21 (m, 1H), 2.44 (m, 1H), 2.72-3.9 (bs, 5H), 4.28 (d, 2H), 4.31-4.98 (m, 6H), 5.67 (m, 1H), 9.22 (s, 2H).

EXAMPLE 20

(8S)-9-[2-(2-methyl-2H-pyrazol-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 69)

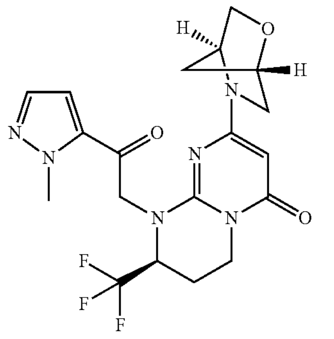 [SMILES: Cn1nccc1C(=O)CN1c2nc(N3C[C@@H]4C[C@H]3CO4)cc(=O)n2CC[C@H]1C(F)(F)F]

Step 20.1: 2-methyl-2H-pyrazole-3-carbonyl chloride

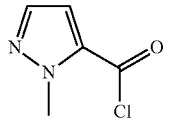

A suspension of 800 mg (6.03 mmol) of 2-methyl-2H-pyrazole-3-carboxylic acid in 30 mL of DCM is placed under argon and cooled to 0° C. When the temperature is reached, 1.32 mL (15.07 mmol) of oxalyl chloride and a catalytic amount of DMF are added. The reaction mixture is stirred at room temperature for 2 hours and then evaporated to dryness and the residue is taken up in DCM and evaporated again to give 850 mg of 2-methyl-2H-pyrazole-3-carbonyl chloride, the characteristics of which are as follows:

$^1$H NMR (300 MHz, δ in ppm, $CDCl_3$): 4.10 (s, 3H), 6.82 (s, 1H), 7.50 (s, 1H).

Step 20.2: N-methoxy-N-methyl-2-methyl-2H-pyrazole-3-carboxamide

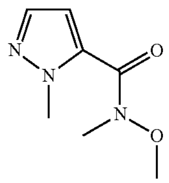

The procedure used is the same as that of step 4.1.

850 mg (5.88 mmol) of 2-methyl-2H-pyrazole-3-carbonyl chloride are used in the reaction. 890 mg of N-methoxy-N-methylbenzo[1,2,3]thiadiazole-5-carboxamide are obtained, the characteristics of which are as follows:

LC/MS (method G): ESI+ [M+H]+: m/z 170 tr (min)=1.03

$^1$H NMR (300 MHz, δ in ppm, $CDCl_3$): 3.27 (s, 3H), 3.63 (s, 3H), 3.96 (s, 3H), 6.71 (s, 1H), 7.5 (s, 1H).

Step 20.3: 1-(2-methyl-2H-pyrazol-3-yl)ethanone

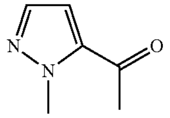

The procedure used is the same as that of step 4.2.

890 mg (2.78 mmol) of N-methoxy-N-methylbenzo[1,2,3]thiadiazole-5-carboxamide were used in the reaction. The mixture is taken up in water and a few drops of 1 N HCl, basified with aqueous 1 N NaOH solution and extracted with ethyl acetate. The organic phase is dried over magnesium sulfate and evaporated to dryness to give 570 mg of 1-(2-methyl-2H-pyrazol-3-yl)ethanone, corresponding to the following characteristics:

LC/MS (method G): ESI+ [M+H]+: m/z 125 tr (min)=0.93

$^1$H NMR (300 MHz, δ in ppm, $CDCl_3$): 2.5 (s, 3H) 4.04 (s, 3H) 7.13 (s, 1H) 7.53 (s, 1H)

Step 20.4: 1-(2-methyl-2H-pyrazol-3-yl)ethanone hydrobromide

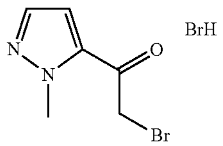

The procedure used is the same as that of step 12.2.

550 mg (4.43 mmol) of 1-(2-methyl-2H-pyrazol-3-yl)ethanone were used in the reaction. The precipitate corresponding to 1-(2-methyl-2H-pyrazol-3-yl)ethanone hydrobromide is filtered off, washed with ethyl ether and dried. The 1.15 g of product obtained have the following characteristics:

LC/MS (method G): ESI+ [M+H]+: m/z 203 tr (min)=1.19

$^1$H NMR (300 MHz, δ in ppm, $CDCl_3$): 4.78 (s, 2H), 7.19 (s, 1H), 7.56 (s, 1H).

Step 20.5: (8S)-2-chloro-9-[2-(2-methyl-2H-pyrazol-3-yl)-2-oxoethyl]-8-trifluoromethyl-6,7,8,9-tetrahyhdropyrimido[1,2-a]pyrimidin-4-one

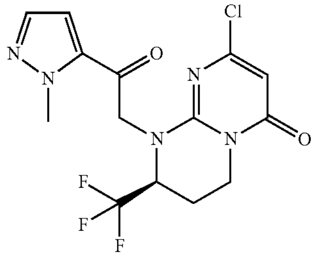 [SMILES: Cn1nccc1C(=O)CN1c2nc(Cl)cc(=O)n2CC[C@H]1C(F)(F)F]

The procedure used is the same as that of step 12.3.

180 mg (0.71 mmol) of (8S)-2-chloro-8-trifluoromethyl-6,7,8,9-tetrahydropyrimido[1,2-a]pyrimidin-4-one and 262 mg (0.92 mmol) of 1-(2-methyl-2H-pyrazol-3-yl)ethanone hydrobromide were used in the reaction. After purification by chromatography on silica gel (eluent: 80/20 DCM/MeOH), 230 mg of (8S)-2-chloro-9-[2-(2-methyl-2H-pyrazol-3-yl)-2-oxoethyl]-8-trifluoromethyl-6,7,8,9-tetrahydropyrimido[1,2-a]pyrimidin-4-one are obtained, the characteristics of which are as follows:

LC/MS (method G): ESI+ [M+H]+: m/z 376 tr (min)=1.98

$^1$H NMR (300 MHz, δ in ppm, $CDCl_3$): 2.28 (m, 1H), 3.4 (m, 2H), 4.06 (s, 3H), 4.39 (m, 1H), 4.66-4.84 (m, 2H), 5.41 (d, 1H), 5.96 (s, 1H), 7.36 (s, 1H), 7.63 (s, 1H).

Step 20.6: (8S)-9-[2-(2-methyl-2H-pyrazol-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

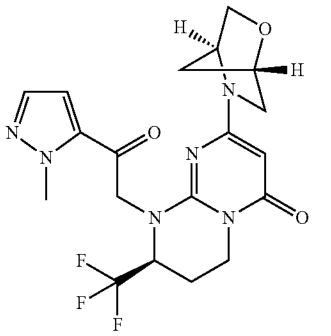 [SMILES: Cn1nccc1C(=O)CN1c2nc(N3C[C@@H]4C[C@H]3CO4)cc(=O)n2CC[C@H]1C(F)(F)F]

The procedure used is the same as that of step 12.4.

230 mg (0.61 mmol) of (8S)-2-chloro-9-[2-(2-methyl-2H-pyrazol-3-yl)-2-oxoethyl]-8-trifluoromethyl-6,7,8,9-tetrahydropyrimido[1,2-a]pyrimidin-4-one and 107.90 mg (0.79 mmol) of (1S,4S)-2-oxa-5-azabicyclo[2.2.1]heptane hydrochloride were used in the reaction. After purification by chromatography on silica gel (eluent: 60/40 DCM/MeOH), 160 mg of (8S)-9-[2-(2-methyl-2H-pyrazol-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one are obtained, the characteristics of which are as follows:

LC/MS (method A): ESI+ [M+H]+: m/z 439 tr (min)=0.54

$^1$H NMR (600 MHz, δ in ppm, DMSO-$d_6$): 1.48-1.8 (bs, 2H), 2.22 (m, 1H), 2.43 (d, 1H), 2.66-3.26 (bs, 5H), 4 (s, 3H), 4.28-4.88 (bs, 6H), 5.5 (d, 1H), 7.42 (s, 1H), 7.59 (s, 1H).

EXAMPLE 21 ethyl {5-[2-((S)8-(1S,4S)-2-oxa-5-azabicyclo[2.2.]hept-5-yl-6-oxo-2-trifluoromethyl-3,4-dihydro-2H,6H-pyrimido[1,2-a]pyrimidin-1-yl)acetyl]pyrid-2-yl}carbamate (Compound 57

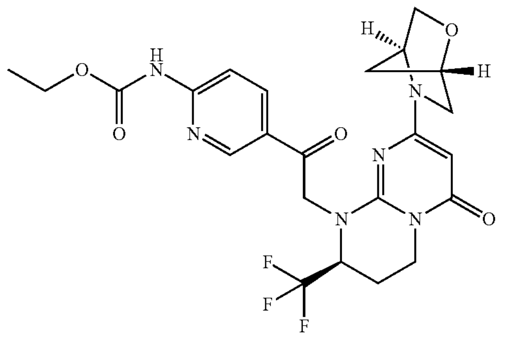 [SMILES: CCOC(=O)Nc1ccc(C(=O)CN2c3nc(N4C[C@@H]5C[C@H]4CO5)cc(=O)n3CC[C@H]2C(F)(F)F)cn1]

Step 21.1: 1-(6-aminopyrid-3-yl)ethanone

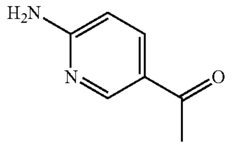

2 g (11.57 mmol) of 1-(6-chloropyrid-3-yl)ethanone and 70 mL of ammonium hydroxide are placed in a Parr reactor. The solution is heated at 130° C. overnight. The mixture obtained is evaporated to dryness, and the residue is taken up in ethyl acetate and washed with water and with saturated NaCl solution. The organic phase is dried over sodium sulfate and evaporated to dryness to give 1.14 g of 1-(6-aminopyrid-3-yl)ethanone, the characteristics of which are as follows:

LC/MS (method G): ESI+ [M+H]+: m/z 137 tr (min)=0.35

$^1$H NMR (300 MHz, δ in ppm, $CDCl_3$): 2.41 (s, 3H), 6.45 (d, 1H), 6.88 (s, 2H), 7.86 (d, 1H), 8.58 (s, 1H).

Step 21.2: 2-bromo-1-(6-aminopyrid-3-yl)ethanone

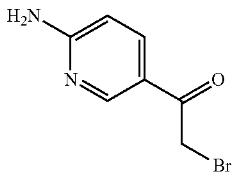 [SMILES: Nc1ccc(C(=O)CBr)cn1]

The procedure used is the same as that of step 12.2.

1.14 g (8.37 mmol) of 1-(6-aminopyrid-3-yl)ethanone were used in the reaction. The reaction mixture is taken up in dichloromethane. The organic phase is washed with aqueous $K_2CO_3$ solution and with saturated NaCl solution, dried and evaporated to dryness. After purification by chromatography on silica gel (eluent: 60/40 DCM/EtOAc), 530 mg of 2-bromo-1-(6-chloropyrid-3-yl)ethanone are obtained, the characteristics of which are as follows:

LC/MS (method G): ESI+ [M+H]+: m/z 215 tr (min)=0.44

$^1$H NMR (300 MHz, δ in ppm, $CDCl_3$): 4.70 (s, 2H), 6.47 (d, 1H), 7.08 (s, 2H), 7.89 (d, 1H), 8.64 (s, 1H).

Step 21.3: (8S)-9-[2-(6-aminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

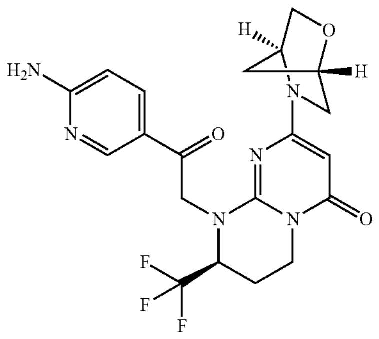 [SMILES: Nc1ccc(C(=O)CN2c3nc(N4C[C@@H]5C[C@H]4CO5)cc(=O)n3CC[C@H]2C(F)(F)F)cn1]

500 mg (1.58 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one in 10 mL of DMF are added to a suspension of 69.55 mg (1.74 mmol) of sodium hydride in 10 mL of DMF. The reaction mixture is placed under magnetic stirring at room temperature for 15 minutes. A solution of 373.96 mg (1.74 mmol) of 2-bromo-1-(6-chloropyrid-3-yl)ethanone in 5 mL of DMF is added dropwise to the reaction medium. The reaction is stirred at room temperature for 2 hours. The reaction medium is taken up in methanol and evaporated to dryness. The residue is purified by chromatography on silica gel (eluent: 60/40 EtOAc/MeOH) to give 530 mg of (8S)-9-[2-(6-aminopyrid-3-yl)-2-oxoethyl]-2-(1S, 4S)-2-oxa-5-azabicyclo[2.2.1]hept-5-yl-8-trifluoromethyl-6,7,8,9-tetrahydropyrimido[1,2-a]pyrimidin-4-one, the characteristics of which are as follows:

LC/MS (method A): ESI+ [M+H]+: m/z 451 tr (min)=0.38

$^1$H NMR (600 MHz, δ in ppm, $CDCl_3$): 1.5-1.81 (m, 2H), 2.23 (m, 1H), 2.41 (m, 1H), 2.74-3.33 (bs, 5H), 4.23-4.76 (m, 6H), 5.6 (d, 1H), 6.47 (d, 1H), 6.97 (s, 2H), 7.92 (d, 1H) 8.71 (s, 1H).

Step 21.4: ethyl {5-[2-((S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl) acetyl]pyrid-2-yl}carbamate

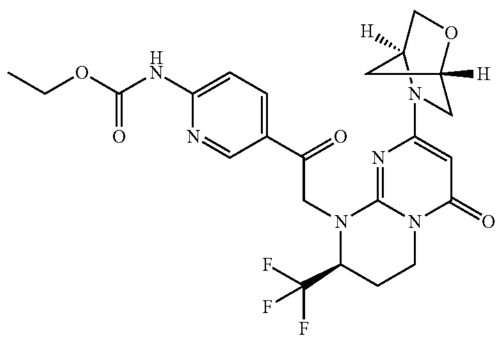 [SMILES: CCOC(=O)Nc1ccc(C(=O)CN2c3nc(N4C[C@@H]5C[C@H]4CO5)cc(=O)n3CC[C@H]2C(F)(F)F)cn1]

168 μl (1 mmol) of N,N-diisopropylethylamine and 65 μl (0.66 mmol) of ethyl chloroformate are added to a solution of 150 mg (0.33 mmol) of (8S)-9-[2-(6-aminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one in 5 mL of DCM.

The heterogeneous mixture is stirred at room temperature for 15 minutes. The solution is taken up in DCM and washed with water and with saturated NaCl solution. The organic phase is dried over sodium sulfate and evaporated to dryness. The residue is dissolved in 10 mL of ethanol, and aqueous 1 N NaOH solution is added. The mixture is stirred for 30 minutes at room temperature and then evaporated to dryness. The crude product is taken up in ethyl acetate and washed with water and with saturated NaCl solution. The organic phase is dried over sodium sulfate and evaporated to dryness. After purification by chromatography on silica gel (eluent: 60/40 DCM/MeOH), 120 mg of ethyl {5-[2-((S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)acetyl]pyrid-2-yl}carbamate are obtained, the characteristics of which are as follows:

LC/MS (method A): ESI+ [M+H]+: m/z 523 tr (min)=0.6

$^1$H NMR (600 MHz, δ in ppm, DMSO-$d_6$): 1.27 (t, 3H), 1.61 (s, 1H), 1.7 (d, 1H), 2.24 (m, 1H), 2.44 (d, 1H), 2.57-3.17 (bs, 3H), 3.24 (m, 2H), 4.2 (q, 2H), 4.29-4.52 (m, 3H), 4.59 (m, 3H), 5.69 (d, 1H), 7.98 (d, 1H), 8.36 (d, 1H), 8.97 (s, 1H), 10.62 (s, 1H).

EXAMPLE 22

(8S)-2-(8-oxa-3-azabicyclo[3.2.1]oct-3-yl)-9-(3-phenylpropyl)-8-trifluoromethyl-6,7,8,9-tetrahydro-pyrimido[1,2-a]pyrimidin-4-one (Compound 84)

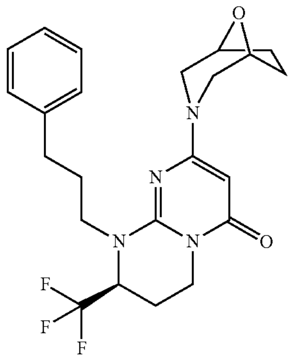 [SMILES: O=c1cc(N2CC3CCC(C2)O3)nc2n1CC[C@@H](C(F)(F)F)N2CCCc1ccccc1]

Step 22.1: (8S)-2-(8-oxa-3-azabicyclo[3.2.1]oct-3-yl)-8-trifluoromethyl-6,7,8,9-tetrahydropyrimido[1,2-a]pyrimidin-4-one

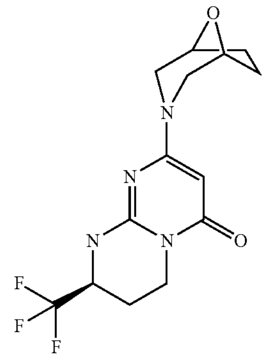 [SMILES: O=c1cc(N2CC3CCC(C2)O3)nc2n1CC[C@@H](C(F)(F)F)N2]

500 mg (1.97 mmol) of (8S)-2-chloro-8-trifluoromethyl-6,7,8,9-tetrahydropyrimido[1,2-a]pyrimidin-4-one, 884 mg (5.91 mmol) of 8-oxa-3-azabicyclo[3.2.1]octane and 820 μl (5.91 mmol) of triethylamine are placed in a microwave tube. The mixture is irradiated for 10 minutes at 150° C. The reaction medium is purified directly by passing through an RP18 reverse-phase column (eluent: $H_2O$: 100% to $CH_3CN$: 100%) to give 600 mg of (8S)-2-(8-oxa-3-azabicyclo[3.2.1]oct-3-yl)-8-trifluoromethyl-6,7,8,9-tetrahydropyrimido[1,2-a]pyrimidin-4-one, the characteristics of which are as follows:

LC/MS (method A): ESI+ [M+H]+: m/z 331 tr (min)=0.53

$^1$H NMR (600 MHz, δ in ppm, DMSO-$d_6$): 1.66 (m, 2H), 1.81 (m, 2H), 2.09 (m, 1H), 2.2 (m, 1H), 2.89 (d, 2H), 3.34 (m, 1H), 3.75 (m, 2H), 4.14 (m, 1H), 4.26 (s, 1H), 4.37 (s, 2H), 4.84 (s, 1H), 8.17 (s, 1H).

Step 22.2: (8S)-2-(8-oxa-3-azabicyclo[3.2.1]oct-3-yl)-9-(3-phenylpropyl)-8-trifluoromethyl-6,7,8,9-tetrahydropyrimido[1,2-a]pyrimidin-4-one

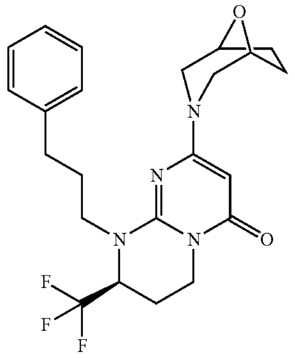 [SMILES: O=c1cc(N2CC3CCC(C2)O3)nc2n1CC[C@@H](C(F)(F)F)N2CCCc1ccccc1]

A solution of 200 mg (0.61 mmol) of (8S)-2-(8-oxa-3-azabicyclo[3.2.1]oct-3-yl)-8-trifluoromethyl-6,7,8,9-tetrahydropyrimido[1,2-a]pyrimidin-4-one and 790 mg (2.42 mmol) of cesium carbonate in 10 mL of DMF is heated at 90° C. for 10 minutes. After addition of 600 µl (1.21 mmol) of (3-bromopropyl)benzene, the reaction is continued for 2 hours at 90° C. The solvent is evaporated off. The residue is purified by RP18 reverse-phase chromatography (eluent: $H_2O$ 100% to $CH_3CN$ 100%) to give 100 mg of (8S)-2-(8-oxa-3-azabicyclo[3.2.1]oct-3-yl)-9-(3-phenylpropyl)-8-trifluoromethyl-6,7,8,9-tetrahydropyrimido[1,2-a]pyrimidin-4-one, the characteristics of which are as follows:

LC/MS (method B): ESI+ [M+H]+: m/z 449 tr (min)=0.85

$^1$H NMR (600 MHz, δ in ppm, DMSO-$d_6$): 1.57 (m, 2H), 1.79 (m, 3H), 2 (m, 2H), 2.31 (d, 1H), 2.62 (m, 2H), 2.8 (d, 2H), 3.13 (m, 2H), 3.53 (m, 2H), 3.94 (m, 1H), 4.15 (m, 1H), 4.31 (s, 2H), 4.62 (m, 1H), 4.82 (s, 1H), 7.18 (m, 3H), 7.27 (m, 2H).

EXAMPLE 23

(8S)-2-(8-oxa-3-azabicyclo[3.2.1]oct-3-yl)-9-(2-oxo-2-pyrid-4-ylethyl)-8-trifluoromethyl-6,7,8,9-tetrahydropyrimido[1,2-a]pyrimidin-4-one (Compound 75)

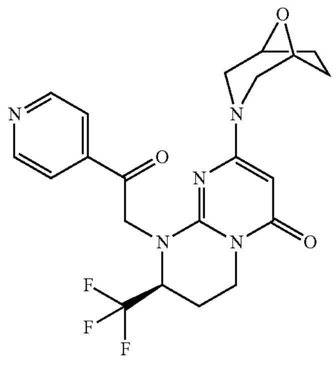 [SMILES: O=C(CN1c2nc(N3CC4CCC(C3)O4)cc(=O)n2CC[C@H]1C(F)(F)F)c1ccncc1]

A solution of 200 mg (0.61 mmol) of (8S)-2-(8-oxa-3-azabicyclo[3.2.1]oct-3-yl)-8-trifluoromethyl-6,7,8,9-tetrahydropyrimido[1,2-a]pyrimidin-4-one and 1.18 g (3.63 mmol) of cesium carbonate in 10 mL of DMF is heated at 90° C. for 10 minutes. The mixture is cooled to 0° C. and 340 mg (1.21 mmol) of 2-bromo-1-pyrid-4-ylethanone are then added. The reaction is continued for 2 hours at room temperature. The solvent is evaporated off. The residue is purified by chromatography on a column of silica (eluent: 90/10 DCM/MeOH). The isolated fraction is recrystallized from acetonitrile to give 16 mg of (8S)-2-(8-oxa-3-azabicyclo[3.2.1]oct-3-yl)-9-(2-oxo-2-pyrid-4-ylethyl)-8-trifluoromethyl-6,7,8,9-tetrahydropyrimido[1,2-a]pyrimidin-4-one, the characteristics of which are as follows:

LC/MS (method B): ESI+ [M+H]+: m/z 450 tr (min)=0.55

$^1$H NMR (600 MHz, δ in ppm, DMSO-$d_6$): 1.32 (m, 1H) 1.5 (m, 1H) 1.62 (m, 2H) 2.2 (m, 1H) 2.42 (d, 1H) 2.51 (d, 1H) 2.69 (d, 1H) 3.2 (m, 1H) 3.38 (d, 2H) 4.05 (d, 2H) 4.31 (d, 1H) 4.61 (m, 1H) 4.85 (s, 2H) 5.45 (d, 1H) 7.89 (s, 2H) 8.85 (s, 2H)

EXAMPLE 24

(8S)-9-((S)-2-hydroxy-2-phenylethyl)-2-(8-oxa-3-azabicyclo[3.2.1]oct-3-yl)-8-trifluoromethyl-6,7,8,9-tetrahydropyrimido[1,2-a]pyrimidin-4-one (Compound 80)

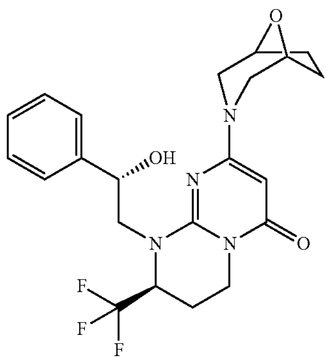 [SMILES: O=c1cc(N2CC3CCC(C2)O3)nc2n1CC[C@@H](C(F)(F)F)N2C[C@@H](O)c1ccccc1]

200 mg (0.61 mmol) of (8S)-2-(8-oxa-3-azabicyclo[3.2.1]oct-3-yl)-8-trifluoromethyl-6,7,8,9-tetrahydropyrimido[1,2-a]pyrimidin-4-one in 5 mL of DMF are added to a suspension of 60 mg (1.51 mmol) of sodium hydride in 5 mL of DMF. The reaction mixture is heated at 50° C. for 10 minutes. After addition of 142 mg (0.91 mmol) of (S)-2-chloro-1-phenylethanol, the reaction is continued at 90° C. overnight. The reaction medium is evaporated to dryness. The residue is purified by chromatography on a column of silica (eluent: 90/10 DCM/MeOH). The isolated fraction is recrystallized from acetonitrile to give 33 mg of (8S)-9-((S)-2-hydroxy-2-phenylethyl)-2-(8-oxa-3-azabicyclo[3.2.1]oct-3-yl)-8-trifluoromethyl-6,7,8,9-tetrahydropyrimido[1,2-a]pyrimidin-4-one, the characteristics of which are as follows:

LC/MS (method B): ESI+ [M+H]+: m/z 451 tr (min)=0.68

$^1$H NMR (600 MHz, δ in ppm, DMSO-$d_6$): 1.70 (m, 2H) 1.84 (m, 2H) 2.25 (m, 1H) 2.4 (m, 1H) 3.02 (m, 3H) 3.2 (m, 1H) 3.77 (m, 2H) 4.26 (m, 2H) 4.41 (s, 2H) 4.80 (m, 1H) 4.92 (s, 1H) 5.01 (m, 1H) 5.71 (d, 1H) 7.37 (m, 5H)

EXAMPLE 25

(8S)-9-[2-(6-dimethylaminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 6)

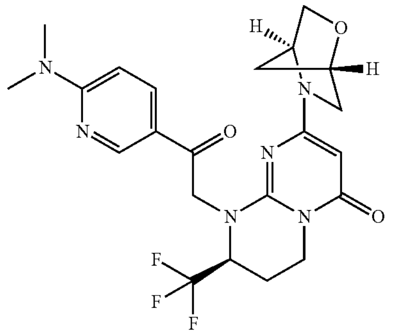 [SMILES: CN(C)c1ccc(C(=O)CN2c3nc(N4C[C@@H]5C[C@H]4CO5)cc(=O)n3CC[C@H]2C(F)(F)F)cn1]

Step 25.1: 1-(6-dimethylaminopyrid-3-yl)ethanone

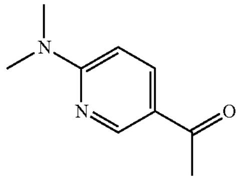

500 mg (2.89 mmol) of 1-(6-chloropyrid-3-yl)ethanone, 2 mL of ethanol and 7.23 mL (14.46 mmol) of 2 M dimethylamine in tetrahydrofuran are placed in a 20 mL microwave reactor. The solution is irradiated with microwaves for 10 minutes at 130° C. The mixture obtained is taken up in water and extracted with ethyl acetate. The organic phase is dried over sodium sulfate and evaporated to dryness to give 470 mg of 1-(6-dimethylaminopyrid-3-yl)ethanone, the characteristics of which are as follows:

$^1$H NMR (300 MHz, δ in ppm, $CDCl_3$): 2.44 (s, 3H), 3.12 (s, 6H), 6.68 (d, 1H), 7.96 (d, 1H), 8.72 (s, 1H).

Step 25.2: 2-bromo-1-(6-dimethylaminopyrid-3-yl)ethanone hydrobromide

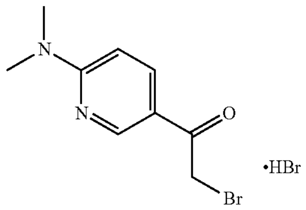

The procedure used is the same as that of step 12.2.

514 mg (3.13 mmol) of 1-(6-dimethylaminopyrid-3-yl)ethanone were used in the reaction. The precipitate corresponding to 2-bromo-1-(6-dimethylaminopyrid-3-yl)ethanone hydrobromide is filtered off, washed with ether and dried. The 950 mg of product obtained have the following characteristics:

$^1$H NMR (300 MHz, δ in ppm, $CDCl_3$): 3.22 (s, 6H), 4.80 (s, 2H), 6.95 (d, 1H), 8.10 (d, 1H), 8.68 (s, 1H).

Step 25.3: (8S)-9-[2-(6-dimethylaminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

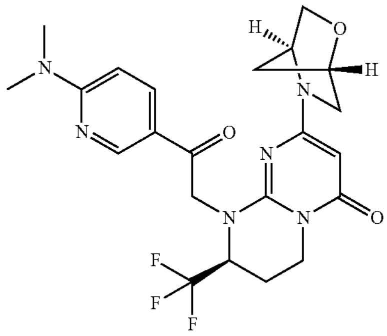 [SMILES: CN(C)c1ccc(C(=O)CN2c3nc(N4C[C@@H]5C[C@H]4CO5)cc(=O)n3CC[C@H]2C(F)(F)F)cn1]

100 mg (0.32 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one in 2 mL of DMF are added to a suspension of 13.91 mg (0.35 mmol) of sodium hydride in 3 mL of DMF. The reaction mixture is placed under magnetic stirring at room temperature for 15 minutes. A solution of 84.55 mg (0.35 mmol) of 2-bromo-1-(6-dimethylaminopyrid-3-yl)ethanone in 5 mL of DMF is added dropwise to the reaction medium. The reaction is stirred at room temperature for 5 minutes. The reaction medium is taken up in ethanol and evaporated to dryness. The residue is purified by chromatography on silica gel (eluent: 95/5 DCM/MeOH) to give 34 mg of (8S)-9-[2-(6-dimethylaminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one, the characteristics of which are as follows:

LC/MS (method A): ESI+ [M+H]+: m/z 479 tr (min)=0.48

$^1$H NMR (600 MHz, δ in ppm, DMSO-$d_6$): 1.62 (bs, 1H), 1.73 (d, 1H), 2.24 (m, 1H), 2.42 (m, 1H), 2.66-3.27 (m, 11H), 4.05-4.96 (m, 6H), 5.63 (d, 1H), 6.71 (d, 1H), 8.03 (d, 1H), 8.83 (s, 1H).

EXAMPLE 26

(8S)-9-(3,3-dimethyl-2-oxobutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 29)

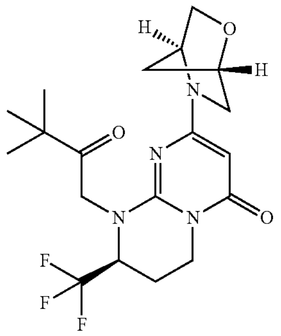 [SMILES: CC(C)(C)C(=O)CN1c2nc(N3C[C@@H]4C[C@H]3CO4)cc(=O)n2CC[C@H]1C(F)(F)F]

Step 26.1: (8S)-2-chloro-9-(3,3-dimethyl-2-oxobutyl)-8-trifluoromethyl-6,7,8,9-tetrahydropyrimido[1,2-a]pyrimidin-4-one

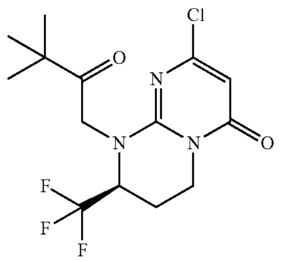 [SMILES: CC(C)(C)C(=O)CN1c2nc(Cl)cc(=O)n2CC[C@H]1C(F)(F)F]

The procedure used is the same as that of step 12.3.

150 mg (0.591 mmol) of (8S)-2-chloro-8-trifluoromethyl-6,7,8,9-tetrahydropyrimido[1,2-a]pyrimidin-4-one, 578.71 mg (1.77 mmol) of cesium carbonate, 99 μl (0.709 mmol) of 1-bromopinacolone and 10 mL of acetonitrile were used in the reaction. After purification by chromatography on silica gel (eluent A/B: DCM/MeOH, gradient A/B: t 0 min 0% B, t 12 min 4% B, t 15 min 4% B, t 30 min 10% B), 188 mg of (8S)-2-chloro-9-(3,3-dimethyl-2-oxobutyl)-8-trifluoromethyl-6,7,8,9-tetrahydropyrimido[1,2-a]pyrimidin-4-one were obtained, corresponding to the following characteristics:

LC/MS (method G): ESI+ [M+H]+: m/z 352 tr (min)=2.38

$^1$H NMR (300 MHz, δ in ppm, DMSO-$d_6$): 1.17 (s, 9H), 2.20 (m, 1H), 2.45 (m, 1H), 3.25 (m, 2H), 4.35 (d, 1H), 4.63 (m, 1H), 5.05 (d, 1H), 5.92 (s, 1H).

Step 26.2: (8S)-9-(3,3-dimethyl-2-oxobutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one

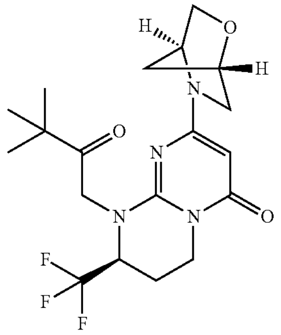 [SMILES: CC(C)(C)C(=O)CN1c2nc(N3C[C@@H]4C[C@H]3CO4)cc(=O)n2CC[C@H]1C(F)(F)F]

The procedure used is the same as that of step 12.4.

180 mg (0.511 mmol) of (8S)-2-chloro-9-(3,3-dimethyl-2-oxobutyl)-8-trifluoromethyl-6,7,8,9-tetrahydropyrimido[1,2-a]pyrimidin-4-one, 76.32 mg (0.563 mmol) of (1S,4S)-2-oxa-5-azabicyclo[2.2.1]heptane hydrochloride and 179 μl (1.28 mmol) of triethylamine were used in the reaction. After purification by chromatography on silica gel (eluent A/B: DCM/MeOH, gradient A/B: t 0 min 0% B, t 15 min 4% B, t 18 min 4% B, t 33 min 10% B), 130 mg of (8S)-9-(3,3-dimethyl-2-oxobutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one were obtained, corresponding to the following characteristics:

LC/MS (method A): ESI+ [M+H]+: m/z 415 tr (min)=0.67

$^1$H NMR (600 MHz, δ in ppm, DMSO-$d_6$): 1.15 (s, 9H), 1.80 (m, 2H), 2.22 (m, 1H), 2.37 (m, 1H), 3.13 (m, 1H), 3.25 (m, 2H), 3.52 (m, 1H), 3.65 (m, 1H), 4.25 (d, 1H), 4.34 (m, 2H), 4.58 (m, 1H), 4.67 (m, 2H), 5.32 (d, 1H).

EXAMPLE 27

(8S)-2-(1S,4S)-2-oxa-5-azabicyclo[2.2.1]hept-5-yl-9-(2-oxo-2-pyrid-4-ylethyl)-8-trifluoromethyl-6,7,8,9-tetrahydropyrimido[1,2-a]pyrimidin-4-one (Compound 2)

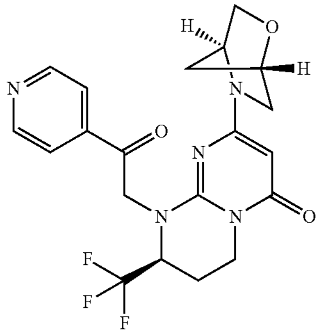 [SMILES: O=C(CN1c2nc(N3C[C@@H]4C[C@H]3CO4)cc(=O)n2CC[C@H]1C(F)(F)F)c1ccncc1]

Step 27.1: (8S)-2-chloro-9-(2-oxo-2-pyrid-4-ylethyl)-8-trifluoromethyl-6,7,8,9-tetrahydropyrimido[1,2-a]pyrimidin-4-one

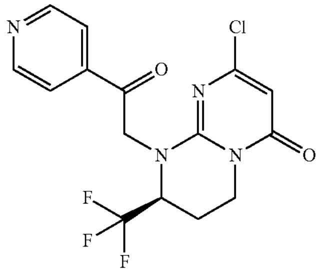 [SMILES: O=C(CN1c2nc(Cl)cc(=O)n2CC[C@H]1C(F)(F)F)c1ccncc1]

The procedure used is the same as that of step 12.3.

1 g (3.94 mmol) of (8S)-2-chloro-8-trifluoromethyl-6,7,8,9-tetrahydropyrimido[1,2-a]pyrimidin-4-one, 3.85 g (11.83 mmol) of cesium carbonate, 1.33 g (4.73 mmol) of 2-bromo-1-pyrid-4-ylethanone hydrobromide and 100 mL of acetonitrile were used in the reaction. After purification by chromatography on silica gel (eluent A/B: heptane/EtOAc, gradient A/B: t 0 min 60% B, t 25 min 100% B, t 30 min 100% B), 804 mg of (8S)-2-chloro-9-(2-oxo-2-pyrid-4-ylethyl)-8-trifluoromethyl-6,7,8,9-tetrahydropyrimido[1,2-a]pyrimidin-4-one were obtained, corresponding to the following characteristics:

LC/MS (method G): ESI+ [M+H]+: m/z 373 tr (min)=1.77

$^1$H NMR (300 MHz, δ in ppm, DMSO-$d_6$): 2.28 (m, 1H), 3.36 (m, 2H), 4.40 (m, 1H), 4.73 (m, 1H), 4.98 (d, 1H), 5.54 (d, 1H), 5.95 (s, 1H), 7.92 (m, 2H), 8.87 (m, 2H).

Step 27.2: (8S)-2-(1S,4S)-2-oxa-5-azabicyclo[2.2.1]hept-5-yl-9-(2-oxo-2-pyrid-4-ylethyl)-8-trifluoromethyl-6,7,8,9-tetrahydropyrimido[1,2-a]pyrimidin-4-one

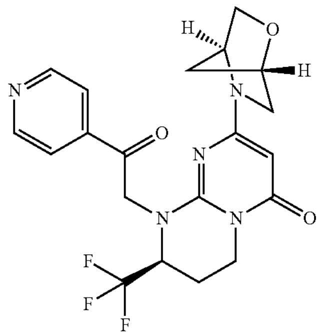 [SMILES: O=C(CN1c2nc(N3C[C@@H]4C[C@H]3CO4)cc(=O)n2CC[C@H]1C(F)(F)F)c1ccncc1]

The procedure used is the same as that of step 12.4.

250 mg (0.67 mmol) of (8S)-2-chloro-9-(2-oxo-2-pyrid-4-ylethyl)-8-trifluoromethyl-6,7,8,9-tetrahydropyrimido[1,2-a]pyrimidin-4-one, 109 mg (0.80 mmol) of (1S,4S)-2-oxa-5-azabicyclo[2.2.1]heptane hydrochloride and 230 μl (1.68 mmol) of triethylamine were used in the reaction. After purification by chromatography on silica gel (eluent A/B: DCM/MeOH, gradient A/B: t 0 min 0% B, t 25 min 10% B, t 30 min 10%) 230 mg of (8S)-2-(1S,4S)-2-oxa-5-azabicyclo[2.2.1]hept-5-yl-9-(2-oxo-2-pyrid-4-ylethyl)-8-trifluoromethyl-6,7,8,9-tetrahydropyrimido[1,2-a]pyrimidin-4-one were obtained, corresponding to the following characteristics:

LC/MS (method A): ESI+ [M+H]+: m/z 436 tr (min)=0.50

$^1$H NMR (600 MHz, δ in ppm, DMSO-$d_6$): 1.65 (m, 1H), 1.72 (m, 1H), 2.25 (m, 1H), 2.45 (m, 1H), 3.00 (m, 1H), 3.10 (m, 1H), 3.20 (m, 1H), 3.30 (m, 2H), 4.38 (m, 1H), 4.42 (m, 1H), 4.48 (m, 1H), 4.62 (m, 1H), 4.37 (m, 1H), 4.75 (d, 1H), 5.58 (d, 1H), 7.88 (m, 2H), 8.85 (m, 2H).

EXAMPLE 28

(8S)-9-[2-(6-methyl pyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 4)

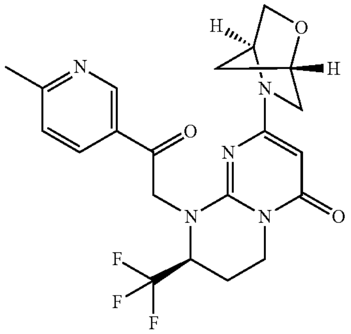 [SMILES: Cc1ccc(C(=O)CN2c3nc(N4C[C@@H]5C[C@H]4CO5)cc(=O)n3CC[C@H]2C(F)(F)F)cn1]

Step 28.1: 2-bromo-1-(6-methylpyrid-3-yl)ethanone hydrobromide

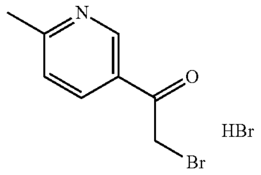

The procedure used is the same as that of step 12.2.

500 mg (3.59 mmol) of 1-(6-methylpyrid-3-yl)ethanone, 590 μl (3.59 mmol) of hydrobromic acid, 204 μl (3.95 mmol) of bromine and 10 mL of glacial acetic acid were used in the reaction. After precipitation with ethyl ether and filtration, 1.02 g of 2-bromo-1-(6-methylpyrid-3-yl)ethanone hydrobromide are obtained, the characteristics of which are as follows:

LC/MS (method G): ESI+ [M+H]+: m/z 214 tr (min)=1.00

Step 28.2: (8S)-2-chloro-9-[2-(6-methylpyrid-3-yl)-2-oxoethyl]-8-trifluoromethyl-6,7,8,9-tetrahydropyrimido[1,2-a]pyrimidin-4-one

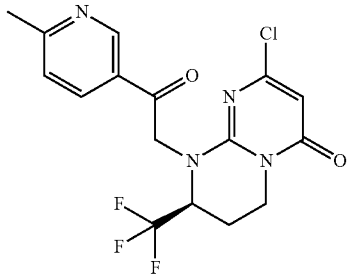 [SMILES: Cc1ccc(C(=O)CN2c3nc(Cl)cc(=O)n3CC[C@H]2C(F)(F)F)cn1]

1 g (3.94 mmol) of (8S)-2-chloro-8-trifluoromethyl-6,7,8,9-tetrahydropyrimido[1,2-a]pyrimidin-4-one is added to a suspension of 394.27 mg (9.86 mmol) of sodium hydride in 40 mL of DMF. The reaction mixture is placed under magnetic stirring at room temperature for 15 minutes. A solution of 1.16 g (3.94 mmol) of 2-bromo-1-(6-methylpyrid-3-yl)ethanone hydrobromide in 10 mL of DMF is added dropwise to the reaction medium at 0° C. The reaction is stirred at room temperature overnight. The reaction medium is evaporated to dryness. The crude product is taken up in water and extracted with ethyl acetate. The organic phase is dried over magnesium sulfate and evaporated to dryness. After purification by chromatography on silica gel (eluent A/B: heptane/EtOAc, gradient A/B: t 0 min 30% B, t 35 min 60% B, t 40 min 60% B), 480 mg of (8S)-2-chloro-9-[2-(6-methylpyrid-3-yl)-2-oxoethyl]-8-trifluoromethyl-6,7,8,9-tetrahydropyrimido[1,2-a]pyrimidin-4-one were obtained, corresponding to the following characteristics:

LC/MS (method G): ESI+ [M+H]+: m/z 387 tr (min)=1.85

$^1$H NMR (300 MHz, δ in ppm, DMSO-$d_6$): 2.30 (m, 1H), 2.58 (s, 3H), 3.29 (m, 2H), 4.40 (m, 1H), 4.75 (m, 1H), 4.93 (d, 1H), 5.55 (d, 1H), 5.94 (s, 1H), 7.46 (m, 1H), 8.26 (m, 1H), 9.09 (m, 1H).

Step 28.3: (8S)-9-[2-(6-methyl pyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

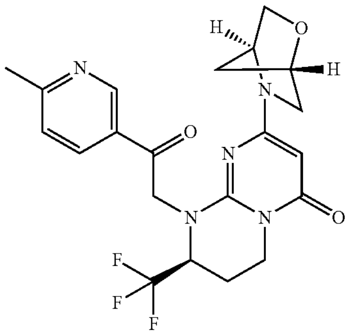 [SMILES: Cc1ccc(C(=O)CN2c3nc(N4C[C@@H]5C[C@H]4CO5)cc(=O)n3CC[C@H]2C(F)(F)F)cn1]

The procedure used is the same as that of step 12.4.

480 mg (1.24 mmol) of (8S)-2-chloro-9-[2-(6-methylpyrid-3-yl)-2-oxoethyl]-8-trifluoromethyl-6,7,8,9-tetrahydropyrimido[1,2-a]pyrimidin-4-one, 201.94 mg (1.49 mmol) of (1S,4S)-2-oxa-5-azabicyclo[2.2.1]heptane hydrochloride and 313.97 mg (3.10 mmol) of triethylamine were used in the reaction. After purification by chromatography on silica gel (eluent A/B: heptane/EtOAc, gradient A/B: t 0 min 30% B, t 35 min 60% B, t 40 min 60% B), 335 mg of (8S)-9-[2-(6-methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one were obtained, corresponding to the following characteristics:

LC/MS (method A): ESI+ [M+H]+: m/z 450 tr (min)=0.49

$^1$H NMR (600 MHz, δ in ppm, DMSO-$d_6$): 1.65 (m, 2H), 2.30 (m, 1H), 2.42 (m, 1H), 2.55 (s, 3H), 2.70-3.10 (bs, 3H), 3.20 (m, 2H), 4.40 (m, 3H), 4.65 (m, 3H), 5.70 (m, 1H), 7.49 (m, 1H), 8.30 (m, 1H), 9.10 (m, 1H).

EXAMPLE 29

2-methyl-1-[2-(6-methylpyrid-3-yl)-2-oxoethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one (Compound 17)

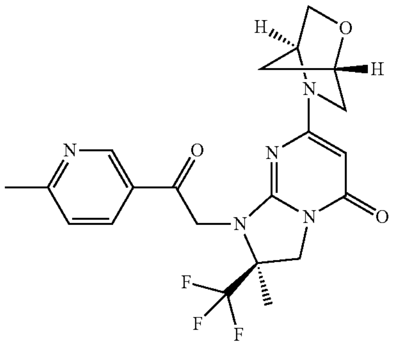 [SMILES: Cc1ccc(C(=O)CN2c3nc(N4C[C@@H]5C[C@H]4CO5)cc(=O)n3C[C@@]2(C)C(F)(F)F)cn1]

Step 29.1: (S)-7-chloro-2-methyl-1-[2-(6-methylpyrid-3-yl)-2-oxoethyl]-2-trifluoromethyl-2,3-dihydro-1H-imidazo[1,2-a]pyrimidin-5-one

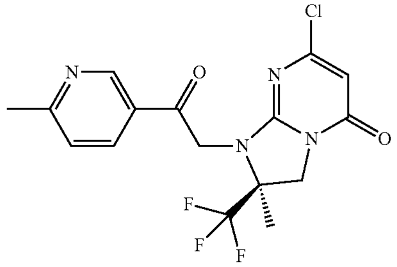 [SMILES: Cc1ccc(C(=O)CN2c3nc(Cl)cc(=O)n3C[C@@]2(C)C(F)(F)F)cn1]

500 mg (1.97 mmol) of (S)-7-chloro-2-methyl-2-trifluoromethyl-2,3-dihydro-1H-imidazo[1,2-a]pyrimidin-5-one are added to a suspension of 141.94 mg (5.91 mmol) of sodium hydride in 20 mL of DMF. The reaction mixture is placed under magnetic stirring at room temperature for 15 minutes. A solution of 872.32 mg (2.96 mmol) of 2-bromo-1-(6-methylpyrid-3-yl)ethanone hydrobromide in 10 mL of DMF is added dropwise to the reaction medium at 0° C. The reaction is stirred at room temperature overnight. The reaction medium is evaporated to dryness. The crude product is taken up in water and extracted with ethyl acetate. The organic phase is dried over magnesium sulfate and evaporated to dryness. After purification by chromatography on silica gel (eluent A/B: heptane/EtOAc, gradient A/B: t 0 min 30% B, t 35 min 60% B, t 40 min 60% B), 150 mg of (S)-7-chloro-2-methyl-1-[2-(6-methylpyrid-3-yl)-2-oxoethyl]-2-trifluoromethyl-2,3-dihydro-1H-imidazo[1,2-a]pyrimidin-5-one were obtained, corresponding to the following characteristics:

LC/MS (method G): ESI+ [M+H]+: m/z 387 tr (min)=1.79

$^1$H NMR (300 MHz, δ in ppm, DMSO-$d_6$): 1.54 (s, 3H), 2.46 (s, 3H), 4.10 (d, 1H), 4.27 (d, 1H), 4.88 (d, 1H), 5.20 (d, 1H), 5.83 (s, 1H), 7.36 (m, 1H), 7.8.17 (m, 1H), 9.00 (m, 1H).

Step 29.2: 2-methyl-1-[2-(6-methyl pyrid-3-yl)-2-oxoethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one

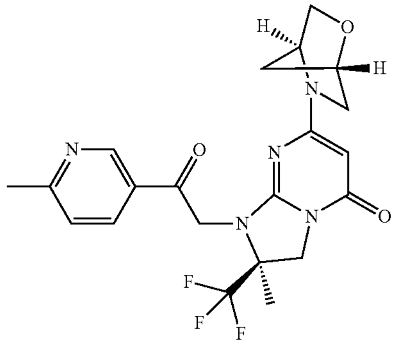 [SMILES: Cc1ccc(C(=O)CN2c3nc(N4C[C@@H]5C[C@H]4CO5)cc(=O)n3C[C@@]2(C)C(F)(F)F)cn1]

The procedure used is the same as that of step 12.4.

150 mg (0.388 mmol) of (S)-7-chloro-2-methyl-1-[2-(6-methyl pyrid-3-yl)-2-oxoethyl]-2-trifluoromethyl-2,3-dihydro-1H-imidazo[1,2-a]pyrimidin-5-one, 63.11 mg (0.465 mmol) of (1S,4S)-2-oxa-5-azabicyclo[2.2.1]heptane hydrochloride and 98.61 mg (0.970 mmol) of triethylamine were used in the reaction. After purification by chromatography on silica gel (eluent A/B: DCM/MeOH, gradient A/B: t 0 min 0% B, t 35 min 10% B, t 40 min 10% B), 65 mg of 2-methyl-1-[2-(6-methylpyrid-3-yl)-2-oxoethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one were obtained, corresponding to the following characteristics:

LC/MS (method A): ESI+ [M+H]+: m/z 450 tr (min)=0.49

$^1$H NMR (600 MHz, δ in ppm, DMSO-$d_6$): 1.65 (s, 3H), 1.67-1.76 (bs, 2H), 2.96-3.24 (bs, 2H), 3.28 (m, 2H), 2.58 (s, 3H), 4.02 (d, 1H), 4.24 (d, 1H), 4.48 (m, 3H), 4.85 (d, 1H), 5.20 (d, 1H), 7.49 (m, 1H), 8.30 (m, 1H), 9.10 (m, 1H).

EXAMPLE 30

2-methyl-7-(1S,4S)-2-oxa-5-azabicyclo[2.2.1]hept-5-yl-1-(2-oxo-2-pyrid-3-ylethyl)-2-((S)-trifluoromethyl)-2,3-dihydro-1H-imidazo[1,2-a]pyrimidin-5-one (Compound 21)

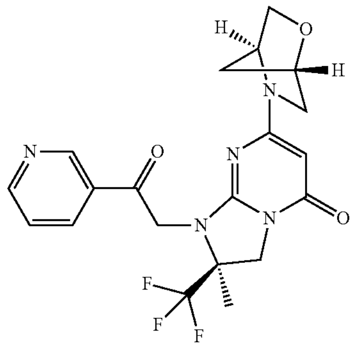 [SMILES: C[C@@]1(C(F)(F)F)Cn2c(nc(N3C[C@@H]4C[C@H]3CO4)cc2=O)N1CC(=O)c1cccnc1]

150 mg (0.474 mmol) of 2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one are added to a suspension of 47.42 mg (1.19 mmol) of sodium hydride in 10 mL of DMF. The reaction mixture is placed under magnetic stirring at room temperature for 15 minutes. A solution of 168.31 mg (0.569 mmol) of 2-bromo-1-pyrid-3-ylethanone hydrobromide in 5 mL of DMF is added dropwise to the reaction medium at 0° C. The reaction is stirred at room temperature overnight. The reaction medium is evaporated to dryness. The crude product is taken up in water and extracted with ethyl acetate. The organic phase is dried over magnesium sulfate and evaporated to dryness. After purification by chromatography on silica gel (eluent A/B: DCM/MeOH, gradient A/B: t 0 min 0% B, t 35 min 10% B, t 40 min 10% B), 58 mg of 2-methyl-7-(1S,4S)-2-oxa-5-azabicyclo[2.2.1]hept-5-yl-1-(2-oxo-2-pyrid-3-ylethyl)-2-((S)-trifluoromethyl)-2,3-dihydro-1H-imidazo[1,2-a]pyrimidin-5-one were obtained, corresponding to the following characteristics:

LC/MS (method A): ESI+ [M+H]+: m/z 436 tr (min)=0.51

$^1$H NMR (600 MHz, δ in ppm, DMSO-$d_6$): 1.58 (s, 3H), 1.62 (m, 2H), 2.80-3.25 (bs, 5H) 3.95 (d, 1H), 4.15 (d, 1H), 4.50 (m, 2H), 4.80 (d, 1H), 5.15 (d, 1H), 7.51 (m, 1H), 8.30 (m, 1H), 8.78 (m, 1H), 9.20 (m, 1H).

EXAMPLE 31

(8S)-2-(1S,4S)-2-oxa-5-azabicyclo[2.2.1]hept-5-yl-9-(2-pyrid-3-ylethyl)-8-trifluoromethyl-6,7,8,9-tetrahydropyrimido[1,2-a]pyrimidin-4-one (Compound 12)

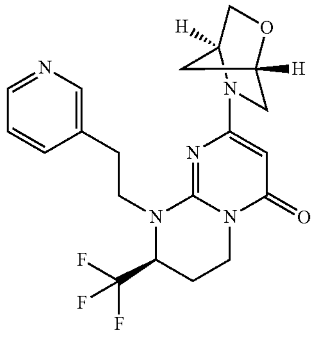 [SMILES: O=c1cc(N2C[C@@H]3C[C@H]2CO3)nc2n1CC[C@@H](C(F)(F)F)N2CCc1cccnc1]

Step 31.1: 2-pyrid-3-ylethyl toluene-4-sulfonate

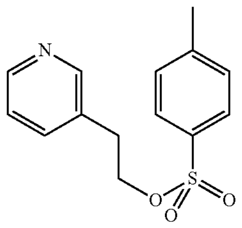 [SMILES: Cc1ccc(S(=O)(=O)OCCc2cccnc2)cc1]

6.62 mL (47.26 mmol) of triethylamine and 8.26 g (43.32 mmol) of 4-methylbenzenesulfonyl chloride are added at 0° C. to a solution of 5 g (39.38 mmol) of 2-pyrid-3-ylethanol in 300 mL of dichloromethane. After allowing the reaction medium to warm to room temperature and stirring overnight, it is washed with water and with saturated NaCl solution. The organic phase is dried over magnesium sulfate and evaporated to dryness. After purification by chromatography on silica gel (eluent: 4/6 heptane/EtOAc), 8 g of 2-pyrid-3-ylethyl toluene-4-sulfonate were obtained, corresponding to the following characteristics:

$^1$H NMR (300 MHz, δ in ppm, DMSO-$d_6$): 2.41 (s, 3H), 2.91 (m, 2H), 4.27 (m, 2H), 7.27 (m, 1H), 7.43 (m, 2H), 7.56 (m, 1H), 7.68 (m, 2H), 8.40 (m, 2H).

Step 31.2: (8S)-2-(1S,4S)-2-oxa-5-azabicyclo[2.2.1]hept-5-yl-9-(2-pyrid-3-ylethyl)-8-trifluoromethyl-6,7,8,9-tetrahydropyrimido[1,2-a]pyrimidin-4-one

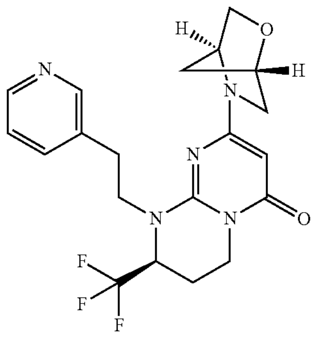 [SMILES: O=c1cc(N2C[C@@H]3C[C@H]2CO3)nc2n1CC[C@@H](C(F)(F)F)N2CCc1cccnc1]

A suspension of 150 mg (0.474 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one and 170.15 mg (0.522 mmol) of cesium carbonate in 10 mL of acetonitrile is stirred for 15 minutes at 85° C. 131.53 mg (0.474 mmol) of 2-pyrid-3-ylethyl toluene-4-sulfonate are then added. After stirring overnight at 85° C., the reaction mixture is evaporated and the residue is taken up in water and extracted with ethyl acetate. The organic phase is dried over magnesium sulfate and evaporated to dryness. After purification by chromatography on silica gel (eluent A/B: DCM/MeOH, gradient A/B: t 0 min 0% B, t 35 min 10% B, t 40 min 10% B) 145 mg of (8S)-2-(1S,4S)-2-oxa-5-azabicyclo[2.2.1]hept-5-yl-9-(2-pyrid-3-ylethyl)-8-trifluoromethyl-6,7,8,9-tetrahydropyrimido[1,2-a]pyrimidin-4-one were obtained, the characteristics of which are as follows:

LC/MS (method A): ESI+ [M+H]+: m/z 422 tr (min)=0.39

$^1$H NMR (600 MHz, δ in ppm, DMSO-$d_6$): 1.25 (m, 2H), 1.85 (m, 2H), 2.01 (m, 1H), 2.35 (m, 1H), 2.95 (m, 3H), 3.15 (m, 1H), 3.42 (m, 1H), 3.75 (m, 2H), 4.22 (m, 2H), 4.72 (m, 3H), 7.35 (m, 1H), 7.65 (m, 1H), 8.45 (m, 2H).

EXAMPLE 32

(8S)-9-[2-(6-methoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 45)

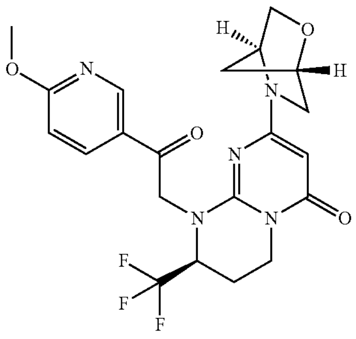 [SMILES: COc1ccc(C(=O)CN2c3nc(N4C[C@@H]5C[C@H]4CO5)cc(=O)n3CC[C@H]2C(F)(F)F)cn1]

Step 32.1: 1-(6-methoxypyrid-3-yl)ethanone

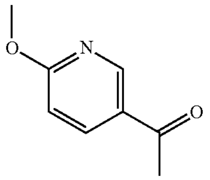

A mixture of 15 mL of methanol, 500 mg (2.89 mmol) of 1-(6-chloropyrid-3-yl)ethanone and 1.17 g (21.69 mmol) of sodium methoxide is heated in a microwave reactor at 160° C. for 4 hours. The reaction medium is evaporated to dryness. After purification by chromatography on silica gel (eluent A/B: heptane/EtOAc, gradient A/B: t 0 min 0% B, t 5 min 20% B, t 30 min 40% B), 230 mg of 1-(6-methoxypyrid-3-yl)ethanone were obtained, corresponding to the following characteristics:

LC/MS (method G): ESI+ [M+H]+: m/z 152 tr (min)=1.33

$^1$H NMR (300 MHz, δ in ppm, DMSO-$d_6$): 2.50 (s, 3H), 3.94 (s, 3H), 6.92 (m, 1H), 8.18 (m, 1H), 8.83 (m, 1H).

Step 32.2: 2-bromo-1-(6-methoxypyrid-3-yl)ethanone hydrobromide

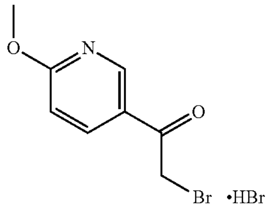

The procedure used is the same as that of step 12.2.

230 mg (1.52 mmol) of 1-(6-methoxypyrid-3-yl)ethanone, 413 μl (7.61 mmol) of hydrobromic acid, 87 μl (1.67 mmol) of bromine and 5 mL of glacial acetic acid were used in the reaction. After precipitation with ethyl ether and filtration, 430 mg of 2-bromo-1-(6-methoxypyrid-3-yl)ethanone hydrobromide are obtained, the characteristics of which are as follows:

LC/MS (method G): ESI+ [M+H]+: m/z 230 tr (min)=1.61

$^1$H NMR (300 MHz, δ in ppm, DMSO-$d_6$): 3.96 (s, 3H), 4.91 (s, 2H), 6.96 (m, 1H), 8.21 (m, 1H), 8.88 (m, 1H).

Step 32.3: (8S)-9-[2-(6-methoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

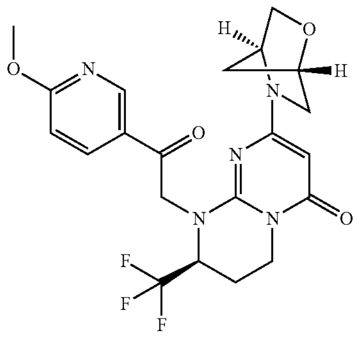 [SMILES: COc1ccc(C(=O)CN2c3nc(N4C[C@@H]5C[C@H]4CO5)cc(=O)n3CC[C@H]2C(F)(F)F)cn1]

The procedure used is the same as that of step 12.3.

150 mg (0.474 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one, 464.04 mg (1.42 mmol) of cesium carbonate, 176.98 mg (0.569 mmol) of 2-bromo-1-(6-methoxypyrid-3-yl)ethanone hydrobromide and 10 mL of acetonitrile were used in the reaction. After purification by chromatography on silica gel (eluent A/B: DCM/MeOH, gradient A/B: t 0 min 0% B, t 25 min 10% B, t 30 min 10% B), 100 mg of (8S)-9-[2-(6-methoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one were obtained, corresponding to the following characteristics:

LC/MS (method A): ESI+ [M+H]+: m/z 466 tr (min)=0.61

$^1H$ NMR (600 MHz, δ in ppm, DMSO-$d_6$): 1.62 (m, 1H), 1.71 (m, 1H), 2.25 (m, 1H), 2.41 (m, 1H), 2.61-3.17 (bs, 3H), 3.25 (m, 2H), 3.95 (s, 3H), 3.38 (m, 1H), 4.48 (m, 2H), 4.62 (m, 3H), 5.70 (m, 1H), 6.97 (m, 1H), 8.28 (m, 1H), 8.98 (s, 1H).

EXAMPLE 33

(S)-9-{2-[6-(2-fluoroethoxy)pyrid-3-yl]-2-oxoethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 63)

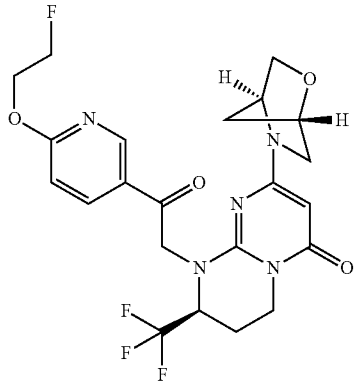 [SMILES: O=C(CN1c2nc(N3C[C@@H]4C[C@H]3CO4)cc(=O)n2CC[C@H]1C(F)(F)F)c1ccc(OCCF)nc1]

Step 33.1: 1-[6-(2-fluoroethoxy)pyrid-3-yl]ethanone

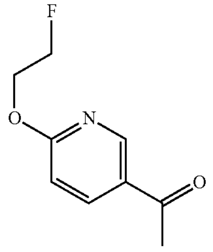

530 μl (8.68 mmol) of 2-fluoroethanol are added to a suspension of 347.05 mg (8.68 mmol) of sodium hydride in 10 mL of DMF. The reaction mixture is placed under magnetic stirring at room temperature for 15 minutes. A solution of 500 mg (2.89 mmol) of 1-(6-chloropyrid-3-yl)ethanone in 3 mL of DMF is added dropwise to the reaction medium. The reaction is stirred at room temperature overnight. The reaction medium is evaporated to dryness. The crude product is taken up in water and extracted with ethyl acetate. The organic phase is dried over magnesium sulfate and evaporated to dryness. After purification by chromatography on silica gel (eluent A/B: heptane/EtOAc, gradient A/B: t 0 min 0% B, t 5 min 10% B, t 30 min 30% B), 362 mg of 1-[6-(2-fluoroethoxy)pyrid-3-yl]ethanone were obtained, corresponding to the following characteristics:

LC/MS (method G): ESI+ [M+H]+: m/z 184 tr (min)=1.41

$^1H$ NMR (300 MHz, δ in ppm, DMSO-$d_6$): 2.57 (s, 3H), 4.56 (m, 1H), 4.67 (m, 1H), 4.86 (m, 1H), 7.00 (m, 1H), 8.21 (m, 1H), 8.83 (m, 1H).

Step 33.2: 2-bromo-1-[6-(2-fluoroethoxy)pyrid-3-yl]ethanone hydrobromide

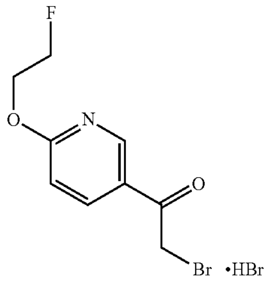 [SMILES: O=C(CBr)c1ccc(OCCF)nc1 ; Br]

The procedure used is the same as that of step 12.2.

362 mg (1.98 mmol) of 1-[6-(2-fluoroethoxy)pyrid-3-yl]ethanone, 413 μl (7.61 mmol) of hydrobromic acid, 537 μl (9.88 mmol) of bromine and 5 mL of glacial acetic acid were used in the reaction. After precipitation with ethyl ether and filtration, 602 mg of 2-bromo-1-[6-(2-fluoroethoxy)pyrid-3-yl]ethanone hydrobromide are obtained, the characteristics of which are as follows:

LC/MS (method G): ESI+ [M+H]+: m/z 264 tr (min)=1.69

$^1H$ NMR spectrum (300 MHz, δ in ppm, DMSO-$d_6$): 4.56 (m, 1H), 4.69 (m, 1H), 4.86 (m, 1H), 4.92 (s, 2H), 7.00 (m, 1H), 8.23 (m, 1H), 8.85 (m, 1H), 9.80 (bs, 1H).

Step 33.3: (8S)-9-{2-[6-(2-fluoroethoxy)pyrid-3-yl]-2-oxoethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one

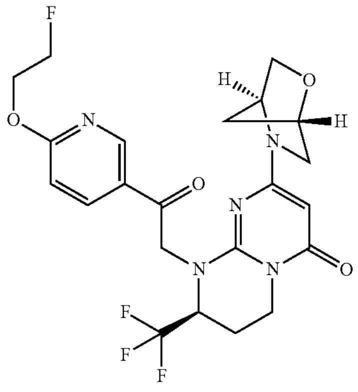 [SMILES: O=C(CN1c2nc(N3C[C@@H]4C[C@H]3CO4)cc(=O)n2CC[C@H]1C(F)(F)F)c1ccc(OCCF)nc1]

The procedure used is the same as that of step 12.3.

150 mg (0.474 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one, 464.04 mg (1.42 mmol) of cesium carbonate, 195.20 mg (0.569 mmol) of 2-bromo-1-[6-(2-fluoroethoxy)pyrid-3-yl]ethanone hydrobromide and 10 mL of acetonitrile were used in the reaction. After purification by chromatography on silica gel (eluent A/B: DCM/MeOH, gradient A/B: t 0 min 0% B, t 25 min 10% B, t 30 min 10% B), 130 mg of (8S)-9-{2-[6-(2-fluoroethoxy)pyrid-3-yl]-2-oxoethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one were obtained, corresponding to the following characteristics:

LC/MS (method A): ESI+ $[M+H]^+$: m/z 498 tr (min)=0.62

$^1H$ NMR (600 MHz, δ in ppm, DMSO-$d_6$): 1.62 (m, 1H), 1.72 (m, 1H), 2.25 (m, 1H), 2.45 (m, 1H), 2.61-3.17 (bs, 3H), 2.25 (m, 2H), 4.38 (m, 1H), 4.50 (m, 2H), 4.55-4.70 (m, 5H), 4.74 (m, 1H), 4.83 (m, 1H), 5.70 (m, 1H), 7.12 (m, 1H), 8.30 (m, 1H), 8.97 (m, 1H).

EXAMPLE 34

(8S)-9-[(S)-2-(4-fluoro-2-methoxyphenyl)-2-hydroxyethyl]-2-(8-oxa-3-azabicyclo[3.2.1]oct-3-yl)-8-trifluoromethyl-6,7,8,9-tetrahydropyrimido[1,2-a]pyrimidin-4-one (Compound 71)

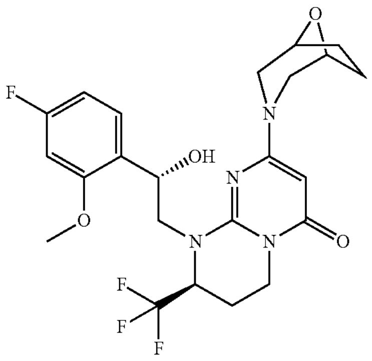 [SMILES: COc1cc(F)ccc1[C@H](O)CN1c2nc(N3CC4CCC(C3)O4)cc(=O)n2CC[C@H]1C(F)(F)F]

200 mg (0.61 mmol) of (8S)-2-(8-oxa-3-azabicyclo[3.2.1]oct-3-yl)-8-trifluoromethyl-6,7,8,9-tetrahydropyrimido[1,2-a]pyrimidin-4-one in 5 mL of DMF are added to a suspension of 60 mg (1.51 mmol) of sodium hydride in 10 mL of DMF. The reaction mixture is heated at 50° C. for 10 minutes. After addition of 162 mg (0.79 mmol) of (S)-2-chloro-1-(4-fluoro-2-methoxyphenyl)ethanol, the reaction is continued at room temperature overnight. The reaction medium is evaporated to dryness. The residue is purified by chromatography on a column of silica (eluent: 90/10 DCM/MeOH). 40 mg of (8S)-9-[(S)-2-(4-fluoro-2-methoxyphenyl)-2-hydroxyethyl]-2-(8-oxa-3-azabicyclo[3.2.1]oct-3-yl)-8-trifluoromethyl-6,7,8,9-tetrahydropyrimido[1,2-a]pyrimidin-4-one were obtained, corresponding to the following characteristics:

LC/MS (method B): ESI+ [M+H]+: m/z 499 tr (min)=0.71

$^1H$ NMR (600 MHz, δ in ppm, DMSO-$d_6$): 1.65 (m, 2H), 1.83 (m, 2H), 2.25 (m, 1H), 2.35 (m, 1H), 2.92 (m, 3H), 3.22 (m, 1H), 3.75 (m, 1H), 3.75 (s, 3H), 3.85 (m, 1H), 4.15 (m, 1H), 4.35 (m, 3H), 4.71 (m, 1H), 4.89 (s, 1H), 5.35 (m, 1H), 5.53 (m, 1H), 6.78 (m, 1H), 6.87 (m, 1H), 7.51 (m, 1H).

EXAMPLE 35

(S)-1-[2-(4-hydroxyphenyl)ethyl]-2-methyl-7-(8-oxa-3-azabicyclo[3.2.1]oct-3-yl)-2-trifluoromethyl-2,3-dihydro-1H-imidazo[1,2-a]pyrimidin-5-one (Compound 72)

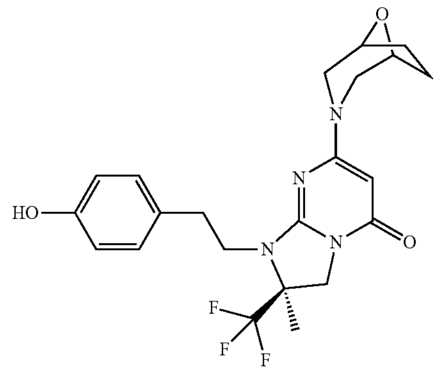 [SMILES: C[C@@]1(C(F)(F)F)Cn2c(nc(N3CC4CCC(C3)O4)cc2=O)N1CCc1ccc(O)cc1]

Step 35.1: (S)-1-[2-(4-benzyloxyphenyl)ethyl]-7-chloro-2-methyl-2-trifluoromethyl-2,3-dihydro-1H-imidazo[1,2-a]pyrimidin-5-one

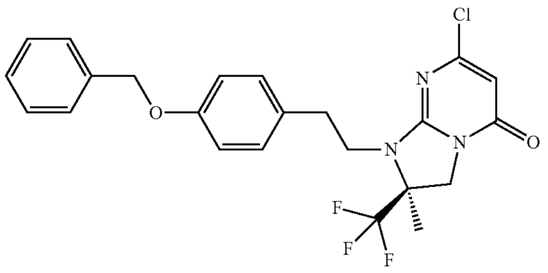 [SMILES: C[C@@]1(C(F)(F)F)Cn2c(nc(Cl)cc2=O)N1CCc1ccc(OCc2ccccc2)cc1]

A mixture of 40 mL of DMF, 2 g (7.89 mmol) of (S)-7-chloro-2-methyl-2-trifluoromethyl-2,3-dihydro-1H-imidazo[1,2-a]pyrimidin-5-one, 3.44 g (11.84 mmol) of 1-benzyloxy-4-(2-bromoethyl)benzene and 5.14 g (15.78 mmol) of cesium carbonate is heated in a Biotage microwave reactor at 120° C. for 20 minutes. The reaction medium is evaporated to dryness. After purification by chromatography on silica gel (eluent A/B: heptane/EtOAc, gradient A/B: t 0 min 20% B, t 25 min 50% B, t 35 min 50% B), 2.8 g of (S)-1-[2-(4-benzyloxyphenyl)ethyl]-7-chloro-2-methyl-2-trifluoromethyl-2,3-dihydro-1H-imidazo[1,2-a]pyrimidin-5-one were obtained, corresponding to the following characteristics:

LC/MS (method G): ESI+ [M+H]+: m/z 464 tr (min)=2.91

$^1H$ NMR (300 MHz, δ in ppm, $CDCl_3$): 1.36 (s, 3H), 2.90 (m, 1H), 3.11 (m, 1H), 3.49 (m, 1H), 3.75 (m, 1H), 4.38 (d, 1H), 5.07 (m, 2H), 5.32 (s, 1H), 5.97 (s, 1H), 6.94 (m, 2H), 7.12 (m, 2H), 7.43 (m, 5H).

Step 35.2: (S)-1-[2-(4-benzyloxyphenyl)ethyl]-2-methyl-7-(8-oxa-3-azabicyclo[3.2.1]oct-3-yl)-2-trifluoromethyl-2,3-dihydro-1H-imidazo[1,2-a]pyrimidin-5-one

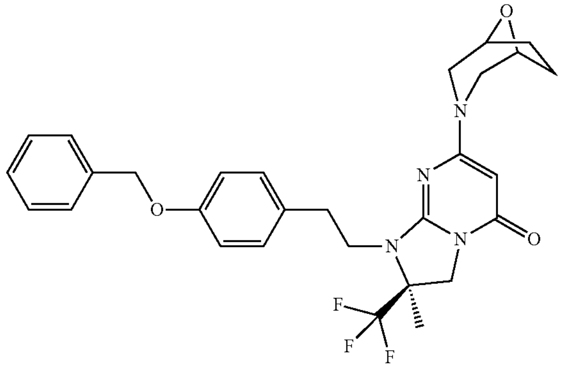 [SMILES: C[C@@]1(C(F)(F)F)Cn2c(nc(N3CC4CCC(C3)O4)cc2=O)N1CCc1ccc(OCc2ccccc2)cc1]

The procedure used is the same as that of step 12.4.

1.40 g (3.02 mmol) of (S)-1-[2-(4-benzyloxyphenyl)ethyl]-7-chloro-2-methyl-2-trifluoromethyl-2,3-dihydro-1H-imidazo[1,2-a]pyrimidin-5-one, 903 mg (6.04 mmol) of 8-oxa-3-azabicyclo[3.2.1]octane hydrochloride and 763 mg (7.54 mmol) of triethylamine were used in the reaction. After purification by chromatography on silica gel (eluent A/B: 2/8 heptane/EtOAc), 1.2 g of (S)-1-[2-(4-benzyloxyphenyl)ethyl]-2-methyl-7-(8-oxa-3-azabicyclo[3.2.1]oct-3-yl)-2-trifluoromethyl-2,3-dihydro-1H-imidazo[1,2-a]pyrimidin-5-one were obtained, corresponding to the following characteristics:

LC/MS (method G): ESI+ [M+H]+: m/z 541 tr (min)=2.84

$^1$H NMR (300 MHz, δ in ppm, DMSO-$d_6$): 1.49 (s, 3H), 1.66 (m, 2H), 1.83 (m, 2H), 2.79 (m, 1H), 2.96 (m, 3H), 3.45 (m, 2H), 3.86 (m, 3H), 4.10 (d, 1H), 4.39 (m, 2H), 4.78 (m, 1H), 5.08 (s, 2H), 6.96 (m, 2H), 7.15 (m, 2H), 7.41 (m, 5H).

Step 35.3: (S)-1-[2-(4-hydroxyphenyl)ethyl]-2-methyl-7-(8-oxa-3-azabicyclo[3.2.1]oct-3-yl)-2-trifluoromethyl-2,3-dihydro-1H-imidazo[1,2-a]pyrimidin-5-one

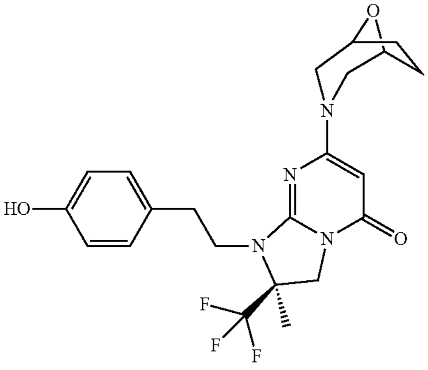 [SMILES: C[C@@]1(C(F)(F)F)Cn2c(nc(N3CC4CCC(C3)O4)cc2=O)N1CCc1ccc(O)cc1]

700 mg (11.10 mmol) of ammonium formate and 156 mg (0.22 mmol) of 20% palladium hydroxide are added at 0° C. to a solution of 1.20 g (2.22 mmol) of (S)-1-[2-(4-benzyloxyphenyl)ethyl]-2-methyl-7-(8-oxa-3-azabicyclo[3.2.1]oct-3-yl)-2-trifluoromethyl-2,3-dihydro-1H-imidazo[1,2-a]pyrimidin-5-one in 15 mL of methanol. The mixture is refluxed for 1 hour and then allowed to cool to room temperature. The reaction medium is filtered through Celite and the filtrate is then evaporated to dryness. After purification by chromatography on silica gel (eluent A/B: DCM/MeOH, gradient A/B: t 0 min 0% B, t 25 min 10% B, t 30 min 10% B), 732 mg of (S)-1-[2-(4-hydroxyphenyl)ethyl]-2-methyl-7-(8-oxa-3-azabicyclo[3.2.1]oct-3-yl)-2-trifluoromethyl-2,3-dihydro-1H-imidazo[1,2-a]pyrimidin-5-one were obtained, corresponding to the following characteristics:

LC/MS (method B): ESI+ [M+H]+: m/z 451 tr (min)=0.68

$^1$H NMR (600 MHz, δ in ppm, DMSO-$d_6$): 1.48 (s, 3H), 1.64 (m, 2H), 1.80 (m, 2H), 2.72 (m, 1H), 2.87 (m, 1H), 3.00 (m, 2H), 3.35 (m, 1H), 3.52 (m, 1H), 3.78 (m, 3H), 4.09 (d, 1H), 4.39 (m, 2H), 4.77 (s, 1H), 6.68 (m, 2H), 6.97 (m, 2H), 9.16 (s, 1H).

EXAMPLE 36

(S)-1-{2-[4-(2-dimethylaminoethoxy)phenyl]ethyl}-2-methyl-7-(8-oxa-3-azabicyclo[3.2.1]oct-3-yl)-2-trifluoromethyl-2,3-dihydro-1H-imidazo[1,2-a]pyrimidin-5-one (Compound 74)

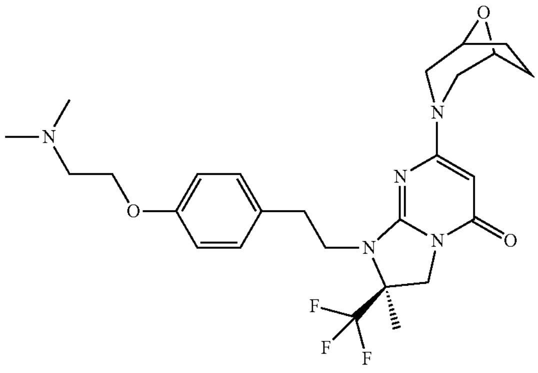 [SMILES: CN(C)CCOc1ccc(CCN2c3nc(N4CC5CCC(C4)O5)cc(=O)n3C[C@@]2(C)C(F)(F)F)cc1]

282 mg (0.87 mmol) of cesium carbonate are added to a solution of 130 mg (0.29 mmol) of (S)-1-[2-(4-hydroxyphenyl)ethyl]-2-methyl-7-(8-oxa-3-azabicyclo[3.2.1]oct-3-yl)-2-trifluoromethyl-2,3-dihydro-1H-imidazo[1,2-a]pyrimidin-5-one in 10 mL of DMF. After heating at 80° C. for 20 minutes, 62.40 mg (0.43 mmol) of (2-chloroethyl)dimethylamine are added. The reaction medium is heated at 80° C. overnight. The reaction medium is evaporated to dryness. After purification by chromatography on silica gel (eluent A/B: DCM/MeOH, gradient A/B: t 0 min 0% B, t 25 min 10% B, t 30 min 10% B), 116 mg of (S)-1-{2-[4-(2-dimethylaminoethoxyl)phenyl]ethyl}-2-methyl-7-(8-oxa-3-azabicyclo[3.2.1]oct-3-yl)-2-trifluoromethyl-2,3-dihydro-1H-imidazo[1,2-a]pyrimidin-5-one were obtained, corresponding to the following characteristics:

LC/MS (method B): ESI+ [M+H]+: m/z 522 tr (min)=0.56

$^1$H NMR (600 MHz, δ in ppm, DMSO-$d_6$): 1.48 (s, 3H), 1.62 (m, 2H), 1.77 (m, 2H), 2.77 (m, 7H), 2.88 (m, 1H), 2.93 (m, 2H), 3.40 (m, 4H), 3.57-378 (bs, 2H), 3.82 (m, 1H), 4.06 (m, 1H), 4.26 (m, 2H), 4.33 (m, 2H), 4.72 (s, 1H), 6.90 (m, 2H), 7.12 (m, 2H), 10.2 (bs, 1H).

EXAMPLE 37

N, N-dimethyl-2-(4-{2-[(S)-2-methyl-7-(8-oxa-3-azabicyclo[3.2.1]oct-3-yl)-5-oxo-2-trifluoromethyl-2,3-dihydro-5H-imidazo[1,2-a]pyrimidin-1-yl]ethyl}phenoxy)acetamide (Compound 70)

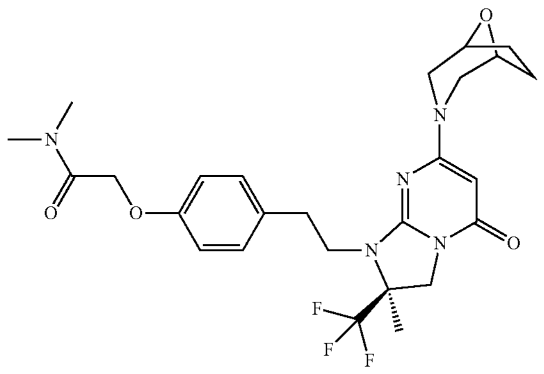 [SMILES: CN(C)C(=O)COc1ccc(CCN2c3nc(N4CC5CCC(C4)O5)cc(=O)n3C[C@@]2(C)C(F)(F)F)cc1]

235 mg (0.72 mmol) of cesium carbonate are added to a solution of 130 mg (0.29 mmol) of (S)-1-[2-(4-hydroxyphenyl)ethyl]-2-methyl-7-(8-oxa-3-azabicyclo[3.2.1]oct-3-yl)-2-trifluoromethyl-2,3-dihydro-1H-imidazo[1,2-a]pyrimidin-5-one in 10 mL of DMF. After heating at 80° C. for 20 minutes, 52.60 mg (0.43 mmol) of 2-chloro-N,N-dimethylacetamide and 43.30 mg (0.29 mmol) of sodium iodide are added. The reaction medium is heated at 80° C. overnight. The reaction medium is evaporated to dryness. After purification by chromatography on silica gel (eluent A/B: DCM/MeOH, gradient A/B: t 0 min 0% B, t 25 min 10% B, t 30 min 10% B), 138 mg of N,N-dimethyl-2-(4-{2-[(S)-2-methyl-7-(8-oxa-3-azabicyclo[3.2.1]oct-3-yl)-5-oxo-2-trifluoromethyl-2,3-dihydro-5H-imidazo[1,2-a]pyrimidin-1-yl]ethyl}phenoxy)acetamide were obtained, corresponding to the following characteristics:

LC/MS (method B): ESI+ [M+H]+: m/z 536 tr (min)=0.69

$^1$H NMR (600 MHz, δ in ppm, DMSO-$d_6$): 1.53 (s, 3H), 1.68 (m, 2H), 1.82 (m, 2H), 2.75 (m, 1H), 2.81 (s, 3H), 2.95 (m, 3H), 2.97 (s, 3H), 3.38 (m, 1H), 3.52 (m, 1H), 3.73 (m, 2H), 3.82 (d, 1H), 4.13 (d, 1H), 4.41 (m, 2H), 4.74 (s, 2H), 4.76 (s, 1H), 6.85 (m, 2H), 7.12 (m, 2H).

EXAMPLE 38

(8S)-9-(2-ethyl-2-hydroxybutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 54)

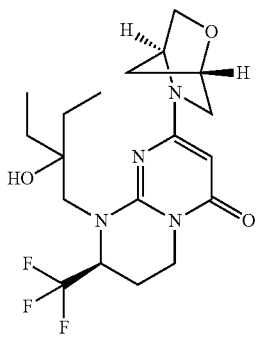 [SMILES: CCC(O)(CC)CN1c2nc(N3C[C@@H]4C[C@H]3CO4)cc(=O)n2CC[C@H]1C(F)(F)F]

Step 38.1: methyl ((8S)-8-(1S,4S)-2-oxa-5-azabicyclo[2.2.]hept-5-yl-6-oxo-2-trifluoromethyl-3,4-dihydro-2H,6H-pyrimido[1,2-a]pyrimidin-1-yl)acetate

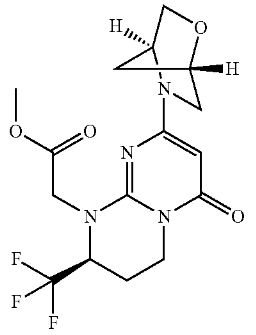 [SMILES: COC(=O)CN1c2nc(N3C[C@@H]4C[C@H]3CO4)cc(=O)n2CC[C@H]1C(F)(F)F]

150 mg (0.474 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one in 3 mL of DMF are added to a suspension of 18.97 mg (0.474 mmol) of sodium hydride in 7 mL of DMF. The reaction mixture is stirred at room temperature for 10 minutes. After addition of 45 μl (0.474 mmol) of methyl bromoacetate, the reaction is stirred at room temperature overnight. The reaction medium is evaporated to dryness. The residue is purified by chromatography on a column of silica (eluent: 95/5 DCM/MeOH). 147 mg of methyl ((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)acetate were obtained, corresponding to the following characteristics:

LC/MS (method G): ESI+ [M+H]+: m/z 389 tr (min)=1.70

$^1$H NMR (300 MHz, δ in ppm, DMSO-$d_6$): 1.81 (m, 2H), 2.11 (m, 1H), 2.40 (m, 1H), 3.13 (m, 3H), 3.50 (m, 1H), 3.57 (s, 3H), 3.69 (m, 1H), 4.16 (m, 1H), 4.27 (m, 1H), 4.50 (m, 1H), 4.68 (m, 4H).

Step 38.2: (8S)-9-(2-ethyl-2-hydroxybutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one

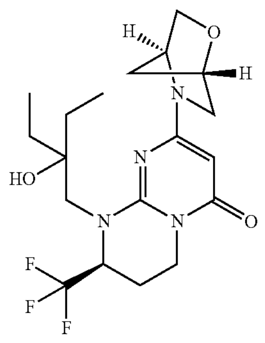 [SMILES: CCC(O)(CC)CN1c2nc(N3C[C@@H]4C[C@H]3CO4)cc(=O)n2CC[C@H]1C(F)(F)F]

631 μl (1.89 mmol) of a 3 M solution of ethylmagnesium bromide in ethyl ether are added at 0° C. to a solution of 147 mg (0.38 mmol) of methyl ((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)acetate in 10 mL of THF. The reaction medium is stirred at 0° C. for 4 hours, followed by addition of 10 mL of saturated ammonium chloride solution. The resulting mixture is extracted with ethyl acetate and the organic phase is then dried over magnesium sulfate and evaporated to dryness. After purification by chromatography on silica gel (eluent A/B: DCM/MeOH, gradient A/B: t 0 min 0% B, t 25 min 10% B, t 30 min 10% B), 80 mg of (8S)-9-(2-ethyl-2-hydroxybutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one were obtained, corresponding to the following characteristics:

LC/MS (method A): ESI+ [M+H]+: m/z 417 tr (min)=0.63

$^1$H NMR (600 MHz, δ in ppm, DMSO-$d_6$): 0.76 (m, 3H), 0.83 (m, 3H), 1.30 (m, 1H), 1.36 (m, 1H), 1.42 (m, 2H), 1.83 (m, 2H), 2.25 (m, 1H), 2.39 (m, 1H), 2.99 (m, 1H), 3.24 (m, 1H), 3.30 (m, 2H), 3.57 (m, 1H), 3.70 (m, 1H), 4.13 (m, 1H), 4.61 (m, 3H), 4.72 (m, 1H), 4.98 (m, 1H).

EXAMPLE 39

(8S)-9-(3-ethyl-3-hydroxypentyl)-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 49)

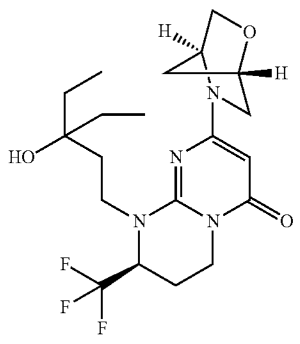 [SMILES: CCC(O)(CC)CCN1c2nc(N3C[C@@H]4C[C@H]3CO4)cc(=O)n2CC[C@H]1C(F)(F)F]

Step 39.1: methyl 3-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)-propionate

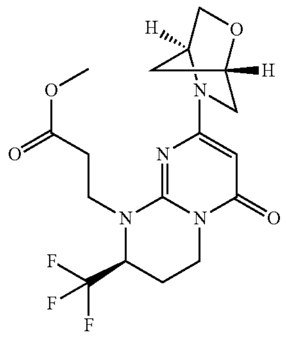 [SMILES: COC(=O)CCN1c2nc(N3C[C@@H]4C[C@H]3CO4)cc(=O)n2CC[C@H]1C(F)(F)F]

1 μl (0.006 mmol) of DBU and 274.94 mg (3.16 mmol) of methyl acrylate are added to a solution of 200 mg (0.632 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one in 5 mL of DMF. The reaction mixture is stirred at room temperature overnight. The reaction medium is evaporated to dryness. The residue is purified by chromatography on a column of silica (eluent: 95/5 DCM/MeOH). 245 mg of methyl 3-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)-propionate were obtained, corresponding to the following characteristics:

LC/MS (method G): ESI+ [M+H]+: m/z 403 tr (min)=1.83

$^1$H NMR (300 MHz, δ in ppm, DMSO-$d_6$): 1.61 (m, 2H), 1.85 (m, 1H), 2.11 (m, 1H), 2.43 (m, 1H), 2.61 (m, 1H), 2.88 (m, 2H), 3.09 (m, 2H), 3.35 (m, 4H), 3.48 (m, 1H), 3.95 (m, 2H), 4.45 (m, 4H).

Step 39.2: (8S)-9-(3-ethyl-3-hydroxypentyl)-2-(1S,4S)-2-oxa-5-azabicyclo[2.2.1]hept-5-yl-8-trifluoromethyl-6,7,8,9-tetrahydropyrimido[1,2-a]pyrimidin-4-one

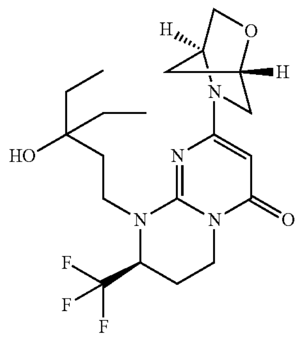 [SMILES: CCC(O)(CC)CCN1c2nc(N3C[C@@H]4C[C@H]3CO4)cc(=O)n2CC[C@H]1C(F)(F)F]

911 μl (2.73 mmol) of a 3 M solution of ethylmagnesium bromide in ethyl ether are added at 0° C. to a solution of 220 mg (0.55 mmol) of methyl 3-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)-propionate in 10 mL of THF. The reaction medium is stirred at 0° C. for 2 hours. 10 mL of saturated ammonium chloride solution are added to the reaction medium. The resulting mixture is extracted with ethyl acetate and the organic phase is then dried over magnesium sulfate and evaporated to dryness. After purification by chromatography on silica gel (eluent A/B: DCM/MeOH, gradient A/B: t 0 min 0% B, t 25 min 10% B, t 30 min 10% B), 128 mg of (8S)-9-(3-ethyl-3-hydroxypentyl)-2-(1S,4S)-2-oxa-5-azabicyclo[2.2.1]hept-5-yl-8-trifluoromethyl-6,7,8,9-tetrahydropyrimido[1,2-a]pyrimidin-4-one were obtained, corresponding to the following characteristics:

LC/MS (method A): ESI+ [M+H]+: m/z 431 tr (min)=0.63

$^1$H NMR (600 MHz, δ in ppm, DMSO-$d_6$): 0.80 (m, 6H), 1.36 (m, 4H), 1.63 (m, 1H), 1.71 (m, 1H), 1.82 (m, 2H), 2.05 (m, 1H), 2.34 (m, 1H), 3.15 (m, 1H), 3.23 (m, 1H), 3.62 (m, 1H), 3.70 (m, 1H), 3.99 (m, 1H), 4.19 (m, 2H), 4.51 (m, 2H), 4.64 (m, 2H), 5.01-5.12 (bs, 1H).

EXAMPLE 40

(8S)-2-(1S,4S)-2-oxa-5-azabicyclo[2.2.1]hept-5-yl-9-(2-oxo-2-pyrid-2-ylethyl)-8-trifluoromethyl-6,7,8,9-tetrahydropyrimido[1,2-a]pyrimidin-4-one (Compound 68)

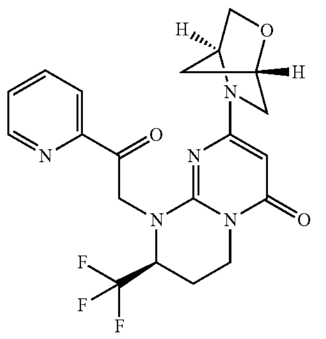 [SMILES: O=C(CN1c2nc(N3C[C@@H]4C[C@H]3CO4)cc(=O)n2CC[C@H]1C(F)(F)F)c1ccccn1]

Step 40.1: (8S)-2-chloro-9-(2-oxo-2-pyrid-2-ylethyl)-8-trifluoromethyl-6,7,8,9-tetrahydropyrimido[1,2-a]pyrimidin-4-one

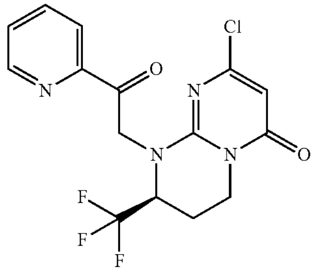 [SMILES: O=C(CN1c2nc(Cl)cc(=O)n2CC[C@H]1C(F)(F)F)c1ccccn1]

The procedure used is the same as that of step 12.3.

150 mg (0.591 mmol) of (8S)-2-chloro-8-trifluoromethyl-6,7,8,9-tetrahydropyrimido[1,2-a]pyrimidin-4-one, 578.71 mg (1.77 mmol) of cesium carbonate, 199.40 mg (0.709 mmol) of 2-bromo-1-pyrid-2-ylethanone hydrobromide and 10 mL of acetonitrile were used in the reaction. After purification by chromatography on silica gel (eluent A/B: heptane/EtOAc, gradient A/B: t 0 min 0% B, t 15 min 50% B, t 25 min 70% B), 218 mg of (8S)-2-chloro-9-(2-oxo-2-pyrid-2-ylethyl)-8-trifluoromethyl-6,7,8,9-tetrahydropyrimido[1,2-a]pyrimidin-4-one were obtained, corresponding to the following characteristics:

LC/MS (method G): ESI+ [M+H]+: m/z 373 tr (min)=2.14

$^1$H NMR (300 MHz, δ in ppm, DMSO-$d_6$): 2.28 (m, 1H), 3.40 (m, 1H), 4.40 (m, 1H), 4.80 (m, 1H), 5.11 (d, 1H), 5.61 (d, 1H), 5.77 (m, 1H), 5.93 (s, 1H), 7.76 (m, 1H), 8.00 (m, 1H), 8.08 (m, 1H), 8.79 (m, 1H).

Step 40.2: (8S)-2-(1S,4S)-2-oxa-5-azabicyclo[2.2.1]hept-5-yl-9-(2-oxo-2-pyrid-2-ylethyl)-8-trifluoromethyl-6,7,8,9-tetrahydropyrimido[1,2-a]pyrimidin-4-one

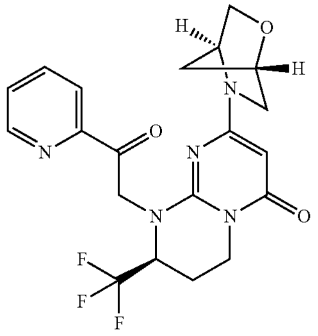 [SMILES: O=C(CN1c2nc(N3C[C@@H]4C[C@H]3CO4)cc(=O)n2CC[C@H]1C(F)(F)F)c1ccccn1]

The procedure used is the same as that of step 12.4.

218 mg (0.58 mmol) of (8S)-2-chloro-9-(2-oxo-2-pyrid-2-ylethyl)-8-trifluoromethyl-6,7,8,9-tetrahydropyrimido[1,2-a]pyrimidin-4-one, 95.17 mg (0.702 mmol) of (1S,4S)-2-oxa-5-azabicyclo[2.2.1]heptane hydrochloride and 205 μl (1.46 mmol) of triethylamine were used in the reaction. After purification by chromatography on silica gel (eluent A/B: 95/5 DCM/MeOH), 103 mg of (8S)-2-(1S,4S)-2-oxa-5-azabicyclo[2.2.1]hept-5-yl-9-(2-oxo-2-pyrid-2-ylethyl)-8-trifluoromethyl-6,7,8,9-tetrahydropyrimido[1,2-a]pyrimidin-4-one were obtained, corresponding to the following characteristics:

LC/MS (method A): ESI+ [M+H]+: m/z 436 tr (min)=0.59

$^1$H NMR (600 MHz, δ in ppm, DMSO-$d_6$): 1.59 (m, 1H), 1.68 (m, 1H), 2.24 (m, 1H), 2.44 (m, 1H), 2.90 (m, 2H), 3.08-3.20 (bs, 2H), 3.25 (m, 1H), 4.26 (m, 1H), 4.37 (m, 1H), 4.47 (m, 1H), 4.62 (m, 1H), 4.72 (m, 1H), 4.82 (m, 1H), 5.70 (m, 1H), 7.73 (m, 1H), 7.98 (m, 1H), 8.07 (m, 1H), 8.78 (m, 1H).

EXAMPLE 41

(8S)-9-{2-[6-(2-hydroxyethylamino)pyrid-3-yl]-2-oxoethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 14)

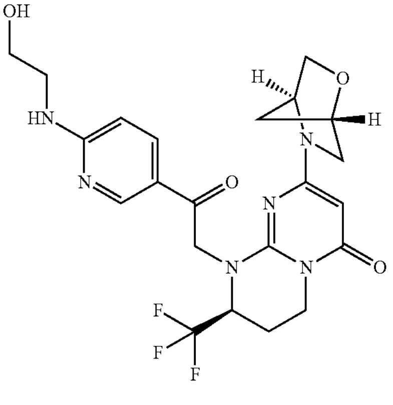 [SMILES: O=C(CN1c2nc(N3C[C@@H]4C[C@H]3CO4)cc(=O)n2CC[C@H]1C(F)(F)F)c1ccc(NCCO)nc1]

Step 41.1: (8S)-9-[2-(6-chloropyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

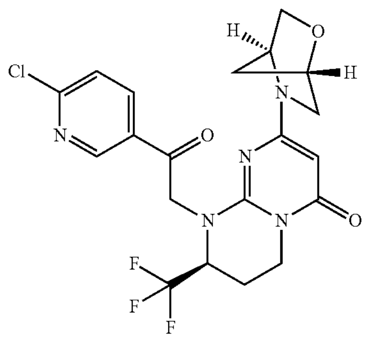 [SMILES: O=C(CN1c2nc(N3C[C@@H]4C[C@H]3CO4)cc(=O)n2CC[C@H]1C(F)(F)F)c1ccc(Cl)nc1]

100 mg (0.32 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one in 3 mL of DMF are added to a suspension of 41.73 mg (1.04 mmol) of sodium hydride in 5 mL of DMF. The reaction mixture is stirred at room temperature for 10 minutes. After addition of 244.65 mg (1.04 mmol) of 2-bromo-1-(6-chloropyrid-3-yl)ethanone, the reaction is continued at room temperature overnight. The reaction medium is evaporated to dryness. The residue is purified by chromatography on a column of silica (eluent: 90/10 DCM/MeOH). 85 mg of (8S)-9-[2-(6-chloropyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one were obtained, corresponding to the following characteristics:

LC/MS (method G): ESI+ [M+H]+: m/z 470 tr (min)=1.86

$^{1}$H NMR (600 MHz, δ in ppm, DMSO-$d_6$): 1.65 (m, 2H), 2.28 (m, 1H), 2.93 (m, 3H), 3.19 (m, 3H), 4.45 (m, 3H), 4.71 (m, 3H), 5.74 (m, 1H), 7.78 (m, 1H), 8.41 (m, 1H), 9.10 (m, 1H).

Step 41.2: (8S)-9-{2-[6-(2-hydroxyethylamino)pyrid-3-yl]-2-oxoethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one

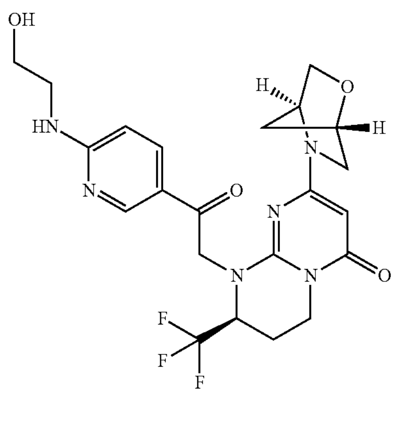 [SMILES: O=C(CN1c2nc(N3C[C@@H]4C[C@H]3CO4)cc(=O)n2CC[C@H]1C(F)(F)F)c1ccc(NCCO)nc1]

A mixture of 0.50 mL of ethanol, 33 mg (0.070 mmol) of (8S)-9-[2-(6-chloropyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one and 21.41 μl (0.352 mmol) of ethanolamine is heated in a Biotage microwave reactor at 130° C. for 30 minutes. The reaction mixture is evaporated to dryness and the residue is then taken up in 10 mL of water. The precipitate is filtered off and then dried under vacuum. 17 mg of (8S)-9-{2-[6-(2-hydroxyethylamino)pyrid-3-yl]-2-oxoethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one are obtained, the characteristics of which are as follows:

LC/MS (method A): ESI+ [M+H]+: m/z 495 tr (min)=0.40

$^{1}$H NMR (600 MHz, δ in ppm, DMSO-$d_6$): 1.62 (m, 1H), 1.73 (m, 1H), 2.23 (m, 1H), 2.41 (m, 1H), 2.91-3.12 (bs, 3H), 3.23 (m, 1H), 3.42 (m, 2H), 3.54 (m, 2H), 4.36 (m, 2H), 4.49 (m, 2H), 4.60 (m, 2H), 4.74 (m, 1H), 5.60 (d, 1H), 6.58 (d, 1H), 7.53 (m, 1H), 7.88 (m, 1H), 8.77 (m, 1H).

EXAMPLE 42

(8S)-9-[2-(6-methylaminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 5)

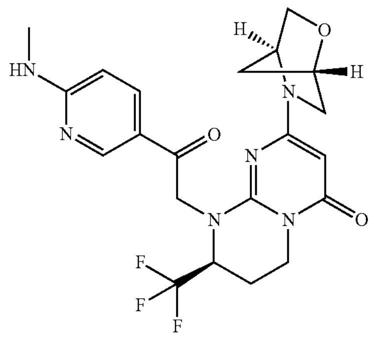 [SMILES: CNc1ccc(C(=O)CN2c3nc(N4C[C@@H]5C[C@H]4CO5)cc(=O)n3CC[C@H]2C(F)(F)F)cn1]

Step 42.1: 1-(6-methylaminopyrid-3-yl)ethanone

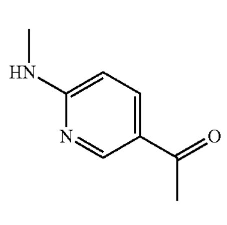

A mixture of 2 mL of ethanol, 280 mg (1.80 mmol) of 1-(6-chloropyrid-3-yl)ethanone and 4.50 mL (9 mmol) of a 2 M solution of methylamine in THF is heated in a Biotage microwave reactor at 130° C. for 30 minutes. The reaction medium is evaporated to dryness. The crude product is taken up in water and extracted with EtOAc. The organic phase is dried over magnesium sulfate and evaporated to dryness. 258 mg of 1-(6-methylaminopyrid-3-yl)ethanone are obtained, the characteristics of which are as follows:

$^1H$ NMR (300 MHz, δ in ppm, DMSO-$d_6$): 2.42 (s, 3H), 2.84 (s, 3H), 6.47 (m, 1H), 7.42 (m, 1H), 7.85 (m, 1H), 8.65 (m, 1H).

Step 42.2: 2-bromo-1-(6-methylaminopyrid-3-yl)ethanone

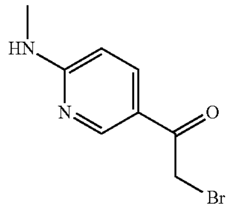

The procedure used is the same as that of step 12.2.

380 mg (2.53 mmol) of 1-(6-methylaminopyrid-3-yl)ethanone, 416 μl (2.53 mmol) of hydrobromic acid, 130 μl (2.53 mmol) of bromine and 5 mL of glacial acetic acid were used in the reaction. After precipitation with ethyl ether and filtration, the precipitate is taken up in water. The solution is basified with saturated $NaHCO_3$ solution. The precipitate formed is filtered off, washed with water and then dried under vacuum. 370 mg of 2-bromo-1-(6-methylaminopyrid-3-yl) ethanone are obtained, the characteristics of which are as follows:

$^1H$ NMR spectrum (300 MHz, δ in ppm, DMSO-$d_6$): 2.85 (s, 3H), 4.70 (s, 2H), 6.50 (m, 1H), 7.62 (m, 1H), 7.87 (m, 1H), 8.71 (m, 1H).

Step 42.3: (8S)-9-[2-(6-methylaminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

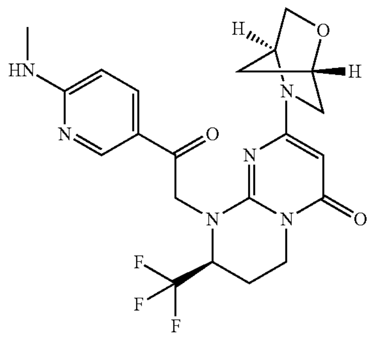

100 mg (0.32 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one in 3 mL of DMF are added to a suspension of 13.91 mg (0.35 mmol) of sodium hydride in 5 mL of DMF. The reaction mixture is stirred at room temperature for 15 minutes. After dropwise addition of 79.67 mg (0.35 mmol) of 2-bromo-1-(6-methylaminopyrid-3-yl)ethanone dissolved in 3 mL of DMF, the reaction is continued at room temperature for 1 hour. The reaction medium is evaporated to dryness. The residue is purified by chromatography on a column of silica (eluent A/B: DCM/MeOH, gradient A/B: t 0 min 0% B, t 25 min 10% B, t 30 min 15% B). 75 mg of (8S)-9-[2-(6-methylaminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one were obtained, corresponding to the following characteristics:

LC/MS (method A): ESI+ [M+H]+: m/z 465 tr (min)=0.41

$^1H$ NMR spectrum (600 MHz, δ in ppm, DMSO-$d_6$): 1.62 (m, 1H), 1.73 (m, 1H), 2.23 (m, 1H), 2.42 (m, 1H), 2.86 (s, 3H), 2.92-3.16 (bs, 3H), 3.23 (m, 2H), 4.37 (m, 2H), 4.49 (m, 2H), 4.60 (m, 2H), 5.60 (m, 1H), 6.51 (m, 1H), 7.47 (m, 1H), 7.92 (m, 1H), 8.78 (m, 1H).

EXAMPLE 43

2-methyl-1-[2-(6-methylaminopyrid-3-yl)-2-oxoethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one (Compound 9)

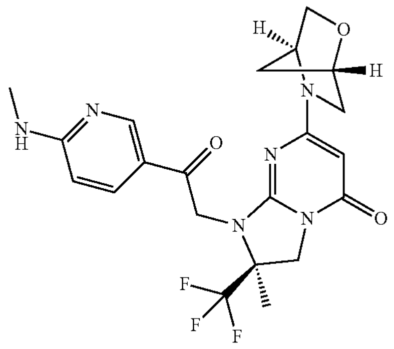 [SMILES: CNc1ccc(C(=O)CN2c3nc(N4C[C@@H]5C[C@H]4CO5)cc(=O)n3C[C@@]2(C)C(F)(F)F)cn1]

100 mg (0.32 mmol) of 2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one in 3 mL of DMF are added to a suspension of 13.91 mg (0.35 mmol) of sodium hydride in 5 mL of DMF. The reaction mixture is stirred at room temperature for 15 minutes. After dropwise addition of 79.67 mg (0.35 mmol) of 2-bromo-1-(6-methylaminopyrid-3-yl)ethanone dissolved in 3 mL of DMF, the reaction is continued at room temperature for 1 hour. The reaction medium is evaporated to dryness. The residue is purified by chromatography on a column of silica (eluent A/B: DCM/MeOH, gradient A/B: t 0 min 0% B, t 25 min 10% B, t 30 min 15% B). 100 mg of 2-methyl-1-[2-(6-methylaminopyrid-3-yl)-2-oxoethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one were obtained, corresponding to the following characteristics:

LC/MS (method A): ESI+ [M+H]+: m/z 465 tr (min)=0.42

$^1H$ NMR (600 MHz, δ in ppm, DMSO-$d_6$): 1.61 (s, 3H), 1.70 (m, 1H), 1.75 (m, 1H), 2.86 (d, 3H), 2.93-3.26 (bs, 3H), 3.35 (m, 1H), 3.98 (m, 1H), 4.22 (m, 1H), 4.53 (m, 3H), 4.64 (d, 1H), 5.05 (d, 1H), 6.51 (m, 1H), 7.50 (m, 1H), 7.91 (m, 1H), 8.79 (m, 1H).

EXAMPLE 44

4-[2-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)ethyl]piperidine-1-carbaldehyde (Compound 90)

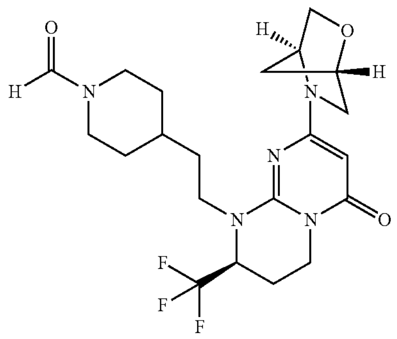 [SMILES: O=CN1CCC(CCN2c3nc(N4C[C@@H]5C[C@H]4CO5)cc(=O)n3CC[C@H]2C(F)(F)F)CC1]

Step 44.1: tert-butyl 4-[2-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)ethyl]piperidine-1-carboxylate

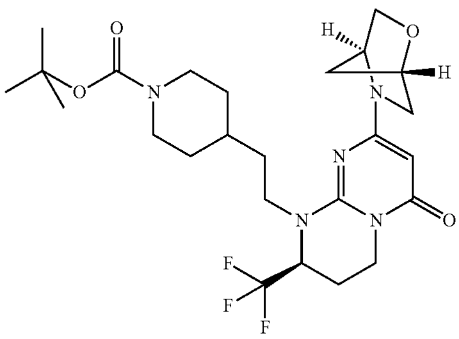 [SMILES: CC(C)(C)OC(=O)N1CCC(CCN2c3nc(N4C[C@@H]5C[C@H]4CO5)cc(=O)n3CC[C@H]2C(F)(F)F)CC1]

1.03 g (3.54 mmol) of tert-butyl 4-(2-bromoethyl)piperidine-1-carboxylate and 530 mg (3.54 mmol) of sodium iodide are added to a solution of 800 mg (2.53 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one and 2.47 g (7.59 mmol) of cesium carbonate in 15 mL of acetonitrile. The reaction mixture is heated in a Biotage microwave reactor at 100° C. for 1 hour 15 minutes. The reaction medium is evaporated to dryness and the residue is taken up in EtOAc and washed with water and with saturated NaCl. The organic phase is dried over magnesium sulfate and evaporated to dryness. The residue is purified by chromatography on silica gel (eluent: 90/10 DCM/MeOH) to give 730 mg of tert-butyl 4-[2-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)ethyl]piperidine-1-carboxylate, the characteristics of which are as follows:

LC/MS (method G): ESI+ [M+H]+: m/z 528 tr (min)=2.57

$^1$H NMR spectrum (300 MHz, δ in ppm, DMSO-$d_6$): 0.98 (m, 2H), 1.24 (m, 1H), 1.38 (s, 9H), 1.47 (m, 1H), 1.61 (m, 3H), 1.84 (m, 2H), 2.03 (m, 1H), 2.33 (m, 1H), 2.68 (m, 2H), 3.13 (m, 3H), 3.32 (m, 3H), 3.57-3.75 (dd, 2H), 3.88 (m, 2H), 7.92 (m, 1H), 4.18 (m, 2H), 4.63 (m, 2H).

Step 44.2: (8S)-2-(1S,4S)-2-oxa-5-azabicyclo[2.2.1]hept-5-yl-9-(2-piperidin-4-ylethyl)-8-trifluoromethyl-6,7,8,9-tetrahydropyrimido[1,2-a]pyrimidin-4-one

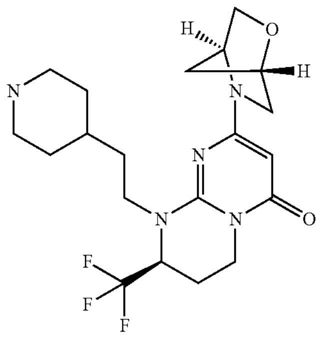 [SMILES: O=c1cc(N2C[C@@H]3C[C@H]2CO3)nc2n1CC[C@@H](C(F)(F)F)N2CCC1CCNCC1]

A solution of 250 mg (0.473 mmol) of tert-butyl 4-[2-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)ethyl]piperidine-1-carboxylate in 10 mL of formic acid is stirred for 1 hour 30 minutes at room temperature.

The reaction mixture is evaporated to dryness and the residue is taken up in DCM and evaporated to give 224 mg of (8S)-2-(1S,4S)-2-oxa-5-azabicyclo[2.2.1]hept-5-yl-9-(2-piperid-4-ylethyl)-8-trifluoromethyl-6,7,8,9-tetrahydropyrimido[1,2-a]pyrimidin-4-one, the characteristics of which are as follows:

LC/MS (method G): ESI+ [M+H]+: m/z 428 tr (min)=1.34

Step 44.3: 4-[2-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)ethyl]piperidine-1-carbaldehyde

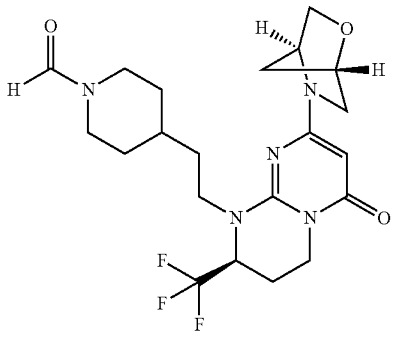 [SMILES: O=CN1CCC(CCN2c3nc(N4C[C@@H]5C[C@H]4CO5)cc(=O)n3CC[C@H]2C(F)(F)F)CC1]

33 mg (0.521 mmol) of ammonium formate are added to a suspension of 224 mg (0.474 mmol) of (8S)-2-(1S,4S)-2-oxa-5-azabicyclo[2.2.1]hept-5-yl-9-(2-piperid-4-ylethyl)-8-trifluoromethyl-6,7,8,9-tetrahydropyrimido[1,2-a]pyrimidin-4-one in 10 mL of 1,4-dioxane. The reaction mixture is heated at 100° C. for 4 hours and then evaporated to dryness. The residue is taken up in DCM and the solution is washed with water and with saturated NaCl. The organic phase is dried over sodium sulfate and evaporated to dryness. The product obtained is purified by chromatography on silica gel (eluent: 90/10 DCM/MeOH) to give 85 mg of 4-[2-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)ethyl]piperidine-1-carbaldehyde, the characteristics of which are as follows:

LC/MS (method A): ESI+ [M+H]+: m/z 456 tr (min)=0.54

$^1$H NMR (600 MHz, δ in ppm, DMSO-$d_6$): 0.83-1.11 (m, 2H), 1.5 (m, 2H), 1.58-1.77 (m, 3H), 1.85 (m, 2H), 2.04 (m, 1H), 2.34 (m, 1H), 2.57 (m, 1H), 2.99 (m, 1H), 3.02-3.23 (m, 3H), 3.33 (m, 1H), 3.59-3.75 (m, 3H), 4.07-4.21 (m, 3H), 4.55-4.99 (m, 4H), 7.95 (s, 1H).

EXAMPLE 45

(8S)-2-(1S,4S)-2-oxa-5-azabicyclo[2.2.1]hept-5-yl-9-[2-(tetrahydropyran-4-yl)ethyl]-8-trifluoromethyl-6,7,8,9-tetrahydropyrimido[1,2-a]pyrimidin-4-one (Compound 92)

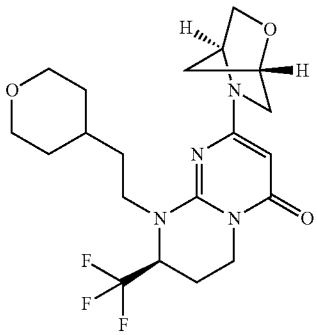

Step 45.1: 2-(tetrahydro-2H-pyran-4-yl)ethyl 4-methylbenzenesulfonate

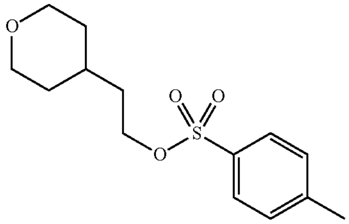 [SMILES: Cc1ccc(S(=O)(=O)OCCC2CCOCC2)cc1]

629 μL (4.47 mmol) of triethylamine and 813 mg (4.10 mmol) of p-toluenesulfonyl chloride are added to a solution of 500 mg (3.73 mmol) of 2-(tetrahydropyran-4-yl)ethanol in 15 mL of DCM previously cooled to 0° C.

The reaction mixture is stirred at room temperature overnight. The solution is taken up in DCM, washed with aqueous $NaHCO_3$ solution, dried over magnesium sulfate and then evaporated to dryness. The residue is purified by chromatography on silica gel (eluent: 20/80 EtOAc/heptane) to give 840 mg of 2-(tetrahydro-2H-pyran-4-yl)ethyl 4-methylbenzenesulfonate, corresponding to the following characteristics:

$^1$H NMR (300 MHz, δ in ppm, $CDCl_3$): 1.15-1.32 (m, 2H), 1.45-1.74 (m, 5H), 2.47 (s, 3H), 3.33 (td, 2H), 3.88-3.96 (m, 2H), 4.09 (t, 2H), 7.37 (d, 2H), 7.82 (d, 2H).

Step 45.2: (8S)-2-(1S,4S)-2-oxa-5-azabicyclo[2.2.1]hept-5-yl-9-[2-(tetrahydropyran-4-yl)ethyl]-8-trifluoromethyl-6,7,8,9-tetrahydropyrimido[1,2-a]pyrimidin-4-one

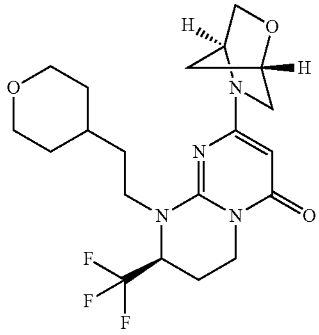

198 mg (0.698 mmol) of 2-(tetrahydro-2H-pyran-4-yl)ethyl 4-methylbenzenesulfonate and 104 mg (0.698 mmol) of sodium iodide are added to a solution of 170 mg (0.537 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one and 525 mg (1.61 mmol) of cesium carbonate in 5 mL of acetonitrile. The reaction mixture is heated in a Biotage microwave reactor at 100° C. for 1 hour 15 minutes. The reaction medium is evaporated to dryness and the residue is taken up in EtOAc and washed with water and with saturated NaCl. The organic phase is dried over magnesium sulfate and evaporated to dryness. The residue is purified by chromatography on silica gel (eluent: 95/5 DCM/MeOH) to give 140 mg of (8S)-2-(1S,4S)-2-oxa-5-azabicyclo[2.2.1]hept-5-yl-9-[2-(tetrahydropyran-4-yl)ethyl]-8-trifluoromethyl-6,7,8,9-tetrahydropyrimido[1,2-a]pyrimidin-4-one, the characteristics of which are as follows:

LC/MS (method A): ESI+ [M+H]+: m/z 429 tr (min)=0.61

$^1$H NMR spectrum (600 MHz, δ in ppm, DMSO-$d_6$): 1.09-1.25 (m, 2H), 1.46-1.57 (m, 3H), 1.58-1.67 (m, 2H), 1.82-1.89 (m, 2H), 2.04 (m, 1H), 2.34 (m, 1H), 2.96-2-3.22 (m, 3H), 3.23-3.37 (m, 4H), 3.63 (m, 1H), 3.73 (m, 1H), 3.82 (m, 2H), 4.11 (m, 1H), 4.21 (m, 1H), 4.57-5.01 (m, 3H).

EXAMPLE 46

(8S)-2-(1S,4S)-2-oxa-5-azabicyclo[2.2.1]hept-5-yl-9-(tetrahydropyran-4-ylmethyl)-8-trifluoromethyl-6,7,8,9-tetrahydropyrimido[1,2-a]pyrimidin-4-one (Compound 93)

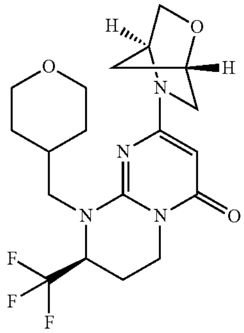 [SMILES: O=c1cc(N2C[C@@H]3C[C@H]2CO3)nc2n1CC[C@@H](C(F)(F)F)N2CC1CCOCC1]

Step 46.1: (8S)-2-chloro-9-(tetrahydropyran-4-ylmethyl)-8-trifluoromethyl-6,7,8,9-tetrahydropyrimido [1,2-a]pyrimidin-4-one

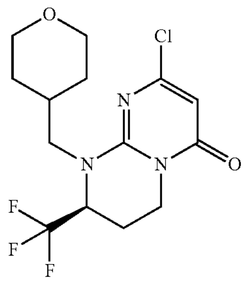 [SMILES: O=c1cc(Cl)nc2n1CC[C@@H](C(F)(F)F)N2CC1CCOCC1]

A suspension of 200 mg (0.788 mmol) of (8S)-2-chloro-8-trifluoromethyl-6,7,8,9-tetrahydropyrimido[1,2-a]pyrimidin-4-one and 771 mg (2.37 mmol) of cesium carbonate in 10 mL of acetonitrile is stirred for 15 minutes at room temperature. 187 mg (0.788 mmol) of (bromomethyl)tetrahydropyran are then added.

The reaction mixture is heated in a Biotage microwave reactor at 100° C. for 50 minutes. The crude product is evaporated and the residue is taken up in water and extracted with ethyl acetate. The organic phase is dried over magnesium sulfate and evaporated to dryness. The residue is purified by chromatography on silica gel (eluent: 95/5 DCM/MeOH) to give 220 mg of (8S)-2-chloro-9-(tetrahydropyran-4-ylmethyl)-8-trifluoromethyl-6,7,8,9-tetrahydropyrimido[1,2-a] pyrimidin-4-one, corresponding to the following characteristics:

LC/MS (method G): ESI+ [M+H]+: m/z 352 tr (min)=2.08

$^1$H NMR spectrum (300 MHz, δ in ppm, DMSO-$d_6$): 1.04-1.42 (m, 2H), 1.42-1.57 (m, 2H), 2.04-2.33 (m, 2H), 2.34-2.46 (m, 1H), 2.95-3.07 (m, 1H), 3.17-3.30 (m, 3H), 3.79-3.89 (m, 2H), 4.04-4.21 (m, 2H), 4.72 (m, 1H), 5.89 (s, 1H).

Step 46.2: (8S)-2-(1S,4S)-2-oxa-5-azabicyclo[2.2.1] hept-5-yl-9-(tetrahydropyran-4-ylmethyl)-8-trifluoromethyl-6,7,8,9-tetrahydropyrimido[1,2-a]pyrimidin-4-one

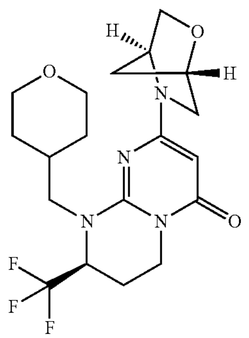 [SMILES: O=c1cc(N2C[C@@H]3C[C@H]2CO3)nc2n1CC[C@@H](C(F)(F)F)N2CC1CCOCC1]

220 mg (0.62 mmol) of (8S)-2-chloro-9-(tetrahydropyran-4-ylmethyl)-8-trifluoromethyl-6,7,8,9-tetrahydropyrimido[1,2-a]pyrimidin-4-one and 127 mg (0.93 mmol) of (1S,4S)-2-oxa-5-azabicyclo[2.2.1]heptane hydrochloride are mixed together. The powder obtained is placed in a tube and 244 μL (1.75 mmol) of triethylamine are added. The tube is sealed and heated at 130° C. in an oil bath for 4 hours. The crude product obtained is taken up in ethyl acetate and the organic phase is washed with water, dried over magnesium sulfate and then evaporated to dryness. The residue is purified by chromatography on silica gel (eluent: 95/5 DCM/MeOH) to give 180 mg of (8S)-2-(1S,4S)-2-oxa-5-azabicyclo[2.2.1]hept-5-yl-9-(tetrahydropyran-4-ylmethyl)-8-trifluoromethyl-6,7,8,9-tetrahydropyrimido[1,2-a]pyrimidin-4-one, the characteristics of which are as follows:

LC/MS (method A): ESI+ [M+H]+: m/z 415 tr (min)=0.57

$^1$H NMR (600 MHz, δ in ppm, DMSO-$d_6$): 1.10-1.38 (m, 2H), 1.40-1.56 (m, 2H), 1.79-1.89 (m, 2H), 2.06-2.22 (m, 2H), 2.32 (m, 1H), 2.89 (m, 1H), 2.95-3.14 (m, 2H), 3.20 (m, 3H), 3.61 (m, 1H), 3.73 (m, 1H), 3.83 (m, 2H), 4.07-4.17 (m, 2H), 4.56 (m, 1H), 4.60-4.96 (m, 3H).

EXAMPLE 47

4-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-ylmethyl)piperidine-1-carbaldehyde (Compound 95)

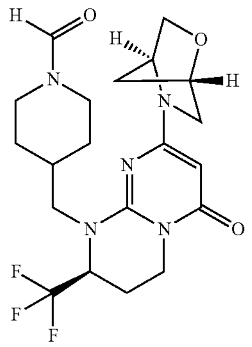 [SMILES: O=CN1CCC(CN2c3nc(N4C[C@@H]5C[C@H]4CO5)cc(=O)n3CC[C@H]2C(F)(F)F)CC1]

Step 47.1: tert-butyl 4-bromomethylpiperidine-1-carboxylate

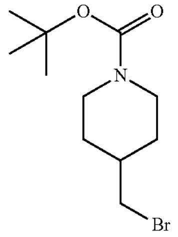

A solution of 1 g (4.41 mmol) of tert-butyl 4-hydroxymethylpiperidine-1-carboxylate in 25 mL of THF is cooled to 0° C. 1.34 g (5.07 mmol) of triphenylphosphine and 2.02 g (5.96 mmol) of carbon tetrabromide are then added.

The reaction mixture is stirred at room temperature over the weekend.

The solution is taken up in ethyl ether, the insoluble matter is filtered off and the organic phase is evaporated to dryness. The residue is purified by chromatography on silica gel (eluent: 80/20 EtOAc/heptane) to give 960 mg of tert-butyl 4-bromomethylpiperidine-1-carboxylate, the characteristics of which are as follows:

LC/MS (method G): ESI+ [M+H]+: m/z 279 tr (min)=2.13

$^1$H NMR (300 MHz, δ in ppm, $CDCl_3$): 1.09-1.29 (m, 2H), 1.47 (s, 9H), 1.71-1.88 (m, 3H), 2.62-2.78 (m, 2H), 3.31 (d, 2H), 4.07-4.25 (m, 2H).

Step 47.2: tert-butyl 4-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-ylmethyl)piperidine-1-carboxylate

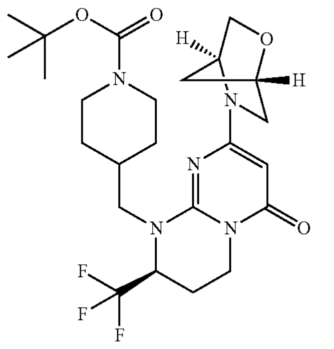 [SMILES: CC(C)(C)OC(=O)N1CCC(CN2c3nc(N4C[C@@H]5C[C@H]4CO5)cc(=O)n3CC[C@H]2C(F)(F)F)CC1]

788 mg (2.84 mmol) of tert-butyl 4-bromomethylpiperidine-1-carboxylate and 425 mg (2.84 mmol) of sodium iodide are added to a solution of 690 mg (2.18 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one and 2.13 g (6.54 mmol) of cesium carbonate in 10 mL of acetonitrile. The reaction mixture is heated in a Biotage microwave reactor at 100° C. for 3 hours. The reaction medium is evaporated to dryness and the residue is taken up in EtOAc and washed with water and with saturated NaCl. The organic phase is dried over magnesium sulfate and evaporated to dryness. The residue is purified by chromatography on silica gel (eluent: 95/5 DCM/MeOH) to give 510 mg of tert-butyl 4-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-ylmethyl)piperidine-1-carboxylate, the characteristics of which are as follows:

LC/MS (method G): ESI+ [M+H]+: m/z 514 tr (min)=2.45

$^1$H NMR (300 MHz, δ in ppm, DMSO-$d_6$): 0.93-1.03 (m, 1H), 1.11-1.32 (m, 3H), 1.38 (s, 9H), 1.44-1.64 (m, 2H), 1.76-1.91 (m, 2H), 1.99-2.39 (m, 3H), 2.78-3.32 (m, 5H), 3.60 (m, 1H), 3.71 (m, 1H), 3.86-3.99 (m, 2H), 4.06-4.19 (m, 2H), 4.48-4.92 (m, 3H).

Step 47.3: (8S)-2-(1S,4S)-2-oxa-5-azabicyclo[2.2.1]hept-5-yl-9-piperid-4-ylmethyl-8-trifluoromethyl-6,7,8,9-tetrahydropyrimido[1,2-a]pyrimidin-4-one

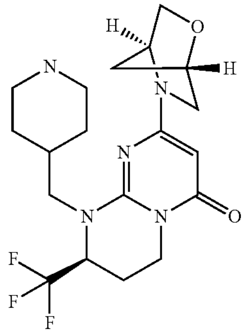

A solution of 280 mg (0.545 mmol) of tert-butyl 4-((S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-ylmethyl)piperidine-1-carboxylate in 10 mL of formic acid is stirred for 2 hours at room temperature. The reaction mixture is evaporated to dryness and the residue is taken up in DCM and evaporated to give 250 mg of (8S)-2-(1S,4S)-2-oxa-5-azabicyclo[2.2.1]hept-5-yl-9-piperid-4-ylmethyl-8-trifluoromethyl-6,7,8,9-tetrahydropyrimido[1,2-a]pyrimidin-4-one, the characteristics of which are as follows:

LC/MS (method G): ESI+ [M+H]+: m/z 414 tr (min)=1.31

Step 47.4: 4-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-ylmethyl)piperidine-1-carbaldehyde

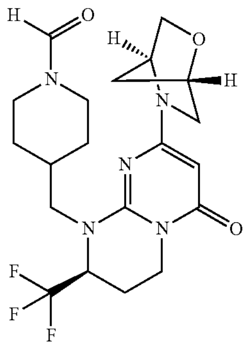 [SMILES: O=CN1CCC(CN2c3nc(N4C[C@@H]5C[C@H]4CO5)cc(=O)n3CC[C@H]2C(F)(F)F)CC1]

41 mL (0.817 mmol) of ammonium formate are added to a suspension of 250 mg (0.545 mmol) of (8S)-2-(1S,4S)-2-oxa-5-azabicyclo[2.2.1]hept-5-yl-9-piperid-4-ylmethyl-8-trifluoromethyl-6,7,8,9-tetrahydropyrimido[1,2-a]pyrimidin-4-one in 10 mL of 1,4-dioxane. The reaction mixture is heated at 100° C. for 2 hours and then evaporated to dryness. The residue is taken up in EtOAc and washed with aqueous $NaHCO_3$ solution and with saturated NaCl. The organic phase is dried over sodium sulfate and evaporated to dryness. The product obtained is purified by chromatography on silica gel (eluent: 90/10 DCM/MeOH) to give 120 mg of 4-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-ylmethyl)piperidine-1-carbaldehyde, the characteristics of which are as follows:

LC/MS (method D): ESI+ [M+H]+: m/z 442 tr (min)=0.82

$^1$H NMR (600 MHz, δ in ppm, DMSO-$d_6$): 0.91-1.24 (m, 2H), 1.56-1.75 (m, 2H), 1.81-1.91 (m, 2H), 2.14-2.29 (m, 2H), 2.36 (m, 1H), 2.54 (m, 1H), 2.96 (m, 2H), 3.15 (m, 1H), 3.21-3.40 (m, 2H), 3.66 (m, 2H), 3.74 (m, 1H), 4.10-4.23 (m, 3H), 4.51 (m, 1H), 4.58-4.84 (m, 3H), 7.99 (m, 1H).

EXAMPLE 48

(8S)-2-(1S,4S)-2-oxa-5-azabicyclo[2.2.1]hept-5-yl-9-(3,3,3-trifluoro-2-hydroxy-2-trifluoromethylpropyl)-8-trifluoromethyl-6,7,8,9-tetrahydropyrimido[1,2-a]pyrimidin-4-one (Compound 96)

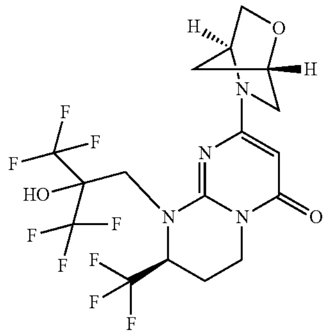 [SMILES: O=c1cc(N2C[C@@H]3C[C@H]2CO3)nc2n1CC[C@@H](C(F)(F)F)N2CC(O)(C(F)(F)F)C(F)(F)F]

264 mg (1.42 mmol) of bis(trifluoromethyl)oxirane are added to a solution of 300 mg (0.948 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one and 1.66 ml (1.66 mmol) of 1 M sodium hydroxide in 5 mL of 1,4-dioxane. The reaction mixture is heated in a Biotage microwave reactor at 130° C. for 2 hours. The reaction medium is evaporated to dryness and the residue is taken up in EtOAc and washed with water and with saturated NaCl. The organic phase is dried over magnesium sulfate and evaporated to dryness. The residue is purified by chromatography on silica gel (eluent: 95/5 DCM/MeOH) to give 250 mg of (8S)-2-(1S,4S)-2-oxa-5-azabicyclo[2.2.1]hept-5-yl-9-(3,3,3-trifluoro-2-hydroxy-2-trifluoromethylpropyl)-8-trifluoromethyl-6,7,8,9-tetrahydropyrimido[1,2-a]pyrimidin-4-one, the characteristics of which are as follows:

LC/MS (method A): ESI+ [M+H]+: m/z 497 tr (min)=0.71

$^1$H NMR (600 MHz, δ in ppm, DMSO-$d_6$): 1.81-1.95 (m, 2H), 2.21 (m, 1H), 2.44 (m, 1H), 2.95-3.36 (m, 3H), 3.47-3.64 (m, 2H), 3.69 (m, 1H), 4.08 (m, 1H), 4.57-5.05 (m, 4H), 5.40 (m, 1H), 8.74 (m, 1H).

EXAMPLE 49

(8S)-2-(1S,4S)-2-oxa-5-azabicyclo[2.2.1]hept-5-yl-9-[2-(3-oxa-8-azabicyclo[3.2.1]oct-8-yl)-2-oxoethyl]-8-trifluoromethyl-6,7,8,9-tetrahydropyrimido[1,2-a]pyrimidin-4-one (Compound 99)

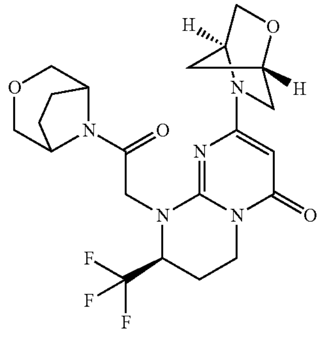 [SMILES: O=C(CN1c2nc(N3C[C@@H]4C[C@H]3CO4)cc(=O)n2CC[C@H]1C(F)(F)F)N1C2CCC1COC2]

Step 49.1: ((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)acetic acid

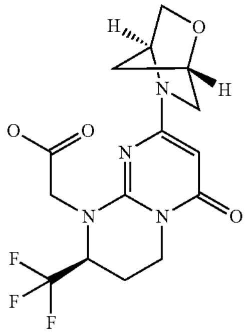 [SMILES: O=C(O)CN1c2nc(N3C[C@@H]4C[C@H]3CO4)cc(=O)n2CC[C@H]1C(F)(F)F]

95 mg (2.22 mmol) of lithium hydroxide monohydrate are added to a solution of 720 mg (1.85 mmol) of methyl ((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)acetate (preparation described in Step 38.1) in 20 mL of THF/water (1/1: v/v). The reaction mixture is stirred at room temperature for 2 hours, after which the THF is evaporated off and the solution is acidified with 1 N HCl and extracted with EtOAc. The organic phase is washed with water and with saturated NaCl, dried over magnesium sulfate and then evaporated to dryness to give 690 mg of ((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)acetic acid, the characteristics of which are as follows:

LC/MS (method A): ESI+ [M+H]+: m/z 375 tr (min)=1.63

$^1$H NMR (300 MHz, δ in ppm, DMSO-$d_6$): 1.81 (m, 2H), 2.02-2.18 (m, 1H), 2.32-2.43 (m, 1H), 3.10-3.32 (m, 3H), 3.49-3.59 (m, 1H), 3.68 (m, 1H), 3.98-4.08 (m, 1H), 4.24-4.35 (m, 1H), 4.37-4.47 (m, 1H), 4.57-4.86 (m, 4H), 12.71 (m, 1H).

Step 49.2: (8S)-2-(1S,4S)-2-oxa-5-azabicyclo[2.2.1]hept-5-yl-9-[2-(3-oxa-8-azabicyclo[3.2.1]oct-8-yl)-2-oxoethyl]-8-trifluoromethyl-6,7,8,9-tetrahydropyrimido[1,2-a]pyrimidin-4-one

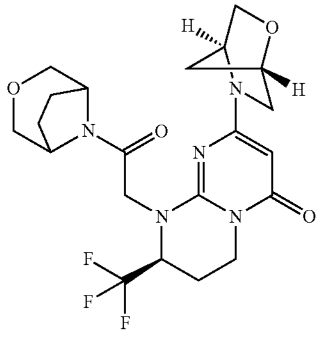 [SMILES: O=C(CN1c2nc(N3C[C@@H]4C[C@H]3CO4)cc(=O)n2CC[C@H]1C(F)(F)F)N1C2CCC1COC2]

98 μL (0.881 mmol) of N-methylmorpholine, 86 mg (0.44 mmol) of 1-(3-dimethylaminopropyl)-3-ethylcarbodiimide hydrochloride and 69 mg (0.44 mmol) of 1-hydroxybenzotriazole hydrate are added to a solution of 150 mg (0.4 mmol) of ((2S)-8-(1S,4S)-2-oxa-5-azabicyclo[2.2.1]hept-5-yl-6- oxo-2-trifluoromethyl-3,4-dihydro-2H,6H-pyrimido[1,2-a]pyrimidin-1-yl)acetic acid in 10 mL of DMF. The reaction mixture is stirred for 10 minutes at room temperature, followed by addition of 66 mg (0.44 mmol) of (1R,5S)-3-oxa-8-azabicyclo[3.2.1]octane hydrochloride. The reaction is continued at room temperature for 5 hours. The DMF is evaporated off and the residue obtained is purified by chromatography on silica gel (eluent: 95/5 DCM/MeOH) to give 130 mg of (8S)-2-(1S,4S)-2-oxa-5-azabicyclo[2.2.1]hept-5-yl-9-[2-(3-oxa-8-azabicyclo[3.2.1]oct-8-yl)-2-oxoethyl]-8-trifluoromethyl-6,7,8,9-tetrahydropyrimido[1,2-a]pyrimidin-4-one, the characteristics of which are as follows:

LC/MS (method A): ESI+ [M+H]+: m/z 470 tr (min)=0.5

$^1$H NMR (600 MHz, δ in ppm, DMSO-$d_6$) performed at 140° C.: 1.77-1.95 (m, 6H), 2.21-2.43 (m, 2H), 3.14-3.38 (m, 3H), 3.53-3.72 (m, 6H), 3.98 (d, 1H), 4.27-4.48 (m, 4H), 4.62 (s, 1H), 4.71 (s, 1H), 4.76 (s, 1H), 5.11 (d, 1H).

EXAMPLE 50

(8S)-9-(3-hydroxy-3-methylbutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 50)

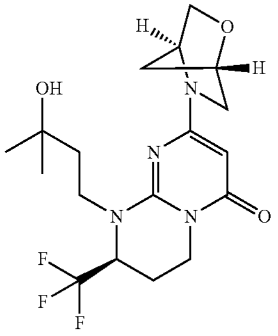 [SMILES: CC(C)(O)CCN1c2nc(N3C[C@@H]4C[C@H]3CO4)cc(=O)n2CC[C@H]1C(F)(F)F]

430 μL (1.29 mmol) of a 3 M solution of methylmagnesium bromide in ethyl ether are added at 0° C. to a solution of 173 mg (0.43 mmol) of methyl 3-((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)-propionate (preparation described in Step 39.1) in 10 mL of THF. The reaction medium is stirred at 0° C. for 2 hours. 10 mL of saturated ammonium chloride solution are added to the reaction medium. The resulting mixture is extracted with ethyl acetate and the organic phase is dried over magnesium sulfate and evaporated to dryness. After purification by chromatography on silica gel (eluent: 95/5 DCM/MeOH), 128 mg of (8S)-9-(3-hydroxy-3-methylbutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one are obtained, corresponding to the following characteristics:

LC/MS (method A): ESI+ [M+H]+: m/z 403 tr (min)=0.53

$^1$H NMR (600 MHz, δ in ppm, DMSO-$d_6$): 1.09 (s, 3H), 1.12 (s, 3H), 1.64-1.76 (m, 2H), 1.78-1.87 (m, 2H), 2.02 (m, 1H), 2.33 (m, 1H), 3.13 (m, 1H), 3.24-3.35 (m, 2H), 3.63 (m, 1H), 3.69 (m, 1H), 4.12 (m, 1H), 4.20 (m, 1H), 4.25 (s, 1H), 4.53 (m, 1H), 4.59-5.03 (m, 4H).

EXAMPLE 51

(8S)-9-(1-hydroxycyclopropylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 104)

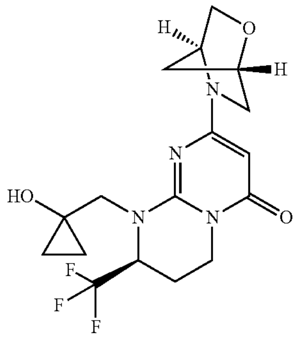 [SMILES: O=c1cc(N2C[C@@H]3C[C@H]2CO3)nc2n1CC[C@@H](C(F)(F)F)N2CC1(O)CC1]

146 mg (0.515 mmol) of titanium (IV) isopropoxide are added to a solution of 200 mg (0.515 mmol) of methyl ((2S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)acetate (preparation described in Step 38.1) in 3 mL of THF. The solution is cooled to 0° C., followed by dropwise addition of 858 μL (2.58 mmol) of 3 M ethylmagnesium bromide in ethyl ether. The reaction mixture is stirred for 30 minutes at room temperature. 10 mL of saturated ammonium chloride solution are added to the reaction medium. The resulting mixture is extracted with ethyl acetate and the organic phase is dried over magnesium sulfate and evaporated to dryness. After purification by chromatography on silica gel (eluent: 95/5 DCM/MeOH), 80 mg of (8S)-9-(1-hydroxycyclopropylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one are obtained, corresponding to the following characteristics:

LC/MS (method A): ESI+ [M+H]+: m/z 387 tr (min)=0.52

$^1$H NMR (600 MHz, δ in ppm, DMSO-$d_6$): 0.52-0.71 (m, 4H), 1.77-1.86 (m, 2H), 2.27 (m, 1H), 2.40 (m, 1H), 3.20-3.29 (m, 3H), 3.45 (d, 1H), 3.59 (m, 1H), 3.72 (m, 1H), 4.18 (m, 1H), 4.37 (m, 1H), 4.59-5.01 (m, 4H), 5.54 (s, 1H).

EXAMPLE 52

(8S)-2-(1S,4S)-2-oxa-5-azabicyclo[2.2.1]hept-5-yl-9-quinolin-5-ylmethyl-8-trifluoromethyl-6,7,8,9-tetrahydropyrimido[1,2-a]pyrimidin-4-one (Compound 106)

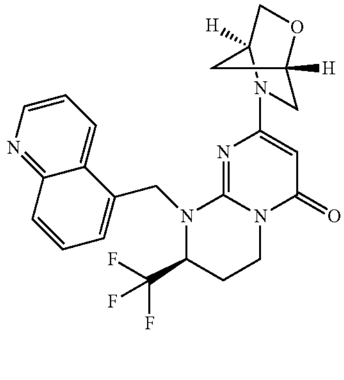 [SMILES: O=c1cc(N2C[C@@H]3C[C@H]2CO3)nc2n1CC[C@@H](C(F)(F)F)N2Cc1cccc2ncccc12]

Step 52.1: Quinolin-5-ylmethanol

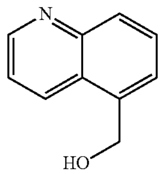 [SMILES: OCc1cccc2ncccc12]

A suspension of 171 mg (4.49 mmol) of lithium aluminum hydride in 20 ml of THF is cooled to 0° C. A solution of 700 mg (3.74 mmol) of methyl quinoline-5-carboxylate in 5 ml of THF is then added dropwise. The reaction mixture is stirred at 0° C. for 1 hour and then hydrolysed with, in this order, 0.17 ml of $H_2O$, 0.17 ml of NaOH and 3×0.17 ml of $H_2O$. The precipitate formed is filtered off and washed with THF and then with EtOAc. The organic phase is washed with saturated NaCl solution, dried and evaporated. After purification by chromatography on silica gel (eluent: 95/5 DCM/MeOH), 190 mg of quinolin-5-ylmethanol are obtained, corresponding to the following characteristics:

LC/MS (method G): ESI+ [M+H]+: m/z 160 tr (min)=0.43

$^1$H NMR (300 MHz, δ in ppm, DMSO-$d_6$): 4.97 (d, 2H), 5.40 (t, 1H), 7.51-7.65 (m, 2H), 7.72 (t, 1H), 7.93 (d, 1H), 8.53 (d, 1H), 8.88-8.93 (m, 1H).

Step 52.2: 5-chloromethylquinoline hydrochloride

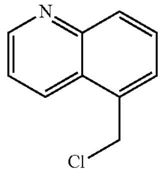 [SMILES: ClCc1cccc2ncccc12]

A solution of 190 mg (1.19 mmol) of quinolin-5-ylmethanol in 5 ml of thionyl chloride is stirred for 10 minutes at room temperature and then refluxed for 2 hours. The reaction mixture is evaporated, the solid obtained is taken up in ethyl ether and the solution is filtered, washed with ethyl ether and dried to give 255 mg of 5-chloromethylquinoline hydrochloride, corresponding to the following characteristics:

LC/MS (method G): ESI+ [M+H]+: m/z 178 tr (min)=1.07

$^1$H NMR (300 MHz, δ in ppm, DMSO-$d_6$): 5.40 (s, 2H), 7.96-8.10 (m, 3H), 8.34 (m, 1H), 9.17 (m, 1H), 9.27 (m, 1H).

Step 52.3: (8S)-2-Chloro-9-quinolin-5-ylmethyl-8-trifluoromethyl-6,7,8,9-tetrahydropyrimido[1,2-a]pyrimidin-4-one

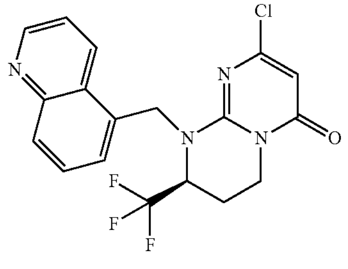 [SMILES: O=c1cc(Cl)nc2n1CC[C@@H](C(F)(F)F)N2Cc1cccc2ncccc12]

A suspension of 180 mg (0.709 mmol) of (8S)-2-chloro-8-trifluoromethyl-6,7,8,9-tetrahydropyrimido[1,2-a]pyrimidin-4-one and 693 mg (2.13 mmol) of cesium carbonate in 10 mL of acetonitrile is stirred for 15 minutes at room temperature. 182 mg (0.851 mmol) of 5-chloromethylquinoline hydrochloride are then added, along with a catalytic amount of sodium iodide.

The reaction mixture is stirred at room temperature for 5 hours. The crude product is evaporated and the residue is taken up in water and extracted with ethyl acetate. The organic phase is dried over magnesium sulfate and evaporated to dryness. The residue is purified by chromatography on silica gel (eluent: 95/5 DCM/MeOH) to give 160 mg of (8S)-2-chloro-9-quinolin-5-ylmethyl-8-trifluoromethyl-6,7,8,9-tetrahydropyrimido[1,2-a]pyrimidin-4-one, corresponding to the following characteristics:

LC/MS (method G): ESI+ [M+H]+: m/z 395 tr (min)=2.00

$^1$H NMR spectrum (300 MHz, δ in ppm, DMSO-$d_6$): 2.24-2.46 (m, 2H), 3.35-3.47 (m, 1H), 4.26-4.36 (m, 1H), 4.66-4.80 (m, 1H), 5.04 (d, 1H), 5.83 (d, 1H), 5.98 (s, 1H), 7.42 (d, 1H), 7.61 (m, 1H), 7.73 (t, 1H), 7.97 (d, 1H), 8.57 (d, 1H), 8.95 (m, 1H).

Step 52.4: (8S)-2-(1S,4S)-2-oxa-5-azabicyclo[2.2.1]hept-5-yl-9-quinolin-5-ylmethyl-8-trifluoromethyl-6,7,8,9-tetrahydropyrimido[1,2-a]pyrimidin-4-one

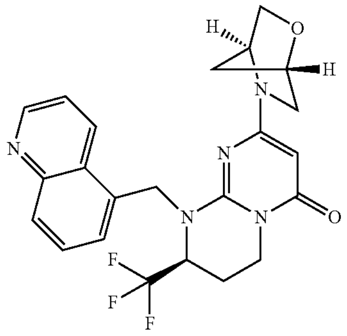 [SMILES: O=c1cc(N2C[C@@H]3C[C@H]2CO3)nc2n1CC[C@@H](C(F)(F)F)N2Cc1cccc2ncccc12]

160 mg (0.40 mmol) of (8S)-2-chloro-9-quinolin-5-ylmethyl-8-trifluoromethyl-6,7,8,9-tetrahydropyrimido[1,2-a]pyrimidin-4-one and 82 mg (0.60 mmol) of (1S,4S)-2-oxa-5-azabicyclo[2.2.1]heptane hydrochloride are mixed together. The powder obtained is placed in a tube and 158 μL (1.13 mmol) of triethylamine are added. The tube is sealed and heated at 130° C. in an oil bath for 7 hours. The crude product obtained is taken up in DCM and the organic phase is washed with water, dried over magnesium sulfate and then evaporated to dryness. The residue is purified by chromatography on silica gel (eluent: 95/5 DCM/MeOH) to give 125 mg of (8S)-2-(1S,4S)-2-oxa-5-azabicyclo[2.2.1]hept-5-yl-9-quinolin-5-ylmethyl-8-trifluoromethyl-6,7,8,9-tetrahydropyrimido[1,2-a]pyrimidin-4-one, the characteristics of which are as follows:

LC/MS (method A): ESI+ [M+H]+: m/z 458 tr (min)=0.47

$^1$H NMR (600 MHz, δ in ppm, DMSO-$d_6$): 1.42-1.67 (bm, 2H), 2.29-2.46 (m, 2H), 2.74-3.20 (bm, 4H), 3.27-3.36 (m, 1H), 4.27 (m, 2H), 4.42 (m, 1H), 4.52-4.80 (bm, 2H), 4.85 (m, 1H), 5.91 (d, 1H), 7.39 (d, 1H), 7.56 (m, 1H), 7.71 (t, 1H), 7.93 (d, 1H), 8.62 (m, 1H), 8.92 (m, 1H).

EXAMPLE 53

(S)-9-[2-(6-difluoromethoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one (Compound 114)

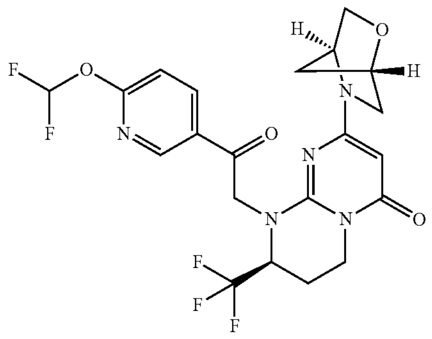 [SMILES: O=C(CN1c2nc(N3C[C@@H]4C[C@H]3CO4)cc(=O)n2CC[C@H]1C(F)(F)F)c1ccc(OC(F)F)nc1]

Step 53.1: 5-bromo-2-difluoromethoxypyridine

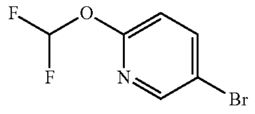 [SMILES: FC(F)Oc1ccc(Br)cn1]

5.42 g (34.48 mmol) of sodium chlorodifluoroacetate are added to a solution of 5 g (28.74 mmol) of 5-bromo-1H-pyrid-2-one in 120 ml of acetonitrile, under argon.

The white suspension obtained is refluxed overnight and then evaporated to dryness. The residue is taken up in aqueous ammonium chloride solution and extracted with EtOAc. The organic phase is dried over magnesium sulfate and then evaporated to dryness. The crude product is purified by chromatography on silica gel (eluent: 0/100 EtOAc/heptane to 20/80 EtOAc/heptane over 35 minutes) to give 2.2 g of 5-bromo-2-difluoromethoxypyridine, corresponding to the following characteristics:

LC/MS (method G): ESI+ [M+H]+: m/z 226 tr (min)=2.08

$^1$H NMR spectrum (300 MHz, δ in ppm, DMSO-$d_6$): 7.12 (d, 1H), 7.67 (t, 1H), 8.15 (dd, 1H), 8.43 (d, 1H).

Step 53.2: 5-(1-butoxyvinyl)-2-difluoromethoxypyridine

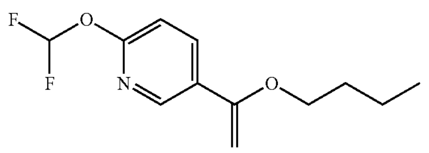 [SMILES: C=C(OCCCC)c1ccc(OC(F)F)nc1]

1 g (4.46 mmol) of 5-bromo-2-difluoromethoxypyridine in 20 mL of $H_2O$/DMF (1/4: v/v), 1.46 mL (11.16 mmol) of N-butyl vinyl ether, 30.68 mg (0.13 mmol) of palladium(II) acetate, 125 mg (0.29 mmol) of 1,3-bis(diphenylphosphino) propane and 746 mg (5.36 mmol) of potassium carbonate are placed in a microwave tube. After microwave irradiation for 1 hour at 120° C., the crude product is taken up in water and extracted with DCM. The organic phase is dried over magnesium sulfate and then evaporated to dryness. The crude product is purified by chromatography on silica gel (eluent: 0/100 EtOAc/heptane to 20/80 EtOAc/heptane over 35 minutes) to give 110 mg of 5-(1-butoxyvinyl)-2-difluoromethoxypyridine, corresponding to the following characteristics:

LC/MS (method G): ESI+ [M+H]+: m/z 244 tr (min)=2.74

$^1$H NMR spectrum (300 MHz, δ in ppm, DMSO-$d_6$): 0.94 (t, 3H), 1.38-1.53 (m, 2H), 1.66-1.78 (m, 2H), 3.86 (t, 2H), 4.38 (d, 1H), 4.85 (d, 1H), 7.09 (d, 1H), 7.71 (t, 1H), 8.09 (dd, 1H), 8.49 (d, 1H).

Step 53.3: 2-bromo-1-(6-difluoromethoxypyrid-3-yl)ethanone

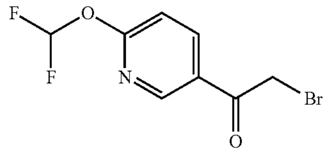 [SMILES: O=C(CBr)c1ccc(OC(F)F)nc1]

A solution of 100 mg (0.41 mmol) of 5-(1-butoxyvinyl)-2-difluoromethoxypyridine in 4 mL of THF/$H_2O$ (3/1: v/v) is cooled to 0° C. 74 mg (0.41 mmol) of N-bromosuccinimide are then added in a single portion. The yellow solution is stirred at 0° C. for 1 hour and then taken up in water and extracted with EtOAc. The organic phase is washed with saturated aqueous $NaHCO_3$ solution and then with saturated NaCl solution, dried over magnesium sulfate and then evaporated to dryness. The crude product is purified by chromatography on silica gel (eluent: 20/80 EtOAc/heptane to 40/60 EtOAc/heptane over 15 minutes) to give 82 mg of 2-bromo-1-(6-difluoromethoxypyrid-3-yl)ethanone, corresponding to the following characteristics:

LC/MS (method G): ESI+ [M+H]+: m/z 266 tr (min)=1.84

$^1$H NMR spectrum (300 MHz, δ in ppm, DMSO-$d_6$): 4.91 (s, 2H), 7.19 (d, 1H), 7.75 (t, 1H), 8.36 (dd, 1H), 8.85 (d, 1H).

Step 53.4: (8S)-9-[2-(6-difluoromethoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one

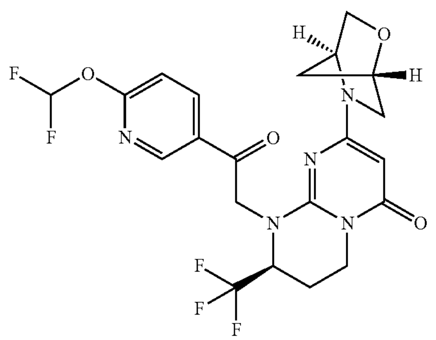 [SMILES: O=C(CN1c2nc(N3C[C@@H]4C[C@H]3CO4)cc(=O)n2CC[C@H]1C(F)(F)F)c1ccc(OC(F)F)nc1]

The procedure used is the same as that of step 12.3. 120 mg (0.38 mmol) of (8S)-2-(1S,4S)-2-oxa-5-azabicyclo[2.2.1]hept-5-yl-8-trifluoromethyl-6,7,8,9-tetrahydropyrimido[1,2-a]pyrimidin-4-one, 371 mg (1.42 mmol) of cesium carbonate, 121 mg (0.45 mmol) of 2-bromo-1-(6-difluoromethoxypyrid-3-yl)ethanone and 15 mL of acetonitrile were used in the reaction. After purification by chromatography on silica gel (eluent A/B: DCM/MeOH, gradient A/B: t 0 min 0% B, t 25 min 10% B, t 30 min 10% B), 38 mg of (8S)-9-[2-(6-difluoromethoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one were obtained, corresponding to the following characteristics:

LC/MS (method A): ESI+ [M+H]+: m/z 502 tr (min)=0.67

$^1H$ NMR (600 MHz, δ in ppm, DMSO-$d_6$): 1.56-1.74 (m, 2H), 2.21 (m, 1H), 2.44 (m, 1H), 2.78-3.09 (m, 3H), 3.23 (m, 1H), 3.47-3.85 (m, 1H), 4.37 (m, 1H), 4.41-4.53 (m, 2H), 4.53-4.71 (m, 3H), 5.66-5.78 (m, 1H), 7.26 (d, 1H), 7.82 (t, 1H), 8.48 (dd, 1H), 9.01 (m, 1H).

The table which follows illustrates the chemical structures and the physical properties of some examples of compounds according to the invention. In this table:

in the "Salt" column, "–" represents a compound in free base form, whereas "HCl" represents a compound in hydrochloride form;

the "Data" column successively indicates the LC/MS analytical method used (A, B, C or F) and detailed in the experimental section, the retention time (tr) of the compound expressed in minutes, and the peak $[M+H]^+$ identified by mass spectrometry.

TABLE

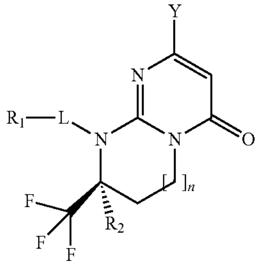

(I)

The asterisk * on $R_1$ and L indicates the atom of attachment of $R_1$ to L.

| No. | n | Y | $R_1$ | L | Salt | Data |
|---|---|---|---|---|---|---|
| 1<br>Ex. 13 | 1 | 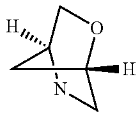 | 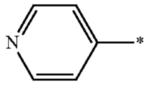 [SMILES: *c1ccncc1] | *—C($CH_3$)$_2$—$CH_2$— | — | Method B:<br>tr (min) = 0.53<br>[M + H]+: 450 |
| 2<br>Ex. 27 | 1 | 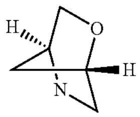 | 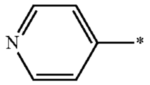 [SMILES: *c1ccncc1] | *—CO—$CH_2$— | — | Method A:<br>tr (min) = 0.50<br>[M + H]+: 436 |
| 3 | 1 | 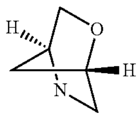 | 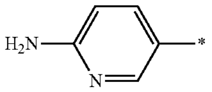 [SMILES: *c1ccc(N)nc1] | *—CO—$CH_2$— | — | Method A:<br>tr (min) = 0.38<br>[M + H]+: 451 |
| 4<br>Ex. 28 | 1 | 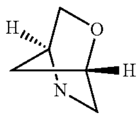 | 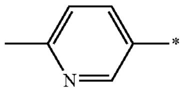 [SMILES: *c1ccc(C)nc1] | *—CO—$CH_2$— | — | Method A:<br>tr (min) = 0.49<br>[M + H]+: 450 |
| 5<br>Ex. 42 | 1 | 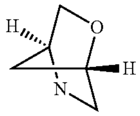 | 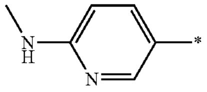 | *—CO—$CH_2$— | — | Method A:<br>tr (min) = 0.41<br>[M + H]+: 465 |
| 6<br>Ex. 25 | 1 | 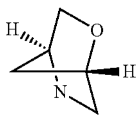 | 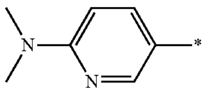 | *—CO—$CH_2$— | — | Method A:<br>tr (min) = 0.48<br>[M + H]+: 479 |
| 7<br>Ex. 6 | 1 | 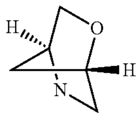 | 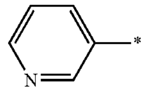 | *—CO—$CH_2$— | — | Method A:<br>tr (min) = 0.51<br>[M + H]+: 436 |

TABLE-continued (I)

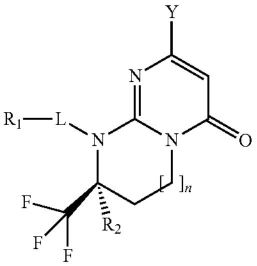

The asterisk * on $R_1$ and L indicates the atom of attachment of $R_1$ to L.

| No. | n | Y | $R_1$ | L | Salt | Data |
|---|---|---|---|---|---|---|
| 8 | 0 | 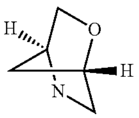 | 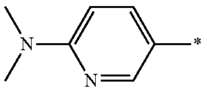 [SMILES: *c1ccc(N(C)C)nc1] | *—CO—$CH_2$— | — | Method A:<br>tr (min) = 0.49<br>[M + H]+: 479 |
| 9<br>Ex. 43 | 0 | 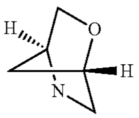 | 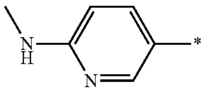 | *—CO—$CH_2$— | — | Method A:<br>tr (min) = 0.42<br>[M + H]+: 465 |
| 10 | 0 | 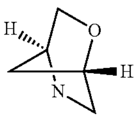 | 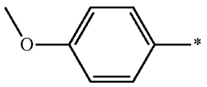 [SMILES: *c1ccc(OC)cc1] | *—$CH_2$—$CH_2$— | — | * Method C:<br>tr (min) = 1.19<br>[M + H]+: 451 |
| 11 | 0 | 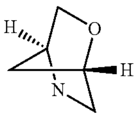 | 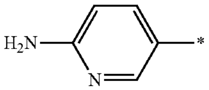 [SMILES: *c1ccc(N)nc1] | *—CO—$CH_2$— | — | Method A:<br>tr (min) = 0.38<br>[M + H]+: 451 |
| 12<br>Ex. 31 | 1 | 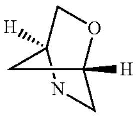 | 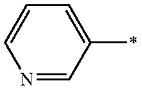 | *—$CH_2$—$CH_2$— | — | Method A:<br>tr (min) = 0.39<br>[M + H]+: 422 |
| 13 | 0 | 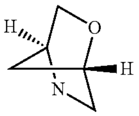 | 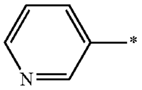 [SMILES: *c1cccnc1] | *—$CH_2$—$CH_2$— | — | Method A:<br>tr (min) = 0.39<br>[M + H]+: 422 |
| 14<br>Ex. 41 | 1 | 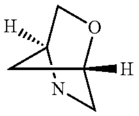 | 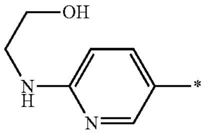 | *—CO—$CH_2$— | — | Method A:<br>tr (min) = 0.40<br>[M + H]+: 495 |
| 15<br>Ex. 3 | 1 | 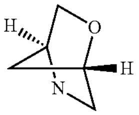 | 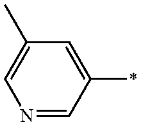 [SMILES: *c1cncc(C)c1] | *—CO—$CH_2$— | — | Method A:<br>tr (min) = 0.51<br>[M + H]+: 450 |
| 16<br>Ex. 7 | 0 | 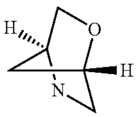 | 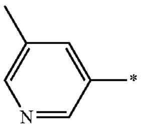 [SMILES: *c1cncc(C)c1] | *—CO—$CH_2$— | — | Method A:<br>tr (min) = 0.52<br>[M + H]+: 450 |

TABLE-continued (I)

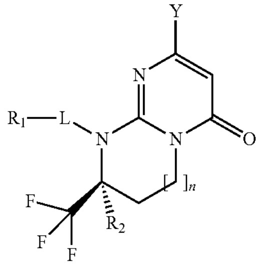

The asterisk * on $R_1$ and L indicates the atom of attachment of $R_1$ to L.

| No. | n | Y | $R_1$ | L | Salt | Data |
|---|---|---|---|---|---|---|
| 17<br>Ex. 29 | 0 | 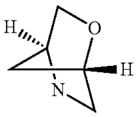 | 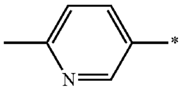 [SMILES: *c1ccc(C)nc1] | *—CO—$CH_2$— | — | Method A:<br>tr (min) = 0.49<br>[M + H]+: 450 |
| 18 | 0 | 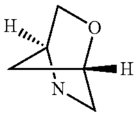 | 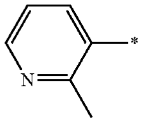 [SMILES: *c1cccnc1C] | *—CO—$CH_2$— | — | Method A:<br>tr (min) = 0.48<br>[M + H]+: 450 |
| 19<br>Ex. 9 | 1 | 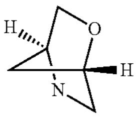 | 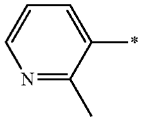 [SMILES: *c1cccnc1C] | *—CO—$CH_2$— | — | Method A:<br>tr (min) = 0.48<br>[M + H]+: 450 |
| 20<br>Ex. 12 | 1 | 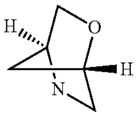 | 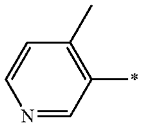 [SMILES: *c1cnccc1C] | *—CO—$CH_2$— | — | Method A:<br>tr (min) = 0.50<br>[M + H]+: 450 |
| 21<br>Ex. 30 | 0 | 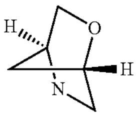 | 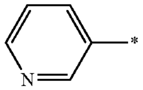 [SMILES: *c1cccnc1] | *—CO—$CH_2$— | — | Method A:<br>tr (min) = 0.51<br>[M + H]+: 436 |
| 22 | 1 | 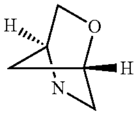 | 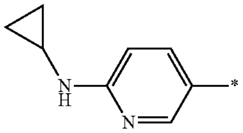 [SMILES: *c1ccc(NC2CC2)nc1] | *—CO—$CH_2$— | — | Method A:<br>tr (min) = 0.45<br>[M + H]+: 491 |
| 23<br>Ex. 14 | 1 | 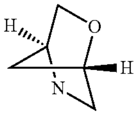 | 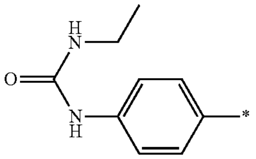 [SMILES: *c1ccc(NC(=O)NCC)cc1] | *—$CH_2$—$CH_2$— | — | Method A:<br>tr (min) = 0.60<br>[M + H]+: 507 |
| 24<br>Ex. 15 | 0 | 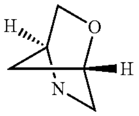 | 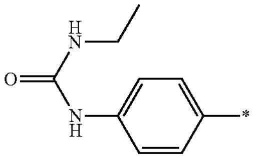 [SMILES: *c1ccc(NC(=O)NCC)cc1] | *—$CH_2$—$CH_2$— | — | Method A:<br>tr (min) = 0.60<br>[M + H]+: 507 |

TABLE-continued (I)

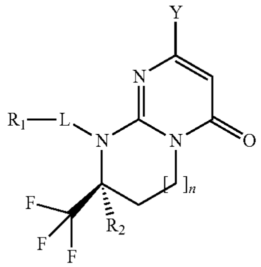

The asterisk * on $R_1$ and L indicates the atom of attachment of $R_1$ to L.

| No. | n | Y | $R_1$ | L | Salt | Data |
|---|---|---|---|---|---|---|
| 25 Ex. 2 | 1 | 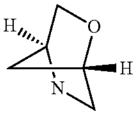 | 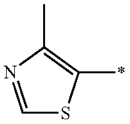 [SMILES: *c1scnc1C] | *—$CH_2$—$CH_2$— | — | Method A: tr (min) = 0.55 [M + H]+: 442 |
| 26 Ex. 8 | 0 | 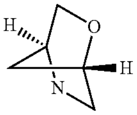 | 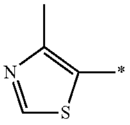 [SMILES: *c1scnc1C] | *—$CH_2$—$CH_2$— | — | Method A: tr (min) = 0.56 [M + H]+: 442 |
| 27 | 1 | 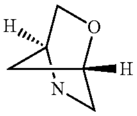 | 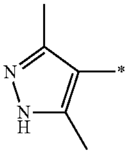 [SMILES: *c1c(C)n[nH]c1C] | *—$CH_2$—$CH_2$— | — | Method A: tr (min) = 0.46 [M + H]+: 439 |
| 28 | 0 | 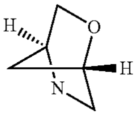 | 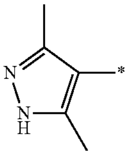 [SMILES: *c1c(C)n[nH]c1C] | *—$CH_2$—$CH_2$— | — | Method A: tr (min) = 0.45 [M + H]+: 439 |
| 29 Ex. 26 | 1 | 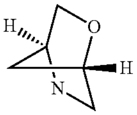 | 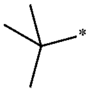 [SMILES: *C(C)(C)C] | *—CO—$CH_2$— | — | Method A: tr (min) = 0.67 [M + H]+: 415 |
| 30 | 0 | 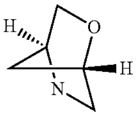 | 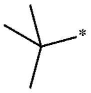 [SMILES: *C(C)(C)C] | *—CO—$CH_2$— | — | Method A: tr (min) = 0.67 [M + H]+: 415 |
| 31 | 1 | 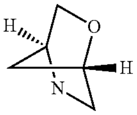 | 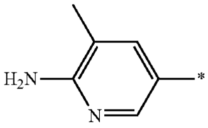 [SMILES: *c1cnc(N)c(C)c1] | *—CO—$CH_2$— | — | Method A: tr (min) = 0.42 [M + H]+: 465 |
| 32 | 0 | 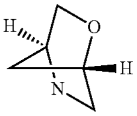 | 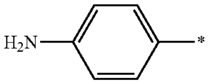 [SMILES: *c1ccc(N)cc1] | *—$CH_2$—$CH_2$— | — | Method A: tr (min) = 0.48 [M + H]+: 436 |
| 33 | 1 | 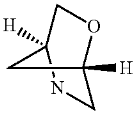 | 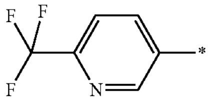 [SMILES: *c1ccc(C(F)(F)F)nc1] | *—CO—$CH_2$— | — | Method A: tr (min) = 0.67 [M + H]+: 504 |

TABLE-continued
(I)
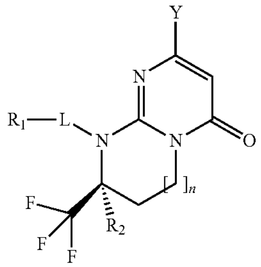
The asterisk * on $R_1$ and L indicates the atom of attachment of $R_1$ to L.
| No. | n | Y | $R_1$ | L | Salt | Data |
|---|---|---|---|---|---|---|
| 34 | 1 | 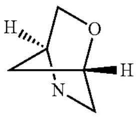 | 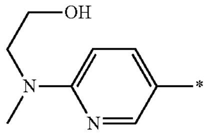 [SMILES: *c1ccc(N(C)CCO)nc1] | *—CO—$CH_2$— | — | Method A: tr (min) = 0.47 [M + H]+: 509 |
| 35 | 1 | 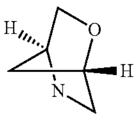 | 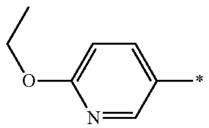 [SMILES: *c1ccc(OCC)nc1] | *—CO—$CH_2$— | — | Method A: tr (min) = 0.67 [M + H]+: 480 |
| 36 | 1 | 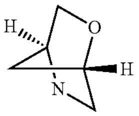 | 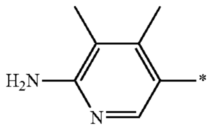 [SMILES: *c1cnc(N)c(C)c1C] | *—CO—$CH_2$— | — | Method A: tr (min) = 0.43 [M + H]+: 479 |
| 37 | 1 | 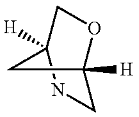 | 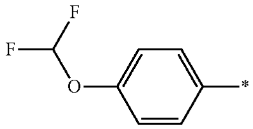 [SMILES: *c1ccc(OC(F)F)cc1] | *—CO—$CH_2$— | — | Method A: tr (min) = 0.69 [M + H]+: 501 |
| 38 Ex. 16 | 1 | 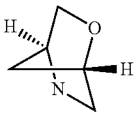 | 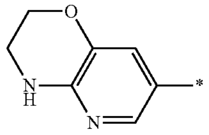 [SMILES: *c1cnc2c(c1)OCCN2] | *—CO—$CH_2$— | — | Method A: tr (min) = 0.49 [M + H]+: 439 |
| 39 | 1 | 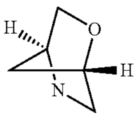 | 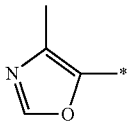 [SMILES: *c1ocnc1C] | *—CO—$CH_2$— | — | Method A: tr (min) = 0.52 [M + H]+: 440 |
| 40 | 1 | 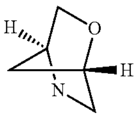 | 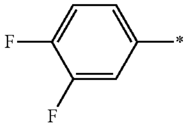 [SMILES: *c1ccc(F)c(F)c1] | *—CO—$CH_2$— | — | Method A: tr (min) = 0.68 [M + H]+: 471 |
| 41 | 1 | 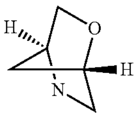 | 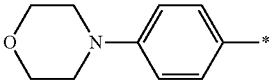 [SMILES: *c1ccc(N2CCOCC2)cc1] | *—CO—$CH_2$— | — | Method A: tr (min) = 0.64 [M + H]+: 520 |
| 42 | 1 | 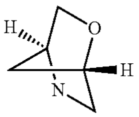 | 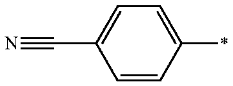 [SMILES: *c1ccc(C#N)cc1] | *—CO—$CH_2$— | — | Method A: tr (min) = 0.62 [M + H]+: 460 |

TABLE-continued
(I)
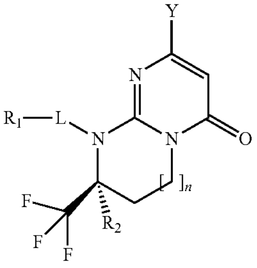
The asterisk * on $R_1$ and L indicates the atom of attachment of $R_1$ to L.
| No. | n | Y | $R_1$ | L | Salt | Data |
|---|---|---|---|---|---|---|
| 43 Ex. 10 | 1 | 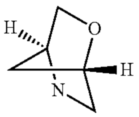 | 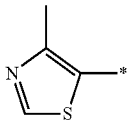 [SMILES: *c1scnc1C] | *—CO—$CH_2$— | — | Method A: tr (min) = 0.55 [M + H]+: 456 |
| 44 | 1 | 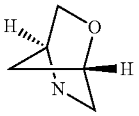 | 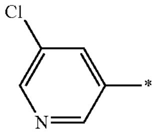 [SMILES: *c1cncc(Cl)c1] | *—CO—$CH_2$— | — | Method A: tr (min) = 0.61 [M + H]+: 470 |
| 45 Ex. 32 | 1 | 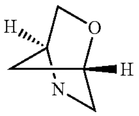 | 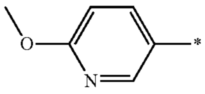 | *—CO—$CH_2$— | — | Method A: tr (min) = 0.61 [M + H]+: 466 |
| 46 | 1 | 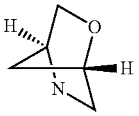 | 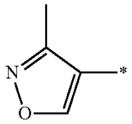 [SMILES: *c1conc1C] | *—CO—$CH_2$— | — | Method A: tr (min) = 0.55 [M + H]+: 440 |
| 47 Ex. 17 | 1 | 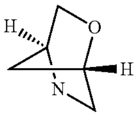 | 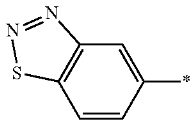 [SMILES: *c1ccc2snnc2c1] | *—CO—$CH_2$— | — | Method A: tr (min) = 0.64 [M + H]+: 493 |
| 48 Ex. 1 | 1 | 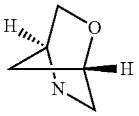 | 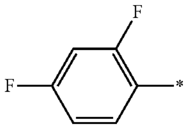 [SMILES: *c1ccc(F)cc1F] | *—CO—$CH_2$— | — | Method A: tr (min) = 0.68 [M + H]+: 471 |
| 49 Ex. 39 | 1 | 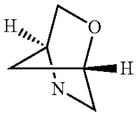 | 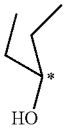 | *—$CH_2$—$CH_2$— | — | Method A: tr (min) = 0.63 [M + H]+: 431 |
| 50 Ex. 50 | 1 | 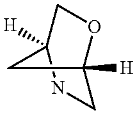 | 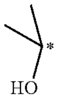 | *—$CH_2$—$CH_2$— | — | Method A: tr (min) = 0.53 [M + H]+: 403 |

TABLE-continued
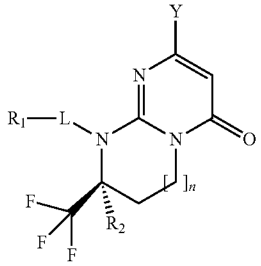
(I)
The asterisk * on $R_1$ and L indicates the atom of attachment of $R_1$ to L.
| No. | n | Y | $R_1$ | L | Salt | Data |
|---|---|---|---|---|---|---|
| 51 Ex. 18 | 1 | 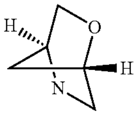 | 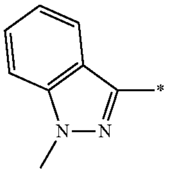 [SMILES: *c1nn(C)c2ccccc12] | *—$CH_2$— | — | Method A: tr (min) = 0.68 [M + H]+: 461 |
| 52 Ex. 19 | 1 | 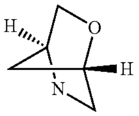 | 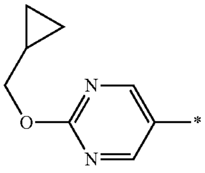 [SMILES: *c1cnc(OCC2CC2)nc1] | *—CO—$CH_2$— | — | Method A: tr (min) = 0.65 [M + H]+: 507 |
| 53 Ex. 4 | 1 | 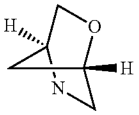 | 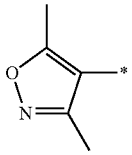 [SMILES: *c1c(C)noc1C] | *—CO—$CH_2$— | — | Method A: tr (min) = 0.58 [M + H]+: 454 |
| 54 Ex. 38 | 1 | 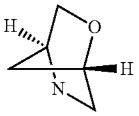 | 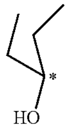 | *—$CH_2$— | — | Method A: tr (min) = 0.63 [M + H]+: 417 |
| 55 | 1 | 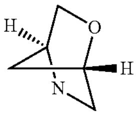 | 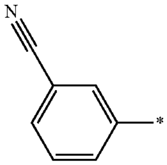 [SMILES: *c1cccc(C#N)c1] | *—CO—$CH_2$— | — | Method A: tr (min) = 0.61 [M + H]+: 460 |
| 56 Ex. 5 | 1 | 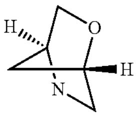 | 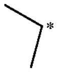 | *—CO—$CH_2$— | — | Method A: tr (min) = 0.60 [M + H]+: 401 |
| 57 Ex. 21 | 1 | 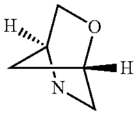 | 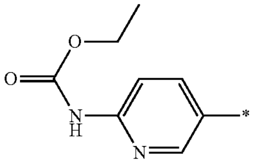 [SMILES: *c1ccc(NC(=O)OCC)nc1] | *—CO—$CH_2$— | — | Method A: tr (min) = 0.60 [M + H]+: 523 |

TABLE-continued (I)

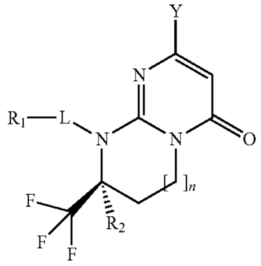

The asterisk * on $R_1$ and L indicates the atom of attachment of $R_1$ to L.

| No. | n | Y | $R_1$ | L | Salt | Data |
|---|---|---|---|---|---|---|
| 58 | 1 | 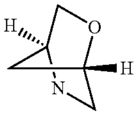 | 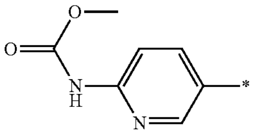 [SMILES: *c1ccc(NC(=O)OC)nc1] | *—CO—$CH_2$— | — | Method A:<br>tr (min) = 0.55<br>[M + H]+: 509 |
| 59 | 1 | 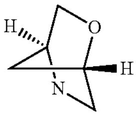 | 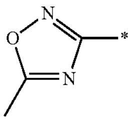 | *—$CH_2$— | — | Method C<br>tr (min) = 0.85<br>[M + H]+: 413 |
| 60 | 1 | 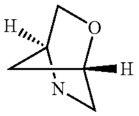 | 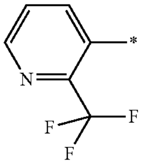 [SMILES: *c1cccnc1C(F)(F)F] | *—CO—$CH_2$— | — | Method A:<br>tr (min) = 0.62<br>[M + H]+: 504 |
| 61 | 1 | 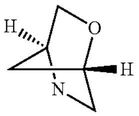 | 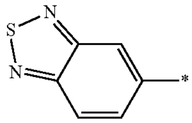 [SMILES: *c1ccc2nsnc2c1] | *—CO—$CH_2$— | — | Method A:<br>tr (min) = 0.64<br>[M + H]+: 493 |
| 62<br>Ex. 11 | 1 | 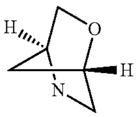 | 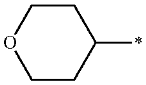 [SMILES: *C1CCOCC1] | *—CO—$CH_2$— | — | Method A:<br>tr (min) = 0.52<br>[M + H]+: 443 |
| 63<br>Ex. 33 | 1 | 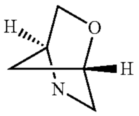 | 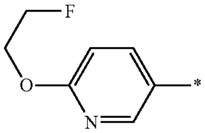 | *—CO—$CH_2$— | — | Method A:<br>tr (min) = 0.62<br>[M + H]+: 498 |
| 64 | 1 | 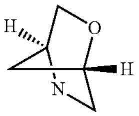 | 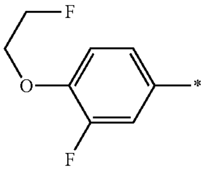 [SMILES: *c1ccc(OCCF)c(F)c1] | *—CO—$CH_2$— | — | Method A:<br>tr (min) = 0.65<br>[M + H]+: 515 |
| 65 | 1 | 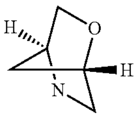 | 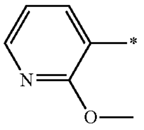 [SMILES: *c1cccnc1OC] | *—CO—$CH_2$— | — | Method A:<br>tr (min) = 0.63<br>[M + H]+: 466 |

TABLE-continued (I)

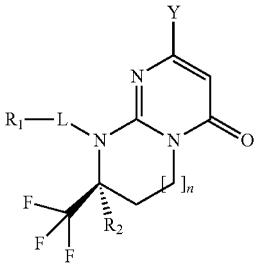

The asterisk * on $R_1$ and L indicates the atom of attachment of $R_1$ to L.

| No. | n | Y | $R_1$ | L | Salt | Data |
|---|---|---|---|---|---|---|
| 66 | 1 | 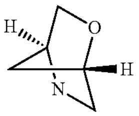 | 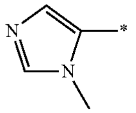 | *—CO—$CH_2$— | — | Method A: tr (min) = 0.40 [M + H]+: 439 |
| 67 | 1 | 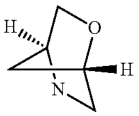 | 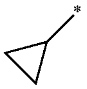 [SMILES: *C1CC1] | *—CO—$CH_2$— | — | Method C tr (min) = 0.88 [M + H]+: 399 |
| 68 Ex. 40 | 1 | 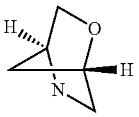 | 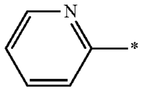 [SMILES: *c1ccccn1] | *—CO—$CH_2$— | — | Method A: tr (min) = 0.59 [M + H]+: 436 |
| 69 Ex. 20 | 1 | 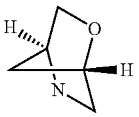 | 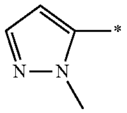 [SMILES: *c1ccnn1C] | *—CO—$CH_2$— | — | Method A: tr (min) = 0.54 [M + H]+: 439 |
| 70 Ex. 37 | 0 | 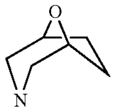 | 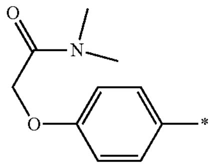 | *—$CH_2$—$CH_2$— | — | Method B: tr (min) = 0.69 [M + H]+: 536 |
| 71 Ex. 34 | 1 | 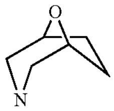 | 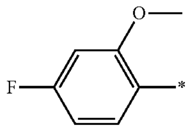 [SMILES: *c1ccc(F)cc1OC] | *—CHOH—$CH_2$— OH abs. conf. (S) | — | Method B: tr (min) = 0.71 [M + H]+: 499 |
| 72 Ex. 35 | 0 | 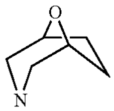 | 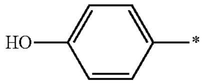 [SMILES: *c1ccc(O)cc1] | *—$CH_2$—$CH_2$— | — | Method B: tr (min) = 0.68 [M + H]+: 451 |
| 73 | 1 | 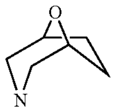 | 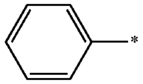 [SMILES: *c1ccccc1] | *—CO—$CH_2$— | — | Method F tr (min) = 0.84 [M + H]+: 449 |
| 74 Ex. 36 | 0 | 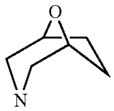 | 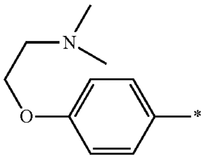 [SMILES: *c1ccc(OCCN(C)C)cc1] | *—$CH_2$—$CH_2$— | HCl | Method B: tr (min) = 0.56 [M + H]+: 522 |

TABLE-continued (I)

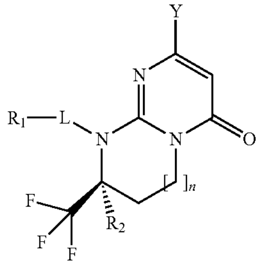

The asterisk * on $R_1$ and L indicates the atom of attachment of $R_1$ to L.

| No. | n | Y | $R_1$ | L | Salt | Data |
|---|---|---|---|---|---|---|
| 75<br>Ex. 23 | 1 | 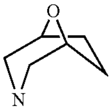 | 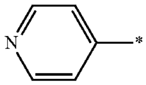 | *—CO—$CH_2$— | — | Method B:<br>tr (min) = 0.55<br>[M + H]+: 450 |
| 76 | 0 | 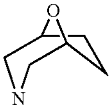 | 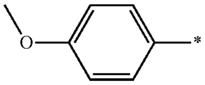 | *—$CH_2$—$CH_2$— | — | Method C<br>tr (min) = 1.26<br>[M + H]+: 465 |
| 77 | 0 | 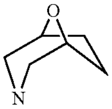 | 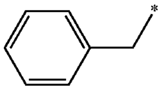 [SMILES: *Cc1ccccc1] | *—$CH_2$—$CH_2$— | — | Method B:<br>tr (min) = 82<br>[M + H]+: 449 |
| 78 | 0 | 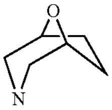 | 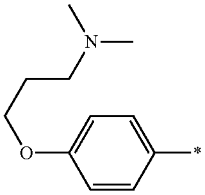 [SMILES: *c1ccc(OCCCN(C)C)cc1] | *—$CH_2$—$CH_2$— | HCl | Method B:<br>tr (min) = 0.58<br>[M + H]+: 536 |
| 79 | 0 | 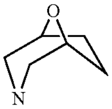 | 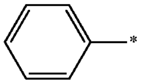 [SMILES: *c1ccccc1] | *—CHOH—$CH_2$—<br>OH abs. conf. (S) | — | Method B:<br>tr (min) = 0.65<br>[M + H]+: 451 |
| 80<br>Ex. 24 | 1 | 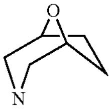 | 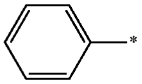 | *—CHOH—$CH_2$—<br>OH abs. conf. (S) | — | Method B:<br>tr (min) = 0.68<br>[M + H]+: 451 |
| 81 | 1 | 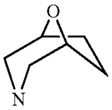 | 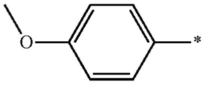 | *—$CH_2$—$CH_2$— | — | Method B:<br>tr (min) = 0.81<br>[M + H]+: 465 |
| 82 | 1 | 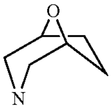 | 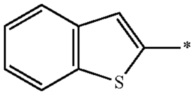 [SMILES: *c1cc2ccccc2s1] | *—CHOH—$CH_2$—<br>OH abs. conf. (R) | — | Method B:<br>tr (min) = 0.85<br>[M + H]+: 507 |
| 83 | 1 | 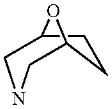 | 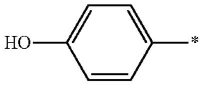 | *—$CH_2$—$CH_2$— | — | Method B:<br>tr (min) = 0.68<br>[M + H]+: 451 |

TABLE-continued (I)

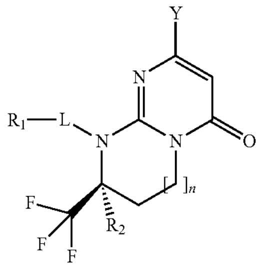

The asterisk * on $R_1$ and L indicates the atom of attachment of $R_1$ to L.

| No. | n | Y | $R_1$ | L | Salt | Data |
|---|---|---|---|---|---|---|
| 84 Ex. 22 | 1 | 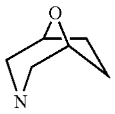 | 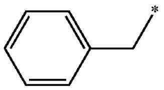 [SMILES: *Cc1ccccc1] | *—$CH_2$—$CH_2$— | — | Method B: tr (min) = 0.85 [M + H]+: 449 |
| 85 | 1 | 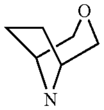 | 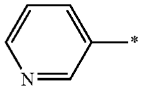 | *—CO—$CH_2$— | — | Method B: tr (min) = 0.52 [M + H]+: 450 |
| 86 | 1 | 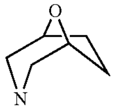 | 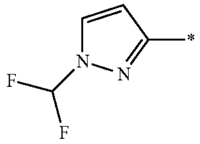 [SMILES: *c1ccn(C(F)F)n1] | *—$CH_2$— | — | Method F tr (min) = 0.83 [M + H]+: 461 |
| 87 | 1 | 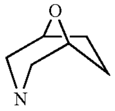 | 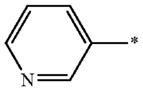 [SMILES: *c1cccnc1] | *—CO—$CH_2$— | — | Method F tr (min) = 0.83 [M + H]+: 450 |
| 88 | 1 | 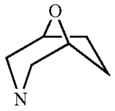 | 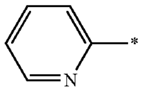 [SMILES: *c1ccccn1] | *—CO—$CH_2$— | — | Method F tr (min) = 1.01 [M + H]+: 450 |
| 89 | 1 | 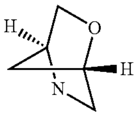 | 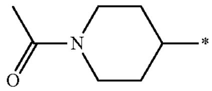 [SMILES: *C1CCN(C(C)=O)CC1] | *—$CH_2$—$CH_2$— | — | Method A: tr (min) = 0.55 [M + H]+: 470 |
| 90 Ex. 44 | 1 | 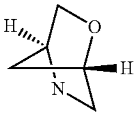 | 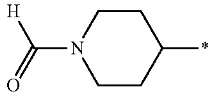 [SMILES: *C1CCN(C=O)CC1] | *—$CH_2$—$CH_2$— | — | Method A: tr (min) = 0.54 [M + H]+: 456 |
| 91 | 1 | 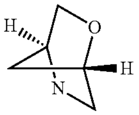 | 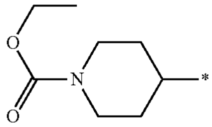 [SMILES: *C1CCN(C(=O)OCC)CC1] | *—CO—$CH_2$— | — | Method A: tr (min) = 0.62 [M + H]+: 514 |
| 92 Ex. 45 | 1 | 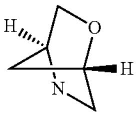 | 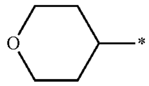 [SMILES: *C1CCOCC1] | *—$CH_2$—$CH_2$— | — | Method A: tr (min) = 0.61 [M + H]+: 429 |

TABLE-continued (I)

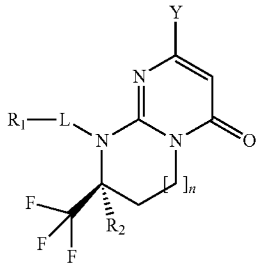

The asterisk * on $R_1$ and L indicates the atom of attachment of $R_1$ to L.

| No. | n | Y | $R_1$ | L | Salt | Data |
|---|---|---|---|---|---|---|
| 93<br>Ex. 46 | 1 | 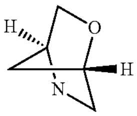 | 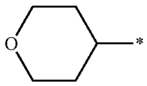 [SMILES: *C1CCOCC1] | *—$CH_2$— | — | Method A:<br>tr (min) = 0.57<br>[M + H]+: 415 |
| 94 | 1 | 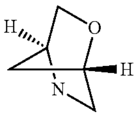 | 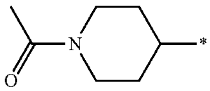 | *—$CH_2$— | — | Method D<br>tr (min) = 0.84<br>[M + H]+: 456 |
| 95<br>Ex. 47 | 1 | 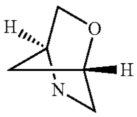 | 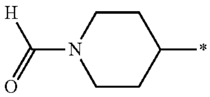 [SMILES: *C1CCN(C=O)CC1] | *—$CH_2$— | — | Method D<br>tr (min) = 1.01<br>[M + H]+: 450 |
| 96<br>Ex. 48 | 1 | 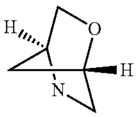 | 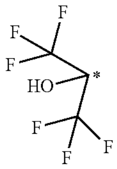 | *—$CH_2$— | — | Method A:<br>tr (min) = 0.71<br>[M + H]+: 497 |
| 97 | 1 | 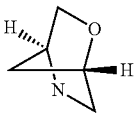 | 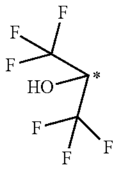 | *—$CH_2$—$CH_2$— | — | Method A:<br>tr (min) = 0.68<br>[M + H]+: 511 |
| 98 | 1 | 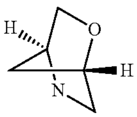 | 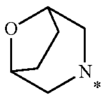 | *—CO—$CH_2$— | — | Method A:<br>tr (min) = 0.51<br>[M + H]+: 470 |
| 99<br>Ex. 49 | 1 | 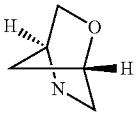 | 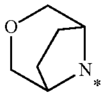 | *—CO—$CH_2$— | — | Method A:<br>tr (min) = 0.5<br>[M + H]+: 470 |
| 100 | 1 | 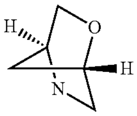 | 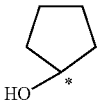 | *—$CH_2$—$CH_2$— | — | Method A:<br>tr (min) = 0.6<br>[M + H]+: 429 |
| 101 | 1 | 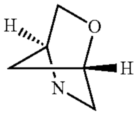 | 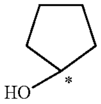 | *—$CH_2$— | — | Method D<br>tr (min) = 0.95<br>[M + H]+: 415 |

TABLE-continued
(I)
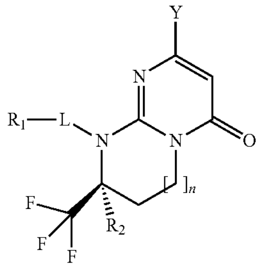
The asterisk * on $R_1$ and L indicates the atom of attachment of $R_1$ to L.
| No. | n | Y | $R_1$ | L | Salt | Data |
|---|---|---|---|---|---|---|
| 102 | 1 | 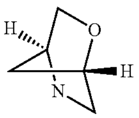 | 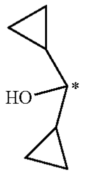 | $*-CH_2-CH_2-$ | — | Method A: tr (min) = 0.68 [M + H]+: 455 |
| 103 | 1 | 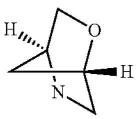 | 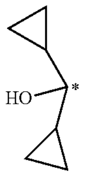 | $*-CH_2-$ | — | Method D tr (min) = 1.13 [M + H]+: 441 |
| 104 Ex. 51 | 1 | 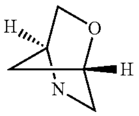 | 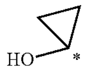 | $*-CH_2-$ | — | Method A: tr (min) = 0.52 [M + H]+: 387 |
| 105 | 1 | 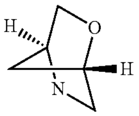 | 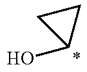 | $*-CH_2-CH_2-$ | — | Method A: tr (min) = 0.53 [M + H]+: 401 |
| 106 Ex. 52 | 1 | 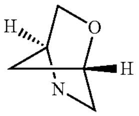 | 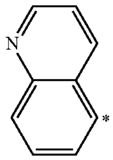 | $*-CH_2-$ | — | Method A: tr (min) = 0.47 [M + H]+: 458 |
| 107 | 1 | 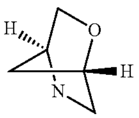 | 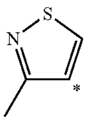 | $*-CO-CH_2-$ | — | Method A: tr (min) = 0.57 [M + H]+: 456 |
| 108 | 1 | 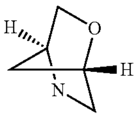 | 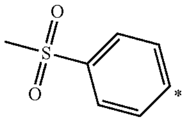 | $*-CO-CH_2-$ | — | Method A: tr (min) = 0.54 [M + H]+: 513 |
| 109 | 1 | 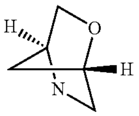 | 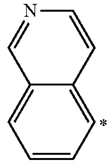 | $*-CH_2-$ | — | Method A: tr (min) = 0.53 [M + H]+: 458 |

TABLE-continued
(I)
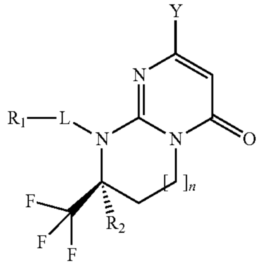
The asterisk * on $R_1$ and L indicates the atom of attachment of $R_1$ to L.
| No. | n | Y | $R_1$ | L | Salt | Data |
| --- | --- | --- | --- | --- | --- | --- |
| 110 | 1 | 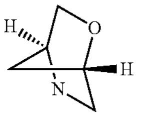 | 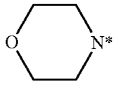 | *—CO—$CH_2$— | — | Method A:<br>tr (min) = 0.56<br>[M + H]+: 444 |
| 111 | 1 | 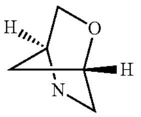 | 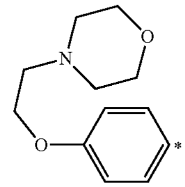 | *—$CH_2$—$CH_2$— | — | Method A:<br>tr (min) = 0.49<br>[M + H]+: 550 |
| 112 | 1 | 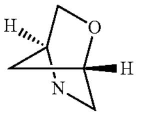 | 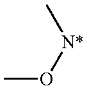 | *—CO—$CH_2$— | — | Method A:<br>tr (min) = 0.53<br>[M + H]+: 418 |
| 113 | 1 | 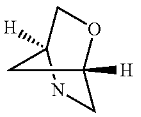 | 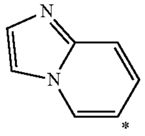 | *—CO—$CH_2$— | — | Method A:<br>tr (min) = 0.38<br>[M + H]+: 475 |
| 114<br>Ex. 53 | 1 | 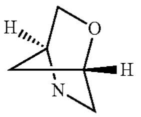 | 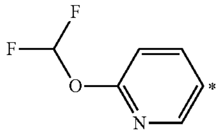 | *—CO—$CH_2$— | — | Method A:<br>tr (min) = 0.67<br>[M + H]+: 502 |
| 115 | 1 | 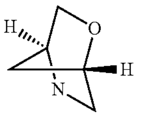 | 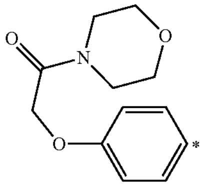 | *—$CH_2$—$CH_2$— | — | Method A:<br>tr (min) = 0.61<br>[M + H]+: 564 |
| 116 | 1 | 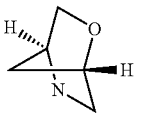 | 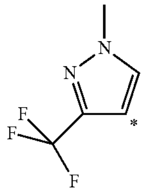 | *—$CH_2$— | — | Method A:<br>tr (min) = 0.67<br>[M + H]+: 479 |

TABLE-continued (I)

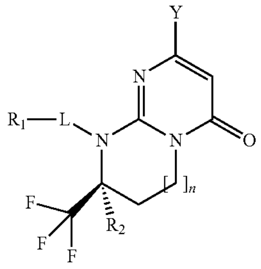

The asterisk * on $R_1$ and L indicates the atom of attachment of $R_1$ to L.

| No. | n | Y | $R_1$ | L | Salt | Data |
|---|---|---|---|---|---|---|
| 117 | 1 | 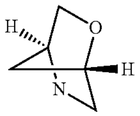 | 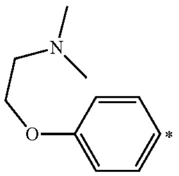 | $*—CH_2—CH_2—$ | — | Method A: tr (min) = 0.49 [M + H]+: 508 |
| 118 | 1 | 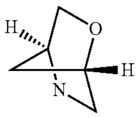 | 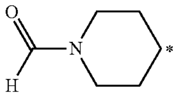 | $*—CO—CH_2—$ | — | Method A: tr (min) = 0.79 [M + H]+: 567 |
| 119 | 1 | 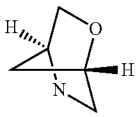 | 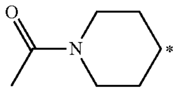 | $*—CO—CH_2—$ | — | Method A: tr (min) = 0.48 [M + H]+: 484 |

The compounds according to the invention underwent pharmacological trials to determine their inhibitory effect on the growth of *Plasmodium falciparum.*

Antimalarial Activity Test

The compounds according to the invention underwent pharmacological trials to determine their inhibitory effect on the growth of *Plasmodium falciparum* (strain NF54 sensitive to inhibition with chloroquine) in an in vitro test using infected human erythrocytes. The growth of the parasites is measured via the incorporation of tritiated hypoxanthine compared with the incorporation in the absence of drug. The tests are performed in 96-well microplates (Falcon™ 96-well microtiter plates, ref. No. 353072) in RPMI 1640 solutions (10.44 g/l) (without hypoxanthine) with HEPES (5.94 g/l), $NaHCO_3$ (2.1 g/l), neomycin (100 g/mL)+AlbumaxR II (5 g/l) supplemented with human erythrocytes with a final hematocrit of 1.25% and a final parasitemia of 0.15%.

The stock solution of the compounds is prepared at 10 mg/mL in DMSO. For the test, fresh solutions at the desired concentrations are prepared in RPMI medium. For the test, 100 μl of compound are mixed with 100 μl of infected blood. For the determination of the $IC_{50}$ values, the compounds are tested in twofold serial dilution.

The plates are incubated at 37° C. under a humid atmosphere with 93% $N_2$, 4% $CO_2$ and 3% $O_2$. After 48 hours, 50 μl of $^3H$-hypoxanthine (=0.5 μCi) in RPMI medium are added to each well and incubation is continued for a further 24 hours. Next, the plates are washed with distilled water and the cell lyzate is transferred onto fiberglass filters. The filters are dried and the radioactivity is determined by liquid scintillation. The results in cpm are converted into percentages of inhibition. The inhibitory activity is given by the concentration that inhibits 50% of the growth of the parasite relative to a control without compound.

The $IC_{50}$ values are between 3 nM and 4000 nM, in particular between 3 nM and 384 nM and even more particularly less than or equal to 200 nM.

The table of results for the antimalarial activity test is given below:

| Compound No. | $IC_{50}$ *Plasmodium falciparum* NF54 |
|---|---|
| 1 | 20 nM |
| 2 | 15 nM |
| 3 | 13 nM |
| 4 | 58 nM |
| 5 | 95 nM |
| 6 | >200 nM |
| 7 | 10 nM |
| 8 | >200 nM |
| 9 | >200 nM |
| 10 | 11 nM |
| 11 | 40 nM |
| 12 | 9 nM |
| 13 | 21 nM |
| 14 | 70 nM |
| 15 | 150 nM |
| 16 | >200 nM |
| 17 | 160 nM |
| 18 | 93 nM |
| 19 | 24 nM |
| 20 | 35 nM |

-continued

| Compound No. | $IC_{50}$ *Plasmodium falciparum* NF54 |
|---|---|
| 21 | 82 nM |
| 22 | >200 nM |
| 23 | 3 nM |
| 24 | 8 nM |
| 25 | <3.4 nM |
| 26 | 10 nM |
| 27 | <4.5 nM |
| 28 | 9 nM |
| 29 | 46 nM |
| 30 | >240 nM |
| 31 | 75 nM |
| 32 | 4 nM |
| 33 | 4000 nM |
| 34 | >200 nM |
| 35 | >210 nM |
| 36 | 240 nM |
| 37 | 230 nM |
| 38 | 140 nM |
| 39 | 98 nM |
| 40 | 80 nM |
| 41 | 930 nM |
| 42 | 80 nM |
| 43 | 42 nM |
| 44 | 106 nM |
| 45 | 112 nM |
| 46 | 398 nM |
| 47 | 13 nM |
| 48 | 27 nM |
| 49 | 6 nM |
| 50 | 8 nM |
| 51 | 65 nM |
| 52 | 130 nM |
| 53 | 870 nM |
| 54 | 10 nM |
| 55 | 28 nM |
| 56 | 45 nM |
| 57 | 65 nM |
| 58 | 53 nM |
| 59 | 87 nM |
| 60 | 19 nM |
| 61 | 130 nM |
| 62 | 11 nM |
| 63 | 384 nM |
| 64 | 39 nM |
| 65 | 21 nM |
| 66 | 73 nM |
| 67 | 43 nM |
| 68 | 27 nM |
| 69 | 96 nM |
| 70 | 12 nM |
| 71 | 23 nM |
| 72 | 37 nM |
| 73 | 44 nM |
| 74 | 68 nM |
| 75 | 80 nM |
| 76 | 93 nM |
| 77 | 160 nM |
| 78 | 360 nM |
| 79 | 640 nM |
| 82 | 9 nM |
| 83 | 10 nM |
| 84 | 110 nM |
| 85 | 150 nM |
| 86 | 170 nM |
| 88 | 140 nM |
| 89 | 3.4 nM |
| 90 | 2 nM |
| 91 | 25 nM |
| 92 | 4 nM |
| 93 | 4 nM |
| 94 | 9 nM |
| 95 | 7 nM |
| 96 | 170 nM |
| 97 | 30 nM |

-continued

| Compound No. | $IC_{50}$ *Plasmodium falciparum* NF54 |
|---|---|
| 98 | 140 nM |
| 99 | 170 nM |
| 100 | 9 nM |
| 101 | 10 nM |
| 102 | 5 nM |
| 103 | 75 nM |
| 104 | 12 nM |
| 105 | 24 nM |
| 106 | 13 nM |
| 107 | 100 nM |
| 108 | 86 nM |
| 109 | 79 nM |
| 110 | 330 nM |
| 111 | 5 nM |
| 112 | 200 nM |
| 113 | 430 nM |
| 114 | 245 nM |
| 115 | 3 nM |
| 116 | 117 nM |
| 117 | 6 nM |
| 118 | 15 nM |
| 119 | 30 nM |

Human PI3Kα Activity Test

The compounds according to the invention underwent pharmacological trials to measure the selectivity toward human lipid kinases and especially human PI3Kα. The test uses a luciferin/luciferase system to measure the concentration of ATP and its consumption during the enzymatic reaction. The test is performed in 96-well format (Corning/Costar 96 black flat-bottomed half-wells plate, ref. 3694) in a total volume of 30 μl.

To 1 μl of inhibitor in 100% DMSO are added (final concentrations) 50 μM of the substrate PIP2 ((L-α-phosphatidyl-D-myoinositol 4,5-bisphosphate, Calbiochem 524644), 2 μM of ATP and 1.7 μg/mL of PI3Kα(p110α/p85α, Invitrogen PV4788) in a buffer of Tris/HCl 50 mM pH 7.5, EGTA 1 mM, $MgCl_2$ 10 mM, Chaps 0.03%, 1 mM DTT). After 90 minutes, the reaction is quenched by adding 20 μl/well of KinaseGlo reagent (Promega V6713). After 10 minutes in the dark, the luminescence is read using a PHERAStar microplate reader (reading at 0.8 sec/well).

The $IC_{50}$ values are determined by the preparation of successive threefold dilutions on at least a scale of more than 10 000. The $IC_{50}$ values are between 190 nM and more than 10 000 nM, in particular between 1040 nM and more than 10 000 nM and even more particularly greater than 2000 nM.

The activity of the other isoforms of human PI3K may be measured in the same manner.

The table of results for the activity of human PI3Kα test is given below:

| No. | $IC_{50}$ Human PI3Kα |
|---|---|
| 1 | 3130 nM |
| 2 | 10000 nM |
| 3 | 7200 nM |
| 4 | >10000 nM |
| 5 | 8200 nM |
| 6 | >10000 nM |
| 7 | 10000 nM |
| 8 | >10000 nM |
| 9 | >10000 nM |
| 10 | 7200 nM |

-continued

| No. | IC50 Human PI3Kα |
|---|---|
| 11 | 10000 nM |
| 12 | 2900 nM |
| 13 | 5750 nM |
| 14 | >10000 nM |
| 15 | >7200 nM |
| 16 | >7200 nM |
| 17 | 10000 nM |
| 18 | >10000 nM |
| 19 | >10000 nM |
| 20 | >10000 nM |
| 21 | >10000 nM |
| 22 | >10000 nM |
| 23 | 1040 nM |
| 24 | 2440 nM |
| 25 | 1000 nM |
| 26 | 2000 nM |
| 27 | 1530 nM |
| 28 | 2260 nM |
| 29 | 7930 nM |
| 30 | >10000 nM |
| 31 | 6350 nM |
| 32 | 3700 nM |
| 33 | >10000 nM |
| 34 | >10000 nM |
| 35 | >10000 nM |
| 36 | >10000 nM |
| 37 | >10000 nM |
| 38 | 5770 nM |
| 39 | >10000 nM |
| 40 | >10000 nM |
| 41 | 4200 nM |
| 42 | >10000 nM |
| 43 | >10000 nM |
| 44 | >10000 nM |
| 45 | >10000 nM |
| 46 | >10000 nM |
| 47 | >10000 nM |
| 48 | >10000 nM |
| 49 | 2740 nM |
| 50 | 4300 nM |
| 51 | >10000 nM |
| 52 | >10000 nM |
| 53 | >10000 nM |
| 54 | 2210 nM |
| 55 | >10000 nM |
| 56 | >10000 nM |
| 57 | >10000 nM |
| 58 | 6400 nM |
| 59 | >10000 nM |
| 60 | >10000 nM |
| 61 | >10000 nM |
| 62 | >10000 nM |
| 63 | >7200 nM |
| 64 | >10000 nM |
| 65 | >10000 nM |
| 66 | >10000 nM |
| 67 | 4000 nM |
| 68 | 6600 nM |
| 69 | >10000 nM |
| 70 | 1000 nM |
| 71 | 810 nM |
| 72 | 730 nM |
| 73 | 2500 nM |
| 74 | 820 nM |
| 75 | 10000 nM |
| 76 | 950 nM |
| 77 | 820 nM |
| 78 | 250 nM |
| 79 | 1600 nM |
| 80 | 1600 nM |
| 81 | 2000 nM |
| 82 | 340 nM |
| 83 | 190 nM |
| 84 | 200 nM |
| 85 | >10000 nM |
| 86 | 7300 nM |

-continued

| No. | IC50 Human PI3Kα |
|---|---|
| 87 | 10000 nM |
| 88 | 1300 nM |
| 89 | 2800 nM |
| 90 | 2400 nM |
| 91 | >10000 nM |
| 92 | 450 nM |
| 93 | 780 nM |
| 94 | 130 nM |
| 95 | 180 nM |
| 96 | 8500 nM |
| 97 | 440 nM |
| 98 | >10000 nM |
| 99 | >10000 nM |
| 100 | 1980 nM |
| 101 | 450 nM |
| 102 | 2500 nM |
| 103 | 840 nM |
| 104 | 930 nM |
| 105 | 1900 nM |
| 106 | >10000 nM |
| 107 | >10000 nM |
| 108 | >10000 nM |
| 109 | 7800 nM |
| 110 | >10000 nM |
| 111 | 330 nM |
| 112 | >10000 nM |
| 113 | >10000 nM |
| 114 | >10000 nM |
| 115 | 590 nM |
| 116 | >10000 nM |
| 117 | 380 nM |
| 118 | >10000 nM |
| 119 | >10000 nM |

The table below shows the human PI3Kα activity test results for known compounds derived from the applications mentioned above WO 2011/001 112 and WO 2011/001 113.

| COMPOUNDS | STRUCTURE | IC50 Human PI3Kα |
|---|---|---|
| Example 1 (p. 39, WO 2011/001 112) | 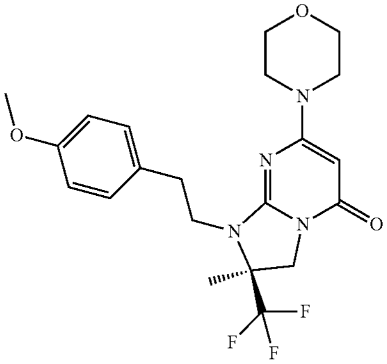 Chiral | 15 nM |

-continued

| COMPOUNDS | STRUCTURE | $IC_{50}$ Human PI3Kα |
|---|---|---|
| Example 10 (p. 61, WO 2011/001 112) | 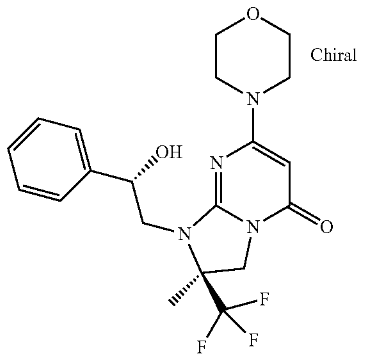 [SMILES: C[C@@]1(C(F)(F)F)Cn2c(nc(N3CCOCC3)cc2=O)N1C[C@@H](O)c1ccccc1] | 17 nM |
| Example 5 (p. 54, WO 2011/001 113) | 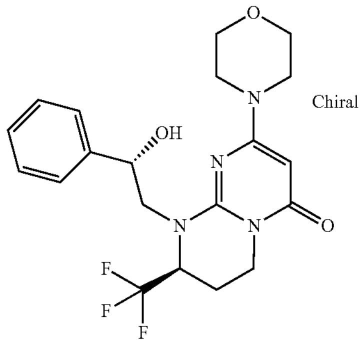 [SMILES: O=c1cc(N2CCOCC2)nc2n1CC[C@@H](C(F)(F)F)N2C[C@@H](O)c1ccccc1] | 6 nM |
| Example 1 (p. 44, WO 2011/001 113) | 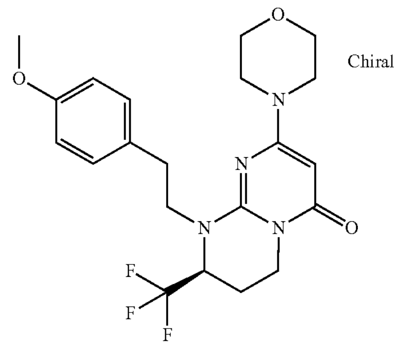 [SMILES: COc1ccc(CCN2c3nc(N4CCOCC4)cc(=O)n3CC[C@H]2C(F)(F)F)cc1] | 9 nM |

It may be seen that although the compounds of the present invention are derived from inhibitors of human PI3K and in particular PI3K, such compounds no longer inhibit, or only sparingly inhibit, this class of human kinases. Thus, they are clearly distinguished from the already-known CF3 pyrimidinones, described in patent applications WO 2011/001 112 and WO 2011/001 113, which are powerful inhibitors of human PI3Kα, which may be used for the treatment of malaria but above all for various cancers in man.

Similar kinomes are present in all species of *Plasmodium*, such as *P. falciparum, P. vivax, P. malariae, P. ovale* and *P. knowlesi*. The compounds of the invention may thus be useful in the treatment of malaria induced by all the parasites mentioned above. In addition, these kinases are found in other parasites, such as *Trypanosoma* (for example *T. brucei, T. cruzei*) and *Leishmania* (for example *L. major, L. donovani*). The compounds of the invention may thus be used in the treatment of sleeping sickness, Chagas disease, the various forms of leishmaniasis and other parasitic infections.

The compounds according to the invention may thus be used for the preparation of medicaments, in particular medicaments for inhibiting parasite growth.

Thus, according to another of its aspects, a subject of the invention is medicaments that comprise a compound of formula (I), or an addition salt of the compound of formula (I) with a pharmaceutically acceptable acid or base.

These medicaments find their use in therapeutics, especially in the treatment of malaria induced by all species of *Plasmodium* such as *P. falciparum, P. vivax, P. malariae, P. ovale* and *P. knowlesi*, but also induced by other species of parasites, for instance *Trypanosoma* such as *T. brucei, T. cruzei* and *Leishmania*, for instance *L. major, L. donovani*. These medicaments also find their use in therapeutics in the treatment of sleeping sickness, Chagas disease, the various forms of leishmaniasis and infections such as schistosomiasis (bilharzia), toxoplasmosis and coccidiosis which are caused by other parasites, respectively schistosomes, toxoplasma and *Eimeria*.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen, according to the pharmaceutical form and the mode of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its salt, can be administered in unit administration form, as a mixture with conventional pharmaceutical excipients, to animals or to human beings for the treatment of the above disorders or diseases.

The appropriate unit administration forms include oral-route forms such as tablets, soft or hard gel capsules, powders, granules and oral solutions or suspensions, sublingual, buccal, intratracheal, intraocular and intranasal administration forms, inhalation forms, topical, transdermal, subcutaneous, intramuscular or intravenous administration forms, rectal administration forms and implants. For topical application, the compounds according to the invention can be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Croscaramellose sodium | 6.0 mg |
| Corn starch | 15.0 mg |
| Hydroxypropylmethylcellulose | 2.25 mg |
| Magnesium stearate | 3.0 mg |

There may be particular cases where higher or lower dosages are appropriate; such dosages do not depart from the context of the invention. According to the usual practice, the dosage appropriate for each patient is determined by the physician according to the method of administration and the weight and response of said patient.

According to another of its aspects, the present invention also relates to a method for treating the pathological conditions indicated above, which comprises the administration, to a patient, of an effective dose of a compound according to the invention, or a pharmaceutically acceptable salt thereof.

The invention claimed is:

1. A compound corresponding to formula (I):

(I)

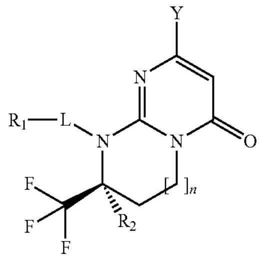

wherein n is 0 or 1;

Y is a bridged morpholine chosen from (a)

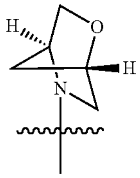

(b)

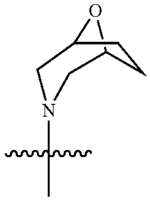

(c)

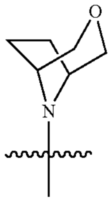

L is a linker —$CH_2$—CO— such that the carbonyl function is attached to the substituent $R_1$, or a ($C_1$-$C_2$)alkyl, said alkyl being optionally substituted with one or more substituents chosen from ($C_1$-$C_3$)alkyl and hydroxyl;

$R_1$ is linear, branched, cyclic or partially cyclic ($C_1$-$C_5$)alkyl, optionally substituted with one or more substituents chosen from hydroxyl, aryl and trifluoromethyl, ($C_3$-$C_6$)cycloalkyl, optionally substituted with hydroxyl, aryl, optionally substituted with one or more substituents chosen from halogen, hydroxyl, cyano, —$NH_2$, —NH—CO—NH—($C_1$-$C_4$)alkyl, morpholine, —$SO_2$—($C_1$-$C_5$)alkyl and ($C_1$-$C_5$)alkoxy, said alkoxy being optionally substituted with one or more substituents chosen from:

halogen, hydroxyl or ($C_1$-$C_5$)alkoxy,

—$COR_3$, in which $R_3$ is heterocycloalkyl or hydroxyl,

—$CONR_4R_{4'}$,

—$NR_4R_{4'}$, heterocycloalkyl comprising one or two heteroelements chosen from nitrogen and oxygen, and heteroaryl optionally substituted with one or more substituents chosen from halogen, ($C_1$-$C_3$)alkyl, hydroxyl and —$NH_2$;

heteroaryl, comprising one or more heteroatoms chosen from nitrogen, sulfur and oxygen, optionally substituted with one or more substituents chosen from:

halogen, ($C_1$-$C_3$)alkyl, optionally substituted with one or more halogen atoms, ($C_1$-$C_5$)alkoxy, optionally substituted with one or more substituents chosen from halogen, ($C_3$-$C_5$) cycloalkyl, and heteroaryl optionally substituted with one or more substituents chosen from halogen, ($C_1$-$C_3$)alkyl, hydroxyl and —$NH_2$, and —$NR_5R_{5'}$, wherein $R_5$ and $R_{5'}$ are independently chosen from hydrogen, —$CO_2$—($C_1$-$C_3$)alkyl, ($C_3$-$C_5$)cycloalkyl and linear or branched ($C_1$-$C_3$)alkyl, said alkyl group being optionally substituted with one or more hydroxyl, pyridine bearing two linked adjacent groups forming, together with the two carbons that bear them, a heterocycle comprising a nitrogen atom and an oxygen atom, heterocycloalkyl comprising one or more heteroatoms chosen from oxygen and nitrogen atoms, said nitrogen atom being optionally substituted with a substituent chosen from formyl, acetyl and a —$CO_2$—($C_1$-$C_4$)alkyl, or —$NR_6R_{6'}$, wherein $R_6$ is ($C_1$-$C_5$)alkyl and $R_{6'}$ is ($C_1$-$C_5$)alkoxy, $R_2$ is hydrogen when n is 1, and methyl when n is 0; and $R_4$ and $R_{4'}$ are independently hydrogen or ($C_1$-$C_3$)alkyl;

in the form of the base or of an addition salt with an acid or with a base.

2. The compound of formula (I) as claimed in claim 1, wherein n is 0 or 1;

Y is bridged morpholine chosen from (a)

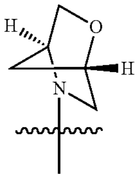

(b)

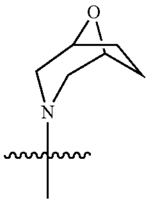

-continued (c)

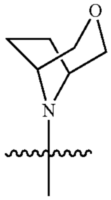

L is a linker —$CH_2$—CO— such that the carbonyl function is attached to the substituent $R_1$, or a ($C_1$-$C_2$)alkyl, optionally substituted with one or more substituents chosen from ($C_1$-$C_3$)alkyl and hydroxyl;

$R_1$ is:

linear or branched ($C_1$-$C_5$)alkyl, optionally substituted with one or more substituents chosen from hydroxyl and aryl, ($C_3$-$C_6$)cycloalkyl, aryl, optionally substituted with one or more substituents chosen from halogen, hydroxyl, cyano, —$NH_2$, —NH—CO—NH—($C_1$-$C_4$)alkyl, morpholine, —$SO_2$—($C_1$-$C_5$)alkyl and ($C_1$-$C_5$)alkoxy, said alkoxy being optionally substituted with one or more substituents chosen from:

halogen, hydroxyl or ($C_1$-$C_5$)alkoxy,

—$COR_3$, wherein $R_3$ is heterocycloalkyl or hydroxyl,

—$CONR_4R_{4'}$,

—$NR_4R_{4'}$, heterocycloalkyl comprising one or two heteroelements chosen from nitrogen and oxygen, and heteroaryl optionally substituted with one or more substituents chosen from halogen, ($C_1$-$C_3$)alkyl, hydroxyl and —$NH_2$;

heteroaryl, comprising one or more heteroatoms chosen from nitrogen, sulfur and oxygen, optionally substituted with one or more substituents chosen from:

halogen, ($C_1$-$C_3$)alkyl, optionally substituted with one or more halogen, ($C_1$-$C_5$)alkoxy, optionally substituted with one or more substituents chosen from halogen, ($C_3$-$C_5$) cycloalkyl, and heteroaryl optionally substituted with one or more substituents chosen from halogen, ($C_1$-$C_3$)alkyl, hydroxyl and —$NH_2$, and —$NR_5R_{5'}$, wherein $R_5$ and $R_{5'}$ are independently chosen from hydrogen, —$CO_2$—($C_1$-$C_3$)alkyl, ($C_3$-$C_5$)cycloalkyl and linear or branched ($C_1$-$C_3$)alkyl, said alkyl group being optionally substituted with one or more hydroxyl, pyridine bearing two linked adjacent groups forming, together with the two carbons that bear them, a heterocycle comprising a nitrogen atom and an oxygen atom, heterocycloalkyl comprising one or more heteroatoms chosen from oxygen and nitrogen atoms, said nitrogen atom being optionally substituted with a substituent chosen from formyl and acetyl, or —$NR_6R_{6'}$, wherein $R_6$ is ($C_1$-$C_5$)alkyl and $R_{6'}$ is ($C_1$-$C_5$) alkoxy, $R_2$ is hydrogen when n is 1, and methyl when n is 0; and $R_4$ and $R_{4'}$ are independently hydrogen or ($C_1$-$C_3$)alkyl;

in the form of the base or of an addition salt with an acid or with a base.

3. The compound of formula (I) as claimed in claim 1, wherein

Y is bridged morpholine (a)

(a)

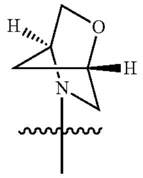

in the form of the base or of an addition salt with an acid or with a base.

4. The compound of formula (I) as claimed in claim 1, wherein n is 0 or 1;

Y is bridged morpholine (a)

(a)

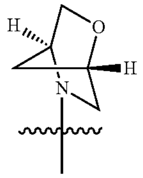

L is a linker —$CH_2$—CO— such that the carbonyl function is attached to the substituent $R_1$, or ($C_1$-$C_2$)alkyl, wherein the alkyl is optionally substituted with one or more ($C_1$-$C_3$)alkyl;

$R_1$ is linear, branched, cyclic or partially cyclic ($C_1$-$C_5$)alkyl, optionally substituted with one or more substituents chosen from hydroxyl, aryl, trifluoromethyl and ($C_3$-$C_6$)cycloalkyl, ($C_3$-$C_6$)cycloalkyl, optionally substituted with hydroxyl, aryl, optionally substituted with one or more substituents chosen from halogen, hydroxyl, —$NH_2$, —NH—CO—NH—($C_1$-$C_4$)alkyl, morpholine, —$SO_2$—($C_1$-$C_5$)alkyl and ($C_1$-$C_5$)alkoxy, said alkoxy being optionally substituted with one or more substituents chosen from:

halogen, hydroxyl or ($C_1$-$C_5$)alkoxy,

—$COR_3$, wherein $R_3$ is heterocycloalkyl or hydroxyl, heterocycloalkyl comprising one or two heteroelements chosen from nitrogen and oxygen, and heteroaryl optionally substituted with one or more substituents chosen from halogen, ($C_1$-$C_3$)alkyl, hydroxyl and —$NH_2$;

heteroaryl, comprising one or more heteroatoms chosen from nitrogen, sulfur and oxygen, optionally substituted with one or more substituents chosen from:

halogen, ($C_1$-$C_3$)alkyl optionally substituted with one or more halogen, ($C_1$-$C_5$)alkoxy group, optionally substituted with one or more substituents chosen from halogen, ($C_3$-$C_5$) cycloalkyl, heteroaryl optionally substituted with one or more substituents chosen from halogen, ($C_1$-$C_3$)alkyl, hydroxyl and —$NH_2$, and —$NR_5R_{5'}$, wherein $R_5$ and $R_{5'}$ are independently chosen from hydrogen, —$CO_2$—($C_1$-$C_3$)alkyl, ($C_3$-$C_5$)cycloalkyl and linear or branched ($C_1$-$C_3$)alkyl, said alkyl group being optionally substituted with one or more hydroxyl, pyridine bearing two linked adjacent groups forming, together with the two carbons that bear them, a heterocycle comprising a nitrogen atom and an oxygen atom, heterocycloalkyl comprising one or more heteroatoms chosen from oxygen and nitrogen atoms, said nitrogen atom being optionally substituted with a substituent chosen from formyl, acetyl and a —$CO_2$—($C_1$-$C_4$)alkyl, or —$NR_6R_{6'}$, wherein $R_6$ is ($C_1$-$C_5$)alkyl and $R_{6'}$ is ($C_1$-$C_5$)alkoxy, $R_2$ is hydrogen when n is 1, and methyl when n is 0; and $R_4$ and $R_{4'}$ are independently hydrogen or ($C_1$-$C_3$)alkyl;

in the form of the base or of an addition salt with an acid or with a base.

5. The compound of formula (I) as claimed in claim 1, wherein n is 0 or 1;

Y is bridged morpholine (a)

(a)

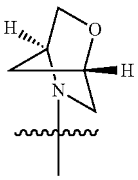

L is a linker —$CH_2$—CO— such that the carbonyl function is attached to the substituent $R_1$, or ($C_1$-$C_2$)alkyl, wherein the alkyl is optionally substituted with one or more ($C_1$-$C_3$)alkyl;

$R_1$ is linear, branched, cyclic or partially cyclic ($C_1$-$C_5$)alkyl, optionally substituted with one or more substituents chosen from hydroxyl and aryl, ($C_3$-$C_6$)cycloalkyl, aryl, optionally substituted with one or more substituents chosen from halogen, hydroxyl, —$NH_2$, —NH—CO—NH—($C_1$-$C_4$)alkyl, morpholine, —$SO_2$—($C_1$-$C_5$)alkyl and ($C_1$-$C_5$)alkoxy, said alkoxy being optionally substituted with one or more substituents chosen from:

halogen, hydroxyl or ($C_1$-$C_5$)alkoxy,

—$COR_3$, wherein $R_3$ is heterocycloalkyl or hydroxyl, heterocycloalkyl comprising one or two heteroelements chosen from nitrogen and oxygen, and heteroaryl optionally substituted with one or more substituents chosen from halogen, ($C_1$-$C_3$)alkyl, hydroxyl and —$NH_2$;

heteroaryl, comprising one or more heteroatoms chosen from nitrogen, sulfur and oxygen, optionally substituted with one or more substituents chosen from:

halogen, ($C_1$-$C_3$)alkyl optionally substituted with one or more halogen, ($C_1$-$C_5$)alkoxy, optionally substituted with one or more substituents chosen from halogen, ($C_3$-$C_5$) cycloalkyl, and heteroaryl optionally substituted with one or more substituents chosen from halogen, ($C_1$-$C_3$)alkyl, hydroxyl and —$NH_2$, and —$NR_5R_{5'}$, wherein $R_5$ and $R_{5'}$ are independently chosen from hydrogen, —$CO_2$—($C_1$-$C_3$)alkyl, ($C_3$-$C_5$)cycloalkyl and linear or branched ($C_1$-$C_3$)alkyl, said alkyl group being optionally substituted with one or more hydroxyl, pyridine bearing two linked adjacent groups forming, together with the two carbons that bear them, a heterocycle comprising a nitrogen atom and an oxygen atom, heterocycloalkyl comprising one or more heteroatoms chosen from oxygen and nitrogen atoms, said nitrogen atom being optionally substituted with a substituent chosen from formyl and acetyl, or —$NR_6R_{6'}$, wherein $R_6$ is ($C_1$-$C_5$)alkyl and $R_{6'}$ is ($C_1$-$C_5$) alkoxy, $R_2$ is hydrogen when n is 1, and methyl when n is 0; and $R_4$ and $R_{4'}$ are independently hydrogen or ($C_1$-$C_3$)alkyl;

in the form of the base or of an addition salt with an acid or with a base.

6. The compound of formula (I) as claimed in claim 1, wherein n is 0 or 1;

Y is bridged morpholine chosen from (b) and (c)

(b)

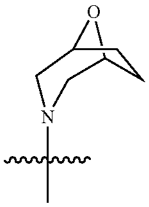

(c)

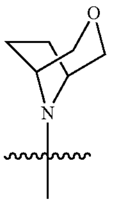

L is a linker —$CH_2$—CO— such that the carbonyl function is attached to the substituent $R_1$, or ($C_1$-$C_2$)alkyl, wherein the alkyl is optionally substituted with a hydroxyl group;

$R_1$ is linear or branched ($C_1$-$C_5$)alkyl, optionally substituted with aryl, aryl, optionally substituted with one or more substituents chosen from halogen, hydroxyl and ($C_1$-$C_5$) alkoxy, said alkoxy being optionally substituted with one or more substituents chosen from:

—$CONR_4R_{4'}$,

—$NR_4R_{4'}$, and heteroaryl comprising one or more heteroatoms chosen from nitrogen, sulfur and oxygen, optionally substituted with one or more ($C_1$-$C_3$)alkyl, optionally substituted with one or more halogen, $R_2$ is hydrogen when n is 1, and methyl when n is 0; and $R_4$ and $R_{4'}$ are independently hydrogen or ($C_1$-$C_3$)alkyl;

in the form of the base or of an addition salt with an acid or with a base.

7. The compound as claimed in claim 1, wherein the linker L is —$CH_2$—CO, in the form of the base or of an addition salt with an acid or with a base.

8. The compound as claimed in claim 1, wherein n is 1, in the form of the base or of an addition salt with an acid or with a base.

9. The compound as claimed in claim 1, wherein n is 0, in the form of the base or of an addition salt with an acid or with a base.

10. The compound as claimed in claim 1, wherein $R_1$ is heteroaryl, in the form of the base or of an addition salt with an acid or with a base.

11. The compound as claimed in claim 1, wherein $R_1$ is heterocycloalkyl comprising one or more heteroatoms chosen from oxygen and nitrogen atoms, said nitrogen atom being optionally substituted with a substituent chosen from formyl, acetyl and a —$CO_2$—($C_1$-$C_4$)alkyl, in the form of the base or of an addition salt with an acid or with a base.

12. A compound of formulae i, N, Q or S:

I

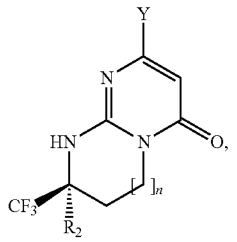

N

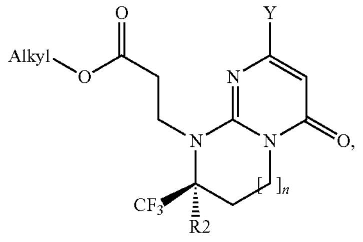

Q

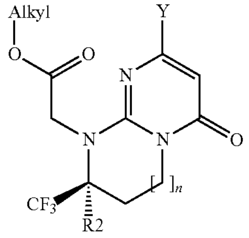

and

S

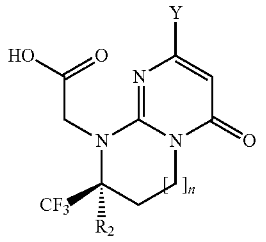

wherein n is 0 or 1;

Y is a bridged morpholine chosen from (a)

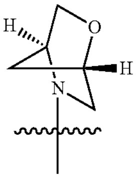

(b)

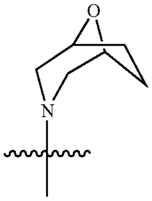

(c)

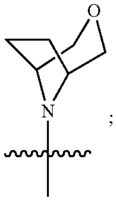

;

and $R_2$ is hydrogen when n is 1, and methyl when n is 0.

13. The compound as claimed in claim 1, wherein the compound is:

(8S)-9-(2-Methyl-2-pyrid-4-ylpropyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-2-(1S,4S)-2-Oxa-5-azabicyclo[2.2.1]hept-5-yl-9-(2-oxo-2-pyrid-4-ylethyl)-8-trifluoromethyl-6,7,8,9-tetrahydropyrimido[1,2-a]pyrimidin-4-one;

(8S)-9-[2-(6-Aminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(6-Methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(6-Methylaminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(6-Dimethylaminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-2-(1S,4S)-2-Oxa-5-azabicyclo[2.2.1]hept-5-yl-9-(2-oxo-2-pyrid-3-ylethyl)-8-trifluoromethyl-6,7,8,9-tetrahydropyrimido[1,2-a]pyrimidin-4-one;

1-[2-(6-Dimethylaminopyrid-3-yl)-2-oxoethyl]-2-(S)-methyl-7-(1S,4S)-2-oxa-5-azabicyclo[2.2.1]hept-5-yl-2-trifluoromethyl-2,3-dihydro-1H-imidazo[1,2-a]pyrimidin-5-one;

2-(S)-Methyl-1-[2-(6-methylaminopyrid-3-yl)-2-oxoethyl]-7-(1S,4S)-2-oxa-5-azabicyclo[2.2.1]hept-5-yl-2-trifluoromethyl-2,3-dihydro-1H-imidazo[1,2-a]pyrimidin-5-one;

(8S)-1-[2-(4-Methoxyphenyl)ethyl]-2-methyl-7-(1S,4S)-2-oxa-5-azabicyclo[2.2.1]hept-5-yl-2-trifluoromethyl-2,3-dihydro-1H-imidazo[1,2-a]pyrimidin-5-one;

(S)-1-[2-(6-Aminopyrid-3-yl)-2-oxoethyl]-2-methyl-7-(1S,4S)-2-oxa-5-azabicyclo[2.2.1]hept-5-yl-2-trifluoromethyl-2,3-dihydro-1H-imidazo[1,2-a]pyrimidin-5-one;

(8S)-2-(1S,4S)-2-Oxa-5-azabicyclo[2.2.1]hept-5-yl-9-(2-pyrid-3-ylethyl)-8-trifluoromethyl-6,7,8,9-tetrahydro-pyrimido[1,2-a]pyrimidin-4-one;

2-Methyl-7-(1S,4S)-2-oxa-5-azabicyclo[2.2.1]hept-5-yl-1-(2-pyrid-3-ylethyl)-2-((S)-trifluoromethyl)-2,3-dihydro-1H-imidazo[1,2-a]pyrimidin-5-one;

(8S)-9-{2-[6-(2-Hydroxyethylamino)pyrid-3-yl]-2-oxo-ethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(5-Methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

2-Methyl-1-[2-(5-methylpyrid-3-yl)-2-oxoethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one;

2-Methyl-1-[2-(6-methylpyrid-3-yl)-2-oxoethyl]-7-(1S,4S)-2-oxa-5-azabicyclo[2.2.1]hept-5-yl-2-trifluoromethyl-2,3-dihydro-1H-imidazo[1,2-a]pyrimidin-5-one;

2-Methyl-1-[2-(2-methylpyrid-3-yl)-2-oxoethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one;

(8S)-9-[2-(2-Methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(4-Methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

2-Methyl-7-(1S,4S)-2-oxa-5-azabicyclo[2.2.1]hept-5-yl-1-(2-oxo-2-pyrid-3-ylethyl)-2-((S)-trifluoromethyl)-2,3-dihydro-1H-imidazo[1,2-a]pyrimidin-5-one;

(8S)-9-[2-(6-Cyclopropylaminopyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

1-Ethyl-3-{4-[2-((S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)ethyl]phenyl}urea;

1-Ethyl-3-{4-[2-((S)-2-methyl-7-(1S,4S)-2-oxa-5-azabicyclo[2.2.1]hept-5-yl-5-oxo-2-trifluoromethyl-2,3-dihydro-5H-imidazo[1,2-a]pyrimidin-1-yl)ethyl]phenyl}urea;

(8S)-9-[2-(4-Methylthiazol-5-yl)ethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

2-Methyl-1-[2-(4-methylthiazol-5-yl)ethyl]-7-(1S,4S)-2-oxa-5-azabicyclo[2.2.1]hept-5-yl-2-((S)-trifluoromethyl)-2,3-dihydro-1H-imidazo[1,2-a]pyrimidin-5-one;

(8S)-9-[2-(3,5-Dimethyl-1H-pyrazol-4-yl)ethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

1-[2-(3,5-Dimethyl-1H-pyrazol-4-yl)ethyl]-2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one;

(8S)-9-(3,3-Dimethyl-2-oxobutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

1-(3,3-Dimethyl-2-oxobutyl)-2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one;

(8S)-9-[2-(6-Amino-5-methylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

1-[2-(4-Aminophenyl)ethyl]-2-methyl-7-(1S,4S)-2-oxa-5-azabicyclo[2.2.1]hept-5-yl-2-((S)-trifluoromethyl)-2,3-dihydro-1H-imidazo[1,2-a]pyrimidin-5-one;

(8S)-2-(1S,4S)-2-Oxa-5-azabicyclo[2.2.1]hept-5-yl-9-[2-oxo-2-(6-trifluoromethylpyrid-3-yl)ethyl]-8-trifluoromethyl-6,7,8,9-tetrahydropyrimido[1,2-a]pyrimidin-4-one;

(8S)-9-(2-{6-[(2-Hydroxyethyl)methylamino]pyrid-3-yl}-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(6-Ethoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(6-Amino-4,5-dimethylpyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(S)-9-[2-(4-Difluoromethoxyphenyl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(3,4-Dihydro-2H-pyrido[3,2-b][1,4]oxazin-7-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(4-Methyloxazol-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(S)-9-[2-(3,4-Difluorophenyl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(4-Morpholin-4-ylphenyl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

4-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)acetyl]benzonitrile;

(8S)-9-[2-(4-Methylthiazol-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(5-Chloropyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(6-Methoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(3-Methylisoxazol-4-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-(2-Benzo[1,2,3]thiadiazol-5-yl-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(2,4-Difluorophenyl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-(3-Ethyl-3-hydroxypentyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-(3-Hydroxy-3-methylbutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-(1-Methyl-1H-indazol-3-ylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(2-Cyclopropylmethoxypyrimidin-5-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(3,5-Dimethylisoxazol-4-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-(2-Ethyl-2-hydroxybutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

3-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)acetyl]benzonitrile;

(8S)-9-(3-Methyl-2-oxobutyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

{5-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)acetyl]pyrid-2-yl}carbamic acid ethyl ester;

{5-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)acetyl]pyrid-2-yl}carbamic acid methyl ester;

(8S)-9-(5-Methyl-[1,2,4]oxadiazol-3-ylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-2-(1S,4S)-2-Oxa-5-azabicyclo[2.2.1]hept-5-yl-9-[2-oxo-2-(2-trifluoromethylpyrid-3-yl)ethyl]-8-trifluoromethyl-6,7,8,9-tetrahydropyrimido[1,2-a]pyrimidin-4-one;

(8S)-9-(2-Benzo[1,2,5]thiadiazol-5-yl-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-2-(1S,4S)-2-Oxa-5-azabicyclo[2.2.1]hept-5-yl-9-[2-oxo-2-(tetrahydropyran-4-yl)ethyl]-8-trifluoromethyl-6,7,8,9-tetrahydropyrimido[1,2-a]pyrimidin-4-one;

(8S)-9-{2-[6-(2-Fluoroethoxy)pyrid-3-yl]-2-oxoethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-{2-[3-Fluoro-4-(2-fluoroethoxyl)phenyl]-2-oxoethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(2-Methoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(3-Methyl-3H-imidazol-4-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-(2-Cyclopropyl-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-2-(1S,4S)-2-Oxa-5-azabicyclo[2.2.1]hept-5-yl-9-(2-oxo-2-pyrid-2-ylethyl)-8-trifluoromethyl-6,7,8,9-tetrahydropyrimido[1,2-a]pyrimidin-4-one;

(8S)-9-[2-(2-Methyl-2H-pyrazol-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

N,N-Dimethyl-2-(4-{2-[(S)-2-methyl-7-(8-oxa-3-azabicyclo[3.2.1]oct-3-yl)-5-oxo-2-trifluoromethyl-2,3-dihydro-5H-imidazo[1,2-a]pyrimidin-1-yl]ethyl}phenoxy)acetamide;

(8S)-9-[(S)-2-(4-Fluoro-2-methoxyphenyl)-2-hydroxyethyl]-2-(8-oxa-3-azabicyclo[3.2.1]oct-3-yl)-8-trifluoromethyl-6,7,8,9-tetrahydropyrimido[1,2-a]pyrimidin-4-one;

(2S)-1-[2-(4-Hydroxyphenyl)ethyl]-2-methyl-7-(8-oxa-3-azabicyclo[3.2.1]oct-3-yl)-2-trifluoromethyl-2,3-dihydro-1H-imidazo[1,2-a]pyrimidin-5-one;

(8S)-2-(8-Oxa-3-azabicyclo[3.2.1]oct-3-yl)-9-(2-oxo-2-phenylethyl)-8-trifluoromethyl-6,7,8,9-tetrahydropyrimido[1,2-a]pyrimidin-4-one;

(2S)-1-{2-[4-(2-Dimethylaminoethoxyl)phenyl]ethyl}-2-methyl-7-(8-oxa-3-azabicyclo[3.2.1]oct-3-yl)-2-trifluoromethyl-2,3-dihydro-1H-imidazo[1,2-a]pyrimidin-5-one;

(8S)-2-(8-Oxa-3-azabicyclo[3.2.1]oct-3-yl)-9-(2-oxo-2-pyrid-4-ylethyl)-8-trifluoromethyl-6,7,8,9-tetrahydropyrimido[1,2-a]pyrimidin-4-one;

(S)-1-[2-(4-Methoxyphenyl)ethyl]-2-methyl-7-(8-oxa-3-azabicyclo[3.2.1]oct-3-yl)-2-trifluoromethyl-2,3-dihydro-1H-imidazo[1,2-a]pyrimidin-5-one;

(S)-2-Methyl-7-(8-oxa-3-azabicyclo[3.2.1]oct-3-yl)-1-(3-phenylpropyl)-2-trifluoromethyl-2,3-dihydro-1H-imidazo[1,2-a]pyrimidin-5-one;

(S)-1-{2-[4-(3-Dimethylaminopropoxyl)phenyl]ethyl}-2-methyl-7-(8-oxa-3-azabicyclo[3.2.1]oct-3-yl)-2-trifluoromethyl-2,3-dihydro-1H-imidazo[1,2-a]pyrimidin-5-one;

(2S)-1-((S)-2-Hydroxy-2-phenylethyl)-2-methyl-7-(8-oxa-3-azabicyclo[3.2.1]oct-3-yl)-2-trifluoromethyl-2,3-dihydro-1H-imidazo[1,2-a]pyrimidin-5-one;

(8S)-9-((S)-2-Hydroxy-2-phenylethyl)-2-(8-oxa-3-azabicyclo[3.2.1]oct-3-yl)-8-trifluoromethyl-6,7,8,9-tetrahydropyrimido[1,2-a]pyrimidin-4-one;

(8S)-9-[2-(4-Methoxyphenyl)ethyl]-2-(8-oxa-3-azabicyclo[3.2.1]oct-3-yl)-8-trifluoromethyl-6,7,8,9-tetrahydropyrimido[1,2-a]pyrimidin-4-one;

(8S)-9-((R)-2-Benzo[b]thiophen-2-yl-2-hydroxyethyl)-2-(8-oxa-3-azabicyclo[3.2.1]oct-3-yl)-8-trifluoromethyl-6,7,8,9-tetrahydropyrimido[1,2-a]pyrimidin-4-one;

(8S)-9-[2-(4-Hydroxyphenyl)ethyl]-2-(8-oxa-3-azabicyclo[3.2.1]oct-3-yl)-8-trifluoromethyl-6,7,8,9-tetrahydropyrimido[1,2-a]pyrimidin-4-one;

(8S)-2-(8-Oxa-3-azabicyclo[3.2.1]oct-3-yl)-9-(3-phenylpropyl)-8-trifluoromethylmethyl-6,7,8,9-tetrahydropyrimido[1,2-a]pyrimidin-4-one;

(8S)-2-(3-Oxa-8-azabicyclo[3.2.1]oct-8-yl)-9-(2-oxo-2-pyrid-3-ylethyl)-8-trifluoromethyl-6,7,8,9-tetrahydropyrimido[1,2-a]pyrimidin-4-one;

(8S)-9-(1-Difluoromethyl-1H-pyrazol-3-ylmethyl)-2-(8-oxa-3-azabicyclo[3.2.1]oct-3-yl)-8-trifluoromethyl-6,7,8,9-tetrahydropyrimido[1,2-a]pyrimidin-4-one;

(8S)-2-(8-Oxa-3-azabicyclo[3.2.1]oct-3-yl)-9-(2-oxo-2-pyrid-3-ylethyl)-8-trifluoromethyl-6,7,8,9-tetrahydropyrimido[1,2-a]pyrimidin-4-one;

(8S)-2-(8-Oxa-3-azabicyclo[3.2.1]oct-3-yl)-9-(2-oxo-2-pyrid-2-ylethyl)-8-trifluoromethyl-6,7,8,9-tetrahydro-pyrimido[1,2-a]pyrimidin-4-one;

(S)-9-[2-(1-Acetylpiperid-4-yl)ethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

4-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)ethyl]piperidine-1-carbaldehyde;

4-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)acetyl]piperidine-1-carboxylic acid ethyl ester;

(8S)-2-(1S,4S)-2-Oxa-5-azabicyclo[2.2.1]hept-5-yl-9-[2-(tetrahydropyran-4-yl)ethyl]-8-trifluoromethyl-6,7,8,9-tetrahydropyrimido[1,2-a]pyrimidin-4-one;

(8S)-2-(1S,4S)-2-Oxa-5-azabicyclo[2.2.1]hept-5-yl-9-(tetrahydropyran-4-ylmethyl)-8-trifluoromethyl-6,7,8,9-tetrahydropyrimido[1,2-a]pyrimidin-4-one;

(8S)-9-(1-Acetylpiperid-4-ylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

4-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-ylmethyl)piperidine-1-carbaldehyde;

(8S)-2-(1S,4S)-2-Oxa-5-azabicyclo[2.2.1]hept-5-yl-9-(3,3,3-trifluoro-2-hydroxy-2-trifluoromethylpropyl)-8-trifluoromethyl-6,7,8,9-tetrahydropyrimido[1,2-a]pyrimidin-4-one;

(8S)-2-(1S,4S)-2-Oxa-5-azabicyclo[2.2.1]hept-5-yl-9-(4,4,4-trifluoro-3-hydroxy-3-trifluoromethylbutyl)-8-trifluoromethyl-6,7,8,9-tetrahydropyrimido[1,2-a]pyrimidin-4-one;

(8S)-2-(1S,4S)-2-Oxa-5-azabicyclo[2.2.1]hept-5-yl-9-[2-(8-oxa-3-azabicyclo[3.2.1]oct-3-yl)-2-oxoethyl]-8-trifluoromethyl-6,7,8,9-tetrahydropyrimido[1,2-a]pyrimidin-4-one;

(8S)-2-(1S,4S)-2-Oxa-5-azabicyclo[2.2.1]hept-5-yl-9-[2-(3-oxa-8-azabicyclo[3.2.1]oct-8-yl)-2-oxoethyl]-8-trifluoromethyl-6,7,8,9-tetrahydropyrimido[1,2-a]pyrimidin-4-one;

(8S)-9-[2-(1-Hydroxycyclopentyl)ethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-(1-Hydroxycyclopentylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-(3,3-Dicyclopropyl-3-hydroxypropyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-(2,2-Dicyclopropyl-2-hydroxyethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-(1-Hydroxycyclopropylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(1-Hydroxycyclopropyl)ethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-2-(1S,4S)-2-Oxa-5-azabicyclo[2.2.1]hept-5-yl-9-quinolin-5-ylmethyl-8-trifluoromethyl-6,7,8,9-tetrahydropyrimido[1,2-a]pyrimidin-4-one;

(8S)-9-[2-(3-Methylisothiazol-4-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(4-Methanesulfonylphenyl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-Isoquinolin-5-ylmethyl-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-(2-Morpholin-4-yl-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-{2-[4-(2-Morpholin-4-ylethoxy)phenyl]ethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one;

N-Methoxy-N-methyl-2-((S)-8-(1S,4S)-2-oxa-5-azabicyclo[2.2.1]hept-5-yl-6-oxo-2-trifluoromethyl-3,4-dihydro-2H,6H-pyrimido[1,2-a]pyrimidin-1-yl)acetamide;

(8S)-9-(2-Imidazo[1,2-a]pyrid-6-yl-2-oxoethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-[2-(6-Difluoromethoxypyrid-3-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

(S)-9-{2-[4-(2-Morpholin-4-yl-2-oxoethoxy)phenyl]ethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-(1-Methyl-3-trifluoromethyl-1H-pyrazol-4-ylmethyl)-2-(1S,4S)-2-oxa-5-azabicyclo[2.2.1]hept-5-yl-8-trifluoromethyl-6,7,8,9-tetrahydropyrimido[1,2-a]pyrimidin-4-one;

(8S)-9-{2-[4-(2-Dimethylaminoethoxy)phenyl]ethyl}-2-(1S,4S)-2-oxa-5-azabicyclo[2.2.1]hept-5-yl-8-trifluoromethyl-6,7,8,9-tetrahydropyrimido[1,2-a]pyrimidin-4-one;

4-[2-((S)-8-(1S,4S)-2-Oxa-5-azabicyclo[2.2.1]hept-5-yl-6-oxo-2-trifluoromethyl-3,4-dihydro-2H,6H-pyrimido[1,2-a]pyrimidin-1-yl)acetyl]piperidine-1-carbaldehyde; or (8S)-9-[2-(1-Acetylpiperid-4-yl)-2-oxoethyl]-2-(1S,4S)-2-oxa-5-azabicyclo[2.2.1]hept-5-yl-8-trifluoromethyl-6,7,8,9-tetrahydropyrimido[1,2-a]pyrimidin-4-one;

in the form of the base or of an addition salt with an acid or with a base.

14. A pharmaceutical composition, comprising a compound as claimed in claim 1, or a pharmaceutically acceptable salt of this compound, and at least one pharmaceutically acceptable excipient.

15. A process for preparing a compound of formula (I) as claimed in claim 1, comprising the reaction of a compound of formula E:

E

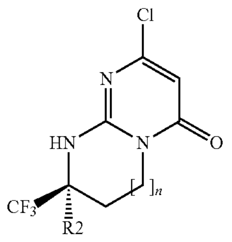

wherein n is 0 or 1 and $R_2$ is hydrogen when n=1, or methyl when n=0;

with a bridged morpholine Y, chosen from (a), (b) and (c) as defined in claim 1; to obtain a compound of formula i:

I

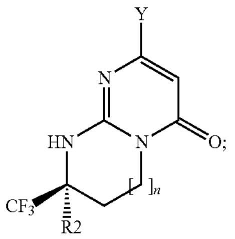

and the alkylation reaction by addition to I of a compound of formula J=$R_1$-L-Lg wherein $R_1$ and L are as defined in claim 1 and Lg is a leaving group.

16. A process for preparing a compound of formula (I) as claimed in claim 1, comprising the alkylation reaction of a compound of formula E:

E

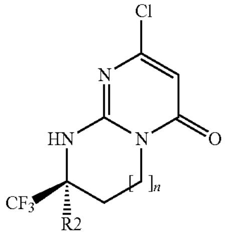

wherein n is 0 or 1 and $R_2$ is a hydrogen atom when n=1 or a methyl group when n=0;

by addition of a compound of formula J=$R_1$-L-Lg wherein $R_1$ and L are as defined in claim 1 and Lg is a leaving group;

to obtain a compound of formula K:

K

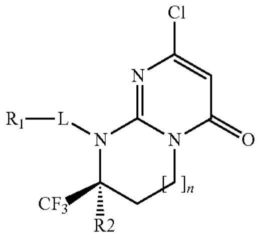

wherein $R_1$, $R_2$, L and n are as defined in claim 1, and a reaction on a compound K with a compound of formula Y being a bridged morpholine chosen from (a), (b) and (c) as defined in claim 1.

17. A process for preparing a compound of formula (I) as claimed in claim 1, wherein the linker L is ethyl, $R_1$ is linear or branched $(C_1\text{-}C_5)$alkyl substituted with hydroxyl, Y is a bridged morpholine chosen from (a), (b) and (c) as defined in claim 1, n is 1 or 0, and $R_2$ is hydrogen when n=1, and methyl when n=0, comprising a Michael addition reaction of a compound of formula E:

E

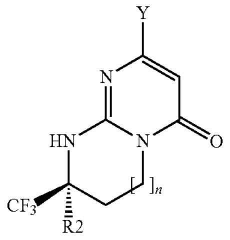

wherein n is 0 or 1 and $R_2$ is hydrogen when n=1, or methyl when n=0;

on a compound of formula M=$CH_2$═$CH_2$—$CO_2$Alkyl, to obtain a compound of formula N:

N

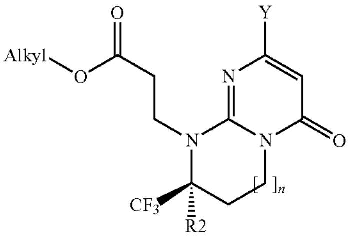

wherein n is 0 or 1 and $R_2$ is hydrogen when n=1, or methyl when n=0, and Y is a bridged morpholine chosen from (a), (b) and (c) as defined in claim 1; and a reaction of alkyl on a compound of formula N with a compound of formula O═Z—Mg—X wherein Z is linear or branched alkyl and X is halogen.

18. A process for preparing a compound of formula (I) as claimed in claim 1, wherein the linker L is methyl, $R_1$ is linear or branched $(C_1\text{-}C_5)$alkyl substituted with hydroxyl, Y is a bridged morpholine chosen from (a), (b) and (c) as defined in claim 1, n is 1 or 0, and $R_2$ is hydrogen when n=1, and methyl when n=0, comprising an addition reaction of a compound of formula E:

E

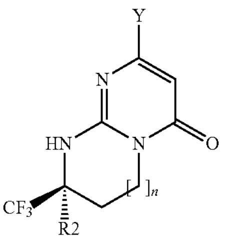

wherein n is 0 or 1 and $R_2$ is hydrogen when n=1, or methyl when n=0, with a compound of formula P═X—$CH_2$—$CO_2$Alkyl wherein X is halogen;

to obtain a compound of formula Q:

Q

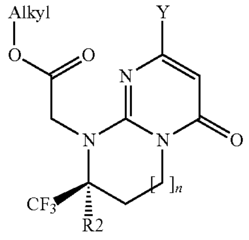

wherein Y is a bridged morpholine chosen from (a), (b) and (c), n is 0 or 1 and $R_2$ is hydrogen when n=1, or methyl when n=0; and an alkylation reaction on a compound of formula Q with a compound of formula O═Z—Mg—X, wherein Z is linear or branched alkyl and X is halogen.

19. A process for preparing a compound of formula (I) as claimed in claim 1, wherein the linker L is methyl, $R_1$ is —$NR_6R_{6'}$, wherein $R_6$ is alkyl and $R_{6'}$ is alkoxy, or $R_6$ and $R_{6'}$ together form a monocyclic or bicyclic heterocycloalkyl, Y is a bridged morpholine chosen from (a), (b) and (c) as defined in claim 1, n is 1 or 0, and $R_2$ is hydrogen when n=1, and methyl when n=0, comprising a hydrolysis reaction of a compound of formula Q:

Q

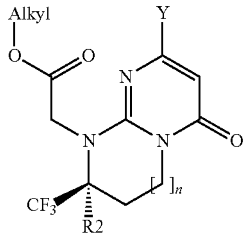

wherein Y is a bridged morpholine chosen from (a), (b) and (c), n is 0 or 1 and $R_2$ is hydrogen when n=1, or methyl when n=0, to obtain a compound of formula S:

S

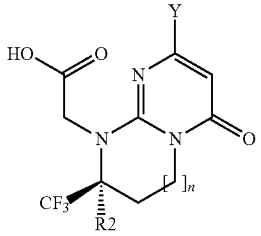

wherein Y is a bridged morpholine chosen from (a), (b) and (c) as defined in claim 1, n is 1 or 0 and $R_2$ is hydrogen when n=1, or methyl when n=0; and a coupling reaction between a compound of formula S and a compound of formula $HNR_6R_{6'}$ wherein $R_6$ is alkyl and $R_{6'}$ is alkoxy, or $R_6$ and $R_{6'}$ together form a monocyclic or bicyclic heterocycloalkyl.

20. A method for treating parasite-induced malaria, the method comprising administrating to a patient in need thereof an effective amount of a compound according to claim 1.

21. A method for the treatment of malaria induced by a species of *Plasmodium*, a species of *Trypanosoma* or a species of *Leishmania*, the treatment of sleeping sickness, the treatment of Chagas disease, the treatment of of leishmaniasis, or the treatment of another parasitic infection, the method comprising administrating to a patient in need thereof an effective amount of a compound according to claim 1.

22. The method of claim 21, wherein the species of *Plasmodium* is *P. falciparum, P. vivax, P. malariae, P. ovale* or *P. knowlesi.*

23. The method of claim 21, wherein the parasitic infection is schistosomiasis (*bilharzia*), toxoplasmosis or coccidiosis.

* * * * *